US012503492B2

(12) United States Patent
Choi et al.

(10) Patent No.: US 12,503,492 B2
(45) Date of Patent: Dec. 23, 2025

(54) CRISPR-Cas-BASED COMPOSITION FOR GENE CORRECTION

(71) Applicant: INDUSTRY-UNIVERSITY COOPERATION FOUNDATION HANYANG UNIVERSITY, Seoul (KR)

(72) Inventors: Je-Min Choi, Seoul (KR); Ja-Hyun Koo, Cheonan-si (KR); Hong-Gyun Lee, Seoul (KR); Jae-Ung Lee, Siheung-si (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 1182 days.

(21) Appl. No.: 17/312,174

(22) PCT Filed: Dec. 27, 2019

(86) PCT No.: PCT/KR2019/018627

§ 371 (c)(1),
(2) Date: Jun. 9, 2021

(87) PCT Pub. No.: WO2020/139031

PCT Pub. Date: Jul. 2, 2020

(65) Prior Publication Data

US 2022/0009968 A1 Jan. 13, 2022

(30) Foreign Application Priority Data

Dec. 27, 2018 (KR) ........................ 10-2018-0170463
Dec. 26, 2019 (KR) ........................ 10-2019-0174907

(51) Int. Cl.

| | |
|---|---|
| ***C07K 14/00*** | (2006.01) |
| ***C12N 9/22*** | (2006.01) |
| ***C12N 15/11*** | (2006.01) |
| ***C12N 15/90*** | (2006.01) |

(52) U.S. Cl.

CPC ................ *C07K 14/00* (2013.01); *C12N 9/22* (2013.01); *C12N 15/11* (2013.01); *C12N 15/902* (2013.01); *C07K 2319/10* (2013.01); *C12N 2310/20* (2017.05)

(58) Field of Classification Search

None

See application file for complete search history.

(56) References Cited

U.S. PATENT DOCUMENTS

2016/0304893 A1 10/2016 Daboussi et al.

FOREIGN PATENT DOCUMENTS

| | | | |
|---|---|---|---|
| KR | 10-0810927 | B1 | 3/2008 |
| KR | 10-2016-0089527 | A | 7/2016 |
| KR | 10-1841211 | B1 | 3/2018 |
| WO | 2018-062866 | A2 | 4/2018 |

OTHER PUBLICATIONS

Written opinion for PCT/KR2019/018627 dated Apr. 14, 2020.
Internal search report for PCT/KR2019/018627 dated Apr. 14, 2020.

*Primary Examiner* — Celine X Qian
(74) *Attorney, Agent, or Firm* — Sughrue Mion, PLLC

(57) ABSTRACT

The present disclosure relates to a composition for enhancing the cell permeability and gene correction efficiency of Cas protein and guide RNA. The currently used CRISPR-Cas-based gene correction technology has the problems of difficult intracellular injection in a complex form, unverified stability and low efficiency even after injection, and the off-target problem. In contrast, the composition for gene correction of the present disclosure can be usefully used for gene therapy due to remarkably high intracellular delivery efficiency, inhibited off-target, and ensured stability.

12 Claims, 21 Drawing Sheets

Specification includes a Sequence Listing.

CRISPR-Cas-BASED COMPOSITION FOR GENE CORRECTION

CROSS-REFERENCE TO RELATED APPLICATIONS

This application is a National Stage of International Application No. PCT/KR2019/018627 filed Dec. 27, 2019, which claims priority under U.S.C. § 119(a) to Korean Patent Application No. 10-2018-0170463 filed on Dec. 27, 2018 and Korean Patent Application No. 10-2019-0174907 filed on Dec. 26, 2019.

SEQUENCE LISTING

The content of the electronically submitted sequence listing, file name: Q264277_Sub_Sequence_Listing_ST25.txt; size: 484.8 KB; and date of creation: Jun. 7, 2025, filed herewith, is incorporated herein by reference in its entirety.

TECHNICAL FIELD

The present disclosure relates to a composition for enhancing the cell permeability and gene correction efficiency of Cas protein and guide RNA. More specifically, the composition of the present disclosure can be used for clinical therapy or cell therapy because it can provide higher gene correction efficiency by delivering genetic scissors into cells in the form of a protein-based RNP complex and can reduce the off-target effect.

BACKGROUND ART

The gene editing technologies include the first generation zinc-finger nucleases (ZFNs), the second generation transcription activator-like effector nucleases (TALENs) and the third generation genetic scissors Cas9 and Cpf1 derived from the CRISPR/Cas system.

The CRISPR/Cas system has originated from the adaptive immunity of microorganisms. It has originated from the immune system which remembers the DNA fragments of a bacteriophage when infected by the bacteriophage and cleaves them with the nuclease Cas9 (CRISPR-associated protein 9: RNA-guided DNA endonuclease enzyme) which serves as genetic scissors when infected again by the bacteriophage. It can conveniently cleave and correct a specific base sequence in a genome that can be recognized by guide RNA (gRNA). However, the third generation genetic scissors has the off-targeting problem of cleaving genes other than the target gene because they are expressed continuously in cells.

Especially, the early gene editing system using Cas9 plasmid requires verification of safety with regard to antibiotic resistance, immune response, etc. when delivered into the body. Although a delivery system prepared in vitro from protein-based genetic scissors (Cas9) and guide RNA was proposed recently as an alternative, it also has the problems of the efficiency of intracellular delivery and the stability of the protein and RNA (Ramakrishna S et al., 2014).

Therefore, the development of a biocompatible protein-based gene correction technology with decreased risk of off-targeting is necessary. For development of novel genetic scissors that can be stably applied to clinical therapy and cell therapy, effective intracellular delivery and reduced cytotoxicity are necessary. However, since the efficiency of intracellular delivery of the Cas9 protein-RNA complex (ribonucleoprotein: RNP) is very limited with around 10%, the existing gene correction technology is limited.

DISCLOSURE

Technical Problem

The present disclosure is directed to providing a cell-penetrating peptide for a Cas protein-RNA complex (ribonucleoprotein: RNP).

The present disclosure is also directed to providing a composition for gene correction, which contains a Cas protein-RNA complex (ribonucleoprotein: RNP).

The present disclosure is also directed to providing a method for preparing a non-human transformant using the composition.

Technical Solution

The present disclosure provides a cell-penetrating peptide for a Cas protein-RNA complex (ribonucleoprotein: RNP), which is represented by General Formula 1.

[General Formula 1]

Arg-Arg-Arg-Trp-Cys-Lys-Arg-Arg-Arg-Ala-Ser-$[\text{Gly}]_m$-$[\text{His-Glu}]_n$ (SEQ ID NO: 85)

In the above formula, m is an integer from 3 to 7, and n is an integer from 5 to 15.

In General Formula 1, n may be an integer from 9 to 15 (SEQ ID NO: 86). More specifically, n may be an integer from 10 to 12 (SEQ ID NO: 87).

The cell-penetrating peptide for a Cas protein-RNA complex (ribonucleoprotein: RNP) may be represented by SEQ ID NO: 6.

The present disclosure also provides a composition for gene correction, which contains a complex (RNP) including: a) a Cas protein to which a cell-penetrating peptide represented by General Formula 1 is bound; and b) a guide RNA

[General Formula 1]

Arg-Arg-Arg-Trp-Cys-Lys-Arg-Arg-Arg-Ala-Ser-$[\text{Gly}]_m$-$[\text{His-Glu}]_n$ (SEQ ID NO: 85 wherein m is an integer from 3 to 7, and n is an integer from 5 to 15.

In General Formula 1, n may be an integer from 9 to 15 (SEQ ID NO: 86). More specifically n may be an integer from 10 to 12 (SEQ ID NO: 87).

The Cas protein may be represented by SEQ ID NO: 9.

The guide RNA may be a dual RNA or a single-stranded guide RNA (sgRNA) including crRNA and tracrRNA.

The composition may induce targeted mutation of single or multiple genes in a prokaryotic cell, a eukaryotic cell or a non-human eukaryotic organism.

The present disclosure also provides a method for preparing a non-human transformant, which includes 1) a step of introducing the composition for gene correction into an isolated prokaryotic cell, eukaryotic cell or non-human eukaryotic organism by a method selected from local injection, microinjection, electroporation and lipofection.

The present disclosure also provides a non-human transformant prepared by the method.

Advantageous Effects

The present disclosure relates to a composition for gene correction, which contains a complex (RNP) of a Cas protein to which a cell-penetrating peptide is bound and a guide RNA. The currently available CRISPR-Cas-based gene correction technology has the problems of difficult intracellular injection in a complex form, unverified stability and low efficiency even after injection, and the off-target problem. In contrast, the composition for gene correction of the present disclosure can be usefully used for gene therapy due to remarkably high intracellular delivery efficiency, inhibited off-target, and ensured stability.

BEST MODE

Figure 1A:
FIG. 1A shows an AP-HE10-SpCas9-inserted pET28a vector prepared in Examples 6 and a CPP-SpCas9-inserted pET28a vector prepared in Comparative Examples 3, 5 and 7.

The inventors of the present disclosure have made efforts to develop an effective gene correction technology capable of overcoming the limitation of the CRISPR-Cas-based gene correction technology and replacing the same. As a result, they have designed a specific gene correction technology utilizing a cell-penetrating peptide in order to effectively deliver a Cas protein-RNA complex (ribonucleoprotein: RNP) into cells, and have completed the present disclosure by identifying that the Cas protein-RNA complex (ribonucleoprotein: RNP) is delivered into cells.

An aspect of the present disclosure relates to a cell-penetrating peptide represented by General Formula 1 for a Cas protein-RNA complex (ribonucleoprotein: RNP).

[General Formula 1]

Arg-Arg-Arg-Trp-Cys-Lys-Arg-Arg-Arg-Ala-Ser-$[Gly]_m$-$[His\text{-}Glu]_n$ (SEQ ID NO: 85

In the above formula, m may be an integer from 3 to 7, and n may be an integer from 5 to 15.

In the above formula, $[Gly]_m$ is a linker which connects peptides, and m may be an integer from 3 to 7, although not being specially limited thereto. If m is larger than 7, cell-penetrating effect may be unsatisfactory because the sequence length is excessively long. And, if it is smaller than 3, sufficient flexibility cannot be ensured. More specifically, m may be from 4 to 6.

If n in the above formula is an integer from 5 to 15, the cell-penetrating peptide may be used as a cell-penetrating peptide. Specifically, when n is an integer from 9 to 15, more specifically an integer from 10 to 12, masking and delivery efficiency are superior by 1.3-1.5 times or more. Further more specifically, n may be an integer which is 10 or larger.

In the present disclosure, a protein capable of providing a new Cas protein-RNA complex (ribonucleoprotein: RNP) by enhancing cell permeability and gene correction efficiency with decreased off-targeting and ensured stability was developed.

Since the cell-penetrating peptide for a Cas protein-RNA complex (ribonucleoprotein: RNP) having an amino acid sequence represented by General Formula 1 used in the present disclosure is the smallest peptide with the most superior delivery efficiency and masking efficiency, it can minimize any biological interference that may occur.

According to an exemplary embodiment, General Formula 1 may be represented by an amino acid sequence represented by any of SEQ ID NOS: 10-17, specifically by any of SEQ ID NOS: 15-17, most specifically by SEQ ID NO: 15. Since the cell-penetrating peptide for a Cas protein-RNA complex (ribonucleoprotein: RNP) includes the attenuator HE in an adequate amount, it does not interfere with the formation of a Cas protein-RNA complex (ribonucleoprotein: RNP) at all. It was confirmed experimentally that, unlike the existing cell-penetrating peptide, the cell-penetrating peptide-bound Cas protein-RNA complex (ribonucleoprotein: RNP) of the present disclosure exhibits the best intracellular delivery efficiency and gene correction efficiency.

Another aspect of the present disclosure relates to a composition for gene correction, which contains a complex (RNP) including: a) a Cas protein to which a cell-penetrating peptide represented by General Formula 1 is bound; and b) a guide RNA.

[General Formula 1]

Arg-Arg-Arg-Trp-Cys-Lys-Arg-Arg-Arg-Ala-Ser-$[Gly]_m$-$[His\text{-}Glu]_n$ (SEQ ID NO: 85)

In the above formula, m is an integer from 3 to 7, and n is an integer from 5 to 15.

In the above formula, $[Gly]_m$ is a linker which connects peptides, and m may be an integer from 3 to 7, although not being specially limited thereto. If m is larger than 7, cell-penetrating effect may be unsatisfactory because the sequence length is excessively long. And, if it is smaller than 3, sufficient flexibility cannot be ensured. More specifically, m may be from 4 to 6.

If n in the above formula is an integer from 5 to 15, the cell-penetrating peptide may be used as a cell-penetrating peptide. Specifically, when n is an integer from 9 to 15, more specifically an integer from 10 to 12, masking and delivery efficiency are superior by 1.3-1.5 times or more. Further more specifically, n may be an integer which is 10 or larger.

The information about the Cas protein or gene may be obtained from a known database such as GenBank of the NCBI (National Center for Biotechnology Information). Specifically, the Cas protein may be Cas9 protein. In addition, the Cas protein may be a Cas protein derived from the genus *Campylobacter*, more specifically from *Campylobacter jejuni*. More specifically, it may be Cas9 protein. As a more specific example, it may be a protein having an amino acid sequence of SEQ ID NO: 9, or a protein having the activity of the protein having the sequence and has homology thereto. In addition, the protein may have a sequence identity of at least 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% to SEQ ID NO: 39, although not being limited thereto.

In addition, the term Cas protein is used in the present disclosure to include, in addition to the natural protein, all variants that may act as activated endonuclease or nickase in cooperation with a guide RNA. Activated endonuclease or nickase can cleave a target DNA and thus can lead to genome correction. In addition, an inactivated variant may lead to regulation of transcription or cleavage of target DNA.

The variant of the Cas protein may be a mutant of Cas9 in which the catalytic aspartate residue or histidine residue is changed with another arbitrary amino acid. Specifically, the another amino acid may be alanine, although not being limited thereto.

More specifically, the Cas protein, specifically the Cas9 protein derived from *C. jejuni* may be one in which the catalytic aspartic acid (D) at position 8 or the histidine (H) residue at position 559 is substituted with another amino acid. Specifically, the another amino acid may be alanine, although not being limited thereto. That is to say, a Cas9 nuclease protein prepared by introducing mutation to only one active site of the Cas9 nuclease protein may act as a nickase when bound to a guide RNA. The nickase is included in the category of RGEN because it may cause double-strand breakage (DSB) by cleaving both DNA strands on both sides when two nickases are used.

In the present disclosure, the term “inactivated Cas protein” refers to a Cas nuclease protein with all or part of the function of the nuclease inactivated. The inactivated Cas is also referred to as dCas.

The term “cleavage” used in the present disclosure includes the breakage of a covalent backbone of a nucleotide molecule.

The Cas protein to which the cell-penetrating peptide represented by General Formula 1 is bound a) is one which is developed to able to function in cells. Specifically, it may be one in which the cell-penetrating peptide represented by General Formula 1 is bound or connected to the Cas protein represented by SEQ ID NO: 9. The cell-penetrating peptide may be represented specifically by SEQ ID NOS 10-17, more specifically by SEQ ID NOS 15-17, most specifically by SEQ ID NO: 15. The Cas protein bound to the cell-penetrating peptide represented by SEQ ID NO: 15 may be represented by SEQ ID NO: 15.

If a peptide other than the cell-penetrating peptide represented by General Formula 1 is connected, gene correction efficiency and intracellular delivery efficiency are decreased significantly as demonstrated in the test examples described below and off-target ratio may increase even when the intracellular delivery efficiency is high.

The Cas protein or a nucleic acid encoding the same may further include a nuclear localization signal (NLS) for importing the Cas protein into the nucleus.

In addition, the nucleic acid encoding the Cas protein may further include a nuclear localization signal (NLS) sequence. Accordingly, an expression cassette including a nucleic acid encoding the Cas protein may include, in addition to a regulatory sequence such as a promoter sequence for expressing the Cas protein, an NLS sequence, although not being limited thereto.

The Cas protein may be linked to a tag which is advantageous for separation and/or purification. Examples of the tag that may be linked include a small peptide tag such as a His tag, a Flag tag, an S tag, etc., a GST (glutathione S-transferase) tag, an MBP (maltose-binding protein) tag, etc., although not being limited thereto.

In the present disclosure, an RNP refers to a ribonucleic acid protein in complex form in which a) a Cas protein to which a cell-penetrating peptide represented by General Formula 1 is bound; and b) a target DNA-specific guide RNA are bound.

In the present disclosure, the RNP may be applied to a cell in the form of a) a Cas protein to which a cell-penetrating peptide represented by General Formula 1 is bound or a nucleic acid encoding the same; and b) a target DNA-specific guide RNA or a DNA encoding the guide RNA, although not being limited thereto. The guide RNA or the DNA encoding the same and the Cas protein to which a cell-penetrating peptide represented by General Formula 1 is bound or a nucleic acid encoding the same a) may be applied to a cell either simultaneously or sequentially.

Accordingly, in the present disclosure, it is the most preferable in terms of stability, gene correction efficiency and delivery efficiency that an RNP complex consisting of a) a Cas protein to which a cell-penetrating peptide represented by General Formula 1 is bound; and b) a guide RNA is delivered into a cell. Particularly, this is advantageous in that there is no risk of genetic modification because a DNA vector is not used.

According to an exemplary embodiment, General Formula 1 may be selected from any of SEQ ID NOS: 10-17, specifically from any of SEQ ID NOS: 15-17. Most specifically, it may be represented by an amino acid sequence represented by SEQ ID NO: 15. Since the cell-penetrating peptide for a Cas protein-RNA complex represented by SEQ ID NO: 15 is the smallest peptide with the most superior delivery efficiency and masking efficiency, it can minimize any biological interference that may occur.

The "guide RNA" refers to an RNA which is specific to a target DNA. It may be combined with the Cas protein to guide the Cas protein to the target DNA. The guide RNA may be prepared to be specific to a target to be cleaved.

In the present disclosure, a guide RNA may be a dual RNA composed of two RNAs, i.e., a crRNA (CRISPR RNA) and a tracrRNA (trans-activating crRNA). Alternatively, the guide RNA may be a sgRNA (single-chain guide RNA) prepared from the fusion of a first part including a sequence capable of forming a base pair with a complementary strand of the target DNA and a second part including a sequence interacting with the Cas protein, more specifically the major parts of a crRNA and a tracrRNA.

The sequence capable of forming a base pair with the complementary strand of the target DNA may have a length of 17-23 bp, 18-23 bp or 19-23 bp, more specifically 20-23 bp, further more specifically 21-23 bp, although not being limited thereto. This applies to both a dual RNA and a sgRNA, more specifically to a sgRNA.

In addition, the guide RNA may have 1-3 additional nucleotides, more specifically 2 or 3 nucleotides, in front of the 5'-end of the sequence capable of forming a base pair with the complementary strand of the target DNA. For example, the nucleotide may be A, T, G or C. The guide RNA may have more specifically 1-3 guanines (G's), further more specifically 2 or 3 G's. This applies to both a dual RNA and a sgRNA, more specifically to a sgRNA.

The sgRNA may include a region having a sequence complementary to the sequence in the target DNA (referred to as Spacer region, target DNA recognition sequence, base pairing region, etc.) and a hairpin structure for binding to the Cas protein. More specifically, it may include a region having a sequence complementary to the sequence in the target DNA, a hairpin structure for binding to the Cas protein, and a terminator sequence. The structures described above may be present sequentially from the 5'-end to the 3'-end, although not being limited thereto.

In the present disclosure, a guide RNA in any form may be used as long as the guide RNA incudes the major parts of a crRNA and a tracrRNA and a region complementary to the target DNA.

The guide RNA may include a first region capable of forming a base pair with the complementary strand of the target DNA sequence; and a second region having a stem or loop structure with a length of 13-18 bp (specifically 5-10 bp).

That is to say, the guide RNA may be selected adequately depending on the type of endonuclease capable of forming a complex depending on the target sequence and/or a microorganism from which it is derived. For example, the guide RNA may be one or more selected from a group consisting of a CRISPR RNA (crRNA), a trans-activating crRNA (tracrRNA) and a single-stranded guide RNA (sgRNA), and may be a double-stranded complex of CRISPR RNA (crRNA) and trans-activating crRNA (tracrRNA) or a single-stranded guide RNA (sgRNA) depending on the type of endonucleotide. The sgRNA may include crRNA and tracrRNA regions.

The composition may be for correction of a single or multiple target DNAs (or genes) in a prokaryotic cell, a eukaryotic cell or a non-human eukaryotic organism.

In the present disclosure, "gene correction (gene editing)" refers to the action of inducing mutation (deletion, substitution, and/or insertion) of one or more nucleotide by causing double-stranded DNA cleavage at the target site in a target gene. In an exemplary embodiment, the gene correction may include inactivation (knock-out) of a target gene by forming a stop codon at a target site or forming a codon encoding a non-wild-type amino acid, introduction of mutation to a non-coding DNA sequence not generating a protein, etc., although not being limited thereto.

In the present disclosure, the 'target gene' refers to a gene which is a target of gene correction, and the 'target site (or target region)' refers to the region where gene correction occurs in the target gene by Cas (or Cas9).

In the present disclosure, the 'target sequence' may be a base sequence of a region including a nucleotide (nt) hybridized by a guide RNA at the target site of the target gene.

The prokaryotic cell or eukaryotic cell may be an isolated cell. The eukaryotic cell may be a cell isolated from yeast, molds, protozoa, plants, higher plants, insects, amphibians or mammals such as CHO, HeLa, HEK 293 and COS-1 cells. The eukaryotic cell may be a cultured (in vitro) cell, a grafted cell, a primarily cultured cell (in vitro and ex vivo), an in vivo, or a mammalian cell isolated from a mammal including human.

The eukaryotic organism may be a eukaryotic cell (e.g., embryonic cell, stem cell, somatic cell, germ cell, etc.) derived from fungi such as yeast, eukaryotic animals (e.g., non-human primates such as monkey, dog, pig, cow, sheep, goat, mouse, rat, etc.) and/or eukaryotic plants (e.g., algae such as green algae, corn, bean, wheat, rice, etc.).

Another aspect of the present disclosure relates to a method for preparing a non-human transformant, which includes 1) a step of introducing the composition for gene correction into an isolated prokaryotic cell, eukaryotic cell or non-human eukaryotic organism by a method selected from local injection, microinjection, electroporation and lipofection.

When a non-human transformant is prepared by the method for preparing a non-human transformant of the present disclosure, the desired transformant can be obtained with high success rate. The success rate of the composition for gene correction of the present disclosure is remarkably improved over the existing composition for gene correction in that the transformant can be obtained successfully.

The present disclosure may provide a pharmaceutical composition containing the composition for gene correction. The pharmaceutical composition of the present disclosure contains a commonly used pharmaceutically acceptable carrier such as lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain, in addition to the above-described ingredients, a lubricant, a wetting agent, a sweetener, a flavorant, an emulsifier, a suspending agent, a preservative, etc. Suitable pharmaceutically acceptable carriers and preparations are described in detail in Remington's Pharmaceutical Sciences (19th ed., 1995).

The pharmaceutical composition of the present disclosure may be administered orally or parenterally. Specifically, it may be parenterally, e.g., by intravenous injection, topical injection, intraperitoneal injection, etc.

An adequate administration dosage of the pharmaceutical composition of the present disclosure varies depending on various factors such as preparation method, administration method, the age, body weight, sex, pathological condition and diet of a patient, administration time, administration route, excretion rate and response sensitivity. An ordinarily skilled physician will easily determine and prescribe an administration dosage effective for the desired treatment or prevention. According to a specific exemplary embodiment of the present disclosure, a daily administration dosage of the pharmaceutical composition of the present disclosure is 0.0001-100 mg/kg.

The pharmaceutical composition of the present disclosure may be prepared into a single-dose or multi-dose formulation using a pharmaceutically acceptable carrier and/or excipient according to methods that may be easily employed by those having ordinary knowledge in the art to which the present disclosure belongs. The formulation may be in the form of a solution in an oily or aqueous medium, a suspension, an emulsion, an extract, a powder, a granule, a tablet or a capsule, and may further contain a dispersant or a stabilizer.

MODE FOR INVENTION

Hereinafter, the present disclosure will be described in detail through examples. However, the following examples are for the purpose of illustrating the present disclosure more specifically only and it will be obvious to those having ordinary knowledge in the art that the scope of the present disclosure is not limited by the examples.

Examples

<Examples 1-8> Preparation of AP-HE-SpCas9 Protein-Containing Composition for Gene Correction 1) Preparation of AP-HE-SpCas9-Inserted pET28a Vector For cloning of a plasmid DNA (SEQ ID NOS: 41-48; FIG. 1A) for expressing the AP-HE-SpCas9 protein (SEQ ID NOS: 10-17), a protein expression vector pET28a was cleaved with NheI and EcoRI restriction enzymes and then a DNA (SEQ ID NO: 49) encoding NheI-SpCas9-EcoRI was inserted using a ligase. In addition, for insertion of AP-$[HE]_m$ (SEQ ID NOS: 1-8), the vector was cleaved with NdeI and NheI restriction enzymes and then a DNA (SEQ ID NOS: 32-39) encoding NdeI-AP-HE-NheI was inserted using a ligase. After transforming the prepared each plasmid DNA into DH5a *E. coli* and inoculating the obtained colony to LB medium, incubation was performed in a shaking incubator for 12 hours at 37° C. under the condition of 200 rpm. After the incubation was completed, *E. coli* was recovered and a plasmid DNA was isolated therefrom. Then, it was confirmed by Cosmo Genetech through DNA sequencing whether the vector was prepared as desired.

2) Expression of AP-HE-SpCas9 Protein in *E. coli* and Purification

Each plasmid DNA prepared in the step 1) was transformed into *E. coli* BL21 (DE3) star pLysS. Each colony was inoculated to 50 mL of LB liquid medium containing chloramphenicol (34 μg/mL) and ampicillin (50 μg/mL) antibiotics and, after culturing at 37° C. for 10 hours, was transferred to 500 mL of fresh LB liquid medium. The culturing was performed until $OD_{600}$ nm measured by a spectrophotometer reached between 0.4 and 0.6. After adding IPTG to a concentration of 0.2 mM and lowering temperature to 20° C., culturing was performed further at 150 rpm for 14 hours. After the culturing was completed, the culture was recovered and centrifuged. Then, after discarding the supernatant, the pellet was resuspended by adding a lysis buffer (0.5 M NaCl, 5 mM imidazole, 20 mM Tris-HCl, pH 8.0). After treating the resuspended solution with an ultrasonic cell disruptor (VCX-130; Sonics & Materials) and then centrifuging the same, the supernatant was separated. The separated supernatant was filtered through a 0.45-μm filter and purified using a 1 M imidazole solution using an AKTA prime protein purification system. Finally, the AP-HE-SpCas9 protein (SEQ ID NOS 10-17) was separated using a PD-10 desalting column. The protein was identified by 12% SDS-PAGE (FIG. 1B).

Figure 1B:
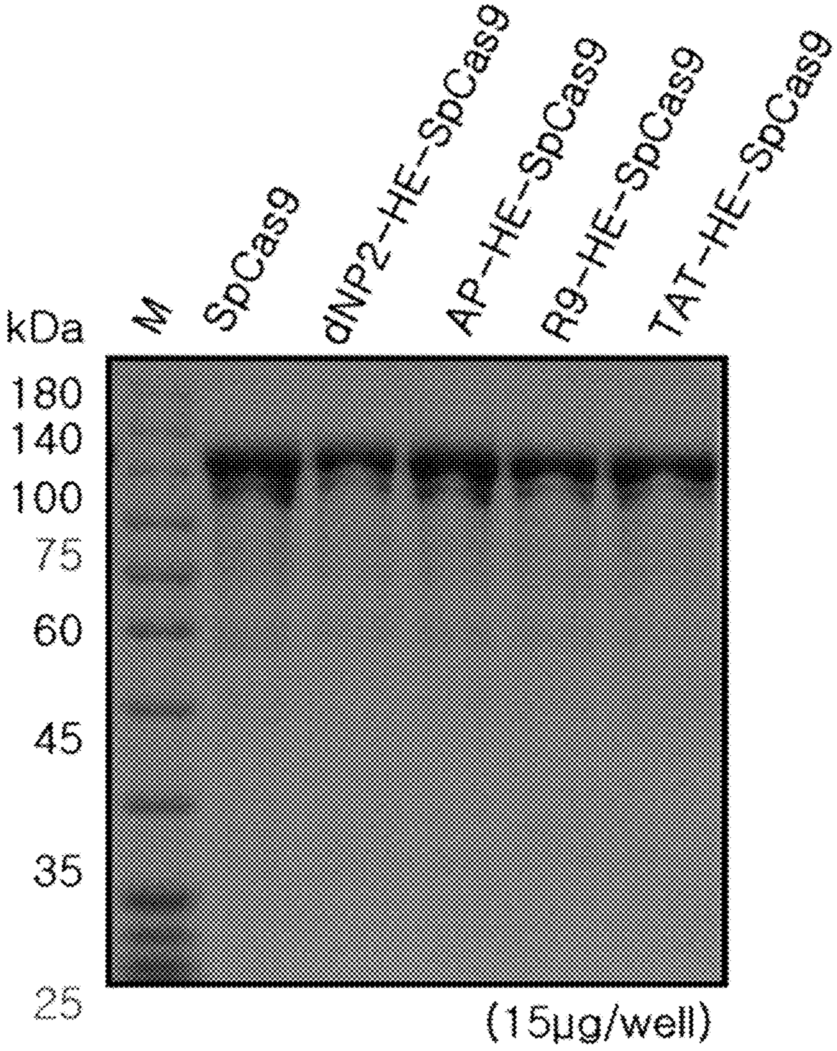
FIG. 1B shows a result of analyzing an AP-HE10-SpCas9 protein (SEQ ID NO: 15) purified in Example 6 and a CPP-SpCas9 protein (SEQ ID NOS: 23, 27 and 31) purified in Comparative Examples 3, 5 and 7 by SDS-PAGE.

FIG. 1A shows the AP-HE10-SpCas9-inserted pET28a vector prepared in Examples 6, and FIG. 1B shows a result of analyzing the AP-HE10-SpCas9 protein (SEQ ID NO: 15) purified in Example 6 by SDS-PAGE. It can be seen that the AP-HE10-SpCas9 protein was purified satisfactorily.

Table 1 shows the name, SEQ ID NO, 'm' and 'n' of Example 1 to 8.

TABLE 1

| | Peptide Name | SEQ ID NO: | m | n |
|---|---|---|---|---|
| Example 1 | AP-HE5-SpCas9 | 10 | 5 | 5 |
| Example2 | AP-HE6-SpCas9 | 11 | 5 | 6 |
| Example3 | AP-HE7-SpCas9 | 12 | 5 | 7 |
| Example4 | AP-HE8-SpCas9 | 13 | 5 | 8 |
| Example5 | AP-HE9-SpCas9 | 14 | 5 | 9 |
| Example6 | AP-HE10-SpCas9 Or AP-HE-SpCas9 | 15 | 5 | 10 |
| Example7 | AP-HE11-SpCas9 | 16 | 5 | 11 |
| Example8 | AP-HE12-SpCas9 | 17 | 5 | 12 |

<Comparative Examples 1-7> Preparation of CPP-SpCas9-Inserted pET28a Vector

1) Preparation of CPP-SpCas9-Inserted pET28a Vector

For cloning of a plasmid DNA (FIGS. 1A and 2) for expressing the CPP-SpCas9 protein, a protein expression vector pET28a was cleaved with NheI and EcoRI restriction enzymes and then a DNA (SEQ ID NO: 40) encoding NheI-SpCas9-EcoRI was inserted using a ligase. In addition, for insertion of CPP (AP, dNP2-HE, dNP2, R9-HE, R9, TAT-HE, TAT), the vector was cleaved with NdeI and NheI restriction enzymes and then a DNA encoding NdeI-CPP-NheI was inserted using a ligase. After transforming the prepared plasmid DNA into DH5a *E. coli* and inoculating the obtained colony to LB medium, incubation was performed in a shaking incubator for 12 hours at 37° C. under the condition of 200 rpm. After the incubation was completed, *E. coli* was recovered and a plasmid DNA was isolated therefrom. Then, it was confirmed by Cosmo Genetech through DNA sequencing whether the vector was prepared as desired.

In Table 2, Ala Ser is the restriction enzyme site (AS: NheI).

TABLE 2

| | Name | SEQ ID NO | Sequence |
|---|---|---|---|
| Comp. Ex. 1 | AP | 18 (protein) | ArgArgArgTrpCysLysArgArgArgAlaSer |
| | | 49 (gene) | ATGGGCAGCAGCCATCATCATCATCATCA<br>CAGCAGCGGCCTGGTGCCGCGCGGCAG<br>CCATATGCGCCGGCGCTGGTGCAAACGC<br>CGCCGG |
| Comp. Ex. 2 | dNP2-HE10 | 22 (protein) | LysIleLysLysValLysLysLysGlyArgLysGlySer<br>LysIleLysLysValLysLysLysGlyArgLysAlaSer<br>GlyGlyGlyGlyGlyHisGluHisGluHisGluHisGlu<br>HisGluHisGluHisGluHisGluHisGluHisGlu |
| | | 53 (gene) | ATGGGCGGTTCTCATCATCATCATCATCA<br>TCATATGAAGATCAAGAAGGTTAAAAAAA<br>AGGGTCGCAAGGGCTCTAAAATTAAAAA<br>AGTCAAGAAGAAAGGAAGAAAAGCTAGC<br>GGTGGTGGTGGAGGTCACGAACATGAAC<br>ATGAACATGAACACGAGCACGAGCATGA<br>GCACGAACACGAACACGAA |
| Comp. Ex. 3 | dNP2 | 20 (protein) | LysIleLysLysValLysLysLysGlyArgLysGlySer<br>LysIleLysLysValLysLysLysGlyArgLysAlaSer |
| | | 51 (gene) | ATGGGCAGCAGCCATCATCATCATCATCA<br>CAGCAGCGGCCTGGTGCCGCGCGGCAG<br>CCATATGAAGATCAAGAAGGTTAAAAAAA<br>AGGGTCGCAAGGGCTCTAAAATTAAAAA<br>AGTCAAGAAGAAAGGAAGAAAA |
| Comp. Ex. 4 | R9-HE10 | 26 (protein) | ArgArgArgArgArgArgArgArgArgAlaSerGlYGly<br>GlyGlyGlyHisGluHisGluHisGluHisGluHisGlu<br>HisGluHisGluHisGluHisGluHisGlu |
| | | 57 (gene) | ATGGGCGGTTCTCATCATCATCATCATCA<br>TCATATGAGACGAAGACGAAGACGTAGA<br>CGTAGAGCTAGCGGTGGTGGTGGAGGT<br>CACGAACATGAACATGAACATGAACACG<br>AGCACGAGCATGAGCACGAACACGAACA<br>CGAA |
| Comp. Ex. 5 | R9 | 24 (protein) | ArgArgArgArgArgArgArgArgArgAlaSer |
| | | 55 (gene) | ATGGGCAGCAGCCATCATCATCATCATCA<br>CAGCAGCGGCCTGGTGCCGCGCGGCAG<br>CCATATGAGACGAAGACGAAGACGTAGA<br>CGTAGA |
| Comp. Ex. 6 | TAT-HE10 | 30 (protein) | TyrGlyArgLysLysArgArgGlnArgArgArgArgAla<br>SerGlyGlyGlyGlyGlyHisGluHisGluHisGluHis<br>GluHisGluHisGluHisGluHisGluHisGluHisGlu |
| | | 61 (gene) | ATGGGCGGTTCTCATCATCATCATCATCA<br>TCATATGTATGGACGCAAGAAGCGCCGC<br>CAGCGCCGCCGCGCTAGCGGTGGTGGT<br>GGAGGTCACGAACATGAACATGAACATG<br>AACACGAGCACGAGCATGAGCACGAACA<br>CGAACACGAA |
| Comp. Ex. 7 | TAT | 28 (protein) | TyrGlyArgLysLysArgArgGlnArgArgArgArgAla<br>Ser |
| | | 59 (gene) | ATGGGCAGCAGCCATCATCATCATCATCA<br>CAGCAGCGGCCTGGTGCCGCGCGGCAG<br>CCATATGTATGGACGCAAGAAGCGCCGC<br>CAGCGCCGCCGC |

2) Expression of CPP-SpCas9 Protein in *E. coli* and Purification

Each plasmid DNA prepared in the step 1) was transformed into *E. coli* BL21 (DE3) star pLysS. Each colony was inoculated to 50 ml of LB liquid medium containing chloramphenicol (34 μg/mL) and ampicillin (50 μg/mL) antibiotics and, after culturing at 37° C. for 10 hours, was transferred to 500 mL of fresh LB liquid medium. The culturing was performed until $OD_{600}$ nm measured by a spectrophotometer reached between 0.4 and 0.6. After adding IPTG to a concentration of 0.2 mM and lowering temperature to 20° C., culturing was performed further at 150 rpm for 14 hours. After the culturing was completed, the culture was recovered and centrifuged. Then, after discarding the supernatant, the pellet was resuspended by adding a lysis buffer (0.5 M NaCl, 5 mM imidazole, 20 mM Tris-HCl, pH 8.0). After treating the resuspended solution with an ultrasonic cell disruptor (VCX-130; Sonics & Materials) and then centrifuging the same, the supernatant was separated. The separated supernatant was filtered through a 0.45-μm filter and purified using a 1 M imidazole solution using an AKTA prime protein purification system. Finally, the CPP-SpCas9 protein (SEQ ID NOS: 19, 21, 23, 25, 27, 29 and 31) was separated using a PD-10 desalting column. The protein was identified by 12% SDS-PAGE (FIGS. 1B and 2).

Figure 2A:
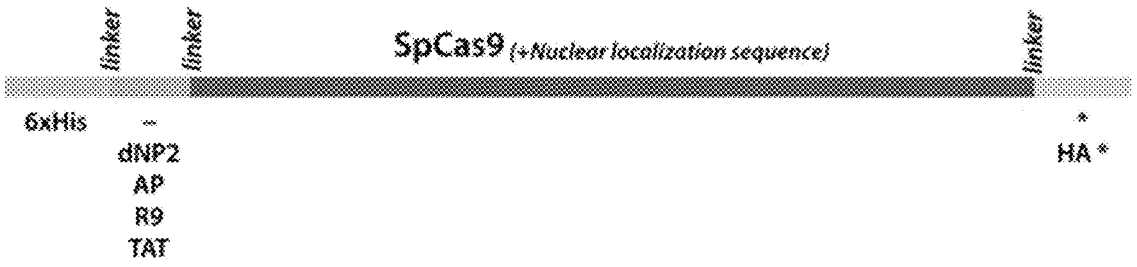
FIG. 2A shows a CPP-SpCas9-inserted pET28a vector prepared in Comparative Examples 1, 2, 4 and 6.
Figure 2B:
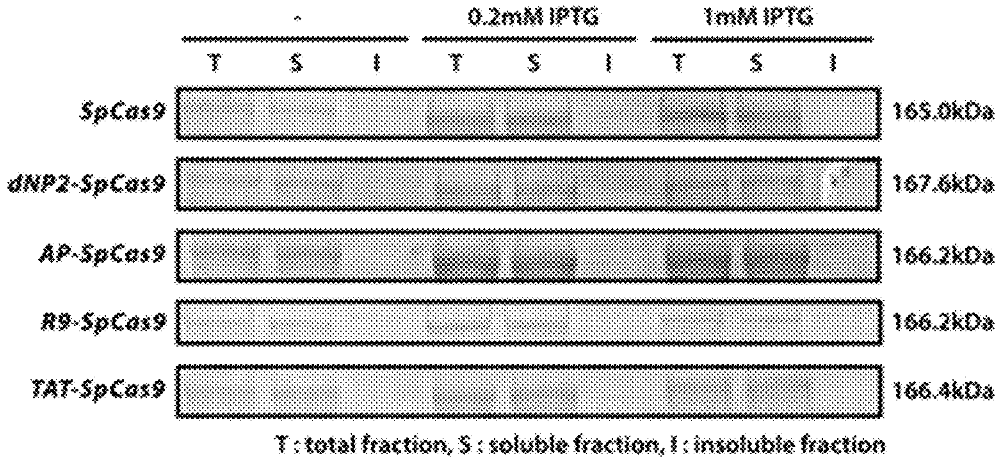
FIG. 2B shows a result of analyzing a CPP-SpCas9 protein (SEQ ID NOS: 19, 21, 25 and 29) purified in Comparative Examples 1, 2, 4 and 6 by SDS-PAGE.

FIG. 1A shows the vector prepared in Comparative Examples 3, 5 and 7. FIG. 2A shows the CPP-SpCas9-inserted pET28a vector prepared in Comparative Examples 1, 2, 4 and 6. FIG. 1B shows a result of analyzing the CPP-SpCas9 protein (SEQ ID NOS: 23, 27 and 31) purified in Comparative Examples 3, 5 and 7 by SDS-PAGE. And, FIG. 2B shows a result of analyzing the CPP-SpCas9 protein (SEQ ID NOS: 19, 21, 25 and 29) purified in Comparative Examples 1, 2, 4 and 6 by SDS-PAGE. It can be seen that the desired proteins were purified satisfactorily.

Figure 2C:
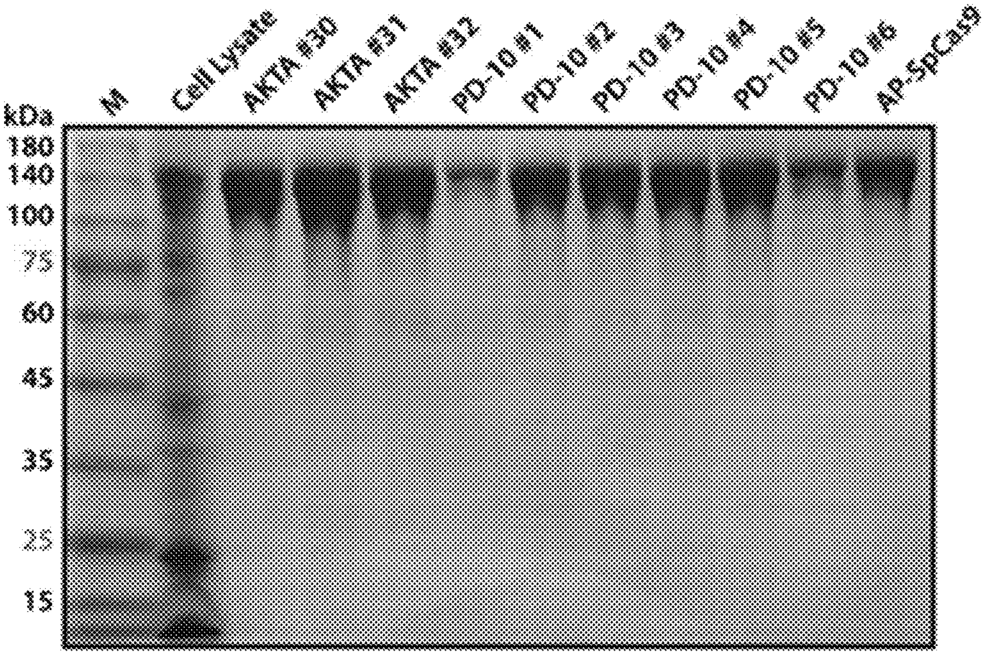
FIG. 2C shows a result of purifying an AP-SpCas9 protein prepared in Comparative Example 1 using various columns and analyzing the same by SDS-PAGE.

FIG. 2C shows the result of purifying the AP-SpCas9 protein prepared in Comparative Example 1 using various columns and analyzing the same by SDS-PAGE. It can be seen that the best result was achieved when the protein was purified according to the method of the present disclosure.

Table 3 shows the name, SEQ ID NO, 'm' and 'n' of Comparative Example 1 to 7.

TABLE 3

| | Peptide Name | SEQ ID NO: | m | n |
|---|---|---|---|---|
| Comparative Example 1 | AP-SpCas9 | 19 | 0 | 0 |
| Comparative Example 2 | dNP2-SpCas9 | 20 | 0 | 0 |
| Comparative Example 3 | dNP2-HE-SpCas9 | 21 | 5 | 10 |
| Comparative Example 4 | R9-SpCas9 | 22 | 0 | 0 |
| Comparative Example 5 | R9-HE-SpCas9 | 23 | 5 | 10 |
| Comparative Example 6 | TAT-SpCas9 | 24 | 0 | 0 |
| Comparative Example 7 | TAT-HE-SpCas9 | 25 | 5 | 10 |

<Comparative Examples 8-15> Preparation of CPP-AsCas12a- and CPP-LbCas12a-Inserted pET28a Vectors 1) Preparation of CPP-AsCas12a- and CPP-LbCas12a-Inserted pET28a Vectors For cloning of plasmid DNAs (FIGS. 3 and 4) for expressing the CPP-AsCas12a and CPP-LbCas12a proteins, a protein expression vector pET28a was cleaved with NheI and EcoRI restriction enzymes and then a DNA (SEQ ID NOS: 63 and 64) encoding NheI-AsCas12a (or LbCas12a)-EcoRI was inserted using a ligase. In addition, for insertion of CPP (AP, dNP2, R9, TAT), the vector was cleaved with NdeI and NheI restriction enzymes and then a DNA encoding NdeI-CPP-NheI was inserted using a ligase. After transforming the prepared plasmid DNA into DH5a *E. coli* and inoculating the obtained colony to LB medium, incubation was performed in a shaking incubator for 12 hours at 37° C. under the condition of 200 rpm. After the incubation was completed, *E. coli* was recovered and a plasmid DNA was isolated therefrom. Then, it was confirmed by Cosmo Genetech through DNA sequencing whether the vector was prepared as desired.

2) Expression of CPP-AsCas12a, CPP-LbCas12a Protein in *E. coli* and Purification Each plasmid DNA prepared in the step 1) was transformed into *E. coli* BL21 (DE3) star pLysS. The obtained colony was inoculated to 50 ml of LB liquid medium containing chloramphenicol (34 μg/mL) and ampicillin (50 μg/mL) antibiotics and, after culturing at 37° C. for 10 hours, was transferred to 500 mL of fresh LB liquid medium. The culturing was performed until $OD_{600}$ nm measured by a spectrophotometer reached between 0.4 and 0.6. After adding IPTG to a concentration of 0.2 mM and lowering temperature to 20° C., culturing was performed further at 150 rpm for 14 hours. After the culturing was completed, the culture was recovered and centrifuged. Then, after discarding the supernatant, the pellet was resuspended by adding a lysis buffer (0.5 M NaCl, 5 mM imidazole, 20 mM Tris-HCl, pH 8.0). After treating the resuspended solution with an ultrasonic cell disruptor (VCX-130; Sonics & Materials) and then centrifuging the same, the supernatant was separated. The separated supernatant was filtered through a 0.45-μm filter and purified using a 1 M imidazole solution using an AKTA prime protein purification system. Finally, the CPP (AP, dNP2, R9, TAT)-AsCas12a (SEQ ID NOS: 69, 70, 71 and 72) (Comparative Examples 8-11 in order) protein and the CPP (AP, dNP2, R9, TAT)-LbCas12a protein (SEQ ID NOS: 73, 74, 75 and 76) (Comparative Examples 12-15 in order) were separated using a PD-10 desalting column. The proteins were identified by 12% SDS-PAGE (FIGS. 3B and 4B).

Figure 3A:
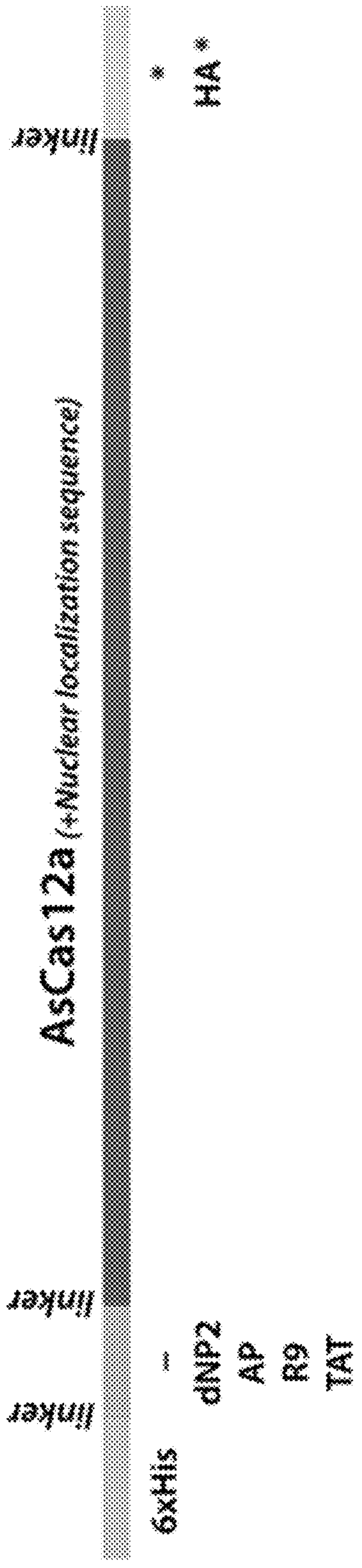
FIG. 3A shows a CPP-AsCas12a-inserted pET28a vector prepared in Comparative Examples 8-11.
Figure 3B:
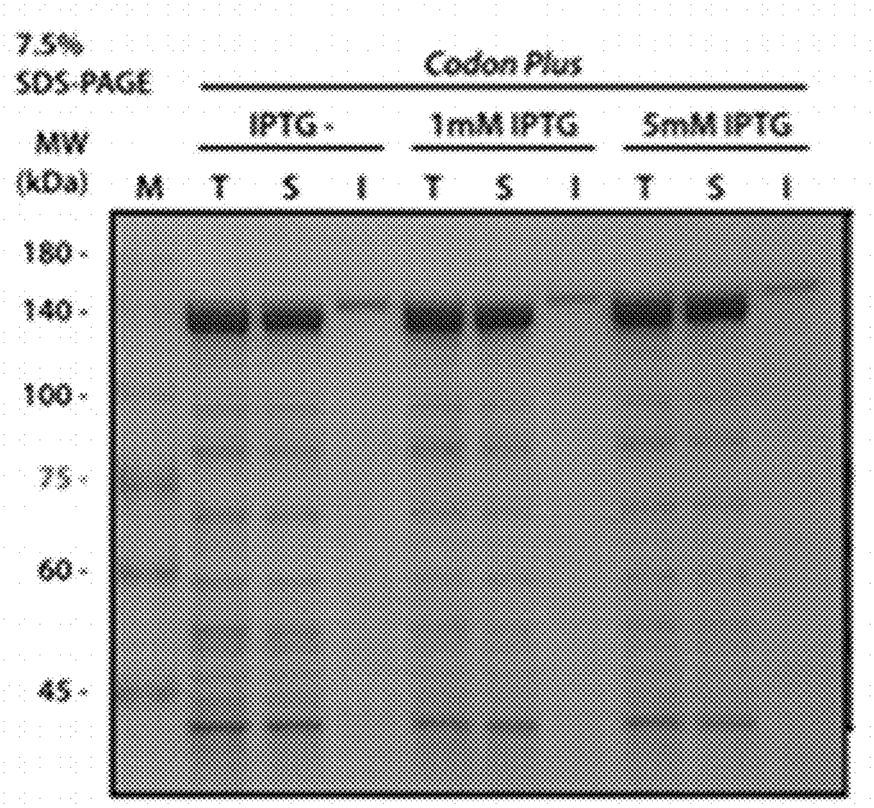
FIG. 3B shows a result of analyzing a CPP-AsCas12a protein (SEQ ID NOS: 69, 70, 71 and 72) purified in Comparative Examples 8-11 by SDS-PAGE.
Figure 4A:
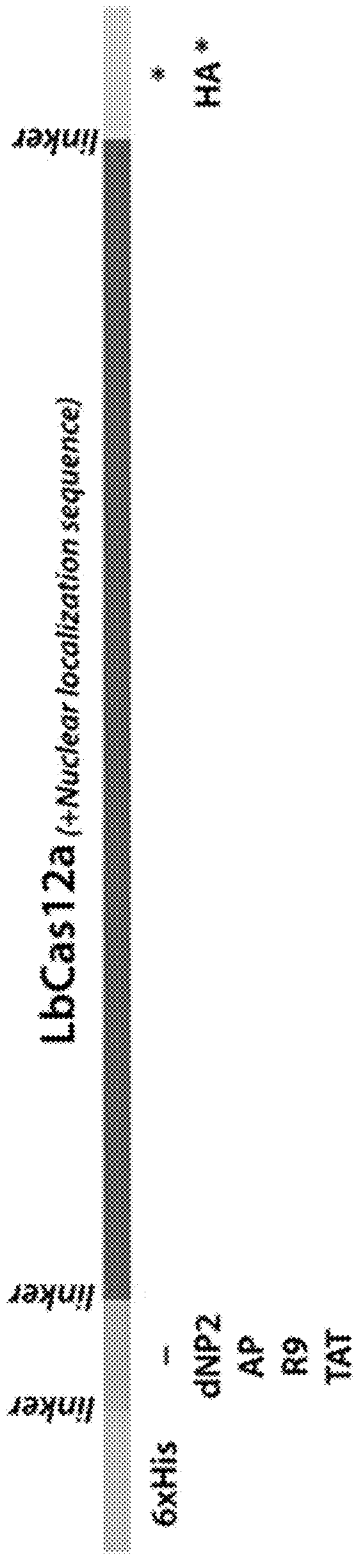
FIG. 4A shows a CPP-LbCas12a-inserted pET28a vector prepared in Comparative Examples 12-16.
Figure 4B:
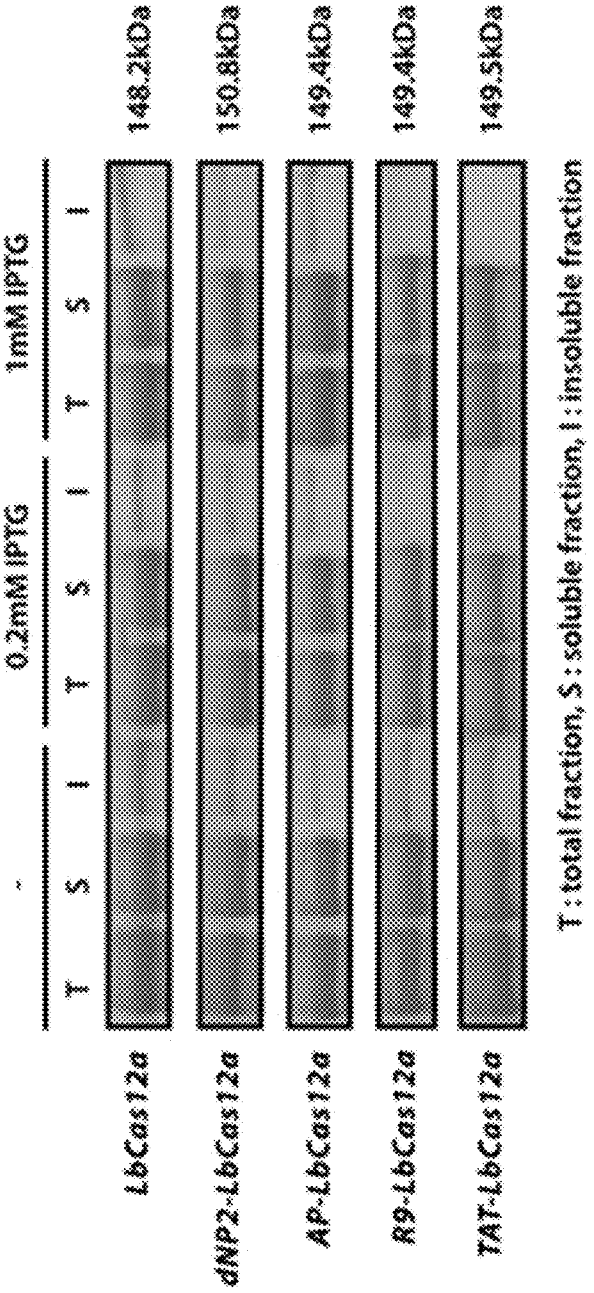
FIG. 4B shows a result of analyzing a CPP-LbCas12a protein (SEQ ID NOS: 73, 74, 75 and 76) prepared in Comparative Examples 12-16 by SDS-PAGE.

FIG. 3A shows the CPP-AsCas12a-inserted pET28a vector prepared in Comparative Examples 8-11, and FIG. 4A shows the CPP-LbCas12a-inserted pET28a vector prepared in Comparative Examples 12-15. FIG. 3B shows a result of analyzing the CPP-AsCas12a protein (SEQ ID NOS: 69, 70, 71 and 72) purified in Comparative Examples 8-11 by SDS-PAGE, and FIG. 4B shows a result of analyzing the CPP-LbCas12a protein (SEQ ID NOS: 73, 74, 75 and 76) prepared in Comparative Examples 12-16 by SDS-PAGE. It can be seen that the desired proteins were purified satisfactorily.

Figure 3C:
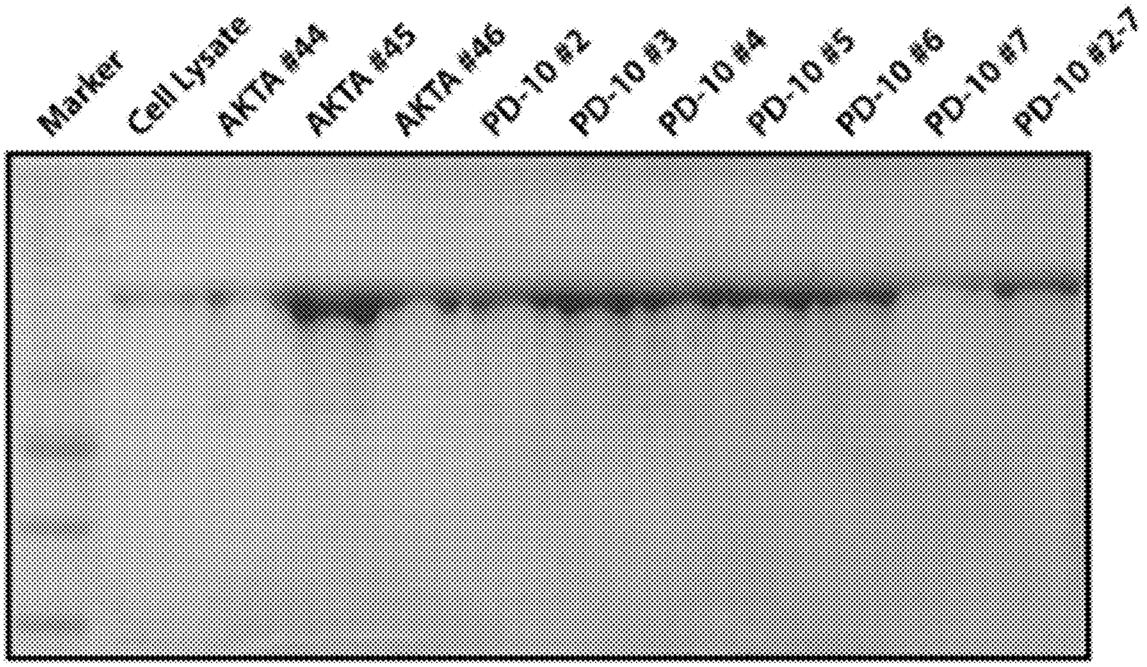
FIG. 3C shows a result of purifying an AP-AsCas12a protein prepared in Comparative Example 8 using various columns and analyzing the same by SDS-PAGE.

FIG. 3C shows a result of purifying the AP-AsCas12a protein prepared in Comparative Example 8 using various columns and analyzing the same by SDS-PAGE. It can be seen that the protein was purified well without impurities.

Table 4 shows the name, SEQ ID NO: of Comparative Example 8 to 15.

TABLE 4

| | Peptide Name | SEQ ID NO: |
|---|---|---|
| Comparative Example 8 | AP-AsCas12a | 69 |
| Comparative Example 9 | dNP2-AsCas12a | 70 |
| Comparative Example 10 | R9-AsCas12a | 71 |
| Comparative Example11 | TAT-ASCas12a | 72 |
| Comparative Example 12 | AP-LbCas12a | 73 |
| Comparative Example 13 | dNP2-LbCas12a | 74 |
| Comparative Example 14 | R9-LbCas12a | 75 |
| Comparative Example 15 | TAT-LbCas12a | 76 |

<Test Example 1> Delivery of Protein into HEK 293 T Cells

Cell-penetrating ability was investigated through an experiment of delivering the AP-HE-SpCas9 protein purified in Example 6 into human HEK 293 T cells. After culturing HEK 293 T cells using DMEM, the cells were plated on a 96-well plate containing 25 μL of DMEM, with $2.5\times10^5$ cells per well. Then, the cells were mixed with the protein of an adequate concentration in 20 μL of D-PBS to a total volume of 200 UL and then incubated with the protein under various conditions.

After treating each well with a mixture of AP-HE-SpCas9 (2 μM) and CQ (1, 10, 50, 100, 250, 500 M), AP-HE-SpCas9 (2 μM) alone or a control (2 μM), the cells were cultured for 2 hours in a 5% $CO_2$ cell incubator at 37° C. The cultured cells were centrifuged and washed twice with a PBS buffer. Then, the protein adhering to the cell surface was removed by treating with a trypsin solution for 5 minutes. Then, after neutralizing using a DMEM solution and then washing with a PBS buffer, delivery efficiency was investigated by measuring intracellular fluorescence by flow cytometry (BD Science FACS Canto II). CQ stands for chloroquine, which was used as a lysosomal degradation inhibitor.

Figure 5:
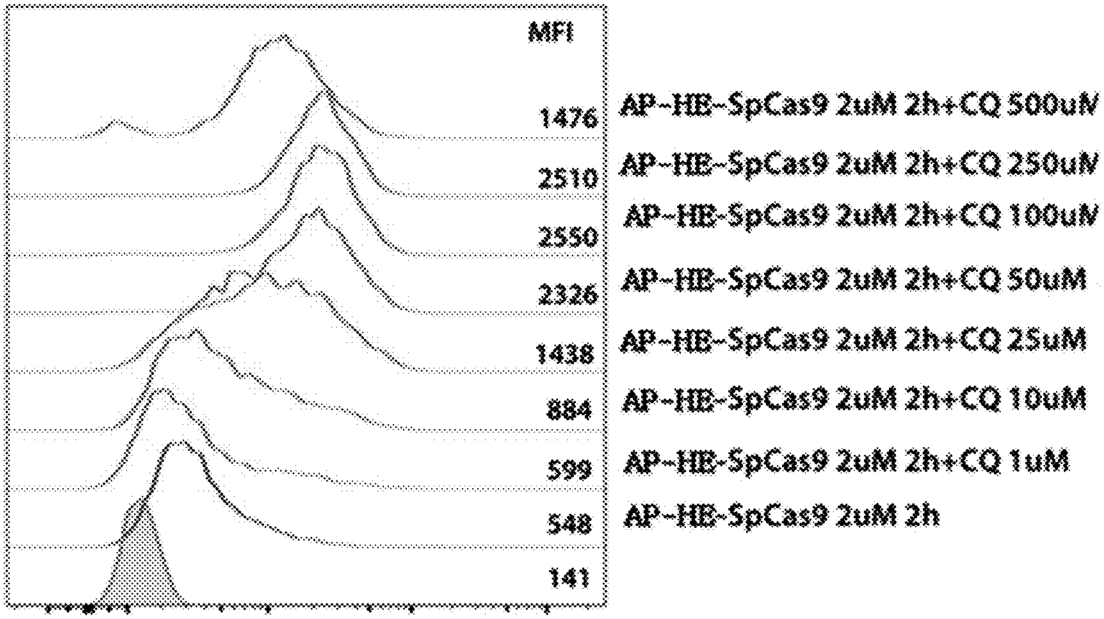
FIG. 5 shows a flow cytometry measurement result after treating with AP-HE-SpCas9 (2 μM; Example 6) alone or in combination with CQ (1, 10, 50, 100, 250, 500 μM), or with a control (2 μM).

FIG. 5 shows the flow cytometry measurement result after treating with AP-HE-SpCas9 (2 μM; Example 6) alone or in combination with CQ (1, 10, 50, 100, 250, 500 μM), or with a control (2 μM). It can be seen that the cell-penetrating effect is increased as the concentration of the AP-HE-SpCas9 protein according to the present disclosure is increased, and the cell-penetrating effect is increased as the concentration of CQ is increased when the protein is mixed with the CQ.

<Test Example 2> Delivery of AP-HE-SpCas9 into HeLa Cancer Cells

It was confirmed in Test Example 1 that the AP-HE-SpCas9 protein of the present disclosure (Example 6) is delivered well into cells. In this test example, the location of the protein after being delivered into the cells was investigated using a microscope.

After placing a 24-$mm^2$ rectangular cover glass on each well of the 6-well plate and plating $1\times10^5$ Hela cells, the cells were allowed to adhere to the cover glass by culturing in DMEM for 24 hours. Then, after removing the DMEM, 900 μL of fresh DMEM was added. Thereafter, the AP-HE-SpCas9 protein prepared in Example 6 was added after mixing with 50 μL of D-PBS to a concentration of 0.5 UM, 1 μM or 2 μM. Then, the cells were cultured for 2 hours at 37° C. in a 5% $CO_2$ cell incubator. After the culturing was completed, the protein and DMEM were removed except the adhering cells and washed twice with a PBS buffer. Then, after fixing the cells in 1 mL of a 4% paraformaldehyde phosphate buffer solution (Wako) and washing again with a PBS buffer, F-actin was stained with a green fluorescent dye (Alexa Fluor 488-conjugated phalloidin; Invitrogen) and the nucleus was stained with Hoechst 33342 (Invitrogen). After washing twice with a PBS buffer and mounting on a slide glass, the location of the AP-HE-SpCas9 protein of the present disclosure (Example 6) in the cells was investigated by fluorescence microscopy (Eclipse 50i, Nikon) or confocal microscopy (TCS SP5, Leica).

Figure 6:
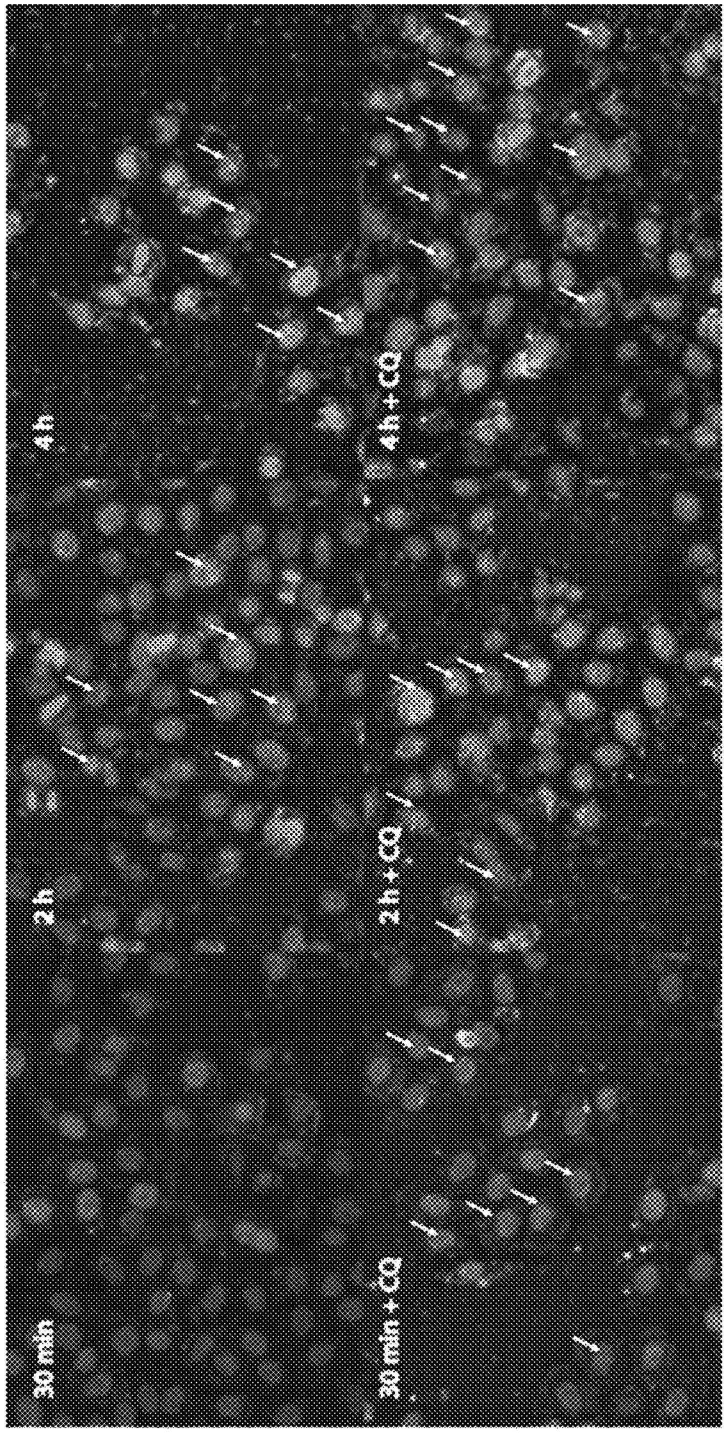
FIG. 6 shows intracellular fluorescence images obtained after treating with AP-HE-SpCas9 (2 M; Example 6) or in combination with CQ (500 UM).

FIG. 6 shows the intracellular fluorescence images obtained after treating with AP-HE-SpCas9 (2 μM; Example 6) or in combination with CQ (500 UM). It was confirmed that the AP-HE-SpCas9 protein of the present disclosure is delivered well into and located in the cells.

<Test Example 3> Gene Correction Efficiency of Cas9 Protein-RNA Complex (Ribonucleoprotein: RNP)

1) Preparation of AP-HE Cas9 Protein-RNA Complex (Ribonucleoprotein: RNP)

An AP-HE-SpCas9 protein-RNA complex (ribonucleoprotein: RNP) was prepared by mixing the AP-HE-SpCas9 protein of Example 6 (5 M) with sgRNA (5 M) at a ratio of 1:1 and conducting reaction at room temperature for 10 minutes, and was named as AP-HE-SpCas9 RNP. crRNP refers to a Cas9 protein-RNA complex (ribonucleoprotein: RNP) regardless of the type of the Cas9 protein.

2) Gene Correction

It was investigated whether the AP-HE-SpCas9 protein of Example 6 prepared in the form of a Cas9 protein-RNA complex (ribonucleoprotein: RNP) exhibit gene correction effect in cells. For this, the RFP/GFP reporter system which express RFP and GFP at the same time when a specific gene is cleaved and T7 endonuclease 1 assay were used. Mouse HEK 293 T cells were cultured in DMEM. After placing 400 μL of DMEM on each well of a 24-well plate, $2.5\times10^5$ cells contained in 50 μL of DMEM were mixed. Then, CQ (50 UM) and AP-HE-SpCas9 RNP were added such that the concentration corresponds to that of D-PBS present in 50 μL of the medium (on day 0). The final volume was adjusted to 500 μL.

On day 1 after the culturing, the HEK 293 T cells in each well were treated with 5 UM AP-HE-SpCas9 RNP and, after culturing for 6 hours in a 5% $CO_2$ cell incubator at 37° C., the medium was replaced with fresh DMEM.

The next day (on day 2), after treating each well with 5 M AP-HE-SpCas9 RNP and incubating for 6 hours in a 5% $CO_2$ cell incubator at 37° C., the medium was replaced with fresh DMEM. On day 3 after the culturing, after treating with AP-HE RNP in the same manner as on day 2 and reacting for 6 hours, the culture was recovered and then centrifuged. After removing the supernatant, the remaining pellet was washed twice with a PBS buffer and the protein attached to the cell surface was removed by treating with trypsin for 5 minutes. After neutralizing by adding an RPMI solution and washing once again with a PBS buffer, gene correction efficiency was investigated by flow cytometry (BD Science FACS Canto II) and T7 endonuclease 1 assay. As a control group, the cells were treated with 250 ng of the CCR5 sgRNA vector and 250 ng of the SpCas9 vector once a day.

Figure 7:
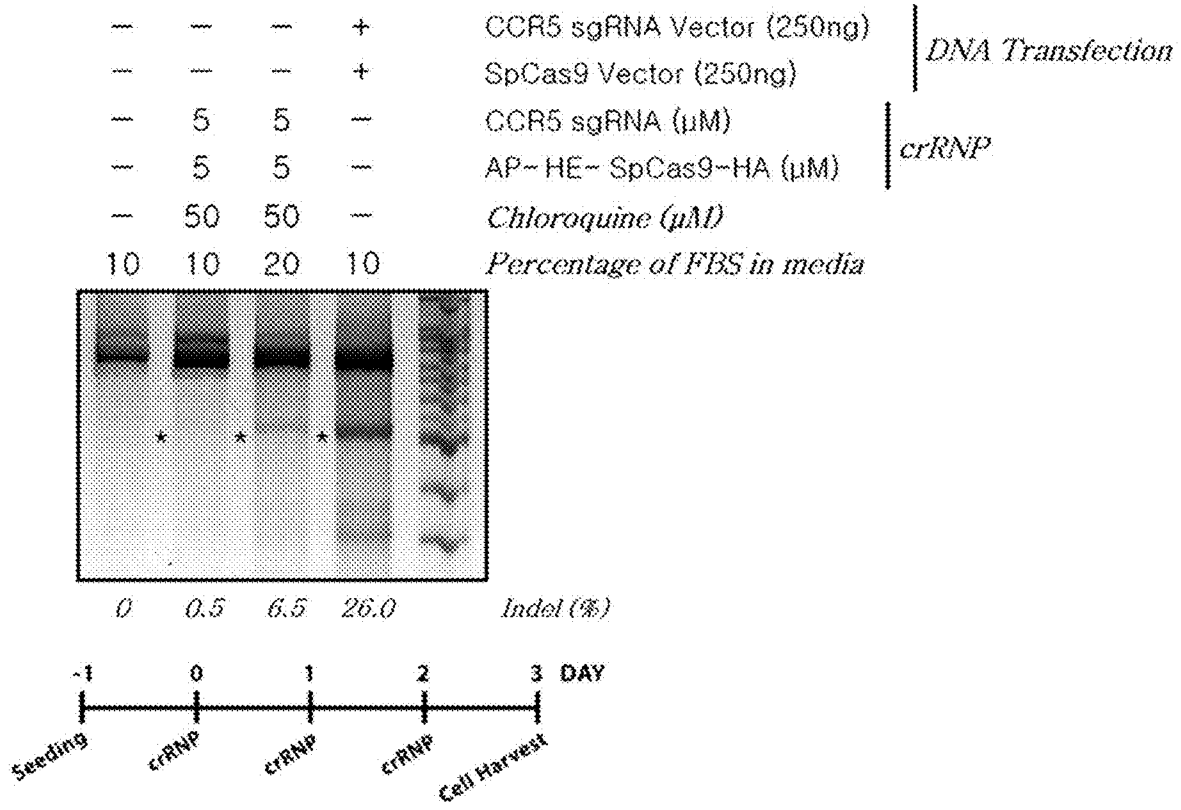
FIG. 7 shows a result of measuring the gene correction efficiency by AP-HE-SpCas9 RNP in HEK 293T cells.

FIG. 7 shows a result of measuring the gene correction efficiency by AP-HE-SpCas9 RNP in the HEK 293T cells. It can be seen that the AP-HE-SpCas9 protein according to the present disclosure-RNA complex (ribonucleoprotein: RNP) resulted in effective gene correction of the cells by 6.5 indel (%) even though it was treated directly to the cells.

<Test Example 4> Gene Correction by AP-SpCas9 in HEK 293 T Cells

It was investigated whether the AP-SpCas9 of Comparative Example 1 exhibits gene correction effect in cells. For this, the RFP/GFP reporter system which express RFP and GFP at the same time when a specific gene is cleaved and T7 endonuclease 1 assay were used. Mouse HEK 293 T cells were cultured in DMEM. After placing 400 μL of DMEM on each well of a 24-well plate, $2.5\times10^5$ cells contained in 50 μL of DMEM were mixed. Then, CQ (50 UM) and the AP-Cas9 of Comparative Example 1 were added such that the concentration corresponds to that of D-PBS present in 50 μL of the medium (on day 0). The final volume was adjusted to 500 μL.

Before the addition of the AP-Cas9 of Comparative Example 1, the HEK 293 T cells were transformed with lipofectamine with a sgRNA plasmid targeting the CCR5 gene.

On day 1 after the culturing, after delivering a sgRNA plasmid targeting the AP-Cas9 plasmid (Comparative Example 1-1) CCR5 gene to the HEK 293 T cells using lipofectamine and culturing for 24 hours in a 5% $CO_2$ cell incubator at 37° C., the medium was replaced with fresh DMEM on day 2. Then, after treating each well with 5 μM AP-SpCas9 protein (Comparative Example 1) and incubating for 6 hours in a 5% $CO_2$ cell incubator at 37° C., the medium was replaced with fresh DMEM. On day 3, after treating each well 5 μM AP-SpCas9 protein (Comparative Example 1) and incubating for 6 hours in a 5% $CO_2$ cell incubator at 37° C., the medium was replaced with fresh DMEM. On day 4, after treating with AP-SpCas9 in the same manner as on day 3 and reacting for 6 hours, the culture was recovered and then centrifuged. After removing the supernatant, the remaining pellet was washed twice with a PBS buffer and the protein attached to the cell surface was removed by treating with trypsin for 5 minutes. After neutralizing by adding an RPMI solution and washing once again with a PBS buffer, gene correction efficiency was investigated by flow cytometry (BD Science FACS Canto II) and T7 endonuclease 1 assay.

Figure 8:
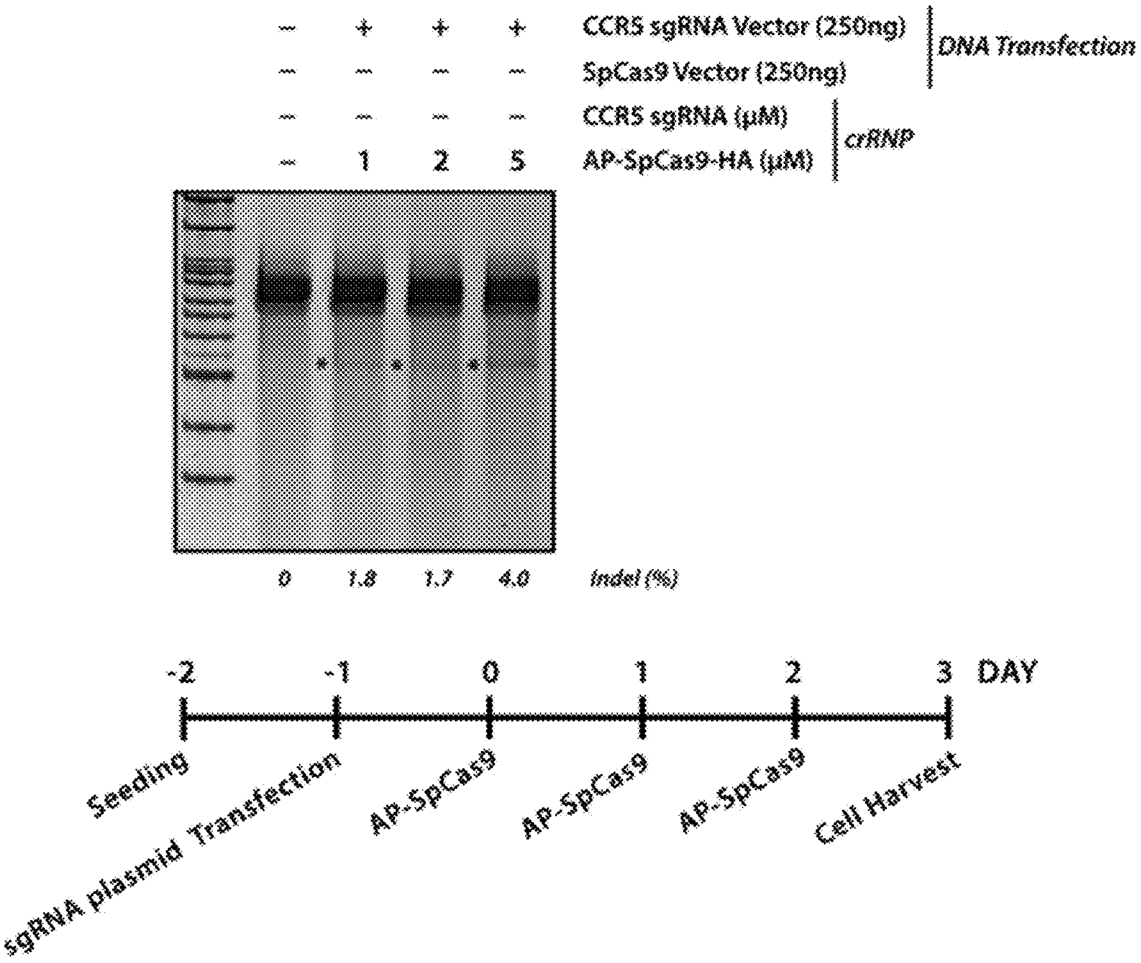
FIG. 8 shows a result of measuring the gene correction efficiency by AP-SpCas9 in HEK 293T cells.

FIG. 8 shows a result of measuring the gene correction efficiency by AP-SpCas9 in HEK 293T cells. It was confirmed that the cells treated with the AP-SpCas9 and sgRNA plasmid according to the present disclosure exhibited an indel (%) of 1.8-4.0.

<Test Example 5> Gene Correction by AP-RNP (Ribonucleoprotein) in HEK 293 T Cells 1) Preparation of AP-HE Cas9 Protein-RNA Complex (Ribonucleoprotein: RNP)

An AP Cas9 protein-RNA complex (ribonucleoprotein: RNP) was prepared by mixing the AP-SpCas9 of Comparative Example 1 protein (5 μM) and a sgRNA (5 μM) at a ratio of 1:1 and reacting at room temperature for 10 minutes, and it was named AP-Cas9 RNP. crRNP refers to a Cas9 protein-RNA complex (ribonucleoprotein: RNP) regardless of the type of the Cas9 protein.

2) Gene Correction

It was investigated whether the AP-SpCas9 protein of Comparative Example 1 prepared in the form of a Cas9 protein-RNA complex (ribonucleoprotein: RNP) exhibit gene correction effect in cells. For this, the RFP/GFP reporter system which express RFP and GFP at the same time when a specific gene is cleaved and T7 endonuclease 1 assay were used. Mouse HEK 293 T cells were cultured in DMEM. After placing 400 μL of DMEM on each well of a 24-well plate, $2.5\times10^5$ cells contained in 50 μL of DMEM were mixed. Then, CQ (50 UM) and AP RNP were added such that the concentration corresponds to that of D-PBS present in 50 μL of the medium (on day 0). The final volume was adjusted to 500 μL.

On day 1 after the culturing, the HEK 293 T cells in each well were treated with 5 UM AP-Cas9 RNP and, after culturing for 6 hours in a 5% $CO_2$ cell incubator at 37° C., the medium was replaced with fresh DMEM. The next day (on day 2), after treating the HEK 293 T cells with 5 UM AP-Cas9 RNP and incubating for 6 hours in a 5% $CO_2$ cell incubator at 37° C., the medium was replaced with fresh DMEM. On day 3 after the culturing, after treating with AP-Cas9 RNP in the same manner as on day 2 and reacting for 6 hours, the culture was recovered and then centrifuged. After removing the supernatant, the remaining pellet was washed twice with a PBS buffer and the protein attached to the cell surface was removed by treating with trypsin for 5 minutes. After neutralizing by adding an RPMI solution and washing once again with a PBS buffer, gene correction efficiency was investigated by flow cytometry (BD Science FACS Canto II) and T7 endonuclease 1 assay. As a control group, the cells were treated with 250 ng of the CCR5 sgRNA vector and 250 ng of the SpCas9 vector once a day.

Figure 9:
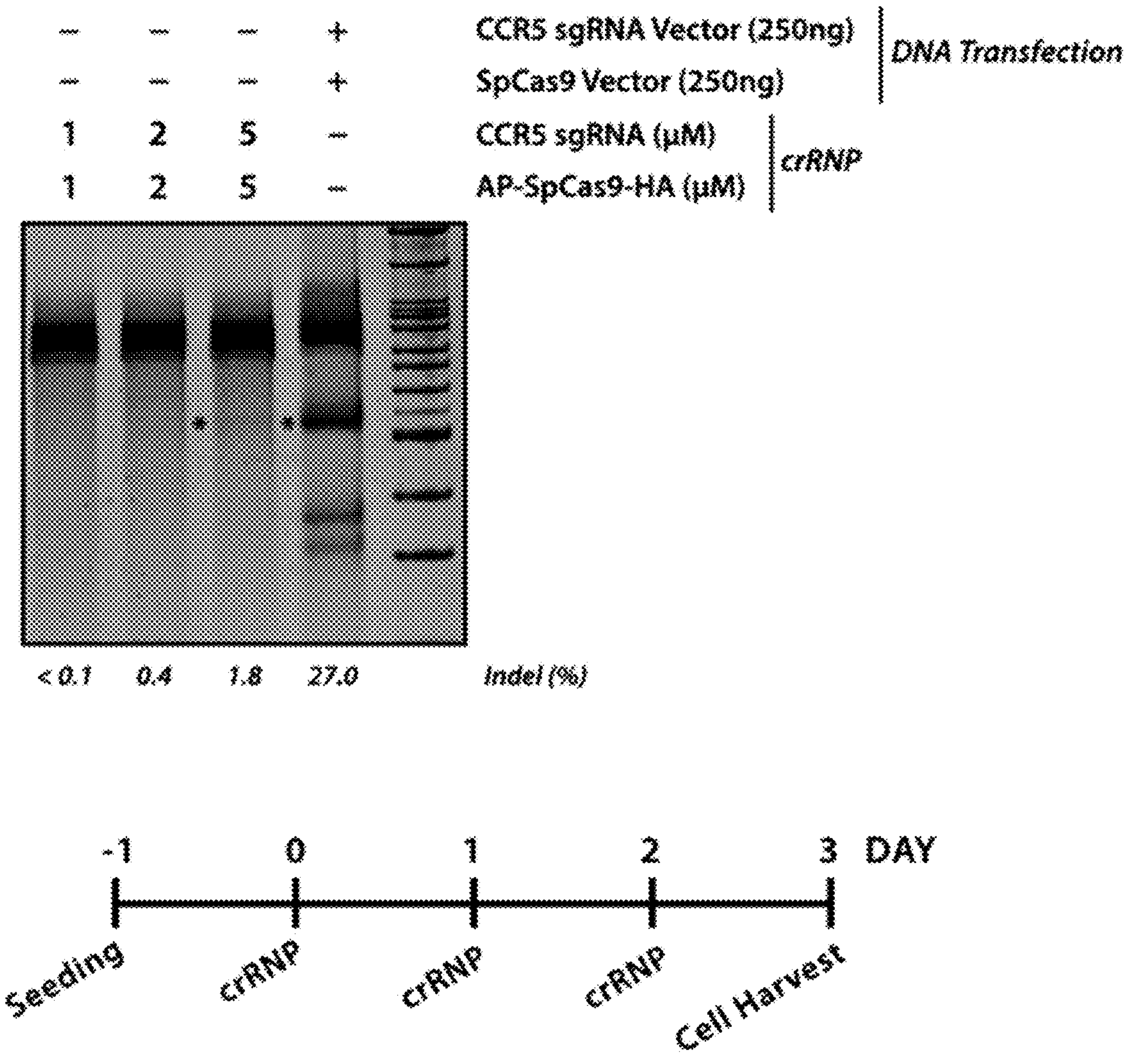
FIG. 9 shows a result of measuring the gene correction efficiency by AP RNP in HEK 293T cells.

FIG. 9 shows a result of measuring the gene correction efficiency by AP-Cas9 RNP in HEK 293T cells. It was confirmed that the cells treated with the AP Cas9 protein-RNA complex (ribonucleoprotein: RNP) according to the present disclosure exhibited an indel (%) of 0.1-1.8, suggesting that the AP-HE-SpCas9 RNP represented by General Formula 1 of the present disclosure, especially the AP-HE-SpCas9 RNP of Example 6, is about 3-6 times more effective.

<Test Example 6> Gene Correction Effect of AP-HE-SpCas9 Prepared In Vitro in Example 6

The AP-HE-SpCas9 protein prepared in Example 6 of the present disclosure includes 10 HEs, which are attenuators, and functions to prevent the + charge of the cell-penetrating peptide. It was investigated in vitro whether the target DNA was cleaved by the AP-HE-SpCas9 protein of Example 1 of the present disclosure. First, a Cas9 protein-RNA complex (ribonucleoprotein: RNP) was prepared by mixing 50 nM of Cas9 (SEQ ID NO: 9), the AP-Cas9 of Comparative Example 1 (SEQ ID NO: 19) or the AP-HE-SpCas9 of Example 6 (SEQ ID NO: 15) with 50 nM of sgRNA and reacting at room temperature for 15 minutes. Then, it was investigated whether a target DNA is cleaved by agarose electrophoresis (0.8% agarose gel) by incubating 300 ng of the target DNA at 37° C. for 15, 30 or 60 minutes.

Figure 10:
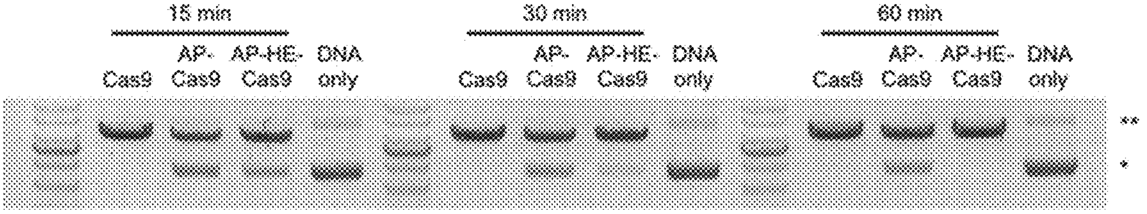
FIG. 10 shows a result of preparing an RNP by mixing Cas9 (SEQ ID NO: 9), AP-Cas9 of Comparative Example 1 (SEQ ID NO: 19) or AP-HE-SpCas9 of Example 6 (SEQ ID NO: 15) with sgDNA and conducting agarose electrophoresis after treating a target DNA with the same for 15, 30 or 60 minutes.

FIG. 10 shows a result of preparing an RNP by mixing Cas9 (SEQ ID NO: 9), the AP-Cas9 of Comparative Example 1 (SEQ ID NO: 19) or the AP-HE-SpCas9 of Example 6 (SEQ ID NO: 15) with sgDNA and conducting agarose electrophoresis after treating a target DNA with the same for 15, 30 or 60 minutes. It can be seen that the complex (RNP) of the AP-HE-SpCas9 of Example 6 (SEQ ID NO: 15) and sgDNA of the present disclosure exhibits the best cleavage effect. That is to say, it can be seen that the protein with the HE sequence added (AP-HE-SpCas9) has an excellent gene correction efficiency as compared to the protein without the HE sequence (AP-Cas9).

<Test Example 7> Gene Correction Effect of Comparative Examples In Vitro

The AP-HE-SpCas9 protein prepared in Example 6 of the present disclosure includes 10 HEs, which are attenuators, and functions to prevent the + charge of the cell-penetrating peptide. It was investigated in vitro whether the target DNA was cleaved by the AP-HE-SpCas9 protein of Example 6 of the present disclosure. First, a Cas9 protein-RNA complex (ribonucleoprotein: RNP) was prepared by mixing 50 nM of Cas9 (SEQ ID NO: 9), the TAT-Cas9 of Comparative Example 7 (SEQ ID NO: 29), the TAT-HE-SpCas9 of Comparative Example 6 (SEQ ID NO: 31), the R9-Cas9 of Comparative Example 5 (SEQ ID NO: 25), the R9-HE-SpCas9 of Comparative Example 4 (SEQ ID NO: 27), the dNP2-Cas9 of Comparative Example 3 (SEQ ID NO: 21) or the dNP2-HE-SpCas9 of Comparative Example 2 (SEQ ID NO: 23) with 50 nM of sgRNA and reacting at room temperature for 15 minutes. Then, it was investigated whether a target DNA is cleaved by agarose electrophoresis (0.8% agarose gel) by incubating 300 ng of the target DNA at 37° C. for 15, 30 or 60 minutes.

Figure 11:
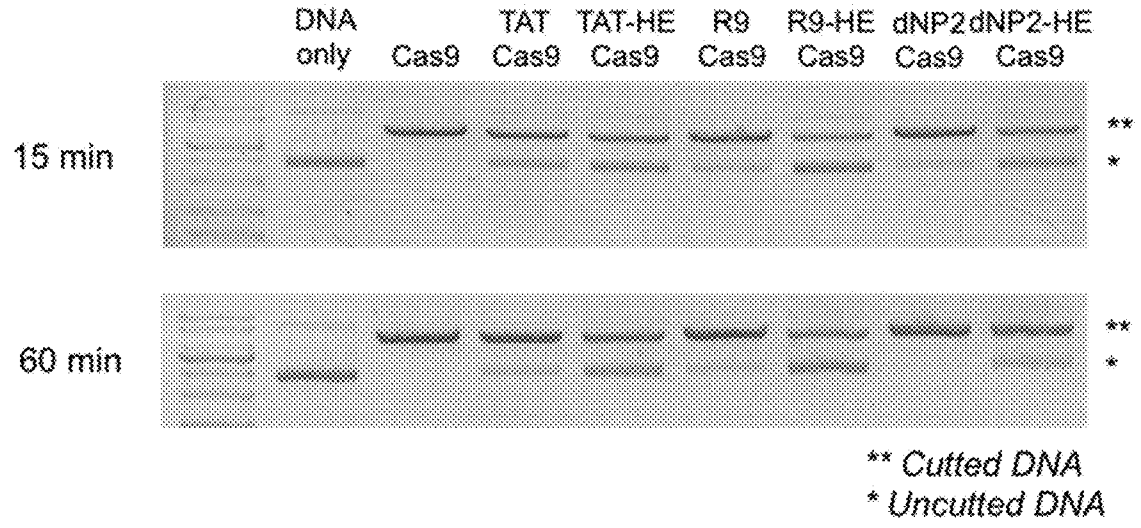
FIG. 11 shows a result of preparing an RNP by mixing Cas9 (SEQ ID NO: 9), TAT-Cas9 of Comparative Example 6 (SEQ ID NO: 29), TAT-HE-SpCas9 of Comparative Example 7 (SEQ ID NO: 31), R9-Cas9 of Comparative Example 4 (SEQ ID NO: 25), R9-HE-SpCas9 of Comparative Example 5 (SEQ ID NO: 27), dNP2-Cas9 of Comparative Example 2 (SEQ ID NO: 21) or dNP2-HE-SpCas9 of Comparative Example 3 (SEQ ID NO: 23) with sgDNA and conducting agarose electrophoresis after treating a target DNA with the same for 15 or 60 minutes.

FIG. 11 shows a result of preparing an RNP by mixing Cas9 (SEQ ID NO: 9), the TAT-Cas9 of Comparative Example 7 (SEQ ID NO: 29), the TAT-HE-SpCas9 of Comparative Example 6 (SEQ ID NO: 31), the R9-Cas9 of Comparative Example 5 (SEQ ID NO: 25), the R9-HE-SpCas9 of Comparative Example 4 (SEQ ID NO: 27), dNP2-Cas9 of Comparative Example 3 (SEQ ID NO: 21) or the dNP2-HE-SpCas9 of Comparative Example 2 (SEQ ID NO: 23) with sgDNA and conducting agarose electrophoresis after treating a target DNA with the same for 15 or 60 minutes. It was confirmed that some target DNAs removed uncleaved for the complexes of the CPP-SpCas9 protein and sgDNA of Comparative Examples 2-7. In summary, it can be seen that the complex (RNP) of the AP-HE-SpCas9 of Example 6 (SEQ ID NO: 15) and sgDNA of the present disclosure exhibits the best cleavage effect.

That is to say, it can be seen that the gene correction effect is decreased on the contrary for the CPP (cell-penetrating peptide) with the HE sequence added, such as TAT, R9, dNP2, etc.

<Test Example 8> Gene Correction Effect Depending on Length of Attenuator HE The gene correction efficiency of a target DNA in vitro was investigated using the AP-HE-SpCas9 protein prepared in Examples 1-8 of the present disclosure. A Cas9 protein-RNA complex (ribonucleoprotein: RNP) was prepared by mixing 50 nM of the AP-HE-SpCas9 protein prepared in Examples 1-8 of the present disclosure with 50 nM of a sgRNA and conducting reaction at room temperature for 15 minutes.

After placing a 24-mm$^2$ rectangular cover glass on each well of a 6-well plate and plating 1×10$^5$ Hela cells, the cells were allowed to adhere to the cover glass by culturing in DMEM for 24 hours. Then, after removing the DMEM, 900 μL of fresh DMEM was added. Thereafter, the AP-HE-SpCas9 protein prepared in Examples 1-8 was added to a concentration of 01, 2 or 5 UM, and the cells were cultured for 1 hour at 37° C. in a 5% $CO_2$ cell incubator under different pH conditions (pH 7.4, 6.5, 6.0). The cultured cells were centrifuged and washed twice with a PBS buffer. Then, the protein attached to the cell surface was removed by treating with a trypsin solution for 5 minutes. Then, after neutralizing with DMEM and washing once again with a PBS buffer, delivery efficiency was investigated by measuring intracellular fluorescence by flow cytometry (BD Science FACS Canto II).

Figure 12:
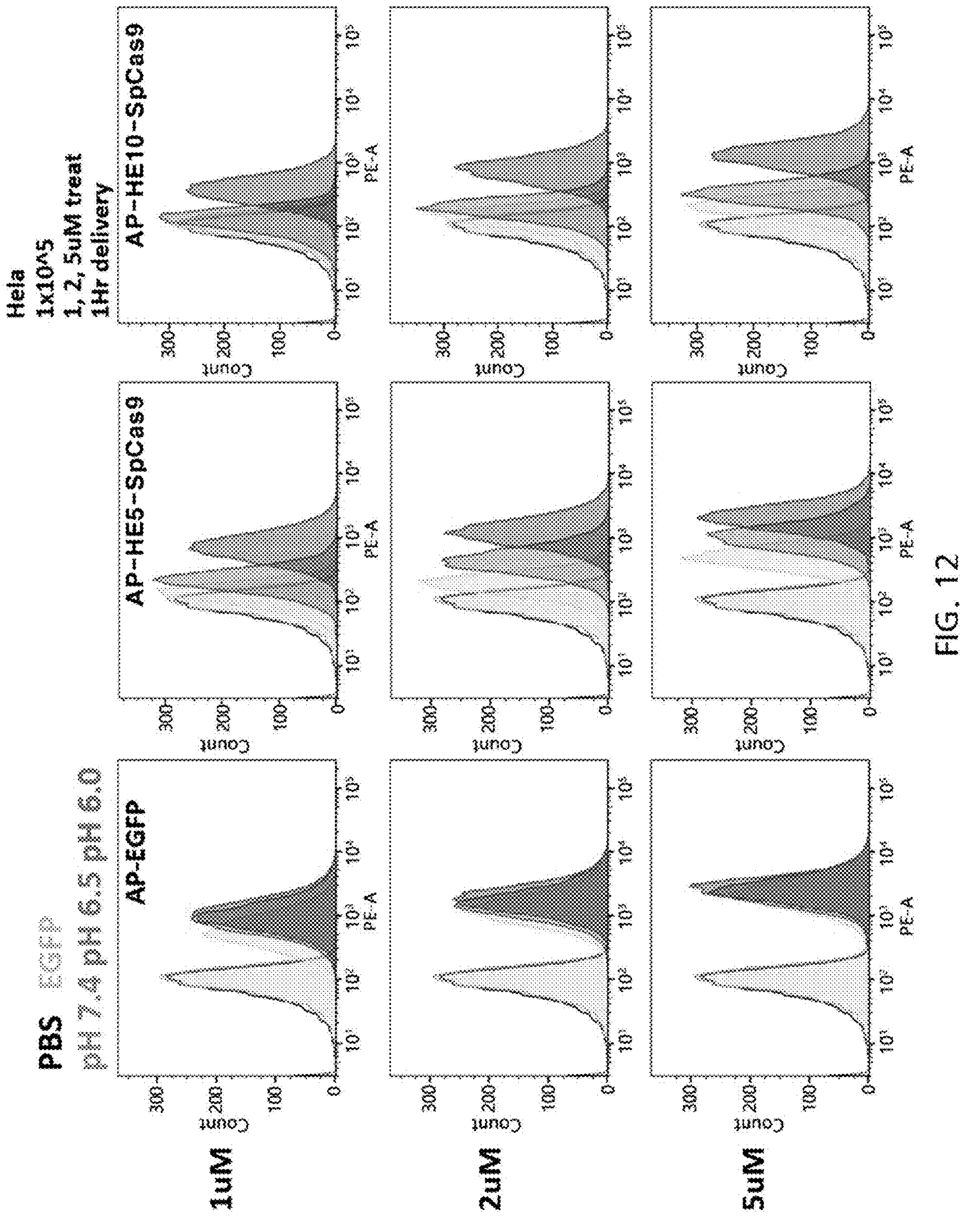
FIG. 12 shows a flow cytometry measurement result after treating with AP-HE5-SpCas9 (SEQ ID NO: 10) and AP-HE10-SpCas9 (SEQ ID NO: 15) prepared in Examples 1 and 6 at various concentrations (1, 2, 5 μM) and pH conditions (pH 7.4, 6.5, 6.0).
Figure 13A:
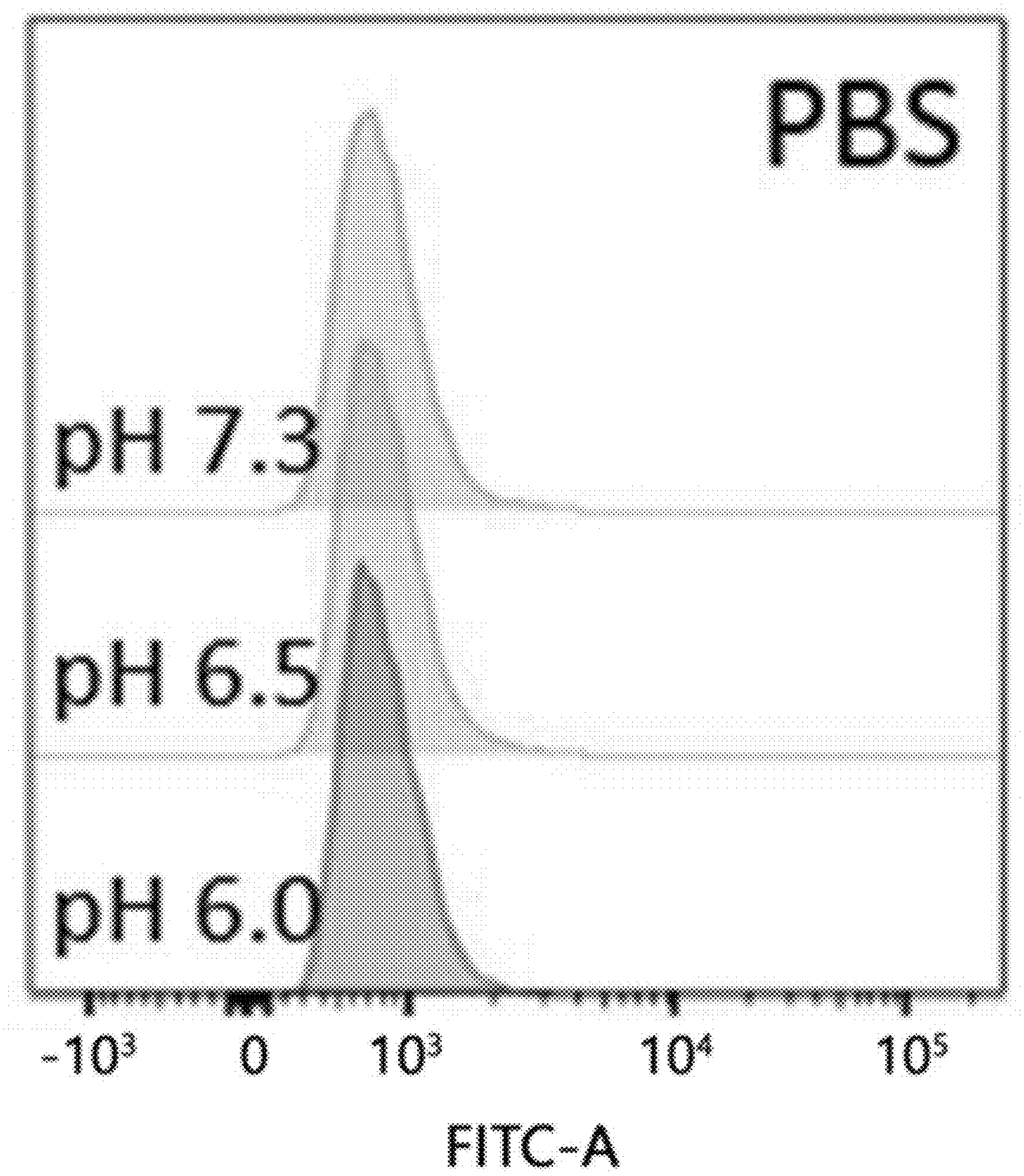
FIGS. 13A to 13G show a flow cytometry measurement result after treating with AP-Cas9 prepared in Comparative Example 1 or AP-HE-SpCas9 prepared in each of Examples 2, 4, 6 and 8 at different concentrations (1, 2, 5 μM) and pH conditions (pH 7.4, 6.5, 6.0).
Figure 13B:
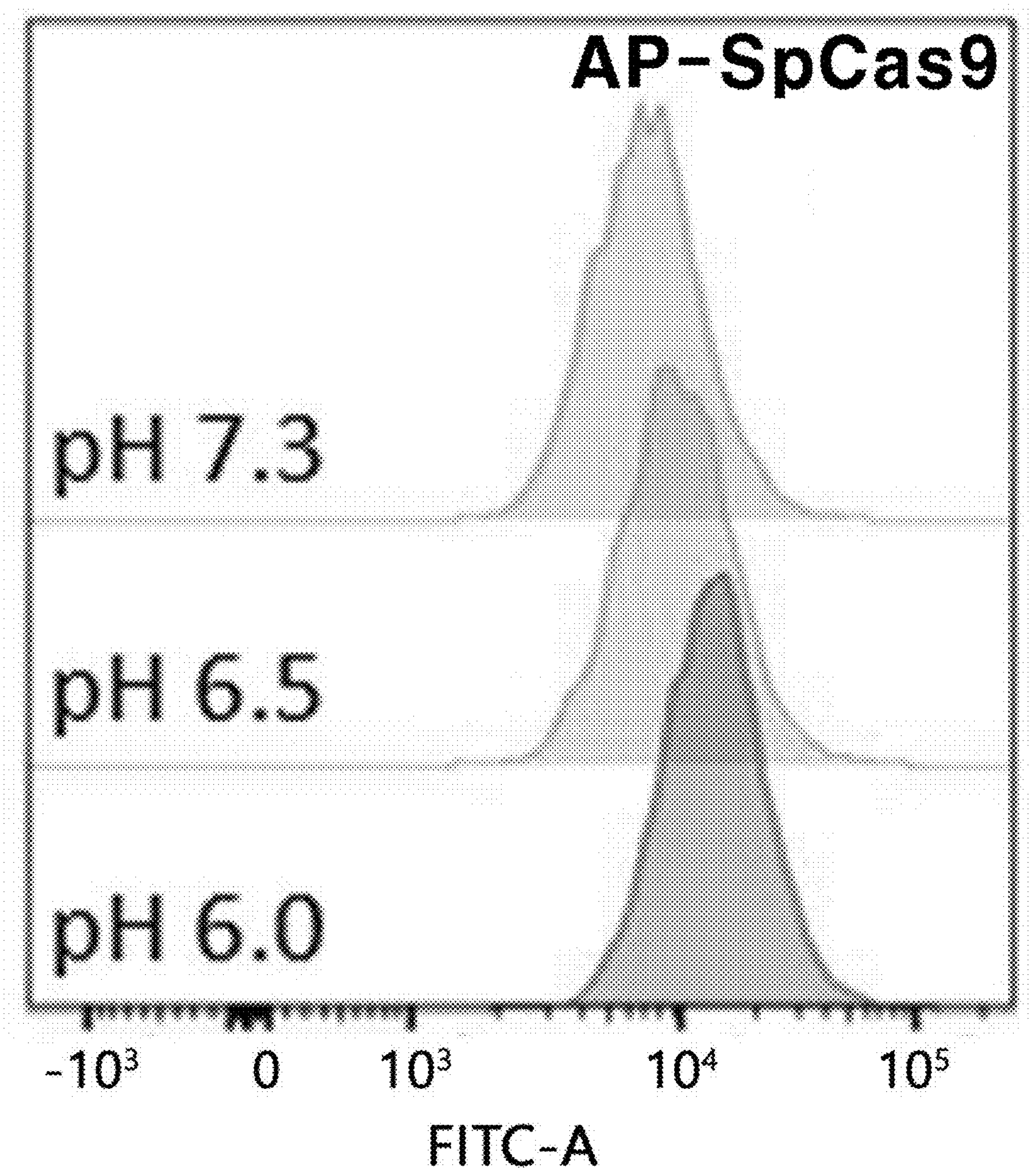
Figure 13C:
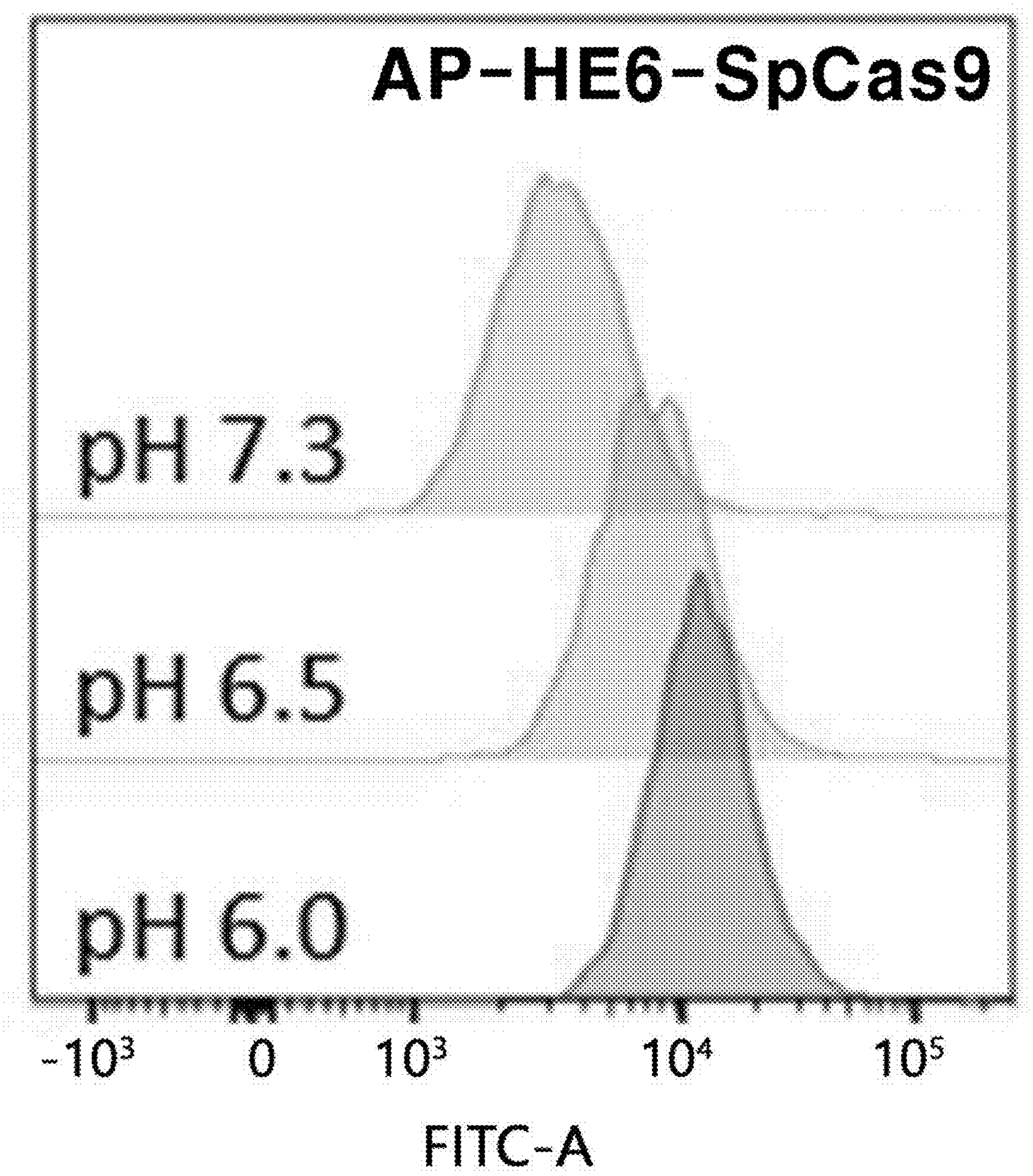
Figure 13D:
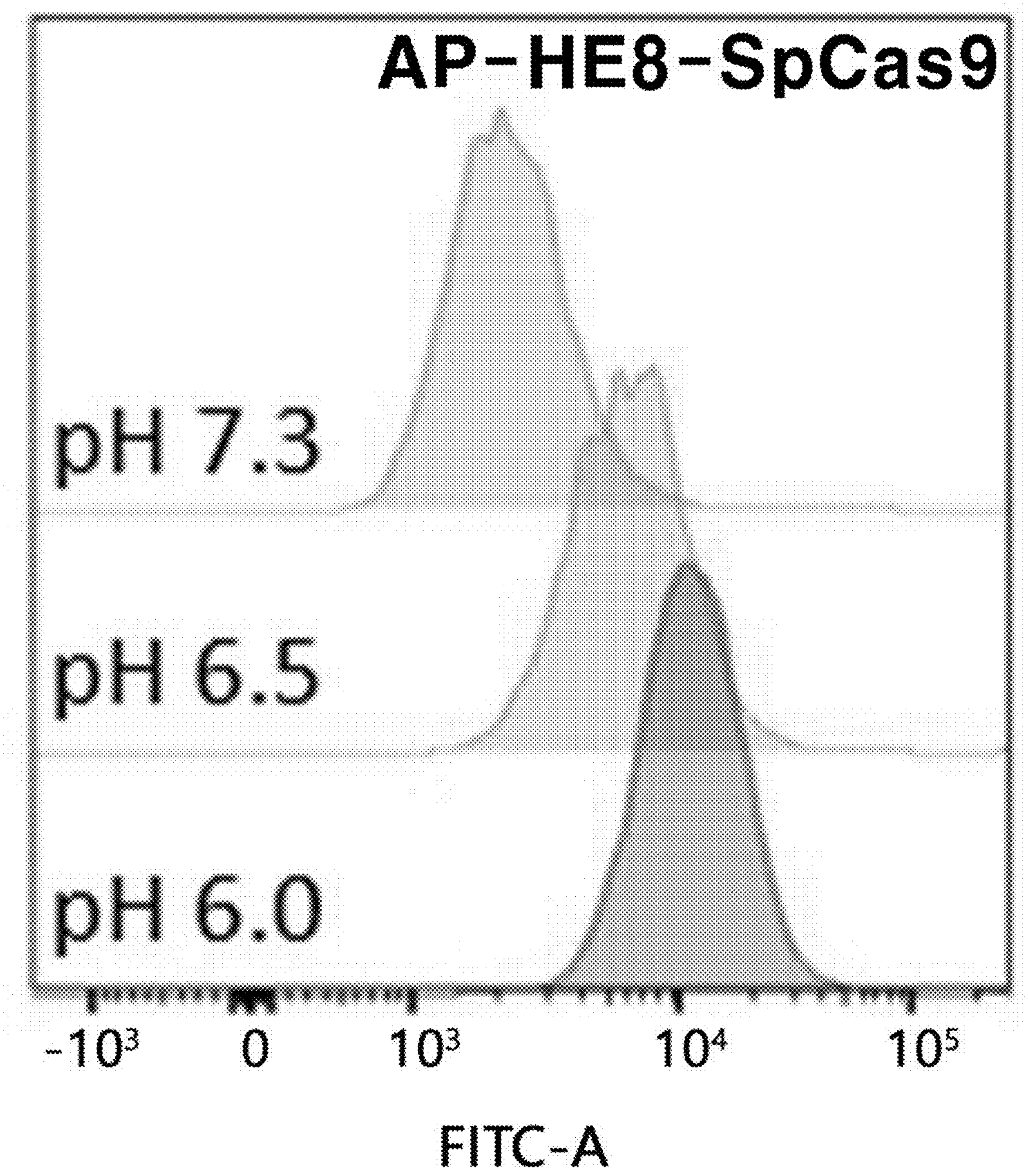
Figure 13E:
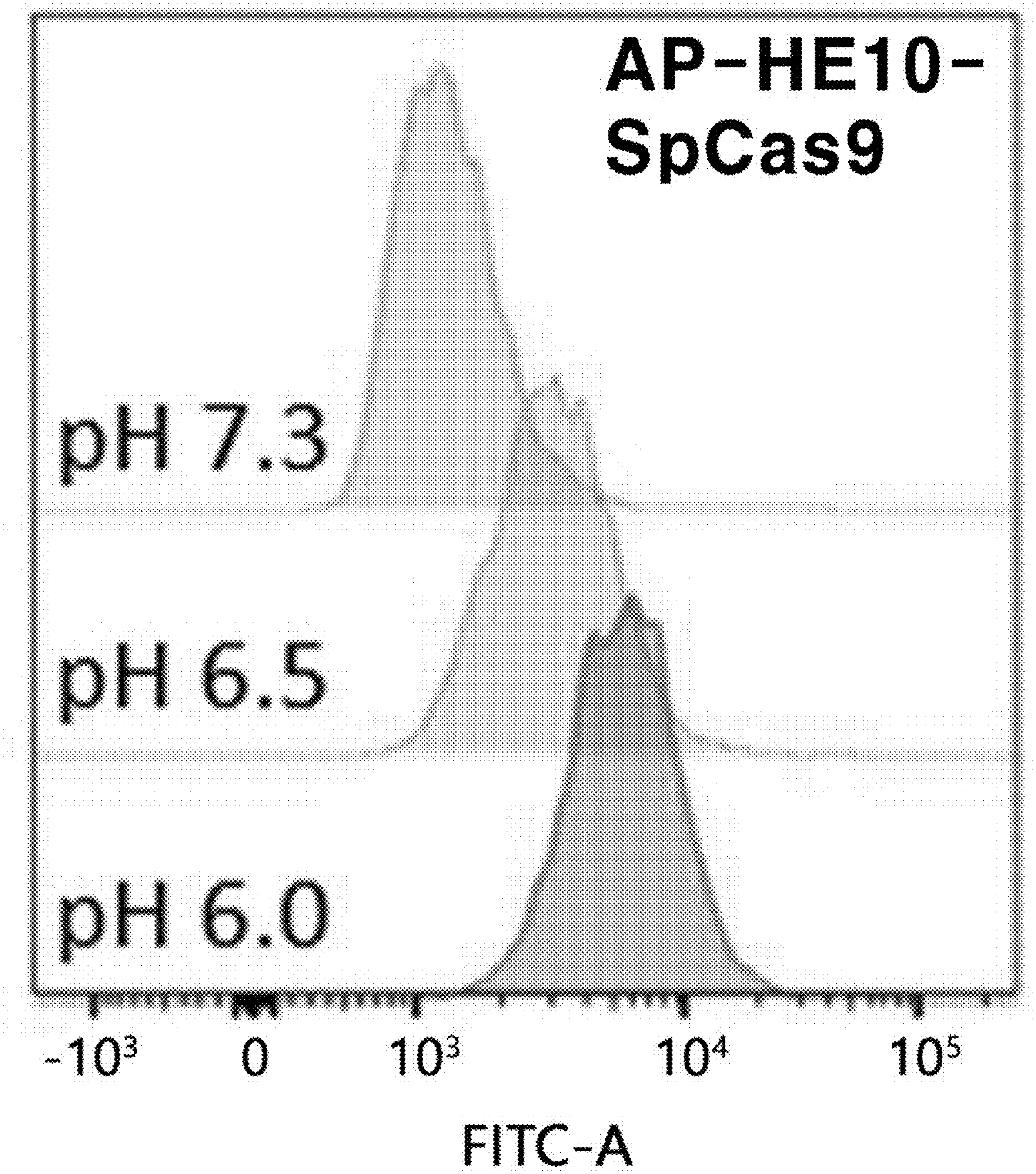
Figure 13F:
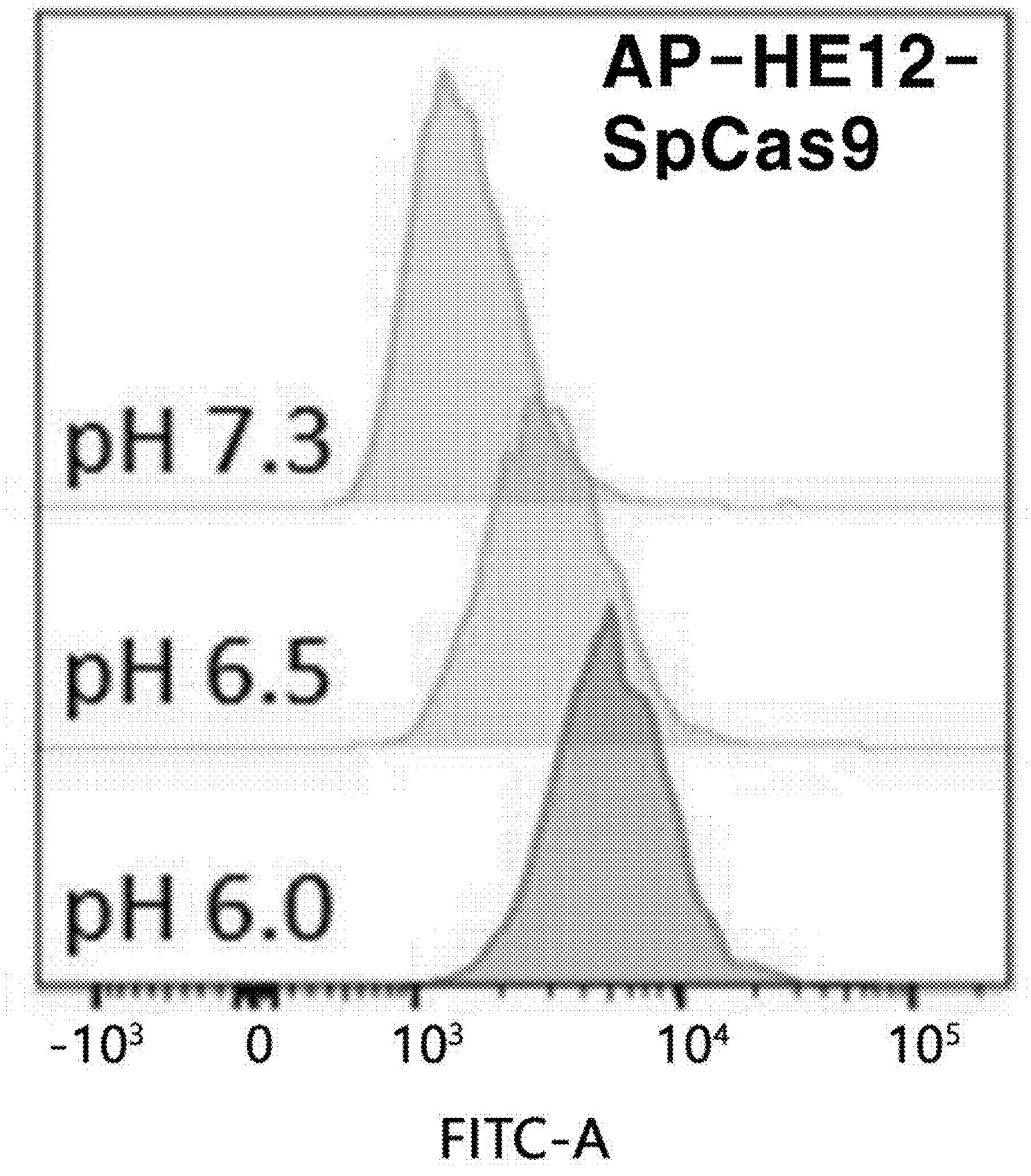
Figure 13G:
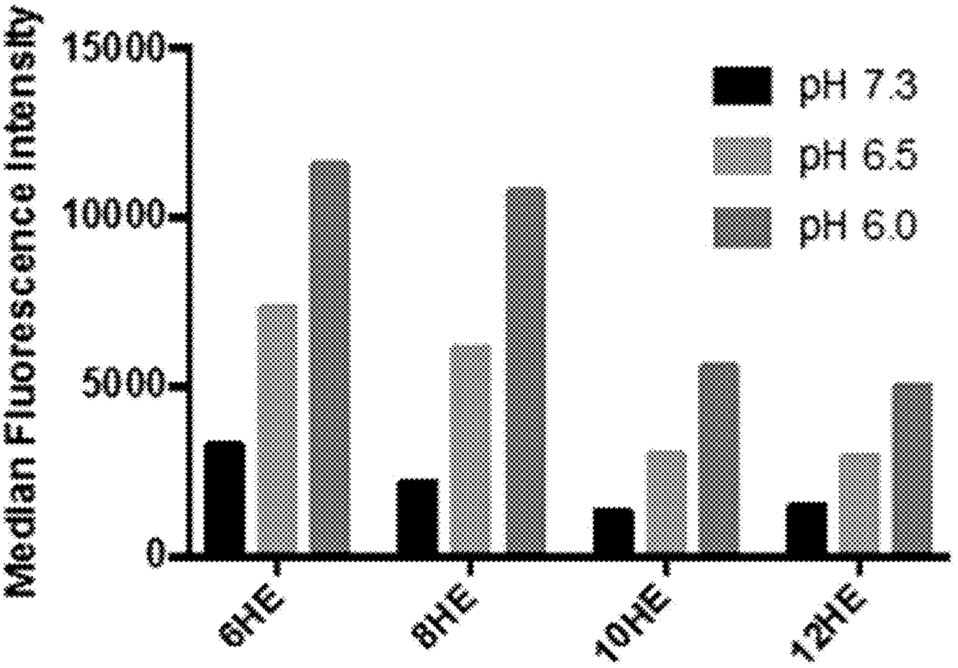

FIG. 12 shows the flow cytometry measurement result after treating with the AP-HE5-SpCas9 (SEQ ID NO: 10) and AP-HE10-SpCas9 (SEQ ID NO: 15) prepared in Examples 1 and 6 at various concentrations (1, 2, 5 μM) and pH conditions (pH 7.4, 6.5, 6.0). It can be seen that the AP-HE10-Cas9 of Example 6 (SEQ ID NO: 15) exhibits remarkably higher masking efficiency than the AP-HE5-Cas9 of Example 1 (SEQ ID NO: 10) under the same condition.

It can also be seen that the AP-HE10-Cas9 of Example 6 (SEQ ID NO: 15) exhibits higher delivery efficiency than the AP-HE5-Cas9 of Example 1 (SEQ ID NO: 10) at pH 7.4 and 6.5.

FIGS. 13A to 13G show the flow cytometry measurement result after treating with the AP-Cas9 prepared in Comparative Example 1 or the AP-HE-SpCas9 prepared in each of Examples 2, 4, 6 and 8 at different concentrations (1, 2, 5 UM) and pH conditions (pH 7.4, 6.5, 6.0).

It was confirmed that the AP-HE10-Cas9 of Example 6 (SEQ ID NO: 15) exhibits remarkably higher masking efficiency than the AP-HE5-Cas9 of Example 1 (SEQ ID NO: 10), the AP-HE6-Cas9 of Example 2 (SEQ ID NO: 11) or the AP-HE8-Cas9 of Example 4 (SEQ ID NO: 13).

In addition, it can be seen that the AP-HE10-Cas9 of Example 6 (SEQ ID NO: 15) exhibits higher delivery efficiency than the AP-HE5-Cas9 of Example 1 (SEQ ID NO: 10), the AP-HE6-Cas9 of Example 2 (SEQ ID NO: 11) or the AP-HE8-Cas9 of Example 4 (SEQ ID NO: 13) at pH 7.4-6.0.

Meanwhile, the AP-HE10-Cas9 of Example 6 (SEQ ID NO: 15) and the AP-HE5-Cas9 of Example 8 (SEQ ID NO: 17) did not show significant difference in masking and delivery efficiency despite the difference in HE sequence length.

That is to say, whereas Example 6 having 10 HE sequences showed excellent masking efficiency as compared to Example 2 or 4 having 6 or 8 HE sequences under various pH conditions, the AP-HE-SpCas9 of Example 6 and Example 9 showed little difference. Through this, it can be seen that there is no significant effect in increasing the number of HE sequences to more than 10, and that the AP-HE10-Cas9 of Example 6 is most preferred.

Although specific exemplary embodiments of the present disclosure have been described in detail above, it is obvious to those having ordinary knowledge in the art that such specific exemplary embodiments are only preferred examples and the scope of the present disclosure is not limited by them. Accordingly, it is to be noted that the substantial scope of the present disclosure is defined by the appended claims and their equivalents.

The invention claimed is:

1. A cell-penetrating peptide for a Cas protein-RNA complex, said cell-penetrating peptide comprising the amino acid sequence of the following Formula 1:

[Formula 1]

Arg-Arg-Arg-Trp-Cys-Lys-Arg-Arg-Arg-Ala-Ser-$[Gly]_m$ -$[His\text{-}Glu]_n$ (SEQ ID NO: 85)

wherein m is an integer from 3 to 7, and n is an integer from 5 to 15.

2. The cell-penetrating peptide for a Cas protein-RNA complex according to claim 1, wherein, in Formula 1, n is an integer from 9 to 15.

3. The cell-penetrating peptide for a Cas protein-RNA complex according to claim 1, wherein, in Formula 1, n is an integer from 10 to 12.

4. The cell-penetrating peptide for a Cas protein-RNA complex according to claim 1, wherein the cell-penetrating peptide for a Cas protein-RNA complex comprises the sequence of SEQ ID NO: 6.

5. A composition for gene correction, comprising a ribonucleoprotein complex (RNP) comprising:

a) a Cas protein to which a cell-penetrating peptide of the Formula 1 is bound:

[Formula 1]

Arg-Arg-Arg-Trp-Cys-Lys-Arg-Arg-Arg-Ala-Ser-$[Gly]_m$ -[His-Glu], (SEQ ID NO: 85)

wherein m is an integer from 3 to 7, and n is an integer from 5 to 15; and b) a guide RNA.

6. The composition for gene correction according to claim 5, wherein, in Formula 1, n is an integer from 10 to 12.

7. The composition for gene correction according to claim 5, wherein, in Formula 1, n is an integer from 9 to 15.

8. The composition for gene correction according to claim 5, wherein, in Formula 1, n is an integer from 10 to 12.

9. The composition for gene correction according to claim 5, wherein the Cas protein comprises the amino acid sequence of SEQ ID NO: 9.

10. The composition for gene correction according to claim 5, wherein the guide RNA is a dual RNA or a single-stranded guide RNA (sgRNA) comprising crRNA and tracrRNA.

11. The composition for gene correction according to claim 5, wherein the composition induces targeted mutation of single or multiple genes in a prokaryotic cell, a eukaryotic cell or a non-human eukaryotic organism.

12. A method for preparing a non-human transformant, comprising 1) a step of introducing the composition for gene correction according to claim 5 into an isolated prokaryotic cell, eukaryotic cell or non-human eukaryotic organism by a method selected from local injection, microinjection, electroporation and lipofection.

* * * * *

SEQUENCE LISTING

<160> NUMBER OF SEQ ID NOS: 87

<210> SEQ ID NO 1
<211> LENGTH: 26
<212> TYPE: PRT
<213> ORGANISM: Artificial Sequence
<220> FEATURE:
<223> OTHER INFORMATION: penetrating peptide; AP-HE5

<400> SEQUENCE: 1

Arg Arg Arg Trp Cys Lys Arg Arg Arg Ala Ser Gly Gly Gly Gly Gly
1               5                   10                  15

His Glu His Glu His Glu His Glu His Glu
            20                  25

<210> SEQ ID NO 2
<211> LENGTH: 28
<212> TYPE: PRT
<213> ORGANISM: Artificial Sequence
<220> FEATURE:

```
<223> OTHER INFORMATION: penetrating peptide; AP-HE6

<400> SEQUENCE: 2

Arg Arg Arg Trp Cys Lys Arg Arg Arg Ala Ser Gly Gly Gly Gly Gly
1               5                   10                  15

His Glu His Glu His Glu His Glu His Glu His Glu
            20                  25


<210> SEQ ID NO 3
<211> LENGTH: 30
<212> TYPE: PRT
<213> ORGANISM: Artificial Sequence
<220> FEATURE:
<223> OTHER INFORMATION: penetrating peptide; AP-HE7

<400> SEQUENCE: 3

Arg Arg Arg Trp Cys Lys Arg Arg Arg Ala Ser Gly Gly Gly Gly Gly
1               5                   10                  15

His Glu His Glu His Glu His Glu His Glu His Glu His Glu
            20                  25                  30


<210> SEQ ID NO 4
<211> LENGTH: 32
<212> TYPE: PRT
<213> ORGANISM: Artificial Sequence
<220> FEATURE:
<223> OTHER INFORMATION: penetrating peptide; AP-HE8

<400> SEQUENCE: 4

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30


<210> SEQ ID NO 5
<211> LENGTH: 34
<212> TYPE: PRT
<213> ORGANISM: Artificial Sequence
<220> FEATURE:
<223> OTHER INFORMATION: penetrating peptide; AP-HE9

<400> SEQUENCE: 5

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu


<210> SEQ ID NO 6
<211> LENGTH: 36
<212> TYPE: PRT
<213> ORGANISM: Artificial Sequence
<220> FEATURE:
<223> OTHER INFORMATION: penetrating peptide; AP-HE10

<400> SEQUENCE: 6

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu His Glu
        35
```

<210> SEQ ID NO 7
<211> LENGTH: 38
<212> TYPE: PRT
<213> ORGANISM: Artificial Sequence
<220> FEATURE:
<223> OTHER INFORMATION: penetrating peptide; AP-HE11

<400> SEQUENCE: 7

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu His Glu His Glu
        35

<210> SEQ ID NO 8
<211> LENGTH: 40
<212> TYPE: PRT
<213> ORGANISM: Artificial Sequence
<220> FEATURE:
<223> OTHER INFORMATION: penetrating peptide; AP-HE12

<400> SEQUENCE: 8

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu His Glu His Glu His Glu
        35                  40

<210> SEQ ID NO 9
<211> LENGTH: 1409
<212> TYPE: PRT
<213> ORGANISM: Artificial Sequence
<220> FEATURE:
<223> OTHER INFORMATION: Cas9

<400> SEQUENCE: 9

Leu Asp Ser Thr Ala Pro Lys Lys Lys Arg Lys Val Gly Ile His Gly
1               5                   10                  15

Val Pro Ala Ala Asp Lys Lys Tyr Ser Ile Gly Leu Asp Ile Gly Thr
            20                  25                  30

Asn Ser Val Gly Trp Ala Val Ile Thr Asp Glu Tyr Lys Val Pro Ser
        35                  40                  45

Lys Lys Phe Lys Val Leu Gly Asn Thr Asp Arg His Ser Ile Lys Lys
    50                  55                  60

Asn Leu Ile Gly Ala Leu Leu Phe Asp Ser Gly Glu Thr Ala Glu Ala
65                  70                  75                  80

Thr Arg Leu Lys Arg Thr Ala Arg Arg Arg Tyr Thr Arg Arg Lys Asn
                85                  90                  95

Arg Ile Cys Tyr Leu Gln Glu Ile Phe Ser Asn Glu Met Ala Lys Val
            100                 105                 110

Asp Asp Ser Phe Phe His Arg Leu Glu Glu Ser Phe Leu Val Glu Glu
        115                 120                 125

Asp Lys Lys His Glu Arg His Pro Ile Phe Gly Asn Ile Val Asp Glu
    130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala

-continued

```
                165                 170                 175

Leu Ala His Met Ile Lys Phe Arg Gly His Phe Leu Ile Glu Gly Asp
            180                 185                 190

Leu Asn Pro Asp Asn Ser Asp Val Asp Lys Leu Phe Ile Gln Leu Val
        195                 200                 205

Gln Thr Tyr Asn Gln Leu Phe Glu Glu Asn Pro Ile Asn Ala Ser Gly
    210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
            260                 265                 270

Ser Asn Phe Asp Leu Ala Glu Asp Ala Lys Leu Gln Leu Ser Lys Asp
        275                 280                 285

Thr Tyr Asp Asp Asp Leu Asp Asn Leu Leu Ala Gln Ile Gly Asp Gln
    290                 295                 300

Tyr Ala Asp Leu Phe Leu Ala Ala Lys Asn Leu Ser Asp Ala Ile Leu
305                 310                 315                 320

Leu Ser Asp Ile Leu Arg Val Asn Thr Glu Ile Thr Lys Ala Pro Leu
                325                 330                 335

Ser Ala Ser Met Ile Lys Arg Tyr Asp Glu His His Gln Asp Leu Thr
            340                 345                 350

Leu Leu Lys Ala Leu Val Arg Gln Gln Leu Pro Glu Lys Tyr Lys Glu
        355                 360                 365

Ile Phe Phe Asp Gln Ser Lys Asn Gly Tyr Ala Gly Tyr Ile Asp Gly
    370                 375                 380

Gly Ala Ser Gln Glu Glu Phe Tyr Lys Phe Ile Lys Pro Ile Leu Glu
385                 390                 395                 400

Lys Met Asp Gly Thr Glu Glu Leu Leu Val Lys Leu Asn Arg Glu Asp
                405                 410                 415

Leu Leu Arg Lys Gln Arg Thr Phe Asp Asn Gly Ser Ile Pro His Gln
            420                 425                 430

Ile His Leu Gly Glu Leu His Ala Ile Leu Arg Arg Gln Glu Asp Phe
        435                 440                 445

Tyr Pro Phe Leu Lys Asp Asn Arg Glu Lys Ile Glu Lys Ile Leu Thr
    450                 455                 460

Phe Arg Ile Pro Tyr Tyr Val Gly Pro Leu Ala Arg Gly Asn Ser Arg
465                 470                 475                 480

Phe Ala Trp Met Thr Arg Lys Ser Glu Glu Thr Ile Thr Pro Trp Asn
                485                 490                 495

Phe Glu Glu Val Val Asp Lys Gly Ala Ser Ala Gln Ser Phe Ile Glu
            500                 505                 510

Arg Met Thr Asn Phe Asp Lys Asn Leu Pro Asn Glu Lys Val Leu Pro
        515                 520                 525

Lys His Ser Leu Leu Tyr Glu Tyr Phe Thr Val Tyr Asn Glu Leu Thr
    530                 535                 540

Lys Val Lys Tyr Val Thr Glu Gly Met Arg Lys Pro Ala Phe Leu Ser
545                 550                 555                 560

Gly Glu Gln Lys Lys Ala Ile Val Asp Leu Leu Phe Lys Thr Asn Arg
                565                 570                 575

Lys Val Thr Val Lys Gln Leu Lys Glu Asp Tyr Phe Lys Lys Ile Glu
            580                 585                 590
```

```
Cys Phe Asp Ser Val Glu Ile Ser Gly Val Glu Asp Arg Phe Asn Ala
        595                 600                 605

Ser Leu Gly Thr Tyr His Asp Leu Leu Lys Ile Ile Lys Asp Lys Asp
    610                 615                 620

Phe Leu Asp Asn Glu Glu Asn Glu Asp Ile Leu Glu Asp Ile Val Leu
625                 630                 635                 640

Thr Leu Thr Leu Phe Glu Asp Arg Glu Met Ile Glu Glu Arg Leu Lys
                645                 650                 655

Thr Tyr Ala His Leu Phe Asp Asp Lys Val Met Lys Gln Leu Lys Arg
            660                 665                 670

Arg Arg Tyr Thr Gly Trp Gly Arg Leu Ser Arg Lys Leu Ile Asn Gly
        675                 680                 685

Ile Arg Asp Lys Gln Ser Gly Lys Thr Ile Leu Asp Phe Leu Lys Ser
    690                 695                 700

Asp Gly Phe Ala Asn Arg Asn Phe Met Gln Leu Ile His Asp Asp Ser
705                 710                 715                 720

Leu Thr Phe Lys Glu Asp Ile Gln Lys Ala Gln Val Ser Gly Gln Gly
                725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Val Asp Glu Leu Val Lys
        755                 760                 765

Val Met Gly Arg His Lys Pro Glu Asn Ile Val Ile Glu Met Ala Arg
    770                 775                 780

Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
                805                 810                 815

Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
        835                 840                 845

Ile Asn Arg Leu Ser Asp Tyr Asp Val Asp His Ile Val Pro Gln Ser
    850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
                885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
        915                 920                 925

Glu Leu Asp Lys Ala Gly Phe Ile Lys Arg Gln Leu Val Glu Thr Arg
    930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
                965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr  His His Ala His Asp  Ala Tyr Leu
        995                 1000                1005
```

```
Asn Ala  Val Val Gly Thr Ala  Leu Ile Lys Lys Tyr  Pro Lys Leu
    1010                 1015                 1020

Glu Ser  Glu Phe Val Tyr Gly  Asp Tyr Lys Val Tyr  Asp Val Arg
    1025                 1030                 1035

Lys Met  Ile Ala Lys Ser Glu  Gln Glu Ile Gly Lys  Ala Thr Ala
    1040                 1045                 1050

Lys Tyr  Phe Phe Tyr Ser Asn  Ile Met Asn Phe Phe  Lys Thr Glu
    1055                 1060                 1065

Ile Thr  Leu Ala Asn Gly Glu  Ile Arg Lys Arg Pro  Leu Ile Glu
    1070                 1075                 1080

Thr Asn  Gly Glu Thr Gly Glu  Ile Val Trp Asp Lys  Gly Arg Asp
    1085                 1090                 1095

Phe Ala  Thr Val Arg Lys Val  Leu Ser Met Pro Gln  Val Asn Ile
    1100                 1105                 1110

Val Lys  Lys Thr Glu Val Gln  Thr Gly Gly Phe Ser  Lys Glu Ser
    1115                 1120                 1125

Ile Leu  Pro Lys Arg Asn Ser  Asp Lys Leu Ile Ala  Arg Lys Lys
    1130                 1135                 1140

Asp Trp  Asp Pro Lys Lys Tyr  Gly Gly Phe Asp Ser  Pro Thr Val
    1145                 1150                 1155

Ala Tyr  Ser Val Leu Val Val  Ala Lys Val Glu Lys  Gly Lys Ser
    1160                 1165                 1170

Lys Lys  Leu Lys Ser Val Lys  Glu Leu Leu Gly Ile  Thr Ile Met
    1175                 1180                 1185

Glu Arg  Ser Ser Phe Glu Lys  Asn Pro Ile Asp Phe  Leu Glu Ala
    1190                 1195                 1200

Lys Gly  Tyr Lys Glu Val Lys  Lys Asp Leu Ile Ile  Lys Leu Pro
    1205                 1210                 1215

Lys Tyr  Ser Leu Phe Glu Leu  Glu Asn Gly Arg Lys  Arg Met Leu
    1220                 1225                 1230

Ala Ser  Ala Gly Glu Leu Gln  Lys Gly Asn Glu Leu  Ala Leu Pro
    1235                 1240                 1245

Ser Lys  Tyr Val Asn Phe Leu  Tyr Leu Ala Ser His  Tyr Glu Lys
    1250                 1255                 1260

Leu Lys  Gly Ser Pro Glu Asp  Asn Glu Gln Lys Gln  Leu Phe Val
    1265                 1270                 1275

Glu Gln  His Lys His Tyr Leu  Asp Glu Ile Ile Glu  Gln Ile Ser
    1280                 1285                 1290

Glu Phe  Ser Lys Arg Val Ile  Leu Ala Asp Ala Asn  Leu Asp Lys
    1295                 1300                 1305

Val Leu  Ser Ala Tyr Asn Lys  His Arg Asp Lys Pro  Ile Arg Glu
    1310                 1315                 1320

Gln Ala  Glu Asn Ile Ile His  Leu Phe Thr Leu Thr  Asn Leu Gly
    1325                 1330                 1335

Ala Pro  Ala Ala Phe Lys Tyr  Phe Asp Thr Thr Ile  Asp Arg Lys
    1340                 1345                 1350

Arg Tyr  Thr Ser Thr Lys Glu  Val Leu Asp Ala Thr  Leu Ile His
    1355                 1360                 1365

Gln Ser  Ile Thr Gly Leu Tyr  Glu Thr Arg Ile Asp  Leu Ser Gln
    1370                 1375                 1380

Leu Gly  Gly Asp Ser Arg Ala  Asp Pro Lys Lys Lys  Arg Lys Val
    1385                 1390                 1395

Glu Phe  Tyr Pro Tyr Asp Val  Pro Asp Tyr Ala
```

1400 1405

<210> SEQ ID NO 10
<211> LENGTH: 1437
<212> TYPE: PRT
<213> ORGANISM: Artificial Sequence
<220> FEATURE:
<223> OTHER INFORMATION: penetrating peptide-linkage-Cas protein; AP-HE5-Cas9

<400> SEQUENCE: 10

Arg Arg Arg Trp Cys Lys Arg Arg Arg Ala Ser Gly Gly Gly Gly Gly
1 5 10 15

His Glu His Glu His Glu His Glu His Glu Ala Ser Leu Asp Ser Thr
20 25 30

Ala Pro Lys Lys Lys Arg Lys Val Gly Ile His Gly Val Pro Ala Ala
35 40 45

Asp Lys Lys Tyr Ser Ile Gly Leu Asp Ile Gly Thr Asn Ser Val Gly
50 55 60

Trp Ala Val Ile Thr Asp Glu Tyr Lys Val Pro Ser Lys Lys Phe Lys
65 70 75 80

Val Leu Gly Asn Thr Asp Arg His Ser Ile Lys Lys Asn Leu Ile Gly
85 90 95

Ala Leu Leu Phe Asp Ser Gly Glu Thr Ala Glu Ala Thr Arg Leu Lys
100 105 110

Arg Thr Ala Arg Arg Arg Tyr Thr Arg Arg Lys Asn Arg Ile Cys Tyr
115 120 125

Leu Gln Glu Ile Phe Ser Asn Glu Met Ala Lys Val Asp Asp Ser Phe
130 135 140

Phe His Arg Leu Glu Glu Ser Phe Leu Val Glu Glu Asp Lys Lys His
145 150 155 160

Glu Arg His Pro Ile Phe Gly Asn Ile Val Asp Glu Val Ala Tyr His
165 170 175

Glu Lys Tyr Pro Thr Ile Tyr His Leu Arg Lys Lys Leu Val Asp Ser
180 185 190

Thr Asp Lys Ala Asp Leu Arg Leu Ile Tyr Leu Ala Leu Ala His Met
195 200 205

Ile Lys Phe Arg Gly His Phe Leu Ile Glu Gly Asp Leu Asn Pro Asp
210 215 220

Asn Ser Asp Val Asp Lys Leu Phe Ile Gln Leu Val Gln Thr Tyr Asn
225 230 235 240

Gln Leu Phe Glu Glu Asn Pro Ile Asn Ala Ser Gly Val Asp Ala Lys
245 250 255

Ala Ile Leu Ser Ala Arg Leu Ser Lys Ser Arg Arg Leu Glu Asn Leu
260 265 270

Ile Ala Gln Leu Pro Gly Glu Lys Lys Asn Gly Leu Phe Gly Asn Leu
275 280 285

Ile Ala Leu Ser Leu Gly Leu Thr Pro Asn Phe Lys Ser Asn Phe Asp
290 295 300

Leu Ala Glu Asp Ala Lys Leu Gln Leu Ser Lys Asp Thr Tyr Asp Asp
305 310 315 320

Asp Leu Asp Asn Leu Leu Ala Gln Ile Gly Asp Gln Tyr Ala Asp Leu
325 330 335

Phe Leu Ala Ala Lys Asn Leu Ser Asp Ala Ile Leu Leu Ser Asp Ile
340 345 350

```
Leu Arg Val Asn Thr Glu Ile Thr Lys Ala Pro Leu Ser Ala Ser Met
        355                 360                 365

Ile Lys Arg Tyr Asp Glu His His Gln Asp Leu Thr Leu Leu Lys Ala
    370                 375                 380

Leu Val Arg Gln Gln Leu Pro Glu Lys Tyr Lys Glu Ile Phe Phe Asp
385                 390                 395                 400

Gln Ser Lys Asn Gly Tyr Ala Gly Tyr Ile Asp Gly Gly Ala Ser Gln
                405                 410                 415

Glu Glu Phe Tyr Lys Phe Ile Lys Pro Ile Leu Glu Lys Met Asp Gly
            420                 425                 430

Thr Glu Glu Leu Leu Val Lys Leu Asn Arg Glu Asp Leu Leu Arg Lys
        435                 440                 445

Gln Arg Thr Phe Asp Asn Gly Ser Ile Pro His Gln Ile His Leu Gly
    450                 455                 460

Glu Leu His Ala Ile Leu Arg Arg Gln Glu Asp Phe Tyr Pro Phe Leu
465                 470                 475                 480

Lys Asp Asn Arg Glu Lys Ile Glu Lys Ile Leu Thr Phe Arg Ile Pro
                485                 490                 495

Tyr Tyr Val Gly Pro Leu Ala Arg Gly Asn Ser Arg Phe Ala Trp Met
            500                 505                 510

Thr Arg Lys Ser Glu Glu Thr Ile Thr Pro Trp Asn Phe Glu Glu Val
        515                 520                 525

Val Asp Lys Gly Ala Ser Ala Gln Ser Phe Ile Glu Arg Met Thr Asn
    530                 535                 540

Phe Asp Lys Asn Leu Pro Asn Glu Lys Val Leu Pro Lys His Ser Leu
545                 550                 555                 560

Leu Tyr Glu Tyr Phe Thr Val Tyr Asn Glu Leu Thr Lys Val Lys Tyr
                565                 570                 575

Val Thr Glu Gly Met Arg Lys Pro Ala Phe Leu Ser Gly Glu Gln Lys
            580                 585                 590

Lys Ala Ile Val Asp Leu Leu Phe Lys Thr Asn Arg Lys Val Thr Val
        595                 600                 605

Lys Gln Leu Lys Glu Asp Tyr Phe Lys Lys Ile Glu Cys Phe Asp Ser
    610                 615                 620

Val Glu Ile Ser Gly Val Glu Asp Arg Phe Asn Ala Ser Leu Gly Thr
625                 630                 635                 640

Tyr His Asp Leu Leu Lys Ile Ile Lys Asp Lys Asp Phe Leu Asp Asn
                645                 650                 655

Glu Glu Asn Glu Asp Ile Leu Glu Asp Ile Val Leu Thr Leu Thr Leu
            660                 665                 670

Phe Glu Asp Arg Glu Met Ile Glu Glu Arg Leu Lys Thr Tyr Ala His
        675                 680                 685

Leu Phe Asp Asp Lys Val Met Lys Gln Leu Lys Arg Arg Arg Tyr Thr
    690                 695                 700

Gly Trp Gly Arg Leu Ser Arg Lys Leu Ile Asn Gly Ile Arg Asp Lys
705                 710                 715                 720

Gln Ser Gly Lys Thr Ile Leu Asp Phe Leu Lys Ser Asp Gly Phe Ala
                725                 730                 735

Asn Arg Asn Phe Met Gln Leu Ile His Asp Asp Ser Leu Thr Phe Lys
            740                 745                 750

Glu Asp Ile Gln Lys Ala Gln Val Ser Gly Gln Gly Asp Ser Leu His
        755                 760                 765

Glu His Ile Ala Asn Leu Ala Gly Ser Pro Ala Ile Lys Lys Gly Ile
```

```
    770                 775                 780

Leu Gln Thr Val Lys Val Val Asp Glu Leu Val Lys Val Met Gly Arg
785                 790                 795                 800

His Lys Pro Glu Asn Ile Val Ile Glu Met Ala Arg Glu Asn Gln Thr
                805                 810                 815

Thr Gln Lys Gly Gln Lys Asn Ser Arg Glu Arg Met Lys Arg Ile Glu
            820                 825                 830

Glu Gly Ile Lys Glu Leu Gly Ser Gln Ile Leu Lys Glu His Pro Val
        835                 840                 845

Glu Asn Thr Gln Leu Gln Asn Glu Lys Leu Tyr Leu Tyr Tyr Leu Gln
    850                 855                 860

Asn Gly Arg Asp Met Tyr Val Asp Gln Glu Leu Asp Ile Asn Arg Leu
865                 870                 875                 880

Ser Asp Tyr Asp Val Asp His Ile Val Pro Gln Ser Phe Leu Lys Asp
                885                 890                 895

Asp Ser Ile Asp Asn Lys Val Leu Thr Arg Ser Asp Lys Asn Arg Gly
            900                 905                 910

Lys Ser Asp Asn Val Pro Ser Glu Glu Val Val Lys Lys Met Lys Asn
        915                 920                 925

Tyr Trp Arg Gln Leu Leu Asn Ala Lys Leu Ile Thr Gln Arg Lys Phe
    930                 935                 940

Asp Asn Leu Thr Lys Ala Glu Arg Gly Gly Leu Ser Glu Leu Asp Lys
945                 950                 955                 960

Ala Gly Phe Ile Lys Arg Gln Leu Val Glu Thr Arg Gln Ile Thr Lys
                965                 970                 975

His Val Ala Gln Ile Leu Asp Ser Arg Met Asn Thr Lys Tyr Asp Glu
            980                 985                 990

Asn Asp Lys Leu Ile Arg Glu Val  Lys Val Ile Thr Leu  Lys Ser Lys
        995                 1000                1005

Leu Val  Ser Asp Phe Arg Lys  Asp Phe Gln Phe Tyr  Lys Val Arg
    1010                1015                1020

Glu Ile  Asn Asn Tyr His His  Ala His Asp Ala Tyr  Leu Asn Ala
    1025                1030                1035

Val Val  Gly Thr Ala Leu Ile  Lys Lys Tyr Pro Lys  Leu Glu Ser
    1040                1045                1050

Glu Phe  Val Tyr Gly Asp Tyr  Lys Val Tyr Asp Val  Arg Lys Met
    1055                1060                1065

Ile Ala  Lys Ser Glu Gln Glu  Ile Gly Lys Ala Thr  Ala Lys Tyr
    1070                1075                1080

Phe Phe  Tyr Ser Asn Ile Met  Asn Phe Phe Lys Thr  Glu Ile Thr
    1085                1090                1095

Leu Ala  Asn Gly Glu Ile Arg  Lys Arg Pro Leu Ile  Glu Thr Asn
    1100                1105                1110

Gly Glu  Thr Gly Glu Ile Val  Trp Asp Lys Gly Arg  Asp Phe Ala
    1115                1120                1125

Thr Val  Arg Lys Val Leu Ser  Met Pro Gln Val Asn  Ile Val Lys
    1130                1135                1140

Lys Thr  Glu Val Gln Thr Gly  Gly Phe Ser Lys Glu  Ser Ile Leu
    1145                1150                1155

Pro Lys  Arg Asn Ser Asp Lys  Leu Ile Ala Arg Lys  Lys Asp Trp
    1160                1165                1170

Asp Pro  Lys Lys Tyr Gly Gly  Phe Asp Ser Pro Thr  Val Ala Tyr
    1175                1180                1185
```

Ser Val Leu Val Val Ala Lys Val Glu Lys Gly Lys Ser Lys Lys
1190 1195 1200

Leu Lys Ser Val Lys Glu Leu Leu Gly Ile Thr Ile Met Glu Arg
1205 1210 1215

Ser Ser Phe Glu Lys Asn Pro Ile Asp Phe Leu Glu Ala Lys Gly
1220 1225 1230

Tyr Lys Glu Val Lys Lys Asp Leu Ile Ile Lys Leu Pro Lys Tyr
1235 1240 1245

Ser Leu Phe Glu Leu Glu Asn Gly Arg Lys Arg Met Leu Ala Ser
1250 1255 1260

Ala Gly Glu Leu Gln Lys Gly Asn Glu Leu Ala Leu Pro Ser Lys
1265 1270 1275

Tyr Val Asn Phe Leu Tyr Leu Ala Ser His Tyr Glu Lys Leu Lys
1280 1285 1290

Gly Ser Pro Glu Asp Asn Glu Gln Lys Gln Leu Phe Val Glu Gln
1295 1300 1305

His Lys His Tyr Leu Asp Glu Ile Ile Glu Gln Ile Ser Glu Phe
1310 1315 1320

Ser Lys Arg Val Ile Leu Ala Asp Ala Asn Leu Asp Lys Val Leu
1325 1330 1335

Ser Ala Tyr Asn Lys His Arg Asp Lys Pro Ile Arg Glu Gln Ala
1340 1345 1350

Glu Asn Ile Ile His Leu Phe Thr Leu Thr Asn Leu Gly Ala Pro
1355 1360 1365

Ala Ala Phe Lys Tyr Phe Asp Thr Thr Ile Asp Arg Lys Arg Tyr
1370 1375 1380

Thr Ser Thr Lys Glu Val Leu Asp Ala Thr Leu Ile His Gln Ser
1385 1390 1395

Ile Thr Gly Leu Tyr Glu Thr Arg Ile Asp Leu Ser Gln Leu Gly
1400 1405 1410

Gly Asp Ser Arg Ala Asp Pro Lys Lys Lys Arg Lys Val Glu Phe
1415 1420 1425

Tyr Pro Tyr Asp Val Pro Asp Tyr Ala
1430 1435

<210> SEQ ID NO 11
<211> LENGTH: 1439
<212> TYPE: PRT
<213> ORGANISM: Artificial Sequence
<220> FEATURE:
<223> OTHER INFORMATION: penetrating peptide-linkage-Cas protein; AP-HE6-Cas9

<400> SEQUENCE: 11

Arg Arg Arg Trp Cys Lys Arg Arg Arg Ala Ser Gly Gly Gly Gly Gly
1 5 10 15

His Glu His Glu His Glu His Glu His Glu His Glu Ala Ser Leu Asp
20 25 30

Ser Thr Ala Pro Lys Lys Lys Arg Lys Val Gly Ile His Gly Val Pro
35 40 45

Ala Ala Asp Lys Lys Tyr Ser Ile Gly Leu Asp Ile Gly Thr Asn Ser
50 55 60

Val Gly Trp Ala Val Ile Thr Asp Glu Tyr Lys Val Pro Ser Lys Lys
65 70 75 80

Phe Lys Val Leu Gly Asn Thr Asp Arg His Ser Ile Lys Lys Asn Leu

-continued

```
                85                  90                  95

Ile Gly Ala Leu Leu Phe Asp Ser Gly Glu Thr Ala Glu Ala Thr Arg
            100                 105                 110

Leu Lys Arg Thr Ala Arg Arg Arg Tyr Thr Arg Arg Lys Asn Arg Ile
        115                 120                 125

Cys Tyr Leu Gln Glu Ile Phe Ser Asn Glu Met Ala Lys Val Asp Asp
    130                 135                 140

Ser Phe Phe His Arg Leu Glu Glu Ser Phe Leu Val Glu Glu Asp Lys
145                 150                 155                 160

Lys His Glu Arg His Pro Ile Phe Gly Asn Ile Val Asp Glu Val Ala
                165                 170                 175

Tyr His Glu Lys Tyr Pro Thr Ile Tyr His Leu Arg Lys Lys Leu Val
            180                 185                 190

Asp Ser Thr Asp Lys Ala Asp Leu Arg Leu Ile Tyr Leu Ala Leu Ala
        195                 200                 205

His Met Ile Lys Phe Arg Gly His Phe Leu Ile Glu Gly Asp Leu Asn
    210                 215                 220

Pro Asp Asn Ser Asp Val Asp Lys Leu Phe Ile Gln Leu Val Gln Thr
225                 230                 235                 240

Tyr Asn Gln Leu Phe Glu Glu Asn Pro Ile Asn Ala Ser Gly Val Asp
                245                 250                 255

Ala Lys Ala Ile Leu Ser Ala Arg Leu Ser Lys Ser Arg Arg Leu Glu
            260                 265                 270

Asn Leu Ile Ala Gln Leu Pro Gly Glu Lys Lys Asn Gly Leu Phe Gly
        275                 280                 285

Asn Leu Ile Ala Leu Ser Leu Gly Leu Thr Pro Asn Phe Lys Ser Asn
    290                 295                 300

Phe Asp Leu Ala Glu Asp Ala Lys Leu Gln Leu Ser Lys Asp Thr Tyr
305                 310                 315                 320

Asp Asp Asp Leu Asp Asn Leu Leu Ala Gln Ile Gly Asp Gln Tyr Ala
                325                 330                 335

Asp Leu Phe Leu Ala Ala Lys Asn Leu Ser Asp Ala Ile Leu Leu Ser
            340                 345                 350

Asp Ile Leu Arg Val Asn Thr Glu Ile Thr Lys Ala Pro Leu Ser Ala
        355                 360                 365

Ser Met Ile Lys Arg Tyr Asp Glu His His Gln Asp Leu Thr Leu Leu
    370                 375                 380

Lys Ala Leu Val Arg Gln Gln Leu Pro Glu Lys Tyr Lys Glu Ile Phe
385                 390                 395                 400

Phe Asp Gln Ser Lys Asn Gly Tyr Ala Gly Tyr Ile Asp Gly Gly Ala
                405                 410                 415

Ser Gln Glu Glu Phe Tyr Lys Phe Ile Lys Pro Ile Leu Glu Lys Met
            420                 425                 430

Asp Gly Thr Glu Glu Leu Leu Val Lys Leu Asn Arg Glu Asp Leu Leu
        435                 440                 445

Arg Lys Gln Arg Thr Phe Asp Asn Gly Ser Ile Pro His Gln Ile His
    450                 455                 460

Leu Gly Glu Leu His Ala Ile Leu Arg Arg Gln Glu Asp Phe Tyr Pro
465                 470                 475                 480

Phe Leu Lys Asp Asn Arg Glu Lys Ile Glu Lys Ile Leu Thr Phe Arg
                485                 490                 495

Ile Pro Tyr Tyr Val Gly Pro Leu Ala Arg Gly Asn Ser Arg Phe Ala
            500                 505                 510
```

```
Trp Met Thr Arg Lys Ser Glu Glu Thr Ile Thr Pro Trp Asn Phe Glu
        515                 520                 525

Glu Val Val Asp Lys Gly Ala Ser Ala Gln Ser Phe Ile Glu Arg Met
    530                 535                 540

Thr Asn Phe Asp Lys Asn Leu Pro Asn Glu Lys Val Leu Pro Lys His
545                 550                 555                 560

Ser Leu Leu Tyr Glu Tyr Phe Thr Val Tyr Asn Glu Leu Thr Lys Val
                565                 570                 575

Lys Tyr Val Thr Glu Gly Met Arg Lys Pro Ala Phe Leu Ser Gly Glu
            580                 585                 590

Gln Lys Lys Ala Ile Val Asp Leu Leu Phe Lys Thr Asn Arg Lys Val
        595                 600                 605

Thr Val Lys Gln Leu Lys Glu Asp Tyr Phe Lys Lys Ile Glu Cys Phe
    610                 615                 620

Asp Ser Val Glu Ile Ser Gly Val Glu Asp Arg Phe Asn Ala Ser Leu
625                 630                 635                 640

Gly Thr Tyr His Asp Leu Leu Lys Ile Ile Lys Asp Lys Asp Phe Leu
                645                 650                 655

Asp Asn Glu Glu Asn Glu Asp Ile Leu Glu Asp Ile Val Leu Thr Leu
            660                 665                 670

Thr Leu Phe Glu Asp Arg Glu Met Ile Glu Glu Arg Leu Lys Thr Tyr
        675                 680                 685

Ala His Leu Phe Asp Asp Lys Val Met Lys Gln Leu Lys Arg Arg Arg
    690                 695                 700

Tyr Thr Gly Trp Gly Arg Leu Ser Arg Lys Leu Ile Asn Gly Ile Arg
705                 710                 715                 720

Asp Lys Gln Ser Gly Lys Thr Ile Leu Asp Phe Leu Lys Ser Asp Gly
                725                 730                 735

Phe Ala Asn Arg Asn Phe Met Gln Leu Ile His Asp Asp Ser Leu Thr
            740                 745                 750

Phe Lys Glu Asp Ile Gln Lys Ala Gln Val Ser Gly Gln Gly Asp Ser
        755                 760                 765

Leu His Glu His Ile Ala Asn Leu Ala Gly Ser Pro Ala Ile Lys Lys
    770                 775                 780

Gly Ile Leu Gln Thr Val Lys Val Val Asp Glu Leu Val Lys Val Met
785                 790                 795                 800

Gly Arg His Lys Pro Glu Asn Ile Val Ile Glu Met Ala Arg Glu Asn
                805                 810                 815

Gln Thr Thr Gln Lys Gly Gln Lys Asn Ser Arg Glu Arg Met Lys Arg
            820                 825                 830

Ile Glu Glu Gly Ile Lys Glu Leu Gly Ser Gln Ile Leu Lys Glu His
        835                 840                 845

Pro Val Glu Asn Thr Gln Leu Gln Asn Glu Lys Leu Tyr Leu Tyr Tyr
    850                 855                 860

Leu Gln Asn Gly Arg Asp Met Tyr Val Asp Gln Glu Leu Asp Ile Asn
865                 870                 875                 880

Arg Leu Ser Asp Tyr Asp Val Asp His Ile Val Pro Gln Ser Phe Leu
                885                 890                 895

Lys Asp Asp Ser Ile Asp Asn Lys Val Leu Thr Arg Ser Asp Lys Asn
            900                 905                 910

Arg Gly Lys Ser Asp Asn Val Pro Ser Glu Glu Val Val Lys Lys Met
        915                 920                 925
```

```
Lys Asn Tyr Trp Arg Gln Leu Leu Asn Ala Lys Leu Ile Thr Gln Arg
    930                 935                 940

Lys Phe Asp Asn Leu Thr Lys Ala Glu Arg Gly Gly Leu Ser Glu Leu
945                 950                 955                 960

Asp Lys Ala Gly Phe Ile Lys Arg Gln Leu Val Glu Thr Arg Gln Ile
                965                 970                 975

Thr Lys His Val Ala Gln Ile Leu Asp Ser Arg Met Asn Thr Lys Tyr
            980                 985                 990

Asp Glu Asn Asp Lys Leu Ile Arg  Glu Val Lys Val Ile  Thr Leu Lys
        995                 1000                1005

Ser Lys  Leu Val Ser Asp Phe  Arg Lys Asp Phe Gln  Phe Tyr Lys
    1010                 1015                1020

Val Arg  Glu Ile Asn Asn Tyr  His His Ala His Asp  Ala Tyr Leu
    1025                 1030                1035

Asn Ala  Val Val Gly Thr Ala  Leu Ile Lys Lys Tyr  Pro Lys Leu
    1040                 1045                1050

Glu Ser  Glu Phe Val Tyr Gly  Asp Tyr Lys Val Tyr  Asp Val Arg
    1055                 1060                1065

Lys Met  Ile Ala Lys Ser Glu  Gln Glu Ile Gly Lys  Ala Thr Ala
    1070                 1075                1080

Lys Tyr  Phe Phe Tyr Ser Asn  Ile Met Asn Phe Phe  Lys Thr Glu
    1085                 1090                1095

Ile Thr  Leu Ala Asn Gly Glu  Ile Arg Lys Arg Pro  Leu Ile Glu
    1100                 1105                1110

Thr Asn  Gly Glu Thr Gly Glu  Ile Val Trp Asp Lys  Gly Arg Asp
    1115                 1120                1125

Phe Ala  Thr Val Arg Lys Val  Leu Ser Met Pro Gln  Val Asn Ile
    1130                 1135                1140

Val Lys  Lys Thr Glu Val Gln  Thr Gly Gly Phe Ser  Lys Glu Ser
    1145                 1150                1155

Ile Leu  Pro Lys Arg Asn Ser  Asp Lys Leu Ile Ala  Arg Lys Lys
    1160                 1165                1170

Asp Trp  Asp Pro Lys Lys Tyr  Gly Gly Phe Asp Ser  Pro Thr Val
    1175                 1180                1185

Ala Tyr  Ser Val Leu Val Val  Ala Lys Val Glu Lys  Gly Lys Ser
    1190                 1195                1200

Lys Lys  Leu Lys Ser Val Lys  Glu Leu Leu Gly Ile  Thr Ile Met
    1205                 1210                1215

Glu Arg  Ser Ser Phe Glu Lys  Asn Pro Ile Asp Phe  Leu Glu Ala
    1220                 1225                1230

Lys Gly  Tyr Lys Glu Val Lys  Lys Asp Leu Ile Ile  Lys Leu Pro
    1235                 1240                1245

Lys Tyr  Ser Leu Phe Glu Leu  Glu Asn Gly Arg Lys  Arg Met Leu
    1250                 1255                1260

Ala Ser  Ala Gly Glu Leu Gln  Lys Gly Asn Glu Leu  Ala Leu Pro
    1265                 1270                1275

Ser Lys  Tyr Val Asn Phe Leu  Tyr Leu Ala Ser His  Tyr Glu Lys
    1280                 1285                1290

Leu Lys  Gly Ser Pro Glu Asp  Asn Glu Gln Lys Gln  Leu Phe Val
    1295                 1300                1305

Glu Gln  His Lys His Tyr Leu  Asp Glu Ile Ile Glu  Gln Ile Ser
    1310                 1315                1320

Glu Phe  Ser Lys Arg Val Ile  Leu Ala Asp Ala Asn  Leu Asp Lys
```

```
    1325                1330                1335

Val Leu  Ser Ala Tyr Asn Lys  His Arg Asp Lys Pro  Ile Arg Glu
    1340                1345                1350

Gln Ala  Glu Asn Ile Ile His  Leu Phe Thr Leu Thr  Asn Leu Gly
    1355                1360                1365

Ala Pro  Ala Ala Phe Lys Tyr  Phe Asp Thr Thr Ile  Asp Arg Lys
    1370                1375                1380

Arg Tyr  Thr Ser Thr Lys Glu  Val Leu Asp Ala Thr  Leu Ile His
    1385                1390                1395

Gln Ser  Ile Thr Gly Leu Tyr  Glu Thr Arg Ile Asp  Leu Ser Gln
    1400                1405                1410

Leu Gly  Gly Asp Ser Arg Ala  Asp Pro Lys Lys Lys  Arg Lys Val
    1415                1420                1425

Glu Phe  Tyr Pro Tyr Asp Val  Pro Asp Tyr Ala
    1430                1435


<210> SEQ ID NO 12
<211> LENGTH: 1441
<212> TYPE: PRT
<213> ORGANISM: Artificial Sequence
<220> FEATURE:
<223> OTHER INFORMATION: penetrating peptide-linkage-Cas protein;
      AP-HE7-Cas9

<400> SEQUENCE: 12

Arg Arg Arg Trp Cys Lys Arg Arg Arg Ala Ser Gly Gly Gly Gly Gly
1               5                   10                  15

His Glu His Glu His Glu His Glu His Glu His Glu His Glu Ala Ser
            20                  25                  30

Leu Asp Ser Thr Ala Pro Lys Lys Lys Arg Lys Val Gly Ile His Gly
        35                  40                  45

Val Pro Ala Ala Asp Lys Lys Tyr Ser Ile Gly Leu Asp Ile Gly Thr
    50                  55                  60

Asn Ser Val Gly Trp Ala Val Ile Thr Asp Glu Tyr Lys Val Pro Ser
65                  70                  75                  80

Lys Lys Phe Lys Val Leu Gly Asn Thr Asp Arg His Ser Ile Lys Lys
                85                  90                  95

Asn Leu Ile Gly Ala Leu Leu Phe Asp Ser Gly Glu Thr Ala Glu Ala
            100                 105                 110

Thr Arg Leu Lys Arg Thr Ala Arg Arg Arg Tyr Thr Arg Arg Lys Asn
        115                 120                 125

Arg Ile Cys Tyr Leu Gln Glu Ile Phe Ser Asn Glu Met Ala Lys Val
    130                 135                 140

Asp Asp Ser Phe Phe His Arg Leu Glu Glu Ser Phe Leu Val Glu Glu
145                 150                 155                 160

Asp Lys Lys His Glu Arg His Pro Ile Phe Gly Asn Ile Val Asp Glu
                165                 170                 175

Val Ala Tyr His Glu Lys Tyr Pro Thr Ile Tyr His Leu Arg Lys Lys
            180                 185                 190

Leu Val Asp Ser Thr Asp Lys Ala Asp Leu Arg Leu Ile Tyr Leu Ala
        195                 200                 205

Leu Ala His Met Ile Lys Phe Arg Gly His Phe Leu Ile Glu Gly Asp
    210                 215                 220

Leu Asn Pro Asp Asn Ser Asp Val Asp Lys Leu Phe Ile Gln Leu Val
225                 230                 235                 240
```

```
Gln Thr Tyr Asn Gln Leu Phe Glu Glu Asn Pro Ile Asn Ala Ser Gly
                245                 250                 255

Val Asp Ala Lys Ala Ile Leu Ser Ala Arg Leu Ser Lys Ser Arg Arg
            260                 265                 270

Leu Glu Asn Leu Ile Ala Gln Leu Pro Gly Glu Lys Lys Asn Gly Leu
        275                 280                 285

Phe Gly Asn Leu Ile Ala Leu Ser Leu Gly Leu Thr Pro Asn Phe Lys
    290                 295                 300

Ser Asn Phe Asp Leu Ala Glu Asp Ala Lys Leu Gln Leu Ser Lys Asp
305                 310                 315                 320

Thr Tyr Asp Asp Asp Leu Asp Asn Leu Leu Ala Gln Ile Gly Asp Gln
                325                 330                 335

Tyr Ala Asp Leu Phe Leu Ala Ala Lys Asn Leu Ser Asp Ala Ile Leu
            340                 345                 350

Leu Ser Asp Ile Leu Arg Val Asn Thr Glu Ile Thr Lys Ala Pro Leu
        355                 360                 365

Ser Ala Ser Met Ile Lys Arg Tyr Asp Glu His His Gln Asp Leu Thr
    370                 375                 380

Leu Leu Lys Ala Leu Val Arg Gln Gln Leu Pro Glu Lys Tyr Lys Glu
385                 390                 395                 400

Ile Phe Phe Asp Gln Ser Lys Asn Gly Tyr Ala Gly Tyr Ile Asp Gly
                405                 410                 415

Gly Ala Ser Gln Glu Glu Phe Tyr Lys Phe Ile Lys Pro Ile Leu Glu
            420                 425                 430

Lys Met Asp Gly Thr Glu Glu Leu Leu Val Lys Leu Asn Arg Glu Asp
        435                 440                 445

Leu Leu Arg Lys Gln Arg Thr Phe Asp Asn Gly Ser Ile Pro His Gln
    450                 455                 460

Ile His Leu Gly Glu Leu His Ala Ile Leu Arg Arg Gln Glu Asp Phe
465                 470                 475                 480

Tyr Pro Phe Leu Lys Asp Asn Arg Glu Lys Ile Glu Lys Ile Leu Thr
                485                 490                 495

Phe Arg Ile Pro Tyr Tyr Val Gly Pro Leu Ala Arg Gly Asn Ser Arg
            500                 505                 510

Phe Ala Trp Met Thr Arg Lys Ser Glu Glu Thr Ile Thr Pro Trp Asn
        515                 520                 525

Phe Glu Glu Val Val Asp Lys Gly Ala Ser Ala Gln Ser Phe Ile Glu
    530                 535                 540

Arg Met Thr Asn Phe Asp Lys Asn Leu Pro Asn Glu Lys Val Leu Pro
545                 550                 555                 560

Lys His Ser Leu Leu Tyr Glu Tyr Phe Thr Val Tyr Asn Glu Leu Thr
                565                 570                 575

Lys Val Lys Tyr Val Thr Glu Gly Met Arg Lys Pro Ala Phe Leu Ser
            580                 585                 590

Gly Glu Gln Lys Lys Ala Ile Val Asp Leu Leu Phe Lys Thr Asn Arg
        595                 600                 605

Lys Val Thr Val Lys Gln Leu Lys Glu Asp Tyr Phe Lys Lys Ile Glu
    610                 615                 620

Cys Phe Asp Ser Val Glu Ile Ser Gly Val Glu Asp Arg Phe Asn Ala
625                 630                 635                 640

Ser Leu Gly Thr Tyr His Asp Leu Leu Lys Ile Ile Lys Asp Lys Asp
                645                 650                 655

Phe Leu Asp Asn Glu Glu Asn Glu Asp Ile Leu Glu Asp Ile Val Leu
```

```
            660                 665                 670

Thr Leu Thr Leu Phe Glu Asp Arg Glu Met Ile Glu Glu Arg Leu Lys
        675                 680                 685

Thr Tyr Ala His Leu Phe Asp Asp Lys Val Met Lys Gln Leu Lys Arg
    690                 695                 700

Arg Arg Tyr Thr Gly Trp Gly Arg Leu Ser Arg Lys Leu Ile Asn Gly
705                 710                 715                 720

Ile Arg Asp Lys Gln Ser Gly Lys Thr Ile Leu Asp Phe Leu Lys Ser
                725                 730                 735

Asp Gly Phe Ala Asn Arg Asn Phe Met Gln Leu Ile His Asp Asp Ser
            740                 745                 750

Leu Thr Phe Lys Glu Asp Ile Gln Lys Ala Gln Val Ser Gly Gln Gly
        755                 760                 765

Asp Ser Leu His Glu His Ile Ala Asn Leu Ala Gly Ser Pro Ala Ile
    770                 775                 780

Lys Lys Gly Ile Leu Gln Thr Val Lys Val Val Asp Glu Leu Val Lys
785                 790                 795                 800

Val Met Gly Arg His Lys Pro Glu Asn Ile Val Ile Glu Met Ala Arg
                805                 810                 815

Glu Asn Gln Thr Thr Gln Lys Gly Gln Lys Asn Ser Arg Glu Arg Met
            820                 825                 830

Lys Arg Ile Glu Glu Gly Ile Lys Glu Leu Gly Ser Gln Ile Leu Lys
        835                 840                 845

Glu His Pro Val Glu Asn Thr Gln Leu Gln Asn Glu Lys Leu Tyr Leu
    850                 855                 860

Tyr Tyr Leu Gln Asn Gly Arg Asp Met Tyr Val Asp Gln Glu Leu Asp
865                 870                 875                 880

Ile Asn Arg Leu Ser Asp Tyr Asp Val Asp His Ile Val Pro Gln Ser
                885                 890                 895

Phe Leu Lys Asp Asp Ser Ile Asp Asn Lys Val Leu Thr Arg Ser Asp
            900                 905                 910

Lys Asn Arg Gly Lys Ser Asp Asn Val Pro Ser Glu Glu Val Val Lys
        915                 920                 925

Lys Met Lys Asn Tyr Trp Arg Gln Leu Leu Asn Ala Lys Leu Ile Thr
    930                 935                 940

Gln Arg Lys Phe Asp Asn Leu Thr Lys Ala Glu Arg Gly Gly Leu Ser
945                 950                 955                 960

Glu Leu Asp Lys Ala Gly Phe Ile Lys Arg Gln Leu Val Glu Thr Arg
                965                 970                 975

Gln Ile Thr Lys His Val Ala Gln Ile Leu Asp Ser Arg Met Asn Thr
            980                 985                 990

Lys Tyr Asp Glu Asn Asp Lys Leu  Ile Arg Glu Val Lys  Val Ile Thr
        995                 1000                1005

Leu Lys  Ser Lys Leu Val Ser  Asp Phe Arg Lys Asp  Phe Gln Phe
    1010                1015                1020

Tyr Lys  Val Arg Glu Ile Asn  Asn Tyr His His Ala  His Asp Ala
    1025                1030                1035

Tyr Leu  Asn Ala Val Val Gly  Thr Ala Leu Ile Lys  Lys Tyr Pro
    1040                1045                1050

Lys Leu  Glu Ser Glu Phe Val  Tyr Gly Asp Tyr Lys  Val Tyr Asp
    1055                1060                1065

Val Arg  Lys Met Ile Ala Lys  Ser Glu Gln Glu Ile  Gly Lys Ala
    1070                1075                1080
```

```
Thr Ala  Lys Tyr Phe Phe Tyr  Ser Asn Ile Met Asn  Phe Phe Lys
    1085                 1090                 1095

Thr Glu  Ile Thr Leu Ala Asn  Gly Glu Ile Arg Lys  Arg Pro Leu
    1100                 1105                 1110

Ile Glu  Thr Asn Gly Glu Thr  Gly Glu Ile Val Trp  Asp Lys Gly
    1115                 1120                 1125

Arg Asp  Phe Ala Thr Val Arg  Lys Val Leu Ser Met  Pro Gln Val
    1130                 1135                 1140

Asn Ile  Val Lys Lys Thr Glu  Val Gln Thr Gly Gly  Phe Ser Lys
    1145                 1150                 1155

Glu Ser  Ile Leu Pro Lys Arg  Asn Ser Asp Lys Leu  Ile Ala Arg
    1160                 1165                 1170

Lys Lys  Asp Trp Asp Pro Lys  Lys Tyr Gly Gly Phe  Asp Ser Pro
    1175                 1180                 1185

Thr Val  Ala Tyr Ser Val Leu  Val Val Ala Lys Val  Glu Lys Gly
    1190                 1195                 1200

Lys Ser  Lys Lys Leu Lys Ser  Val Lys Glu Leu Leu  Gly Ile Thr
    1205                 1210                 1215

Ile Met  Glu Arg Ser Ser Phe  Glu Lys Asn Pro Ile  Asp Phe Leu
    1220                 1225                 1230

Glu Ala  Lys Gly Tyr Lys Glu  Val Lys Lys Asp Leu  Ile Ile Lys
    1235                 1240                 1245

Leu Pro  Lys Tyr Ser Leu Phe  Glu Leu Glu Asn Gly  Arg Lys Arg
    1250                 1255                 1260

Met Leu  Ala Ser Ala Gly Glu  Leu Gln Lys Gly Asn  Glu Leu Ala
    1265                 1270                 1275

Leu Pro  Ser Lys Tyr Val Asn  Phe Leu Tyr Leu Ala  Ser His Tyr
    1280                 1285                 1290

Glu Lys  Leu Lys Gly Ser Pro  Glu Asp Asn Glu Gln  Lys Gln Leu
    1295                 1300                 1305

Phe Val  Glu Gln His Lys His  Tyr Leu Asp Glu Ile  Ile Glu Gln
    1310                 1315                 1320

Ile Ser  Glu Phe Ser Lys Arg  Val Ile Leu Ala Asp  Ala Asn Leu
    1325                 1330                 1335

Asp Lys  Val Leu Ser Ala Tyr  Asn Lys His Arg Asp  Lys Pro Ile
    1340                 1345                 1350

Arg Glu  Gln Ala Glu Asn Ile  Ile His Leu Phe Thr  Leu Thr Asn
    1355                 1360                 1365

Leu Gly  Ala Pro Ala Ala Phe  Lys Tyr Phe Asp Thr  Thr Ile Asp
    1370                 1375                 1380

Arg Lys  Arg Tyr Thr Ser Thr  Lys Glu Val Leu Asp  Ala Thr Leu
    1385                 1390                 1395

Ile His  Gln Ser Ile Thr Gly  Leu Tyr Glu Thr Arg  Ile Asp Leu
    1400                 1405                 1410

Ser Gln  Leu Gly Gly Asp Ser  Arg Ala Asp Pro Lys  Lys Lys Arg
    1415                 1420                 1425

Lys Val  Glu Phe Tyr Pro Tyr  Asp Val Pro Asp Tyr  Ala
    1430                 1435                 1440
```

<210> SEQ ID NO 13
<211> LENGTH: 1443
<212> TYPE: PRT
<213> ORGANISM: Artificial Sequence
<220> FEATURE:

<223> OTHER INFORMATION: penetrating peptide-linkage-Cas protein;
AP-HE8-Cas9

<400> SEQUENCE: 13

Arg Arg Arg Trp Cys Lys Arg Arg Arg Ala Ser Gly Gly Gly Gly Gly
1 5 10 15

His Glu His Glu His Glu His Glu His Glu His Glu His Glu His Glu
20 25 30

Ala Ser Leu Asp Ser Thr Ala Pro Lys Lys Lys Arg Lys Val Gly Ile
35 40 45

His Gly Val Pro Ala Ala Asp Lys Lys Tyr Ser Ile Gly Leu Asp Ile
50 55 60

Gly Thr Asn Ser Val Gly Trp Ala Val Ile Thr Asp Glu Tyr Lys Val
65 70 75 80

Pro Ser Lys Lys Phe Lys Val Leu Gly Asn Thr Asp Arg His Ser Ile
85 90 95

Lys Lys Asn Leu Ile Gly Ala Leu Leu Phe Asp Ser Gly Glu Thr Ala
100 105 110

Glu Ala Thr Arg Leu Lys Arg Thr Ala Arg Arg Arg Tyr Thr Arg Arg
115 120 125

Lys Asn Arg Ile Cys Tyr Leu Gln Glu Ile Phe Ser Asn Glu Met Ala
130 135 140

Lys Val Asp Asp Ser Phe Phe His Arg Leu Glu Glu Ser Phe Leu Val
145 150 155 160

Glu Glu Asp Lys Lys His Glu Arg His Pro Ile Phe Gly Asn Ile Val
165 170 175

Asp Glu Val Ala Tyr His Glu Lys Tyr Pro Thr Ile Tyr His Leu Arg
180 185 190

Lys Lys Leu Val Asp Ser Thr Asp Lys Ala Asp Leu Arg Leu Ile Tyr
195 200 205

Leu Ala Leu Ala His Met Ile Lys Phe Arg Gly His Phe Leu Ile Glu
210 215 220

Gly Asp Leu Asn Pro Asp Asn Ser Asp Val Asp Lys Leu Phe Ile Gln
225 230 235 240

Leu Val Gln Thr Tyr Asn Gln Leu Phe Glu Glu Asn Pro Ile Asn Ala
245 250 255

Ser Gly Val Asp Ala Lys Ala Ile Leu Ser Ala Arg Leu Ser Lys Ser
260 265 270

Arg Arg Leu Glu Asn Leu Ile Ala Gln Leu Pro Gly Glu Lys Lys Asn
275 280 285

Gly Leu Phe Gly Asn Leu Ile Ala Leu Ser Leu Gly Leu Thr Pro Asn
290 295 300

Phe Lys Ser Asn Phe Asp Leu Ala Glu Asp Ala Lys Leu Gln Leu Ser
305 310 315 320

Lys Asp Thr Tyr Asp Asp Asp Leu Asp Asn Leu Leu Ala Gln Ile Gly
325 330 335

Asp Gln Tyr Ala Asp Leu Phe Leu Ala Ala Lys Asn Leu Ser Asp Ala
340 345 350

Ile Leu Leu Ser Asp Ile Leu Arg Val Asn Thr Glu Ile Thr Lys Ala
355 360 365

Pro Leu Ser Ala Ser Met Ile Lys Arg Tyr Asp Glu His His Gln Asp
370 375 380

Leu Thr Leu Leu Lys Ala Leu Val Arg Gln Gln Leu Pro Glu Lys Tyr
385 390 395 400

```
Lys Glu Ile Phe Phe Asp Gln Ser Lys Asn Gly Tyr Ala Gly Tyr Ile
                405                 410                 415

Asp Gly Gly Ala Ser Gln Glu Glu Phe Tyr Lys Phe Ile Lys Pro Ile
            420                 425                 430

Leu Glu Lys Met Asp Gly Thr Glu Glu Leu Leu Val Lys Leu Asn Arg
        435                 440                 445

Glu Asp Leu Leu Arg Lys Gln Arg Thr Phe Asp Asn Gly Ser Ile Pro
    450                 455                 460

His Gln Ile His Leu Gly Glu Leu His Ala Ile Leu Arg Arg Gln Glu
465                 470                 475                 480

Asp Phe Tyr Pro Phe Leu Lys Asp Asn Arg Glu Lys Ile Glu Lys Ile
                485                 490                 495

Leu Thr Phe Arg Ile Pro Tyr Tyr Val Gly Pro Leu Ala Arg Gly Asn
            500                 505                 510

Ser Arg Phe Ala Trp Met Thr Arg Lys Ser Glu Glu Thr Ile Thr Pro
        515                 520                 525

Trp Asn Phe Glu Glu Val Val Asp Lys Gly Ala Ser Ala Gln Ser Phe
    530                 535                 540

Ile Glu Arg Met Thr Asn Phe Asp Lys Asn Leu Pro Asn Glu Lys Val
545                 550                 555                 560

Leu Pro Lys His Ser Leu Leu Tyr Glu Tyr Phe Thr Val Tyr Asn Glu
                565                 570                 575

Leu Thr Lys Val Lys Tyr Val Thr Glu Gly Met Arg Lys Pro Ala Phe
            580                 585                 590

Leu Ser Gly Glu Gln Lys Lys Ala Ile Val Asp Leu Leu Phe Lys Thr
        595                 600                 605

Asn Arg Lys Val Thr Val Lys Gln Leu Lys Glu Asp Tyr Phe Lys Lys
    610                 615                 620

Ile Glu Cys Phe Asp Ser Val Glu Ile Ser Gly Val Glu Asp Arg Phe
625                 630                 635                 640

Asn Ala Ser Leu Gly Thr Tyr His Asp Leu Leu Lys Ile Ile Lys Asp
                645                 650                 655

Lys Asp Phe Leu Asp Asn Glu Glu Asn Glu Asp Ile Leu Glu Asp Ile
            660                 665                 670

Val Leu Thr Leu Thr Leu Phe Glu Asp Arg Glu Met Ile Glu Glu Arg
        675                 680                 685

Leu Lys Thr Tyr Ala His Leu Phe Asp Asp Lys Val Met Lys Gln Leu
    690                 695                 700

Lys Arg Arg Arg Tyr Thr Gly Trp Gly Arg Leu Ser Arg Lys Leu Ile
705                 710                 715                 720

Asn Gly Ile Arg Asp Lys Gln Ser Gly Lys Thr Ile Leu Asp Phe Leu
                725                 730                 735

Lys Ser Asp Gly Phe Ala Asn Arg Asn Phe Met Gln Leu Ile His Asp
            740                 745                 750

Asp Ser Leu Thr Phe Lys Glu Asp Ile Gln Lys Ala Gln Val Ser Gly
        755                 760                 765

Gln Gly Asp Ser Leu His Glu His Ile Ala Asn Leu Ala Gly Ser Pro
    770                 775                 780

Ala Ile Lys Lys Gly Ile Leu Gln Thr Val Lys Val Val Asp Glu Leu
785                 790                 795                 800

Val Lys Val Met Gly Arg His Lys Pro Glu Asn Ile Val Ile Glu Met
                805                 810                 815
```

```
Ala Arg Glu Asn Gln Thr Thr Gln Lys Gly Gln Lys Asn Ser Arg Glu
            820                 825                 830

Arg Met Lys Arg Ile Glu Glu Gly Ile Lys Glu Leu Gly Ser Gln Ile
        835                 840                 845

Leu Lys Glu His Pro Val Glu Asn Thr Gln Leu Gln Asn Glu Lys Leu
    850                 855                 860

Tyr Leu Tyr Tyr Leu Gln Asn Gly Arg Asp Met Tyr Val Asp Gln Glu
865                 870                 875                 880

Leu Asp Ile Asn Arg Leu Ser Asp Tyr Asp Val Asp His Ile Val Pro
                885                 890                 895

Gln Ser Phe Leu Lys Asp Asp Ser Ile Asp Asn Lys Val Leu Thr Arg
            900                 905                 910

Ser Asp Lys Asn Arg Gly Lys Ser Asp Asn Val Pro Ser Glu Glu Val
        915                 920                 925

Val Lys Lys Met Lys Asn Tyr Trp Arg Gln Leu Leu Asn Ala Lys Leu
    930                 935                 940

Ile Thr Gln Arg Lys Phe Asp Asn Leu Thr Lys Ala Glu Arg Gly Gly
945                 950                 955                 960

Leu Ser Glu Leu Asp Lys Ala Gly Phe Ile Lys Arg Gln Leu Val Glu
                965                 970                 975

Thr Arg Gln Ile Thr Lys His Val Ala Gln Ile Leu Asp Ser Arg Met
            980                 985                 990

Asn Thr Lys Tyr Asp Glu Asn Asp  Lys Leu Ile Arg Glu  Val Lys Val
        995                 1000                 1005

Ile Thr  Leu Lys Ser Lys Leu  Val Ser Asp Phe Arg  Lys Asp Phe
    1010                 1015                 1020

Gln Phe  Tyr Lys Val Arg Glu  Ile Asn Asn Tyr His  His Ala His
    1025                 1030                 1035

Asp Ala  Tyr Leu Asn Ala Val  Val Gly Thr Ala Leu  Ile Lys Lys
    1040                 1045                 1050

Tyr Pro  Lys Leu Glu Ser Glu  Phe Val Tyr Gly Asp  Tyr Lys Val
    1055                 1060                 1065

Tyr Asp  Val Arg Lys Met Ile  Ala Lys Ser Glu Gln  Glu Ile Gly
    1070                 1075                 1080

Lys Ala  Thr Ala Lys Tyr Phe  Phe Tyr Ser Asn Ile  Met Asn Phe
    1085                 1090                 1095

Phe Lys  Thr Glu Ile Thr Leu  Ala Asn Gly Glu Ile  Arg Lys Arg
    1100                 1105                 1110

Pro Leu  Ile Glu Thr Asn Gly  Glu Thr Gly Glu Ile  Val Trp Asp
    1115                 1120                 1125

Lys Gly  Arg Asp Phe Ala Thr  Val Arg Lys Val Leu  Ser Met Pro
    1130                 1135                 1140

Gln Val  Asn Ile Val Lys Lys  Thr Glu Val Gln Thr  Gly Gly Phe
    1145                 1150                 1155

Ser Lys  Glu Ser Ile Leu Pro  Lys Arg Asn Ser Asp  Lys Leu Ile
    1160                 1165                 1170

Ala Arg  Lys Lys Asp Trp Asp  Pro Lys Lys Tyr Gly  Gly Phe Asp
    1175                 1180                 1185

Ser Pro  Thr Val Ala Tyr Ser  Val Leu Val Val Ala  Lys Val Glu
    1190                 1195                 1200

Lys Gly  Lys Ser Lys Lys Leu  Lys Ser Val Lys Glu  Leu Leu Gly
    1205                 1210                 1215

Ile Thr  Ile Met Glu Arg Ser  Ser Phe Glu Lys Asn  Pro Ile Asp
```

1220 1225 1230

Phe Leu Glu Ala Lys Gly Tyr Lys Glu Val Lys Lys Asp Leu Ile
1235 1240 1245

Ile Lys Leu Pro Lys Tyr Ser Leu Phe Glu Leu Glu Asn Gly Arg
1250 1255 1260

Lys Arg Met Leu Ala Ser Ala Gly Glu Leu Gln Lys Gly Asn Glu
1265 1270 1275

Leu Ala Leu Pro Ser Lys Tyr Val Asn Phe Leu Tyr Leu Ala Ser
1280 1285 1290

His Tyr Glu Lys Leu Lys Gly Ser Pro Glu Asp Asn Glu Gln Lys
1295 1300 1305

Gln Leu Phe Val Glu Gln His Lys His Tyr Leu Asp Glu Ile Ile
1310 1315 1320

Glu Gln Ile Ser Glu Phe Ser Lys Arg Val Ile Leu Ala Asp Ala
1325 1330 1335

Asn Leu Asp Lys Val Leu Ser Ala Tyr Asn Lys His Arg Asp Lys
1340 1345 1350

Pro Ile Arg Glu Gln Ala Glu Asn Ile Ile His Leu Phe Thr Leu
1355 1360 1365

Thr Asn Leu Gly Ala Pro Ala Ala Phe Lys Tyr Phe Asp Thr Thr
1370 1375 1380

Ile Asp Arg Lys Arg Tyr Thr Ser Thr Lys Glu Val Leu Asp Ala
1385 1390 1395

Thr Leu Ile His Gln Ser Ile Thr Gly Leu Tyr Glu Thr Arg Ile
1400 1405 1410

Asp Leu Ser Gln Leu Gly Gly Asp Ser Arg Ala Asp Pro Lys Lys
1415 1420 1425

Lys Arg Lys Val Glu Phe Tyr Pro Tyr Asp Val Pro Asp Tyr Ala
1430 1435 1440

<210> SEQ ID NO 14
<211> LENGTH: 1445
<212> TYPE: PRT
<213> ORGANISM: Artificial Sequence
<220> FEATURE:
<223> OTHER INFORMATION: penetrating peptide-linkage-Cas protein; AP-HE9-Cas9

<400> SEQUENCE: 14

Arg Arg Arg Trp Cys Lys Arg Arg Arg Ala Ser Gly Gly Gly Gly Gly
1 5 10 15

His Glu His Glu His Glu His Glu His Glu His Glu His Glu His Glu
20 25 30

His Glu Ala Ser Leu Asp Ser Thr Ala Pro Lys Lys Lys Arg Lys Val
35 40 45

Gly Ile His Gly Val Pro Ala Ala Asp Lys Lys Tyr Ser Ile Gly Leu
50 55 60

Asp Ile Gly Thr Asn Ser Val Gly Trp Ala Val Ile Thr Asp Glu Tyr
65 70 75 80

Lys Val Pro Ser Lys Lys Phe Lys Val Leu Gly Asn Thr Asp Arg His
85 90 95

Ser Ile Lys Lys Asn Leu Ile Gly Ala Leu Leu Phe Asp Ser Gly Glu
100 105 110

Thr Ala Glu Ala Thr Arg Leu Lys Arg Thr Ala Arg Arg Arg Tyr Thr
115 120 125

```
Arg Arg Lys Asn Arg Ile Cys Tyr Leu Gln Glu Ile Phe Ser Asn Glu
    130                 135                 140

Met Ala Lys Val Asp Asp Ser Phe Phe His Arg Leu Glu Glu Ser Phe
145                 150                 155                 160

Leu Val Glu Glu Asp Lys Lys His Glu Arg His Pro Ile Phe Gly Asn
                165                 170                 175

Ile Val Asp Glu Val Ala Tyr His Glu Lys Tyr Pro Thr Ile Tyr His
            180                 185                 190

Leu Arg Lys Lys Leu Val Asp Ser Thr Asp Lys Ala Asp Leu Arg Leu
        195                 200                 205

Ile Tyr Leu Ala Leu Ala His Met Ile Lys Phe Arg Gly His Phe Leu
    210                 215                 220

Ile Glu Gly Asp Leu Asn Pro Asp Asn Ser Asp Val Asp Lys Leu Phe
225                 230                 235                 240

Ile Gln Leu Val Gln Thr Tyr Asn Gln Leu Phe Glu Glu Asn Pro Ile
                245                 250                 255

Asn Ala Ser Gly Val Asp Ala Lys Ala Ile Leu Ser Ala Arg Leu Ser
            260                 265                 270

Lys Ser Arg Arg Leu Glu Asn Leu Ile Ala Gln Leu Pro Gly Glu Lys
        275                 280                 285

Lys Asn Gly Leu Phe Gly Asn Leu Ile Ala Leu Ser Leu Gly Leu Thr
    290                 295                 300

Pro Asn Phe Lys Ser Asn Phe Asp Leu Ala Glu Asp Ala Lys Leu Gln
305                 310                 315                 320

Leu Ser Lys Asp Thr Tyr Asp Asp Asp Leu Asp Asn Leu Leu Ala Gln
                325                 330                 335

Ile Gly Asp Gln Tyr Ala Asp Leu Phe Leu Ala Ala Lys Asn Leu Ser
            340                 345                 350

Asp Ala Ile Leu Leu Ser Asp Ile Leu Arg Val Asn Thr Glu Ile Thr
        355                 360                 365

Lys Ala Pro Leu Ser Ala Ser Met Ile Lys Arg Tyr Asp Glu His His
    370                 375                 380

Gln Asp Leu Thr Leu Leu Lys Ala Leu Val Arg Gln Gln Leu Pro Glu
385                 390                 395                 400

Lys Tyr Lys Glu Ile Phe Phe Asp Gln Ser Lys Asn Gly Tyr Ala Gly
                405                 410                 415

Tyr Ile Asp Gly Gly Ala Ser Gln Glu Glu Phe Tyr Lys Phe Ile Lys
            420                 425                 430

Pro Ile Leu Glu Lys Met Asp Gly Thr Glu Glu Leu Leu Val Lys Leu
        435                 440                 445

Asn Arg Glu Asp Leu Leu Arg Lys Gln Arg Thr Phe Asp Asn Gly Ser
    450                 455                 460

Ile Pro His Gln Ile His Leu Gly Glu Leu His Ala Ile Leu Arg Arg
465                 470                 475                 480

Gln Glu Asp Phe Tyr Pro Phe Leu Lys Asp Asn Arg Glu Lys Ile Glu
                485                 490                 495

Lys Ile Leu Thr Phe Arg Ile Pro Tyr Tyr Val Gly Pro Leu Ala Arg
            500                 505                 510

Gly Asn Ser Arg Phe Ala Trp Met Thr Arg Lys Ser Glu Glu Thr Ile
        515                 520                 525

Thr Pro Trp Asn Phe Glu Glu Val Val Asp Lys Gly Ala Ser Ala Gln
    530                 535                 540

Ser Phe Ile Glu Arg Met Thr Asn Phe Asp Lys Asn Leu Pro Asn Glu
```

```
545                 550                 555                 560

Lys Val Leu Pro Lys His Ser Leu Leu Tyr Glu Tyr Phe Thr Val Tyr
                565                 570                 575

Asn Glu Leu Thr Lys Val Lys Tyr Val Thr Glu Gly Met Arg Lys Pro
            580                 585                 590

Ala Phe Leu Ser Gly Glu Gln Lys Lys Ala Ile Val Asp Leu Leu Phe
        595                 600                 605

Lys Thr Asn Arg Lys Val Thr Val Lys Gln Leu Lys Glu Asp Tyr Phe
    610                 615                 620

Lys Lys Ile Glu Cys Phe Asp Ser Val Glu Ile Ser Gly Val Glu Asp
625                 630                 635                 640

Arg Phe Asn Ala Ser Leu Gly Thr Tyr His Asp Leu Leu Lys Ile Ile
                645                 650                 655

Lys Asp Lys Asp Phe Leu Asp Asn Glu Glu Asn Glu Asp Ile Leu Glu
            660                 665                 670

Asp Ile Val Leu Thr Leu Thr Leu Phe Glu Asp Arg Glu Met Ile Glu
        675                 680                 685

Glu Arg Leu Lys Thr Tyr Ala His Leu Phe Asp Asp Lys Val Met Lys
    690                 695                 700

Gln Leu Lys Arg Arg Arg Tyr Thr Gly Trp Gly Arg Leu Ser Arg Lys
705                 710                 715                 720

Leu Ile Asn Gly Ile Arg Asp Lys Gln Ser Gly Lys Thr Ile Leu Asp
                725                 730                 735

Phe Leu Lys Ser Asp Gly Phe Ala Asn Arg Asn Phe Met Gln Leu Ile
            740                 745                 750

His Asp Asp Ser Leu Thr Phe Lys Glu Asp Ile Gln Lys Ala Gln Val
        755                 760                 765

Ser Gly Gln Gly Asp Ser Leu His Glu His Ile Ala Asn Leu Ala Gly
    770                 775                 780

Ser Pro Ala Ile Lys Lys Gly Ile Leu Gln Thr Val Lys Val Val Asp
785                 790                 795                 800

Glu Leu Val Lys Val Met Gly Arg His Lys Pro Glu Asn Ile Val Ile
                805                 810                 815

Glu Met Ala Arg Glu Asn Gln Thr Thr Gln Lys Gly Gln Lys Asn Ser
            820                 825                 830

Arg Glu Arg Met Lys Arg Ile Glu Glu Gly Ile Lys Glu Leu Gly Ser
        835                 840                 845

Gln Ile Leu Lys Glu His Pro Val Glu Asn Thr Gln Leu Gln Asn Glu
    850                 855                 860

Lys Leu Tyr Leu Tyr Tyr Leu Gln Asn Gly Arg Asp Met Tyr Val Asp
865                 870                 875                 880

Gln Glu Leu Asp Ile Asn Arg Leu Ser Asp Tyr Asp Val Asp His Ile
                885                 890                 895

Val Pro Gln Ser Phe Leu Lys Asp Asp Ser Ile Asp Asn Lys Val Leu
            900                 905                 910

Thr Arg Ser Asp Lys Asn Arg Gly Lys Ser Asp Asn Val Pro Ser Glu
        915                 920                 925

Glu Val Val Lys Lys Met Lys Asn Tyr Trp Arg Gln Leu Leu Asn Ala
    930                 935                 940

Lys Leu Ile Thr Gln Arg Lys Phe Asp Asn Leu Thr Lys Ala Glu Arg
945                 950                 955                 960

Gly Gly Leu Ser Glu Leu Asp Lys Ala Gly Phe Ile Lys Arg Gln Leu
                965                 970                 975
```

```
Val Glu Thr Arg Gln Ile Thr Lys His Val Ala Gln Ile Leu Asp Ser
            980                 985                 990

Arg Met Asn Thr Lys Tyr Asp Glu  Asn Asp Lys Leu Ile  Arg Glu Val
        995                 1000                1005

Lys Val  Ile Thr Leu Lys Ser  Lys Leu Val Ser Asp  Phe Arg Lys
    1010                 1015                 1020

Asp Phe  Gln Phe Tyr Lys Val  Arg Glu Ile Asn Asn  Tyr His His
    1025                 1030                 1035

Ala His  Asp Ala Tyr Leu Asn  Ala Val Val Gly Thr  Ala Leu Ile
    1040                 1045                 1050

Lys Lys  Tyr Pro Lys Leu Glu  Ser Glu Phe Val Tyr  Gly Asp Tyr
    1055                 1060                 1065

Lys Val  Tyr Asp Val Arg Lys  Met Ile Ala Lys Ser  Glu Gln Glu
    1070                 1075                 1080

Ile Gly  Lys Ala Thr Ala Lys  Tyr Phe Phe Tyr Ser  Asn Ile Met
    1085                 1090                 1095

Asn Phe  Phe Lys Thr Glu Ile  Thr Leu Ala Asn Gly  Glu Ile Arg
    1100                 1105                 1110

Lys Arg  Pro Leu Ile Glu Thr  Asn Gly Glu Thr Gly  Glu Ile Val
    1115                 1120                 1125

Trp Asp  Lys Gly Arg Asp Phe  Ala Thr Val Arg Lys  Val Leu Ser
    1130                 1135                 1140

Met Pro  Gln Val Asn Ile Val  Lys Lys Thr Glu Val  Gln Thr Gly
    1145                 1150                 1155

Gly Phe  Ser Lys Glu Ser Ile  Leu Pro Lys Arg Asn  Ser Asp Lys
    1160                 1165                 1170

Leu Ile  Ala Arg Lys Lys Asp  Trp Asp Pro Lys Lys  Tyr Gly Gly
    1175                 1180                 1185

Phe Asp  Ser Pro Thr Val Ala  Tyr Ser Val Leu Val  Val Ala Lys
    1190                 1195                 1200

Val Glu  Lys Gly Lys Ser Lys  Lys Leu Lys Ser Val  Lys Glu Leu
    1205                 1210                 1215

Leu Gly  Ile Thr Ile Met Glu  Arg Ser Ser Phe Glu  Lys Asn Pro
    1220                 1225                 1230

Ile Asp  Phe Leu Glu Ala Lys  Gly Tyr Lys Glu Val  Lys Lys Asp
    1235                 1240                 1245

Leu Ile  Ile Lys Leu Pro Lys  Tyr Ser Leu Phe Glu  Leu Glu Asn
    1250                 1255                 1260

Gly Arg  Lys Arg Met Leu Ala  Ser Ala Gly Glu Leu  Gln Lys Gly
    1265                 1270                 1275

Asn Glu  Leu Ala Leu Pro Ser  Lys Tyr Val Asn Phe  Leu Tyr Leu
    1280                 1285                 1290

Ala Ser  His Tyr Glu Lys Leu  Lys Gly Ser Pro Glu  Asp Asn Glu
    1295                 1300                 1305

Gln Lys  Gln Leu Phe Val Glu  Gln His Lys His Tyr  Leu Asp Glu
    1310                 1315                 1320

Ile Ile  Glu Gln Ile Ser Glu  Phe Ser Lys Arg Val  Ile Leu Ala
    1325                 1330                 1335

Asp Ala  Asn Leu Asp Lys Val  Leu Ser Ala Tyr Asn  Lys His Arg
    1340                 1345                 1350

Asp Lys  Pro Ile Arg Glu Gln  Ala Glu Asn Ile Ile  His Leu Phe
    1355                 1360                 1365
```

```
Thr Leu  Thr Asn Leu Gly Ala  Pro Ala Ala Phe Lys  Tyr Phe Asp
    1370                 1375                 1380

Thr Thr  Ile Asp Arg Lys Arg  Tyr Thr Ser Thr Lys  Glu Val Leu
    1385                 1390                 1395

Asp Ala  Thr Leu Ile His Gln  Ser Ile Thr Gly Leu  Tyr Glu Thr
    1400                 1405                 1410

Arg Ile  Asp Leu Ser Gln Leu  Gly Gly Asp Ser Arg  Ala Asp Pro
    1415                 1420                 1425

Lys Lys  Lys Arg Lys Val Glu  Phe Tyr Pro Tyr Asp  Val Pro Asp
    1430                 1435                 1440

Tyr Ala
    1445


<210> SEQ ID NO 15
<211> LENGTH: 1447
<212> TYPE: PRT
<213> ORGANISM: Artificial Sequence
<220> FEATURE:
<223> OTHER INFORMATION: penetrating peptide-linkage-Cas protein;
      AP-HE10-Cas9

<400> SEQUENCE: 15

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu His Glu Ala Ser Leu Asp Ser Thr Ala Pro Lys Lys Lys Arg
        35                  40                  45

Lys Val Gly Ile His Gly Val Pro Ala Ala Asp Lys Lys Tyr Ser Ile
    50                  55                  60

Gly Leu Asp Ile Gly Thr Asn Ser Val Gly Trp Ala Val Ile Thr Asp
65                  70                  75                  80

Glu Tyr Lys Val Pro Ser Lys Lys Phe Lys Val Leu Gly Asn Thr Asp
                85                  90                  95

Arg His Ser Ile Lys Lys Asn Leu Ile Gly Ala Leu Leu Phe Asp Ser
            100                 105                 110

Gly Glu Thr Ala Glu Ala Thr Arg Leu Lys Arg Thr Ala Arg Arg Arg
        115                 120                 125

Tyr Thr Arg Arg Lys Asn Arg Ile Cys Tyr Leu Gln Glu Ile Phe Ser
    130                 135                 140

Asn Glu Met Ala Lys Val Asp Asp Ser Phe Phe His Arg Leu Glu Glu
145                 150                 155                 160

Ser Phe Leu Val Glu Glu Asp Lys Lys His Glu Arg His Pro Ile Phe
                165                 170                 175

Gly Asn Ile Val Asp Glu Val Ala Tyr His Glu Lys Tyr Pro Thr Ile
            180                 185                 190

Tyr His Leu Arg Lys Lys Leu Val Asp Ser Thr Asp Lys Ala Asp Leu
        195                 200                 205

Arg Leu Ile Tyr Leu Ala Leu Ala His Met Ile Lys Phe Arg Gly His
    210                 215                 220

Phe Leu Ile Glu Gly Asp Leu Asn Pro Asp Asn Ser Asp Val Asp Lys
225                 230                 235                 240

Leu Phe Ile Gln Leu Val Gln Thr Tyr Asn Gln Leu Phe Glu Glu Asn
                245                 250                 255

Pro Ile Asn Ala Ser Gly Val Asp Ala Lys Ala Ile Leu Ser Ala Arg
            260                 265                 270
```

```
Leu Ser Lys Ser Arg Arg Leu Glu Asn Leu Ile Ala Gln Leu Pro Gly
        275                 280                 285

Glu Lys Lys Asn Gly Leu Phe Gly Asn Leu Ile Ala Leu Ser Leu Gly
    290                 295                 300

Leu Thr Pro Asn Phe Lys Ser Asn Phe Asp Leu Ala Glu Asp Ala Lys
305                 310                 315                 320

Leu Gln Leu Ser Lys Asp Thr Tyr Asp Asp Asp Leu Asp Asn Leu Leu
                325                 330                 335

Ala Gln Ile Gly Asp Gln Tyr Ala Asp Leu Phe Leu Ala Ala Lys Asn
            340                 345                 350

Leu Ser Asp Ala Ile Leu Leu Ser Asp Ile Leu Arg Val Asn Thr Glu
        355                 360                 365

Ile Thr Lys Ala Pro Leu Ser Ala Ser Met Ile Lys Arg Tyr Asp Glu
    370                 375                 380

His His Gln Asp Leu Thr Leu Leu Lys Ala Leu Val Arg Gln Gln Leu
385                 390                 395                 400

Pro Glu Lys Tyr Lys Glu Ile Phe Phe Asp Gln Ser Lys Asn Gly Tyr
                405                 410                 415

Ala Gly Tyr Ile Asp Gly Gly Ala Ser Gln Glu Glu Phe Tyr Lys Phe
            420                 425                 430

Ile Lys Pro Ile Leu Glu Lys Met Asp Gly Thr Glu Glu Leu Leu Val
        435                 440                 445

Lys Leu Asn Arg Glu Asp Leu Leu Arg Lys Gln Arg Thr Phe Asp Asn
    450                 455                 460

Gly Ser Ile Pro His Gln Ile His Leu Gly Glu Leu His Ala Ile Leu
465                 470                 475                 480

Arg Arg Gln Glu Asp Phe Tyr Pro Phe Leu Lys Asp Asn Arg Glu Lys
                485                 490                 495

Ile Glu Lys Ile Leu Thr Phe Arg Ile Pro Tyr Tyr Val Gly Pro Leu
            500                 505                 510

Ala Arg Gly Asn Ser Arg Phe Ala Trp Met Thr Arg Lys Ser Glu Glu
        515                 520                 525

Thr Ile Thr Pro Trp Asn Phe Glu Glu Val Val Asp Lys Gly Ala Ser
    530                 535                 540

Ala Gln Ser Phe Ile Glu Arg Met Thr Asn Phe Asp Lys Asn Leu Pro
545                 550                 555                 560

Asn Glu Lys Val Leu Pro Lys His Ser Leu Leu Tyr Glu Tyr Phe Thr
                565                 570                 575

Val Tyr Asn Glu Leu Thr Lys Val Lys Tyr Val Thr Glu Gly Met Arg
            580                 585                 590

Lys Pro Ala Phe Leu Ser Gly Glu Gln Lys Lys Ala Ile Val Asp Leu
        595                 600                 605

Leu Phe Lys Thr Asn Arg Lys Val Thr Val Lys Gln Leu Lys Glu Asp
    610                 615                 620

Tyr Phe Lys Lys Ile Glu Cys Phe Asp Ser Val Glu Ile Ser Gly Val
625                 630                 635                 640

Glu Asp Arg Phe Asn Ala Ser Leu Gly Thr Tyr His Asp Leu Leu Lys
                645                 650                 655

Ile Ile Lys Asp Lys Asp Phe Leu Asp Asn Glu Glu Asn Glu Asp Ile
            660                 665                 670

Leu Glu Asp Ile Val Leu Thr Leu Thr Leu Phe Glu Asp Arg Glu Met
        675                 680                 685
```

```
Ile Glu Glu Arg Leu Lys Thr Tyr Ala His Leu Phe Asp Asp Lys Val
    690                 695                 700

Met Lys Gln Leu Lys Arg Arg Arg Tyr Thr Gly Trp Gly Arg Leu Ser
705                 710                 715                 720

Arg Lys Leu Ile Asn Gly Ile Arg Asp Lys Gln Ser Gly Lys Thr Ile
                725                 730                 735

Leu Asp Phe Leu Lys Ser Asp Gly Phe Ala Asn Arg Asn Phe Met Gln
            740                 745                 750

Leu Ile His Asp Asp Ser Leu Thr Phe Lys Glu Asp Ile Gln Lys Ala
        755                 760                 765

Gln Val Ser Gly Gln Gly Asp Ser Leu His Glu His Ile Ala Asn Leu
    770                 775                 780

Ala Gly Ser Pro Ala Ile Lys Lys Gly Ile Leu Gln Thr Val Lys Val
785                 790                 795                 800

Val Asp Glu Leu Val Lys Val Met Gly Arg His Lys Pro Glu Asn Ile
                805                 810                 815

Val Ile Glu Met Ala Arg Glu Asn Gln Thr Thr Gln Lys Gly Gln Lys
            820                 825                 830

Asn Ser Arg Glu Arg Met Lys Arg Ile Glu Glu Gly Ile Lys Glu Leu
        835                 840                 845

Gly Ser Gln Ile Leu Lys Glu His Pro Val Glu Asn Thr Gln Leu Gln
    850                 855                 860

Asn Glu Lys Leu Tyr Leu Tyr Tyr Leu Gln Asn Gly Arg Asp Met Tyr
865                 870                 875                 880

Val Asp Gln Glu Leu Asp Ile Asn Arg Leu Ser Asp Tyr Asp Val Asp
                885                 890                 895

His Ile Val Pro Gln Ser Phe Leu Lys Asp Asp Ser Ile Asp Asn Lys
            900                 905                 910

Val Leu Thr Arg Ser Asp Lys Asn Arg Gly Lys Ser Asp Asn Val Pro
        915                 920                 925

Ser Glu Glu Val Val Lys Lys Met Lys Asn Tyr Trp Arg Gln Leu Leu
    930                 935                 940

Asn Ala Lys Leu Ile Thr Gln Arg Lys Phe Asp Asn Leu Thr Lys Ala
945                 950                 955                 960

Glu Arg Gly Gly Leu Ser Glu Leu Asp Lys Ala Gly Phe Ile Lys Arg
                965                 970                 975

Gln Leu Val Glu Thr Arg Gln Ile Thr Lys His Val Ala Gln Ile Leu
            980                 985                 990

Asp Ser Arg Met Asn Thr Lys Tyr  Asp Glu Asn Asp Lys  Leu Ile Arg
        995                 1000                1005

Glu Val  Lys Val Ile Thr Leu  Lys Ser Lys Leu Val  Ser Asp Phe
    1010                1015                1020

Arg Lys  Asp Phe Gln Phe Tyr  Lys Val Arg Glu Ile  Asn Asn Tyr
    1025                1030                1035

His His  Ala His Asp Ala Tyr  Leu Asn Ala Val Val  Gly Thr Ala
    1040                1045                1050

Leu Ile  Lys Lys Tyr Pro Lys  Leu Glu Ser Glu Phe  Val Tyr Gly
    1055                1060                1065

Asp Tyr  Lys Val Tyr Asp Val  Arg Lys Met Ile Ala  Lys Ser Glu
    1070                1075                1080

Gln Glu  Ile Gly Lys Ala Thr  Ala Lys Tyr Phe Phe  Tyr Ser Asn
    1085                1090                1095

Ile Met  Asn Phe Phe Lys Thr  Glu Ile Thr Leu Ala  Asn Gly Glu
```

```
    1100                1105                1110

Ile Arg  Lys Arg Pro Leu Ile  Glu Thr Asn Gly Glu  Thr Gly Glu
    1115                1120                1125

Ile Val  Trp Asp Lys Gly Arg  Asp Phe Ala Thr Val  Arg Lys Val
    1130                1135                1140

Leu Ser  Met Pro Gln Val Asn  Ile Val Lys Lys Thr  Glu Val Gln
    1145                1150                1155

Thr Gly  Gly Phe Ser Lys Glu  Ser Ile Leu Pro Lys  Arg Asn Ser
    1160                1165                1170

Asp Lys  Leu Ile Ala Arg Lys  Lys Asp Trp Asp Pro  Lys Lys Tyr
    1175                1180                1185

Gly Gly  Phe Asp Ser Pro Thr  Val Ala Tyr Ser Val  Leu Val Val
    1190                1195                1200

Ala Lys  Val Glu Lys Gly Lys  Ser Lys Lys Leu Lys  Ser Val Lys
    1205                1210                1215

Glu Leu  Leu Gly Ile Thr Ile  Met Glu Arg Ser Ser  Phe Glu Lys
    1220                1225                1230

Asn Pro  Ile Asp Phe Leu Glu  Ala Lys Gly Tyr Lys  Glu Val Lys
    1235                1240                1245

Lys Asp  Leu Ile Ile Lys Leu  Pro Lys Tyr Ser Leu  Phe Glu Leu
    1250                1255                1260

Glu Asn  Gly Arg Lys Arg Met  Leu Ala Ser Ala Gly  Glu Leu Gln
    1265                1270                1275

Lys Gly  Asn Glu Leu Ala Leu  Pro Ser Lys Tyr Val  Asn Phe Leu
    1280                1285                1290

Tyr Leu  Ala Ser His Tyr Glu  Lys Leu Lys Gly Ser  Pro Glu Asp
    1295                1300                1305

Asn Glu  Gln Lys Gln Leu Phe  Val Glu Gln His Lys  His Tyr Leu
    1310                1315                1320

Asp Glu  Ile Ile Glu Gln Ile  Ser Glu Phe Ser Lys  Arg Val Ile
    1325                1330                1335

Leu Ala  Asp Ala Asn Leu Asp  Lys Val Leu Ser Ala  Tyr Asn Lys
    1340                1345                1350

His Arg  Asp Lys Pro Ile Arg  Glu Gln Ala Glu Asn  Ile Ile His
    1355                1360                1365

Leu Phe  Thr Leu Thr Asn Leu  Gly Ala Pro Ala Ala  Phe Lys Tyr
    1370                1375                1380

Phe Asp  Thr Thr Ile Asp Arg  Lys Arg Tyr Thr Ser  Thr Lys Glu
    1385                1390                1395

Val Leu  Asp Ala Thr Leu Ile  His Gln Ser Ile Thr  Gly Leu Tyr
    1400                1405                1410

Glu Thr  Arg Ile Asp Leu Ser  Gln Leu Gly Gly Asp  Ser Arg Ala
    1415                1420                1425

Asp Pro  Lys Lys Lys Arg Lys  Val Glu Phe Tyr Pro  Tyr Asp Val
    1430                1435                1440

Pro Asp  Tyr Ala
    1445
```

<210> SEQ ID NO 16
<211> LENGTH: 1449
<212> TYPE: PRT
<213> ORGANISM: Artificial Sequence
<220> FEATURE:
<223> OTHER INFORMATION: penetrating peptide-linkage-Cas protein;
AP-HE11-Cas9

<400> SEQUENCE: 16

Arg Arg Arg Trp Cys Lys Arg Arg Arg Ala Ser Gly Gly Gly Gly Gly
1               5                   10                  15

His Glu His Glu His Glu His Glu His Glu His Glu His Glu His Glu
            20                  25                  30

His Glu His Glu His Glu Ala Ser Leu Asp Ser Thr Ala Pro Lys Lys
        35                  40                  45

Lys Arg Lys Val Gly Ile His Gly Val Pro Ala Ala Asp Lys Lys Tyr
    50                  55                  60

Ser Ile Gly Leu Asp Ile Gly Thr Asn Ser Val Gly Trp Ala Val Ile
65                  70                  75                  80

Thr Asp Glu Tyr Lys Val Pro Ser Lys Lys Phe Lys Val Leu Gly Asn
                85                  90                  95

Thr Asp Arg His Ser Ile Lys Lys Asn Leu Ile Gly Ala Leu Leu Phe
            100                 105                 110

Asp Ser Gly Glu Thr Ala Glu Ala Thr Arg Leu Lys Arg Thr Ala Arg
        115                 120                 125

Arg Arg Tyr Thr Arg Arg Lys Asn Arg Ile Cys Tyr Leu Gln Glu Ile
    130                 135                 140

Phe Ser Asn Glu Met Ala Lys Val Asp Asp Ser Phe Phe His Arg Leu
145                 150                 155                 160

Glu Glu Ser Phe Leu Val Glu Glu Asp Lys Lys His Glu Arg His Pro
                165                 170                 175

Ile Phe Gly Asn Ile Val Asp Glu Val Ala Tyr His Glu Lys Tyr Pro
            180                 185                 190

Thr Ile Tyr His Leu Arg Lys Lys Leu Val Asp Ser Thr Asp Lys Ala
        195                 200                 205

Asp Leu Arg Leu Ile Tyr Leu Ala Leu Ala His Met Ile Lys Phe Arg
    210                 215                 220

Gly His Phe Leu Ile Glu Gly Asp Leu Asn Pro Asp Asn Ser Asp Val
225                 230                 235                 240

Asp Lys Leu Phe Ile Gln Leu Val Gln Thr Tyr Asn Gln Leu Phe Glu
                245                 250                 255

Glu Asn Pro Ile Asn Ala Ser Gly Val Asp Ala Lys Ala Ile Leu Ser
            260                 265                 270

Ala Arg Leu Ser Lys Ser Arg Arg Leu Glu Asn Leu Ile Ala Gln Leu
        275                 280                 285

Pro Gly Glu Lys Lys Asn Gly Leu Phe Gly Asn Leu Ile Ala Leu Ser
    290                 295                 300

Leu Gly Leu Thr Pro Asn Phe Lys Ser Asn Phe Asp Leu Ala Glu Asp
305                 310                 315                 320

Ala Lys Leu Gln Leu Ser Lys Asp Thr Tyr Asp Asp Asp Leu Asp Asn
                325                 330                 335

Leu Leu Ala Gln Ile Gly Asp Gln Tyr Ala Asp Leu Phe Leu Ala Ala
            340                 345                 350

Lys Asn Leu Ser Asp Ala Ile Leu Leu Ser Asp Ile Leu Arg Val Asn
        355                 360                 365

Thr Glu Ile Thr Lys Ala Pro Leu Ser Ala Ser Met Ile Lys Arg Tyr
    370                 375                 380

Asp Glu His His Gln Asp Leu Thr Leu Leu Lys Ala Leu Val Arg Gln
385                 390                 395                 400

Gln Leu Pro Glu Lys Tyr Lys Glu Ile Phe Phe Asp Gln Ser Lys Asn

```
                405                 410                 415

Gly Tyr Ala Gly Tyr Ile Asp Gly Gly Ala Ser Gln Glu Glu Phe Tyr
            420                 425                 430

Lys Phe Ile Lys Pro Ile Leu Glu Lys Met Asp Gly Thr Glu Glu Leu
        435                 440                 445

Leu Val Lys Leu Asn Arg Glu Asp Leu Leu Arg Lys Gln Arg Thr Phe
    450                 455                 460

Asp Asn Gly Ser Ile Pro His Gln Ile His Leu Gly Glu Leu His Ala
465                 470                 475                 480

Ile Leu Arg Arg Gln Glu Asp Phe Tyr Pro Phe Leu Lys Asp Asn Arg
                485                 490                 495

Glu Lys Ile Glu Lys Ile Leu Thr Phe Arg Ile Pro Tyr Tyr Val Gly
            500                 505                 510

Pro Leu Ala Arg Gly Asn Ser Arg Phe Ala Trp Met Thr Arg Lys Ser
        515                 520                 525

Glu Glu Thr Ile Thr Pro Trp Asn Phe Glu Glu Val Val Asp Lys Gly
    530                 535                 540

Ala Ser Ala Gln Ser Phe Ile Glu Arg Met Thr Asn Phe Asp Lys Asn
545                 550                 555                 560

Leu Pro Asn Glu Lys Val Leu Pro Lys His Ser Leu Leu Tyr Glu Tyr
                565                 570                 575

Phe Thr Val Tyr Asn Glu Leu Thr Lys Val Lys Tyr Val Thr Glu Gly
            580                 585                 590

Met Arg Lys Pro Ala Phe Leu Ser Gly Glu Gln Lys Lys Ala Ile Val
        595                 600                 605

Asp Leu Leu Phe Lys Thr Asn Arg Lys Val Thr Val Lys Gln Leu Lys
    610                 615                 620

Glu Asp Tyr Phe Lys Lys Ile Glu Cys Phe Asp Ser Val Glu Ile Ser
625                 630                 635                 640

Gly Val Glu Asp Arg Phe Asn Ala Ser Leu Gly Thr Tyr His Asp Leu
                645                 650                 655

Leu Lys Ile Ile Lys Asp Lys Asp Phe Leu Asp Asn Glu Glu Asn Glu
            660                 665                 670

Asp Ile Leu Glu Asp Ile Val Leu Thr Leu Thr Leu Phe Glu Asp Arg
        675                 680                 685

Glu Met Ile Glu Glu Arg Leu Lys Thr Tyr Ala His Leu Phe Asp Asp
    690                 695                 700

Lys Val Met Lys Gln Leu Lys Arg Arg Arg Tyr Thr Gly Trp Gly Arg
705                 710                 715                 720

Leu Ser Arg Lys Leu Ile Asn Gly Ile Arg Asp Lys Gln Ser Gly Lys
                725                 730                 735

Thr Ile Leu Asp Phe Leu Lys Ser Asp Gly Phe Ala Asn Arg Asn Phe
            740                 745                 750

Met Gln Leu Ile His Asp Asp Ser Leu Thr Phe Lys Glu Asp Ile Gln
        755                 760                 765

Lys Ala Gln Val Ser Gly Gln Gly Asp Ser Leu His Glu His Ile Ala
    770                 775                 780

Asn Leu Ala Gly Ser Pro Ala Ile Lys Lys Gly Ile Leu Gln Thr Val
785                 790                 795                 800

Lys Val Val Asp Glu Leu Val Lys Val Met Gly Arg His Lys Pro Glu
                805                 810                 815

Asn Ile Val Ile Glu Met Ala Arg Glu Asn Gln Thr Thr Gln Lys Gly
            820                 825                 830
```

```
Gln Lys Asn Ser Arg Glu Arg Met Lys Arg Ile Glu Glu Gly Ile Lys
        835                 840                 845

Glu Leu Gly Ser Gln Ile Leu Lys Glu His Pro Val Glu Asn Thr Gln
    850                 855                 860

Leu Gln Asn Glu Lys Leu Tyr Leu Tyr Tyr Leu Gln Asn Gly Arg Asp
865                 870                 875                 880

Met Tyr Val Asp Gln Glu Leu Asp Ile Asn Arg Leu Ser Asp Tyr Asp
                885                 890                 895

Val Asp His Ile Val Pro Gln Ser Phe Leu Lys Asp Asp Ser Ile Asp
            900                 905                 910

Asn Lys Val Leu Thr Arg Ser Asp Lys Asn Arg Gly Lys Ser Asp Asn
        915                 920                 925

Val Pro Ser Glu Glu Val Val Lys Lys Met Lys Asn Tyr Trp Arg Gln
    930                 935                 940

Leu Leu Asn Ala Lys Leu Ile Thr Gln Arg Lys Phe Asp Asn Leu Thr
945                 950                 955                 960

Lys Ala Glu Arg Gly Gly Leu Ser Glu Leu Asp Lys Ala Gly Phe Ile
                965                 970                 975

Lys Arg Gln Leu Val Glu Thr Arg Gln Ile Thr Lys His Val Ala Gln
            980                 985                 990

Ile Leu Asp Ser Arg Met Asn Thr  Lys Tyr Asp Glu Asn  Asp Lys Leu
        995                 1000                 1005

Ile Arg  Glu Val Lys Val Ile  Thr Leu Lys Ser Lys  Leu Val Ser
    1010                 1015                 1020

Asp Phe  Arg Lys Asp Phe Gln  Phe Tyr Lys Val Arg  Glu Ile Asn
    1025                 1030                 1035

Asn Tyr  His His Ala His Asp  Ala Tyr Leu Asn Ala  Val Val Gly
    1040                 1045                 1050

Thr Ala  Leu Ile Lys Lys Tyr  Pro Lys Leu Glu Ser  Glu Phe Val
    1055                 1060                 1065

Tyr Gly  Asp Tyr Lys Val Tyr  Asp Val Arg Lys Met  Ile Ala Lys
    1070                 1075                 1080

Ser Glu  Gln Glu Ile Gly Lys  Ala Thr Ala Lys Tyr  Phe Phe Tyr
    1085                 1090                 1095

Ser Asn  Ile Met Asn Phe Phe  Lys Thr Glu Ile Thr  Leu Ala Asn
    1100                 1105                 1110

Gly Glu  Ile Arg Lys Arg Pro  Leu Ile Glu Thr Asn  Gly Glu Thr
    1115                 1120                 1125

Gly Glu  Ile Val Trp Asp Lys  Gly Arg Asp Phe Ala  Thr Val Arg
    1130                 1135                 1140

Lys Val  Leu Ser Met Pro Gln  Val Asn Ile Val Lys  Lys Thr Glu
    1145                 1150                 1155

Val Gln  Thr Gly Gly Phe Ser  Lys Glu Ser Ile Leu  Pro Lys Arg
    1160                 1165                 1170

Asn Ser  Asp Lys Leu Ile Ala  Arg Lys Lys Asp Trp  Asp Pro Lys
    1175                 1180                 1185

Lys Tyr  Gly Gly Phe Asp Ser  Pro Thr Val Ala Tyr  Ser Val Leu
    1190                 1195                 1200

Val Val  Ala Lys Val Glu Lys  Gly Lys Ser Lys Lys  Leu Lys Ser
    1205                 1210                 1215

Val Lys  Glu Leu Leu Gly Ile  Thr Ile Met Glu Arg  Ser Ser Phe
    1220                 1225                 1230
```

Glu Lys Asn Pro Ile Asp Phe Leu Glu Ala Lys Gly Tyr Lys Glu
1235 1240 1245

Val Lys Lys Asp Leu Ile Ile Lys Leu Pro Lys Tyr Ser Leu Phe
1250 1255 1260

Glu Leu Glu Asn Gly Arg Lys Arg Met Leu Ala Ser Ala Gly Glu
1265 1270 1275

Leu Gln Lys Gly Asn Glu Leu Ala Leu Pro Ser Lys Tyr Val Asn
1280 1285 1290

Phe Leu Tyr Leu Ala Ser His Tyr Glu Lys Leu Lys Gly Ser Pro
1295 1300 1305

Glu Asp Asn Glu Gln Lys Gln Leu Phe Val Glu Gln His Lys His
1310 1315 1320

Tyr Leu Asp Glu Ile Ile Glu Gln Ile Ser Glu Phe Ser Lys Arg
1325 1330 1335

Val Ile Leu Ala Asp Ala Asn Leu Asp Lys Val Leu Ser Ala Tyr
1340 1345 1350

Asn Lys His Arg Asp Lys Pro Ile Arg Glu Gln Ala Glu Asn Ile
1355 1360 1365

Ile His Leu Phe Thr Leu Thr Asn Leu Gly Ala Pro Ala Ala Phe
1370 1375 1380

Lys Tyr Phe Asp Thr Thr Ile Asp Arg Lys Arg Tyr Thr Ser Thr
1385 1390 1395

Lys Glu Val Leu Asp Ala Thr Leu Ile His Gln Ser Ile Thr Gly
1400 1405 1410

Leu Tyr Glu Thr Arg Ile Asp Leu Ser Gln Leu Gly Gly Asp Ser
1415 1420 1425

Arg Ala Asp Pro Lys Lys Lys Arg Lys Val Glu Phe Tyr Pro Tyr
1430 1435 1440

Asp Val Pro Asp Tyr Ala
1445

<210> SEQ ID NO 17
<211> LENGTH: 1451
<212> TYPE: PRT
<213> ORGANISM: Artificial Sequence
<220> FEATURE:
<223> OTHER INFORMATION: penetrating peptide-linkage-Cas protein; AP-HE12-Cas9

<400> SEQUENCE: 17

Arg Arg Arg Trp Cys Lys Arg Arg Arg Ala Ser Gly Gly Gly Gly Gly
1 5 10 15

His Glu His Glu His Glu His Glu His Glu His Glu His Glu His Glu
20 25 30

His Glu His Glu His Glu His Glu Ala Ser Leu Asp Ser Thr Ala Pro
35 40 45

Lys Lys Lys Arg Lys Val Gly Ile His Gly Val Pro Ala Ala Asp Lys
50 55 60

Lys Tyr Ser Ile Gly Leu Asp Ile Gly Thr Asn Ser Val Gly Trp Ala
65 70 75 80

Val Ile Thr Asp Glu Tyr Lys Val Pro Ser Lys Lys Phe Lys Val Leu
85 90 95

Gly Asn Thr Asp Arg His Ser Ile Lys Lys Asn Leu Ile Gly Ala Leu
100 105 110

Leu Phe Asp Ser Gly Glu Thr Ala Glu Ala Thr Arg Leu Lys Arg Thr
115 120 125

```
Ala Arg Arg Arg Tyr Thr Arg Arg Lys Asn Arg Ile Cys Tyr Leu Gln
    130                 135                 140

Glu Ile Phe Ser Asn Glu Met Ala Lys Val Asp Asp Ser Phe Phe His
145                 150                 155                 160

Arg Leu Glu Glu Ser Phe Leu Val Glu Glu Asp Lys Lys His Glu Arg
                165                 170                 175

His Pro Ile Phe Gly Asn Ile Val Asp Glu Val Ala Tyr His Glu Lys
            180                 185                 190

Tyr Pro Thr Ile Tyr His Leu Arg Lys Lys Leu Val Asp Ser Thr Asp
        195                 200                 205

Lys Ala Asp Leu Arg Leu Ile Tyr Leu Ala Leu Ala His Met Ile Lys
    210                 215                 220

Phe Arg Gly His Phe Leu Ile Glu Gly Asp Leu Asn Pro Asp Asn Ser
225                 230                 235                 240

Asp Val Asp Lys Leu Phe Ile Gln Leu Val Gln Thr Tyr Asn Gln Leu
                245                 250                 255

Phe Glu Glu Asn Pro Ile Asn Ala Ser Gly Val Asp Ala Lys Ala Ile
            260                 265                 270

Leu Ser Ala Arg Leu Ser Lys Ser Arg Arg Leu Glu Asn Leu Ile Ala
        275                 280                 285

Gln Leu Pro Gly Glu Lys Lys Asn Gly Leu Phe Gly Asn Leu Ile Ala
    290                 295                 300

Leu Ser Leu Gly Leu Thr Pro Asn Phe Lys Ser Asn Phe Asp Leu Ala
305                 310                 315                 320

Glu Asp Ala Lys Leu Gln Leu Ser Lys Asp Thr Tyr Asp Asp Asp Leu
                325                 330                 335

Asp Asn Leu Leu Ala Gln Ile Gly Asp Gln Tyr Ala Asp Leu Phe Leu
            340                 345                 350

Ala Ala Lys Asn Leu Ser Asp Ala Ile Leu Leu Ser Asp Ile Leu Arg
        355                 360                 365

Val Asn Thr Glu Ile Thr Lys Ala Pro Leu Ser Ala Ser Met Ile Lys
    370                 375                 380

Arg Tyr Asp Glu His His Gln Asp Leu Thr Leu Leu Lys Ala Leu Val
385                 390                 395                 400

Arg Gln Gln Leu Pro Glu Lys Tyr Lys Glu Ile Phe Phe Asp Gln Ser
                405                 410                 415

Lys Asn Gly Tyr Ala Gly Tyr Ile Asp Gly Gly Ala Ser Gln Glu Glu
            420                 425                 430

Phe Tyr Lys Phe Ile Lys Pro Ile Leu Glu Lys Met Asp Gly Thr Glu
        435                 440                 445

Glu Leu Leu Val Lys Leu Asn Arg Glu Asp Leu Leu Arg Lys Gln Arg
    450                 455                 460

Thr Phe Asp Asn Gly Ser Ile Pro His Gln Ile His Leu Gly Glu Leu
465                 470                 475                 480

His Ala Ile Leu Arg Arg Gln Glu Asp Phe Tyr Pro Phe Leu Lys Asp
                485                 490                 495

Asn Arg Glu Lys Ile Glu Lys Ile Leu Thr Phe Arg Ile Pro Tyr Tyr
            500                 505                 510

Val Gly Pro Leu Ala Arg Gly Asn Ser Arg Phe Ala Trp Met Thr Arg
        515                 520                 525

Lys Ser Glu Glu Thr Ile Thr Pro Trp Asn Phe Glu Glu Val Val Asp
    530                 535                 540
```

-continued

```
Lys Gly Ala Ser Ala Gln Ser Phe Ile Glu Arg Met Thr Asn Phe Asp
545                 550                 555                 560

Lys Asn Leu Pro Asn Glu Lys Val Leu Pro Lys His Ser Leu Leu Tyr
                565                 570                 575

Glu Tyr Phe Thr Val Tyr Asn Glu Leu Thr Lys Val Lys Tyr Val Thr
            580                 585                 590

Glu Gly Met Arg Lys Pro Ala Phe Leu Ser Gly Glu Gln Lys Lys Ala
        595                 600                 605

Ile Val Asp Leu Leu Phe Lys Thr Asn Arg Lys Val Thr Val Lys Gln
    610                 615                 620

Leu Lys Glu Asp Tyr Phe Lys Lys Ile Glu Cys Phe Asp Ser Val Glu
625                 630                 635                 640

Ile Ser Gly Val Glu Asp Arg Phe Asn Ala Ser Leu Gly Thr Tyr His
                645                 650                 655

Asp Leu Leu Lys Ile Ile Lys Asp Lys Asp Phe Leu Asp Asn Glu Glu
            660                 665                 670

Asn Glu Asp Ile Leu Glu Asp Ile Val Leu Thr Leu Thr Leu Phe Glu
        675                 680                 685

Asp Arg Glu Met Ile Glu Glu Arg Leu Lys Thr Tyr Ala His Leu Phe
    690                 695                 700

Asp Asp Lys Val Met Lys Gln Leu Lys Arg Arg Arg Tyr Thr Gly Trp
705                 710                 715                 720

Gly Arg Leu Ser Arg Lys Leu Ile Asn Gly Ile Arg Asp Lys Gln Ser
                725                 730                 735

Gly Lys Thr Ile Leu Asp Phe Leu Lys Ser Asp Gly Phe Ala Asn Arg
            740                 745                 750

Asn Phe Met Gln Leu Ile His Asp Asp Ser Leu Thr Phe Lys Glu Asp
        755                 760                 765

Ile Gln Lys Ala Gln Val Ser Gly Gln Gly Asp Ser Leu His Glu His
    770                 775                 780

Ile Ala Asn Leu Ala Gly Ser Pro Ala Ile Lys Lys Gly Ile Leu Gln
785                 790                 795                 800

Thr Val Lys Val Val Asp Glu Leu Val Lys Val Met Gly Arg His Lys
                805                 810                 815

Pro Glu Asn Ile Val Ile Glu Met Ala Arg Glu Asn Gln Thr Thr Gln
            820                 825                 830

Lys Gly Gln Lys Asn Ser Arg Glu Arg Met Lys Arg Ile Glu Glu Gly
        835                 840                 845

Ile Lys Glu Leu Gly Ser Gln Ile Leu Lys Glu His Pro Val Glu Asn
    850                 855                 860

Thr Gln Leu Gln Asn Glu Lys Leu Tyr Leu Tyr Tyr Leu Gln Asn Gly
865                 870                 875                 880

Arg Asp Met Tyr Val Asp Gln Glu Leu Asp Ile Asn Arg Leu Ser Asp
                885                 890                 895

Tyr Asp Val Asp His Ile Val Pro Gln Ser Phe Leu Lys Asp Asp Ser
            900                 905                 910

Ile Asp Asn Lys Val Leu Thr Arg Ser Asp Lys Asn Arg Gly Lys Ser
        915                 920                 925

Asp Asn Val Pro Ser Glu Glu Val Val Lys Lys Met Lys Asn Tyr Trp
    930                 935                 940

Arg Gln Leu Leu Asn Ala Lys Leu Ile Thr Gln Arg Lys Phe Asp Asn
945                 950                 955                 960

Leu Thr Lys Ala Glu Arg Gly Gly Leu Ser Glu Leu Asp Lys Ala Gly
```

```
                965                 970                 975

Phe Ile Lys Arg Gln Leu Val Glu Thr Arg Gln Ile Thr Lys His Val
            980                 985                 990

Ala Gln Ile Leu Asp Ser Arg Met  Asn Thr Lys Tyr Asp  Glu Asn Asp
        995                 1000                1005

Lys Leu  Ile Arg Glu Val Lys  Val Ile Thr Leu Lys  Ser Lys Leu
    1010                 1015                 1020

Val Ser  Asp Phe Arg Lys Asp  Phe Gln Phe Tyr Lys  Val Arg Glu
    1025                 1030                 1035

Ile Asn  Asn Tyr His His Ala  His Asp Ala Tyr Leu  Asn Ala Val
    1040                 1045                 1050

Val Gly  Thr Ala Leu Ile Lys  Lys Tyr Pro Lys Leu  Glu Ser Glu
    1055                 1060                 1065

Phe Val  Tyr Gly Asp Tyr Lys  Val Tyr Asp Val Arg  Lys Met Ile
    1070                 1075                 1080

Ala Lys  Ser Glu Gln Glu Ile  Gly Lys Ala Thr Ala  Lys Tyr Phe
    1085                 1090                 1095

Phe Tyr  Ser Asn Ile Met Asn  Phe Phe Lys Thr Glu  Ile Thr Leu
    1100                 1105                 1110

Ala Asn  Gly Glu Ile Arg Lys  Arg Pro Leu Ile Glu  Thr Asn Gly
    1115                 1120                 1125

Glu Thr  Gly Glu Ile Val Trp  Asp Lys Gly Arg Asp  Phe Ala Thr
    1130                 1135                 1140

Val Arg  Lys Val Leu Ser Met  Pro Gln Val Asn Ile  Val Lys Lys
    1145                 1150                 1155

Thr Glu  Val Gln Thr Gly Gly  Phe Ser Lys Glu Ser  Ile Leu Pro
    1160                 1165                 1170

Lys Arg  Asn Ser Asp Lys Leu  Ile Ala Arg Lys Lys  Asp Trp Asp
    1175                 1180                 1185

Pro Lys  Lys Tyr Gly Gly Phe  Asp Ser Pro Thr Val  Ala Tyr Ser
    1190                 1195                 1200

Val Leu  Val Val Ala Lys Val  Glu Lys Gly Lys Ser  Lys Lys Leu
    1205                 1210                 1215

Lys Ser  Val Lys Glu Leu Leu  Gly Ile Thr Ile Met  Glu Arg Ser
    1220                 1225                 1230

Ser Phe  Glu Lys Asn Pro Ile  Asp Phe Leu Glu Ala  Lys Gly Tyr
    1235                 1240                 1245

Lys Glu  Val Lys Lys Asp Leu  Ile Ile Lys Leu Pro  Lys Tyr Ser
    1250                 1255                 1260

Leu Phe  Glu Leu Glu Asn Gly  Arg Lys Arg Met Leu  Ala Ser Ala
    1265                 1270                 1275

Gly Glu  Leu Gln Lys Gly Asn  Glu Leu Ala Leu Pro  Ser Lys Tyr
    1280                 1285                 1290

Val Asn  Phe Leu Tyr Leu Ala  Ser His Tyr Glu Lys  Leu Lys Gly
    1295                 1300                 1305

Ser Pro  Glu Asp Asn Glu Gln  Lys Gln Leu Phe Val  Glu Gln His
    1310                 1315                 1320

Lys His  Tyr Leu Asp Glu Ile  Ile Glu Gln Ile Ser  Glu Phe Ser
    1325                 1330                 1335

Lys Arg  Val Ile Leu Ala Asp  Ala Asn Leu Asp Lys  Val Leu Ser
    1340                 1345                 1350

Ala Tyr  Asn Lys His Arg Asp  Lys Pro Ile Arg Glu  Gln Ala Glu
    1355                 1360                 1365
```

```
Asn Ile  Ile His Leu Phe Thr  Leu Thr Asn Leu Gly  Ala Pro Ala
    1370                 1375                 1380

Ala Phe  Lys Tyr Phe Asp Thr  Thr Ile Asp Arg Lys  Arg Tyr Thr
    1385                 1390                 1395

Ser Thr  Lys Glu Val Leu Asp  Ala Thr Leu Ile His  Gln Ser Ile
    1400                 1405                 1410

Thr Gly  Leu Tyr Glu Thr Arg  Ile Asp Leu Ser Gln  Leu Gly Gly
    1415                 1420                 1425

Asp Ser  Arg Ala Asp Pro Lys  Lys Lys Arg Lys Val  Glu Phe Tyr
    1430                 1435                 1440

Pro Tyr  Asp Val Pro Asp Tyr  Ala
    1445                 1450
```

<210> SEQ ID NO 18
<211> LENGTH: 11
<212> TYPE: PRT
<213> ORGANISM: Artificial Sequence
<220> FEATURE:
<223> OTHER INFORMATION: penetrating peptide; AP

<400> SEQUENCE: 18

```
Arg Arg Arg Trp Cys Lys Arg Arg Arg Ala Ser
1               5                   10
```

<210> SEQ ID NO 19
<211> LENGTH: 1420
<212> TYPE: PRT
<213> ORGANISM: Artificial Sequence
<220> FEATURE:
<223> OTHER INFORMATION: penetrating peptide-linkage-Cas protein;
      AP-Cas9

<400> SEQUENCE: 19

```
Arg Arg Arg Trp Cys Lys Arg Arg Arg Ala Ser Leu Asp Ser Thr Ala
1               5                   10                  15

Pro Lys Lys Lys Arg Lys Val Gly Ile His Gly Val Pro Ala Ala Asp
            20                  25                  30

Lys Lys Tyr Ser Ile Gly Leu Asp Ile Gly Thr Asn Ser Val Gly Trp
        35                  40                  45

Ala Val Ile Thr Asp Glu Tyr Lys Val Pro Ser Lys Lys Phe Lys Val
    50                  55                  60

Leu Gly Asn Thr Asp Arg His Ser Ile Lys Lys Asn Leu Ile Gly Ala
65                  70                  75                  80

Leu Leu Phe Asp Ser Gly Glu Thr Ala Glu Ala Thr Arg Leu Lys Arg
                85                  90                  95

Thr Ala Arg Arg Arg Tyr Thr Arg Arg Lys Asn Arg Ile Cys Tyr Leu
            100                 105                 110

Gln Glu Ile Phe Ser Asn Glu Met Ala Lys Val Asp Asp Ser Phe Phe
        115                 120                 125

His Arg Leu Glu Glu Ser Phe Leu Val Glu Glu Asp Lys Lys His Glu
    130                 135                 140

Arg His Pro Ile Phe Gly Asn Ile Val Asp Glu Val Ala Tyr His Glu
145                 150                 155                 160

Lys Tyr Pro Thr Ile Tyr His Leu Arg Lys Lys Leu Val Asp Ser Thr
                165                 170                 175

Asp Lys Ala Asp Leu Arg Leu Ile Tyr Leu Ala Leu Ala His Met Ile
            180                 185                 190
```

```
Lys Phe Arg Gly His Phe Leu Ile Glu Gly Asp Leu Asn Pro Asp Asn
        195                 200                 205

Ser Asp Val Asp Lys Leu Phe Ile Gln Leu Val Gln Thr Tyr Asn Gln
    210                 215                 220

Leu Phe Glu Glu Asn Pro Ile Asn Ala Ser Gly Val Asp Ala Lys Ala
225                 230                 235                 240

Ile Leu Ser Ala Arg Leu Ser Lys Ser Arg Arg Leu Glu Asn Leu Ile
            245                 250                 255

Ala Gln Leu Pro Gly Glu Lys Lys Asn Gly Leu Phe Gly Asn Leu Ile
            260                 265                 270

Ala Leu Ser Leu Gly Leu Thr Pro Asn Phe Lys Ser Asn Phe Asp Leu
        275                 280                 285

Ala Glu Asp Ala Lys Leu Gln Leu Ser Lys Asp Thr Tyr Asp Asp Asp
    290                 295                 300

Leu Asp Asn Leu Leu Ala Gln Ile Gly Asp Gln Tyr Ala Asp Leu Phe
305                 310                 315                 320

Leu Ala Ala Lys Asn Leu Ser Asp Ala Ile Leu Leu Ser Asp Ile Leu
                325                 330                 335

Arg Val Asn Thr Glu Ile Thr Lys Ala Pro Leu Ser Ala Ser Met Ile
            340                 345                 350

Lys Arg Tyr Asp Glu His His Gln Asp Leu Thr Leu Leu Lys Ala Leu
        355                 360                 365

Val Arg Gln Gln Leu Pro Glu Lys Tyr Lys Glu Ile Phe Phe Asp Gln
    370                 375                 380

Ser Lys Asn Gly Tyr Ala Gly Tyr Ile Asp Gly Gly Ala Ser Gln Glu
385                 390                 395                 400

Glu Phe Tyr Lys Phe Ile Lys Pro Ile Leu Glu Lys Met Asp Gly Thr
                405                 410                 415

Glu Glu Leu Leu Val Lys Leu Asn Arg Glu Asp Leu Leu Arg Lys Gln
            420                 425                 430

Arg Thr Phe Asp Asn Gly Ser Ile Pro His Gln Ile His Leu Gly Glu
        435                 440                 445

Leu His Ala Ile Leu Arg Arg Gln Glu Asp Phe Tyr Pro Phe Leu Lys
    450                 455                 460

Asp Asn Arg Glu Lys Ile Glu Lys Ile Leu Thr Phe Arg Ile Pro Tyr
465                 470                 475                 480

Tyr Val Gly Pro Leu Ala Arg Gly Asn Ser Arg Phe Ala Trp Met Thr
                485                 490                 495

Arg Lys Ser Glu Glu Thr Ile Thr Pro Trp Asn Phe Glu Glu Val Val
            500                 505                 510

Asp Lys Gly Ala Ser Ala Gln Ser Phe Ile Glu Arg Met Thr Asn Phe
        515                 520                 525

Asp Lys Asn Leu Pro Asn Glu Lys Val Leu Pro Lys His Ser Leu Leu
    530                 535                 540

Tyr Glu Tyr Phe Thr Val Tyr Asn Glu Leu Thr Lys Val Lys Tyr Val
545                 550                 555                 560

Thr Glu Gly Met Arg Lys Pro Ala Phe Leu Ser Gly Glu Gln Lys Lys
                565                 570                 575

Ala Ile Val Asp Leu Leu Phe Lys Thr Asn Arg Lys Val Thr Val Lys
            580                 585                 590

Gln Leu Lys Glu Asp Tyr Phe Lys Lys Ile Glu Cys Phe Asp Ser Val
        595                 600                 605

Glu Ile Ser Gly Val Glu Asp Arg Phe Asn Ala Ser Leu Gly Thr Tyr
```

```
    610                 615                 620

His Asp Leu Leu Lys Ile Ile Lys Asp Lys Asp Phe Leu Asp Asn Glu
625                 630                 635                 640

Glu Asn Glu Asp Ile Leu Glu Asp Ile Val Leu Thr Leu Thr Leu Phe
                645                 650                 655

Glu Asp Arg Glu Met Ile Glu Glu Arg Leu Lys Thr Tyr Ala His Leu
            660                 665                 670

Phe Asp Asp Lys Val Met Lys Gln Leu Lys Arg Arg Arg Tyr Thr Gly
        675                 680                 685

Trp Gly Arg Leu Ser Arg Lys Leu Ile Asn Gly Ile Arg Asp Lys Gln
    690                 695                 700

Ser Gly Lys Thr Ile Leu Asp Phe Leu Lys Ser Asp Gly Phe Ala Asn
705                 710                 715                 720

Arg Asn Phe Met Gln Leu Ile His Asp Asp Ser Leu Thr Phe Lys Glu
                725                 730                 735

Asp Ile Gln Lys Ala Gln Val Ser Gly Gln Gly Asp Ser Leu His Glu
            740                 745                 750

His Ile Ala Asn Leu Ala Gly Ser Pro Ala Ile Lys Lys Gly Ile Leu
        755                 760                 765

Gln Thr Val Lys Val Val Asp Glu Leu Val Lys Val Met Gly Arg His
    770                 775                 780

Lys Pro Glu Asn Ile Val Ile Glu Met Ala Arg Glu Asn Gln Thr Thr
785                 790                 795                 800

Gln Lys Gly Gln Lys Asn Ser Arg Glu Arg Met Lys Arg Ile Glu Glu
                805                 810                 815

Gly Ile Lys Glu Leu Gly Ser Gln Ile Leu Lys Glu His Pro Val Glu
            820                 825                 830

Asn Thr Gln Leu Gln Asn Glu Lys Leu Tyr Leu Tyr Tyr Leu Gln Asn
        835                 840                 845

Gly Arg Asp Met Tyr Val Asp Gln Glu Leu Asp Ile Asn Arg Leu Ser
    850                 855                 860

Asp Tyr Asp Val Asp His Ile Val Pro Gln Ser Phe Leu Lys Asp Asp
865                 870                 875                 880

Ser Ile Asp Asn Lys Val Leu Thr Arg Ser Asp Lys Asn Arg Gly Lys
                885                 890                 895

Ser Asp Asn Val Pro Ser Glu Glu Val Val Lys Lys Met Lys Asn Tyr
            900                 905                 910

Trp Arg Gln Leu Leu Asn Ala Lys Leu Ile Thr Gln Arg Lys Phe Asp
        915                 920                 925

Asn Leu Thr Lys Ala Glu Arg Gly Gly Leu Ser Glu Leu Asp Lys Ala
    930                 935                 940

Gly Phe Ile Lys Arg Gln Leu Val Glu Thr Arg Gln Ile Thr Lys His
945                 950                 955                 960

Val Ala Gln Ile Leu Asp Ser Arg Met Asn Thr Lys Tyr Asp Glu Asn
                965                 970                 975

Asp Lys Leu Ile Arg Glu Val Lys Val Ile Thr Leu Lys Ser Lys Leu
            980                 985                 990

Val Ser Asp Phe Arg Lys Asp Phe  Gln Phe Tyr Lys Val  Arg Glu Ile
        995                 1000                1005

Asn Asn  Tyr His His Ala His  Asp Ala Tyr Leu Asn  Ala Val Val
    1010                1015                1020

Gly Thr  Ala Leu Ile Lys Lys  Tyr Pro Lys Leu Glu  Ser Glu Phe
    1025                1030                1035
```

```
Val Tyr  Gly Asp Tyr Lys Val  Tyr Asp Val Arg Lys  Met Ile Ala
    1040                 1045                 1050

Lys Ser  Glu Gln Glu Ile Gly  Lys Ala Thr Ala Lys  Tyr Phe Phe
    1055                 1060                 1065

Tyr Ser  Asn Ile Met Asn Phe  Phe Lys Thr Glu Ile  Thr Leu Ala
    1070                 1075                 1080

Asn Gly  Glu Ile Arg Lys Arg  Pro Leu Ile Glu Thr  Asn Gly Glu
    1085                 1090                 1095

Thr Gly  Glu Ile Val Trp Asp  Lys Gly Arg Asp Phe  Ala Thr Val
    1100                 1105                 1110

Arg Lys  Val Leu Ser Met Pro  Gln Val Asn Ile Val  Lys Lys Thr
    1115                 1120                 1125

Glu Val  Gln Thr Gly Gly Phe  Ser Lys Glu Ser Ile  Leu Pro Lys
    1130                 1135                 1140

Arg Asn  Ser Asp Lys Leu Ile  Ala Arg Lys Lys Asp  Trp Asp Pro
    1145                 1150                 1155

Lys Lys  Tyr Gly Gly Phe Asp  Ser Pro Thr Val Ala  Tyr Ser Val
    1160                 1165                 1170

Leu Val  Val Ala Lys Val Glu  Lys Gly Lys Ser Lys  Lys Leu Lys
    1175                 1180                 1185

Ser Val  Lys Glu Leu Leu Gly  Ile Thr Ile Met Glu  Arg Ser Ser
    1190                 1195                 1200

Phe Glu  Lys Asn Pro Ile Asp  Phe Leu Glu Ala Lys  Gly Tyr Lys
    1205                 1210                 1215

Glu Val  Lys Lys Asp Leu Ile  Ile Lys Leu Pro Lys  Tyr Ser Leu
    1220                 1225                 1230

Phe Glu  Leu Glu Asn Gly Arg  Lys Arg Met Leu Ala  Ser Ala Gly
    1235                 1240                 1245

Glu Leu  Gln Lys Gly Asn Glu  Leu Ala Leu Pro Ser  Lys Tyr Val
    1250                 1255                 1260

Asn Phe  Leu Tyr Leu Ala Ser  His Tyr Glu Lys Leu  Lys Gly Ser
    1265                 1270                 1275

Pro Glu  Asp Asn Glu Gln Lys  Gln Leu Phe Val Glu  Gln His Lys
    1280                 1285                 1290

His Tyr  Leu Asp Glu Ile Ile  Glu Gln Ile Ser Glu  Phe Ser Lys
    1295                 1300                 1305

Arg Val  Ile Leu Ala Asp Ala  Asn Leu Asp Lys Val  Leu Ser Ala
    1310                 1315                 1320

Tyr Asn  Lys His Arg Asp Lys  Pro Ile Arg Glu Gln  Ala Glu Asn
    1325                 1330                 1335

Ile Ile  His Leu Phe Thr Leu  Thr Asn Leu Gly Ala  Pro Ala Ala
    1340                 1345                 1350

Phe Lys  Tyr Phe Asp Thr Thr  Ile Asp Arg Lys Arg  Tyr Thr Ser
    1355                 1360                 1365

Thr Lys  Glu Val Leu Asp Ala  Thr Leu Ile His Gln  Ser Ile Thr
    1370                 1375                 1380

Gly Leu  Tyr Glu Thr Arg Ile  Asp Leu Ser Gln Leu  Gly Gly Asp
    1385                 1390                 1395

Ser Arg  Ala Asp Pro Lys Lys  Lys Arg Lys Val Glu  Phe Tyr Pro
    1400                 1405                 1410

Tyr Asp  Val Pro Asp Tyr Ala
    1415                 1420
```

<210> SEQ ID NO 20
<211> LENGTH: 24
<212> TYPE: PRT
<213> ORGANISM: Artificial Sequence
<220> FEATURE:
<223> OTHER INFORMATION: penetrating peptide; dNP2

<400> SEQUENCE: 20

Lys Ile Lys Lys Val Lys Lys Lys Gly Arg Lys Gly Ser Lys Ile Lys
1 5 10 15

Lys Val Lys Lys Lys Gly Arg Lys
20

<210> SEQ ID NO 21
<211> LENGTH: 1435
<212> TYPE: PRT
<213> ORGANISM: Artificial Sequence
<220> FEATURE:
<223> OTHER INFORMATION: penetrating peptide-linkage-Cas protein; dNP2-Cas9

<400> SEQUENCE: 21

Lys Ile Lys Lys Val Lys Lys Lys Gly Arg Lys Gly Ser Lys Ile Lys
1 5 10 15

Lys Val Lys Lys Lys Gly Arg Lys Ala Ser Leu Asp Ser Thr Ala Pro
20 25 30

Lys Lys Lys Arg Lys Val Gly Ile His Gly Val Pro Ala Ala Asp Lys
35 40 45

Lys Tyr Ser Ile Gly Leu Asp Ile Gly Thr Asn Ser Val Gly Trp Ala
50 55 60

Val Ile Thr Asp Glu Tyr Lys Val Pro Ser Lys Lys Phe Lys Val Leu
65 70 75 80

Gly Asn Thr Asp Arg His Ser Ile Lys Lys Asn Leu Ile Gly Ala Leu
85 90 95

Leu Phe Asp Ser Gly Glu Thr Ala Glu Ala Thr Arg Leu Lys Arg Thr
100 105 110

Ala Arg Arg Arg Tyr Thr Arg Arg Lys Asn Arg Ile Cys Tyr Leu Gln
115 120 125

Glu Ile Phe Ser Asn Glu Met Ala Lys Val Asp Asp Ser Phe Phe His
130 135 140

Arg Leu Glu Glu Ser Phe Leu Val Glu Glu Asp Lys Lys His Glu Arg
145 150 155 160

His Pro Ile Phe Gly Asn Ile Val Asp Glu Val Ala Tyr His Glu Lys
165 170 175

Tyr Pro Thr Ile Tyr His Leu Arg Lys Lys Leu Val Asp Ser Thr Asp
180 185 190

Lys Ala Asp Leu Arg Leu Ile Tyr Leu Ala Leu Ala His Met Ile Lys
195 200 205

Phe Arg Gly His Phe Leu Ile Glu Gly Asp Leu Asn Pro Asp Asn Ser
210 215 220

Asp Val Asp Lys Leu Phe Ile Gln Leu Val Gln Thr Tyr Asn Gln Leu
225 230 235 240

Phe Glu Glu Asn Pro Ile Asn Ala Ser Gly Val Asp Ala Lys Ala Ile
245 250 255

Leu Ser Ala Arg Leu Ser Lys Ser Arg Arg Leu Glu Asn Leu Ile Ala
260 265 270

Gln Leu Pro Gly Glu Lys Lys Asn Gly Leu Phe Gly Asn Leu Ile Ala

```
        275                 280                 285

Leu Ser Leu Gly Leu Thr Pro Asn Phe Lys Ser Asn Phe Asp Leu Ala
    290                 295                 300

Glu Asp Ala Lys Leu Gln Leu Ser Lys Asp Thr Tyr Asp Asp Asp Leu
305                 310                 315                 320

Asp Asn Leu Leu Ala Gln Ile Gly Asp Gln Tyr Ala Asp Leu Phe Leu
                325                 330                 335

Ala Ala Lys Asn Leu Ser Asp Ala Ile Leu Leu Ser Asp Ile Leu Arg
            340                 345                 350

Val Asn Thr Glu Ile Thr Lys Ala Pro Leu Ser Ala Ser Met Ile Lys
        355                 360                 365

Arg Tyr Asp Glu His His Gln Asp Leu Thr Leu Leu Lys Ala Leu Val
    370                 375                 380

Arg Gln Gln Leu Pro Glu Lys Tyr Lys Glu Ile Phe Phe Asp Gln Ser
385                 390                 395                 400

Lys Asn Gly Tyr Ala Gly Tyr Ile Asp Gly Gly Ala Ser Gln Glu Glu
                405                 410                 415

Phe Tyr Lys Phe Ile Lys Pro Ile Leu Glu Lys Met Asp Gly Thr Glu
            420                 425                 430

Glu Leu Leu Val Lys Leu Asn Arg Glu Asp Leu Leu Arg Lys Gln Arg
        435                 440                 445

Thr Phe Asp Asn Gly Ser Ile Pro His Gln Ile His Leu Gly Glu Leu
    450                 455                 460

His Ala Ile Leu Arg Arg Gln Glu Asp Phe Tyr Pro Phe Leu Lys Asp
465                 470                 475                 480

Asn Arg Glu Lys Ile Glu Lys Ile Leu Thr Phe Arg Ile Pro Tyr Tyr
                485                 490                 495

Val Gly Pro Leu Ala Arg Gly Asn Ser Arg Phe Ala Trp Met Thr Arg
            500                 505                 510

Lys Ser Glu Glu Thr Ile Thr Pro Trp Asn Phe Glu Glu Val Val Asp
        515                 520                 525

Lys Gly Ala Ser Ala Gln Ser Phe Ile Glu Arg Met Thr Asn Phe Asp
    530                 535                 540

Lys Asn Leu Pro Asn Glu Lys Val Leu Pro Lys His Ser Leu Leu Tyr
545                 550                 555                 560

Glu Tyr Phe Thr Val Tyr Asn Glu Leu Thr Lys Val Lys Tyr Val Thr
                565                 570                 575

Glu Gly Met Arg Lys Pro Ala Phe Leu Ser Gly Glu Gln Lys Lys Ala
            580                 585                 590

Ile Val Asp Leu Leu Phe Lys Thr Asn Arg Lys Val Thr Val Lys Gln
        595                 600                 605

Leu Lys Glu Asp Tyr Phe Lys Lys Ile Glu Cys Phe Asp Ser Val Glu
    610                 615                 620

Ile Ser Gly Val Glu Asp Arg Phe Asn Ala Ser Leu Gly Thr Tyr His
625                 630                 635                 640

Asp Leu Leu Lys Ile Ile Lys Asp Lys Asp Phe Leu Asp Asn Glu Glu
                645                 650                 655

Asn Glu Asp Ile Leu Glu Asp Ile Val Leu Thr Leu Thr Leu Phe Glu
            660                 665                 670

Asp Arg Glu Met Ile Glu Glu Arg Leu Lys Thr Tyr Ala His Leu Phe
        675                 680                 685

Asp Asp Lys Val Met Lys Gln Leu Lys Arg Arg Arg Tyr Thr Gly Trp
    690                 695                 700
```

```
Gly Arg Leu Ser Arg Lys Leu Ile Asn Gly Ile Arg Asp Lys Gln Ser
705                 710                 715                 720

Gly Lys Thr Ile Leu Asp Phe Leu Lys Ser Asp Gly Phe Ala Asn Arg
                725                 730                 735

Asn Phe Met Gln Leu Ile His Asp Asp Ser Leu Thr Phe Lys Glu Asp
            740                 745                 750

Ile Gln Lys Ala Gln Val Ser Gly Gln Gly Asp Ser Leu His Glu His
        755                 760                 765

Ile Ala Asn Leu Ala Gly Ser Pro Ala Ile Lys Lys Gly Ile Leu Gln
    770                 775                 780

Thr Val Lys Val Val Asp Glu Leu Val Lys Val Met Gly Arg His Lys
785                 790                 795                 800

Pro Glu Asn Ile Val Ile Glu Met Ala Arg Glu Asn Gln Thr Thr Gln
                805                 810                 815

Lys Gly Gln Lys Asn Ser Arg Glu Arg Met Lys Arg Ile Glu Glu Gly
            820                 825                 830

Ile Lys Glu Leu Gly Ser Gln Ile Leu Lys Glu His Pro Val Glu Asn
        835                 840                 845

Thr Gln Leu Gln Asn Glu Lys Leu Tyr Leu Tyr Tyr Leu Gln Asn Gly
    850                 855                 860

Arg Asp Met Tyr Val Asp Gln Glu Leu Asp Ile Asn Arg Leu Ser Asp
865                 870                 875                 880

Tyr Asp Val Asp His Ile Val Pro Gln Ser Phe Leu Lys Asp Asp Ser
                885                 890                 895

Ile Asp Asn Lys Val Leu Thr Arg Ser Asp Lys Asn Arg Gly Lys Ser
            900                 905                 910

Asp Asn Val Pro Ser Glu Glu Val Val Lys Lys Met Lys Asn Tyr Trp
        915                 920                 925

Arg Gln Leu Leu Asn Ala Lys Leu Ile Thr Gln Arg Lys Phe Asp Asn
    930                 935                 940

Leu Thr Lys Ala Glu Arg Gly Gly Leu Ser Glu Leu Asp Lys Ala Gly
945                 950                 955                 960

Phe Ile Lys Arg Gln Leu Val Glu Thr Arg Gln Ile Thr Lys His Val
                965                 970                 975

Ala Gln Ile Leu Asp Ser Arg Met Asn Thr Lys Tyr Asp Glu Asn Asp
            980                 985                 990

Lys Leu Ile Arg Glu Val Lys Val  Ile Thr Leu Lys Ser  Lys Leu Val
        995                 1000                1005

Ser Asp  Phe Arg Lys Asp Phe  Gln Phe Tyr Lys Val  Arg Glu Ile
    1010                1015                1020

Asn Asn  Tyr His His Ala His  Asp Ala Tyr Leu Asn  Ala Val Val
    1025                1030                1035

Gly Thr  Ala Leu Ile Lys Lys  Tyr Pro Lys Leu Glu  Ser Glu Phe
    1040                1045                1050

Val Tyr  Gly Asp Tyr Lys Val  Tyr Asp Val Arg Lys  Met Ile Ala
    1055                1060                1065

Lys Ser  Glu Gln Glu Ile Gly  Lys Ala Thr Ala Lys  Tyr Phe Phe
    1070                1075                1080

Tyr Ser  Asn Ile Met Asn Phe  Phe Lys Thr Glu Ile  Thr Leu Ala
    1085                1090                1095

Asn Gly  Glu Ile Arg Lys Arg  Pro Leu Ile Glu Thr  Asn Gly Glu
    1100                1105                1110
```

Thr Gly Glu Ile Val Trp Asp Lys Gly Arg Asp Phe Ala Thr Val
1115 1120 1125

Arg Lys Val Leu Ser Met Pro Gln Val Asn Ile Val Lys Lys Thr
1130 1135 1140

Glu Val Gln Thr Gly Gly Phe Ser Lys Glu Ser Ile Leu Pro Lys
1145 1150 1155

Arg Asn Ser Asp Lys Leu Ile Ala Arg Lys Lys Asp Trp Asp Pro
1160 1165 1170

Lys Lys Tyr Gly Gly Phe Asp Ser Pro Thr Val Ala Tyr Ser Val
1175 1180 1185

Leu Val Val Ala Lys Val Glu Lys Gly Lys Ser Lys Lys Leu Lys
1190 1195 1200

Ser Val Lys Glu Leu Leu Gly Ile Thr Ile Met Glu Arg Ser Ser
1205 1210 1215

Phe Glu Lys Asn Pro Ile Asp Phe Leu Glu Ala Lys Gly Tyr Lys
1220 1225 1230

Glu Val Lys Lys Asp Leu Ile Ile Lys Leu Pro Lys Tyr Ser Leu
1235 1240 1245

Phe Glu Leu Glu Asn Gly Arg Lys Arg Met Leu Ala Ser Ala Gly
1250 1255 1260

Glu Leu Gln Lys Gly Asn Glu Leu Ala Leu Pro Ser Lys Tyr Val
1265 1270 1275

Asn Phe Leu Tyr Leu Ala Ser His Tyr Glu Lys Leu Lys Gly Ser
1280 1285 1290

Pro Glu Asp Asn Glu Gln Lys Gln Leu Phe Val Glu Gln His Lys
1295 1300 1305

His Tyr Leu Asp Glu Ile Ile Glu Gln Ile Ser Glu Phe Ser Lys
1310 1315 1320

Arg Val Ile Leu Ala Asp Ala Asn Leu Asp Lys Val Leu Ser Ala
1325 1330 1335

Tyr Asn Lys His Arg Asp Lys Pro Ile Arg Glu Gln Ala Glu Asn
1340 1345 1350

Ile Ile His Leu Phe Thr Leu Thr Asn Leu Gly Ala Pro Ala Ala
1355 1360 1365

Phe Lys Tyr Phe Asp Thr Thr Ile Asp Arg Lys Arg Tyr Thr Ser
1370 1375 1380

Thr Lys Glu Val Leu Asp Ala Thr Leu Ile His Gln Ser Ile Thr
1385 1390 1395

Gly Leu Tyr Glu Thr Arg Ile Asp Leu Ser Gln Leu Gly Gly Asp
1400 1405 1410

Ser Arg Ala Asp Pro Lys Lys Lys Arg Lys Val Glu Phe Tyr Pro
1415 1420 1425

Tyr Asp Val Pro Asp Tyr Ala
1430 1435

<210> SEQ ID NO 22
<211> LENGTH: 51
<212> TYPE: PRT
<213> ORGANISM: Artificial Sequence
<220> FEATURE:
<223> OTHER INFORMATION: penetrating peptide; dNP2-HE

<400> SEQUENCE: 22

Lys Ile Lys Lys Val Lys Lys Lys Gly Arg Lys Gly Ser Lys Ile Lys
1 5 10 15

```
Lys Val Lys Lys Lys Gly Arg Lys Ala Ser Gly Gly Gly Gly Gly His
            20                  25                  30

Glu His Glu His Glu His Glu His Glu His Glu His Glu His Glu His
        35                  40                  45

Glu His Glu
    50


<210> SEQ ID NO 23
<211> LENGTH: 1460
<212> TYPE: PRT
<213> ORGANISM: Artificial Sequence
<220> FEATURE:
<223> OTHER INFORMATION: penetrating peptide-linkage-Cas protein;
      dNP2-HE10-Cas9

<400> SEQUENCE: 23

Lys Ile Lys Lys Val Lys Lys Lys Gly Arg Lys Gly Ser Lys Ile Lys
1               5                   10                  15

Lys Val Lys Lys Lys Gly Arg Lys Ala Ser Gly Gly Gly Gly Gly His
            20                  25                  30

Glu His Glu His Glu His Glu His Glu His Glu His Glu His Glu His
        35                  40                  45

Glu His Glu Leu Asp Ser Thr Ala Pro Lys Lys Lys Arg Lys Val Gly
    50                  55                  60

Ile His Gly Val Pro Ala Ala Asp Lys Lys Tyr Ser Ile Gly Leu Asp
65                  70                  75                  80

Ile Gly Thr Asn Ser Val Gly Trp Ala Val Ile Thr Asp Glu Tyr Lys
                85                  90                  95

Val Pro Ser Lys Lys Phe Lys Val Leu Gly Asn Thr Asp Arg His Ser
            100                 105                 110

Ile Lys Lys Asn Leu Ile Gly Ala Leu Leu Phe Asp Ser Gly Glu Thr
        115                 120                 125

Ala Glu Ala Thr Arg Leu Lys Arg Thr Ala Arg Arg Arg Tyr Thr Arg
    130                 135                 140

Arg Lys Asn Arg Ile Cys Tyr Leu Gln Glu Ile Phe Ser Asn Glu Met
145                 150                 155                 160

Ala Lys Val Asp Asp Ser Phe Phe His Arg Leu Glu Glu Ser Phe Leu
                165                 170                 175

Val Glu Glu Asp Lys Lys His Glu Arg His Pro Ile Phe Gly Asn Ile
            180                 185                 190

Val Asp Glu Val Ala Tyr His Glu Lys Tyr Pro Thr Ile Tyr His Leu
        195                 200                 205

Arg Lys Lys Leu Val Asp Ser Thr Asp Lys Ala Asp Leu Arg Leu Ile
    210                 215                 220

Tyr Leu Ala Leu Ala His Met Ile Lys Phe Arg Gly His Phe Leu Ile
225                 230                 235                 240

Glu Gly Asp Leu Asn Pro Asp Asn Ser Asp Val Asp Lys Leu Phe Ile
                245                 250                 255

Gln Leu Val Gln Thr Tyr Asn Gln Leu Phe Glu Glu Asn Pro Ile Asn
            260                 265                 270

Ala Ser Gly Val Asp Ala Lys Ala Ile Leu Ser Ala Arg Leu Ser Lys
        275                 280                 285

Ser Arg Arg Leu Glu Asn Leu Ile Ala Gln Leu Pro Gly Glu Lys Lys
    290                 295                 300

Asn Gly Leu Phe Gly Asn Leu Ile Ala Leu Ser Leu Gly Leu Thr Pro
305                 310                 315                 320
```

```
Asn Phe Lys Ser Asn Phe Asp Leu Ala Glu Asp Ala Lys Leu Gln Leu
                325                 330                 335

Ser Lys Asp Thr Tyr Asp Asp Asp Leu Asp Asn Leu Leu Ala Gln Ile
            340                 345                 350

Gly Asp Gln Tyr Ala Asp Leu Phe Leu Ala Ala Lys Asn Leu Ser Asp
        355                 360                 365

Ala Ile Leu Leu Ser Asp Ile Leu Arg Val Asn Thr Glu Ile Thr Lys
    370                 375                 380

Ala Pro Leu Ser Ala Ser Met Ile Lys Arg Tyr Asp Glu His His Gln
385                 390                 395                 400

Asp Leu Thr Leu Leu Lys Ala Leu Val Arg Gln Gln Leu Pro Glu Lys
                405                 410                 415

Tyr Lys Glu Ile Phe Phe Asp Gln Ser Lys Asn Gly Tyr Ala Gly Tyr
            420                 425                 430

Ile Asp Gly Gly Ala Ser Gln Glu Glu Phe Tyr Lys Phe Ile Lys Pro
        435                 440                 445

Ile Leu Glu Lys Met Asp Gly Thr Glu Glu Leu Leu Val Lys Leu Asn
    450                 455                 460

Arg Glu Asp Leu Leu Arg Lys Gln Arg Thr Phe Asp Asn Gly Ser Ile
465                 470                 475                 480

Pro His Gln Ile His Leu Gly Glu Leu His Ala Ile Leu Arg Arg Gln
                485                 490                 495

Glu Asp Phe Tyr Pro Phe Leu Lys Asp Asn Arg Glu Lys Ile Glu Lys
            500                 505                 510

Ile Leu Thr Phe Arg Ile Pro Tyr Tyr Val Gly Pro Leu Ala Arg Gly
        515                 520                 525

Asn Ser Arg Phe Ala Trp Met Thr Arg Lys Ser Glu Glu Thr Ile Thr
    530                 535                 540

Pro Trp Asn Phe Glu Glu Val Val Asp Lys Gly Ala Ser Ala Gln Ser
545                 550                 555                 560

Phe Ile Glu Arg Met Thr Asn Phe Asp Lys Asn Leu Pro Asn Glu Lys
                565                 570                 575

Val Leu Pro Lys His Ser Leu Leu Tyr Glu Tyr Phe Thr Val Tyr Asn
            580                 585                 590

Glu Leu Thr Lys Val Lys Tyr Val Thr Glu Gly Met Arg Lys Pro Ala
        595                 600                 605

Phe Leu Ser Gly Glu Gln Lys Lys Ala Ile Val Asp Leu Leu Phe Lys
    610                 615                 620

Thr Asn Arg Lys Val Thr Val Lys Gln Leu Lys Glu Asp Tyr Phe Lys
625                 630                 635                 640

Lys Ile Glu Cys Phe Asp Ser Val Glu Ile Ser Gly Val Glu Asp Arg
                645                 650                 655

Phe Asn Ala Ser Leu Gly Thr Tyr His Asp Leu Leu Lys Ile Ile Lys
            660                 665                 670

Asp Lys Asp Phe Leu Asp Asn Glu Glu Asn Glu Asp Ile Leu Glu Asp
        675                 680                 685

Ile Val Leu Thr Leu Thr Leu Phe Glu Asp Arg Glu Met Ile Glu Glu
    690                 695                 700

Arg Leu Lys Thr Tyr Ala His Leu Phe Asp Asp Lys Val Met Lys Gln
705                 710                 715                 720

Leu Lys Arg Arg Arg Tyr Thr Gly Trp Gly Arg Leu Ser Arg Lys Leu
                725                 730                 735
```

```
Ile Asn Gly Ile Arg Asp Lys Gln Ser Gly Lys Thr Ile Leu Asp Phe
            740                 745                 750

Leu Lys Ser Asp Gly Phe Ala Asn Arg Asn Phe Met Gln Leu Ile His
        755                 760                 765

Asp Asp Ser Leu Thr Phe Lys Glu Asp Ile Gln Lys Ala Gln Val Ser
    770                 775                 780

Gly Gln Gly Asp Ser Leu His Glu His Ile Ala Asn Leu Ala Gly Ser
785                 790                 795                 800

Pro Ala Ile Lys Lys Gly Ile Leu Gln Thr Val Lys Val Val Asp Glu
                805                 810                 815

Leu Val Lys Val Met Gly Arg His Lys Pro Glu Asn Ile Val Ile Glu
            820                 825                 830

Met Ala Arg Glu Asn Gln Thr Thr Gln Lys Gly Gln Lys Asn Ser Arg
        835                 840                 845

Glu Arg Met Lys Arg Ile Glu Glu Gly Ile Lys Glu Leu Gly Ser Gln
    850                 855                 860

Ile Leu Lys Glu His Pro Val Glu Asn Thr Gln Leu Gln Asn Glu Lys
865                 870                 875                 880

Leu Tyr Leu Tyr Tyr Leu Gln Asn Gly Arg Asp Met Tyr Val Asp Gln
                885                 890                 895

Glu Leu Asp Ile Asn Arg Leu Ser Asp Tyr Asp Val Asp His Ile Val
            900                 905                 910

Pro Gln Ser Phe Leu Lys Asp Asp Ser Ile Asp Asn Lys Val Leu Thr
        915                 920                 925

Arg Ser Asp Lys Asn Arg Gly Lys Ser Asp Asn Val Pro Ser Glu Glu
    930                 935                 940

Val Val Lys Lys Met Lys Asn Tyr Trp Arg Gln Leu Leu Asn Ala Lys
945                 950                 955                 960

Leu Ile Thr Gln Arg Lys Phe Asp Asn Leu Thr Lys Ala Glu Arg Gly
                965                 970                 975

Gly Leu Ser Glu Leu Asp Lys Ala Gly Phe Ile Lys Arg Gln Leu Val
            980                 985                 990

Glu Thr Arg Gln Ile Thr Lys His  Val Ala Gln Ile Leu  Asp Ser Arg
        995                 1000                1005

Met Asn  Thr Lys Tyr Asp Glu  Asn Asp Lys Leu Ile  Arg Glu Val
    1010                1015                1020

Lys Val  Ile Thr Leu Lys Ser  Lys Leu Val Ser Asp  Phe Arg Lys
    1025                1030                1035

Asp Phe  Gln Phe Tyr Lys Val  Arg Glu Ile Asn Asn  Tyr His His
    1040                1045                1050

Ala His  Asp Ala Tyr Leu Asn  Ala Val Val Gly Thr  Ala Leu Ile
    1055                1060                1065

Lys Lys  Tyr Pro Lys Leu Glu  Ser Glu Phe Val Tyr  Gly Asp Tyr
    1070                1075                1080

Lys Val  Tyr Asp Val Arg Lys  Met Ile Ala Lys Ser  Glu Gln Glu
    1085                1090                1095

Ile Gly  Lys Ala Thr Ala Lys  Tyr Phe Phe Tyr Ser  Asn Ile Met
    1100                1105                1110

Asn Phe  Phe Lys Thr Glu Ile  Thr Leu Ala Asn Gly  Glu Ile Arg
    1115                1120                1125

Lys Arg  Pro Leu Ile Glu Thr  Asn Gly Glu Thr Gly  Glu Ile Val
    1130                1135                1140

Trp Asp  Lys Gly Arg Asp Phe  Ala Thr Val Arg Lys  Val Leu Ser
```

```
    1145                1150                1155

Met Pro  Gln Val Asn Ile Val  Lys Lys Thr Glu Val  Gln Thr Gly
    1160                1165                1170

Gly Phe  Ser Lys Glu Ser Ile  Leu Pro Lys Arg Asn  Ser Asp Lys
    1175                1180                1185

Leu Ile  Ala Arg Lys Lys Asp  Trp Asp Pro Lys Lys  Tyr Gly Gly
    1190                1195                1200

Phe Asp  Ser Pro Thr Val Ala  Tyr Ser Val Leu Val  Val Ala Lys
    1205                1210                1215

Val Glu  Lys Gly Lys Ser Lys  Lys Leu Lys Ser Val  Lys Glu Leu
    1220                1225                1230

Leu Gly  Ile Thr Ile Met Glu  Arg Ser Ser Phe Glu  Lys Asn Pro
    1235                1240                1245

Ile Asp  Phe Leu Glu Ala Lys  Gly Tyr Lys Glu Val  Lys Lys Asp
    1250                1255                1260

Leu Ile  Ile Lys Leu Pro Lys  Tyr Ser Leu Phe Glu  Leu Glu Asn
    1265                1270                1275

Gly Arg  Lys Arg Met Leu Ala  Ser Ala Gly Glu Leu  Gln Lys Gly
    1280                1285                1290

Asn Glu  Leu Ala Leu Pro Ser  Lys Tyr Val Asn Phe  Leu Tyr Leu
    1295                1300                1305

Ala Ser  His Tyr Glu Lys Leu  Lys Gly Ser Pro Glu  Asp Asn Glu
    1310                1315                1320

Gln Lys  Gln Leu Phe Val Glu  Gln His Lys His Tyr  Leu Asp Glu
    1325                1330                1335

Ile Ile  Glu Gln Ile Ser Glu  Phe Ser Lys Arg Val  Ile Leu Ala
    1340                1345                1350

Asp Ala  Asn Leu Asp Lys Val  Leu Ser Ala Tyr Asn  Lys His Arg
    1355                1360                1365

Asp Lys  Pro Ile Arg Glu Gln  Ala Glu Asn Ile Ile  His Leu Phe
    1370                1375                1380

Thr Leu  Thr Asn Leu Gly Ala  Pro Ala Ala Phe Lys  Tyr Phe Asp
    1385                1390                1395

Thr Thr  Ile Asp Arg Lys Arg  Tyr Thr Ser Thr Lys  Glu Val Leu
    1400                1405                1410

Asp Ala  Thr Leu Ile His Gln  Ser Ile Thr Gly Leu  Tyr Glu Thr
    1415                1420                1425

Arg Ile  Asp Leu Ser Gln Leu  Gly Gly Asp Ser Arg  Ala Asp Pro
    1430                1435                1440

Lys Lys  Lys Arg Lys Val Glu  Phe Tyr Pro Tyr Asp  Val Pro Asp
    1445                1450                1455

Tyr Ala
    1460
```

<210> SEQ ID NO 24
<211> LENGTH: 9
<212> TYPE: PRT
<213> ORGANISM: Artificial Sequence
<220> FEATURE:
<223> OTHER INFORMATION: penetrating peptide; R9

<400> SEQUENCE: 24

```
Arg Arg Arg Arg Arg Arg Arg Arg Arg
1               5
```

```
<210> SEQ ID NO 25
<211> LENGTH: 1420
<212> TYPE: PRT
<213> ORGANISM: Artificial Sequence
<220> FEATURE:
<223> OTHER INFORMATION: penetrating peptide-linkage-Cas protein;
      R9-Cas9

<400> SEQUENCE: 25

Arg Arg Arg Arg Arg Arg Arg Arg Arg Ala Ser Leu Asp Ser Thr Ala
1               5                   10                  15

Pro Lys Lys Lys Arg Lys Val Gly Ile His Gly Val Pro Ala Ala Asp
            20                  25                  30

Lys Lys Tyr Ser Ile Gly Leu Asp Ile Gly Thr Asn Ser Val Gly Trp
        35                  40                  45

Ala Val Ile Thr Asp Glu Tyr Lys Val Pro Ser Lys Lys Phe Lys Val
    50                  55                  60

Leu Gly Asn Thr Asp Arg His Ser Ile Lys Lys Asn Leu Ile Gly Ala
65                  70                  75                  80

Leu Leu Phe Asp Ser Gly Glu Thr Ala Glu Ala Thr Arg Leu Lys Arg
                85                  90                  95

Thr Ala Arg Arg Arg Tyr Thr Arg Arg Lys Asn Arg Ile Cys Tyr Leu
            100                 105                 110

Gln Glu Ile Phe Ser Asn Glu Met Ala Lys Val Asp Asp Ser Phe Phe
        115                 120                 125

His Arg Leu Glu Glu Ser Phe Leu Val Glu Glu Asp Lys Lys His Glu
    130                 135                 140

Arg His Pro Ile Phe Gly Asn Ile Val Asp Glu Val Ala Tyr His Glu
145                 150                 155                 160

Lys Tyr Pro Thr Ile Tyr His Leu Arg Lys Lys Leu Val Asp Ser Thr
                165                 170                 175

Asp Lys Ala Asp Leu Arg Leu Ile Tyr Leu Ala Leu Ala His Met Ile
            180                 185                 190

Lys Phe Arg Gly His Phe Leu Ile Glu Gly Asp Leu Asn Pro Asp Asn
        195                 200                 205

Ser Asp Val Asp Lys Leu Phe Ile Gln Leu Val Gln Thr Tyr Asn Gln
    210                 215                 220

Leu Phe Glu Glu Asn Pro Ile Asn Ala Ser Gly Val Asp Ala Lys Ala
225                 230                 235                 240

Ile Leu Ser Ala Arg Leu Ser Lys Ser Arg Arg Leu Glu Asn Leu Ile
                245                 250                 255

Ala Gln Leu Pro Gly Glu Lys Lys Asn Gly Leu Phe Gly Asn Leu Ile
            260                 265                 270

Ala Leu Ser Leu Gly Leu Thr Pro Asn Phe Lys Ser Asn Phe Asp Leu
        275                 280                 285

Ala Glu Asp Ala Lys Leu Gln Leu Ser Lys Asp Thr Tyr Asp Asp Asp
    290                 295                 300

Leu Asp Asn Leu Leu Ala Gln Ile Gly Asp Gln Tyr Ala Asp Leu Phe
305                 310                 315                 320

Leu Ala Ala Lys Asn Leu Ser Asp Ala Ile Leu Leu Ser Asp Ile Leu
                325                 330                 335

Arg Val Asn Thr Glu Ile Thr Lys Ala Pro Leu Ser Ala Ser Met Ile
            340                 345                 350

Lys Arg Tyr Asp Glu His His Gln Asp Leu Thr Leu Leu Lys Ala Leu
        355                 360                 365
```

```
Val Arg Gln Gln Leu Pro Glu Lys Tyr Lys Glu Ile Phe Phe Asp Gln
    370                 375                 380

Ser Lys Asn Gly Tyr Ala Gly Tyr Ile Asp Gly Gly Ala Ser Gln Glu
385                 390                 395                 400

Glu Phe Tyr Lys Phe Ile Lys Pro Ile Leu Glu Lys Met Asp Gly Thr
                405                 410                 415

Glu Glu Leu Leu Val Lys Leu Asn Arg Glu Asp Leu Leu Arg Lys Gln
            420                 425                 430

Arg Thr Phe Asp Asn Gly Ser Ile Pro His Gln Ile His Leu Gly Glu
        435                 440                 445

Leu His Ala Ile Leu Arg Arg Gln Glu Asp Phe Tyr Pro Phe Leu Lys
    450                 455                 460

Asp Asn Arg Glu Lys Ile Glu Lys Ile Leu Thr Phe Arg Ile Pro Tyr
465                 470                 475                 480

Tyr Val Gly Pro Leu Ala Arg Gly Asn Ser Arg Phe Ala Trp Met Thr
                485                 490                 495

Arg Lys Ser Glu Glu Thr Ile Thr Pro Trp Asn Phe Glu Glu Val Val
            500                 505                 510

Asp Lys Gly Ala Ser Ala Gln Ser Phe Ile Glu Arg Met Thr Asn Phe
        515                 520                 525

Asp Lys Asn Leu Pro Asn Glu Lys Val Leu Pro Lys His Ser Leu Leu
    530                 535                 540

Tyr Glu Tyr Phe Thr Val Tyr Asn Glu Leu Thr Lys Val Lys Tyr Val
545                 550                 555                 560

Thr Glu Gly Met Arg Lys Pro Ala Phe Leu Ser Gly Glu Gln Lys Lys
                565                 570                 575

Ala Ile Val Asp Leu Leu Phe Lys Thr Asn Arg Lys Val Thr Val Lys
            580                 585                 590

Gln Leu Lys Glu Asp Tyr Phe Lys Lys Ile Glu Cys Phe Asp Ser Val
        595                 600                 605

Glu Ile Ser Gly Val Glu Asp Arg Phe Asn Ala Ser Leu Gly Thr Tyr
    610                 615                 620

His Asp Leu Leu Lys Ile Ile Lys Asp Lys Asp Phe Leu Asp Asn Glu
625                 630                 635                 640

Glu Asn Glu Asp Ile Leu Glu Asp Ile Val Leu Thr Leu Thr Leu Phe
                645                 650                 655

Glu Asp Arg Glu Met Ile Glu Glu Arg Leu Lys Thr Tyr Ala His Leu
            660                 665                 670

Phe Asp Asp Lys Val Met Lys Gln Leu Lys Arg Arg Arg Tyr Thr Gly
        675                 680                 685

Trp Gly Arg Leu Ser Arg Lys Leu Ile Asn Gly Ile Arg Asp Lys Gln
    690                 695                 700

Ser Gly Lys Thr Ile Leu Asp Phe Leu Lys Ser Asp Gly Phe Ala Asn
705                 710                 715                 720

Arg Asn Phe Met Gln Leu Ile His Asp Asp Ser Leu Thr Phe Lys Glu
                725                 730                 735

Asp Ile Gln Lys Ala Gln Val Ser Gly Gln Gly Asp Ser Leu His Glu
            740                 745                 750

His Ile Ala Asn Leu Ala Gly Ser Pro Ala Ile Lys Lys Gly Ile Leu
        755                 760                 765

Gln Thr Val Lys Val Val Asp Glu Leu Val Lys Val Met Gly Arg His
    770                 775                 780

Lys Pro Glu Asn Ile Val Ile Glu Met Ala Arg Glu Asn Gln Thr Thr
```

785 790 795 800

Gln Lys Gly Gln Lys Asn Ser Arg Glu Arg Met Lys Arg Ile Glu Glu
805 810 815

Gly Ile Lys Glu Leu Gly Ser Gln Ile Leu Lys Glu His Pro Val Glu
820 825 830

Asn Thr Gln Leu Gln Asn Glu Lys Leu Tyr Leu Tyr Tyr Leu Gln Asn
835 840 845

Gly Arg Asp Met Tyr Val Asp Gln Glu Leu Asp Ile Asn Arg Leu Ser
850 855 860

Asp Tyr Asp Val Asp His Ile Val Pro Gln Ser Phe Leu Lys Asp Asp
865 870 875 880

Ser Ile Asp Asn Lys Val Leu Thr Arg Ser Asp Lys Asn Arg Gly Lys
885 890 895

Ser Asp Asn Val Pro Ser Glu Glu Val Val Lys Lys Met Lys Asn Tyr
900 905 910

Trp Arg Gln Leu Leu Asn Ala Lys Leu Ile Thr Gln Arg Lys Phe Asp
915 920 925

Asn Leu Thr Lys Ala Glu Arg Gly Gly Leu Ser Glu Leu Asp Lys Ala
930 935 940

Gly Phe Ile Lys Arg Gln Leu Val Glu Thr Arg Gln Ile Thr Lys His
945 950 955 960

Val Ala Gln Ile Leu Asp Ser Arg Met Asn Thr Lys Tyr Asp Glu Asn
965 970 975

Asp Lys Leu Ile Arg Glu Val Lys Val Ile Thr Leu Lys Ser Lys Leu
980 985 990

Val Ser Asp Phe Arg Lys Asp Phe Gln Phe Tyr Lys Val Arg Glu Ile
995 1000 1005

Asn Asn Tyr His His Ala His Asp Ala Tyr Leu Asn Ala Val Val
1010 1015 1020

Gly Thr Ala Leu Ile Lys Lys Tyr Pro Lys Leu Glu Ser Glu Phe
1025 1030 1035

Val Tyr Gly Asp Tyr Lys Val Tyr Asp Val Arg Lys Met Ile Ala
1040 1045 1050

Lys Ser Glu Gln Glu Ile Gly Lys Ala Thr Ala Lys Tyr Phe Phe
1055 1060 1065

Tyr Ser Asn Ile Met Asn Phe Phe Lys Thr Glu Ile Thr Leu Ala
1070 1075 1080

Asn Gly Glu Ile Arg Lys Arg Pro Leu Ile Glu Thr Asn Gly Glu
1085 1090 1095

Thr Gly Glu Ile Val Trp Asp Lys Gly Arg Asp Phe Ala Thr Val
1100 1105 1110

Arg Lys Val Leu Ser Met Pro Gln Val Asn Ile Val Lys Lys Thr
1115 1120 1125

Glu Val Gln Thr Gly Gly Phe Ser Lys Glu Ser Ile Leu Pro Lys
1130 1135 1140

Arg Asn Ser Asp Lys Leu Ile Ala Arg Lys Lys Asp Trp Asp Pro
1145 1150 1155

Lys Lys Tyr Gly Gly Phe Asp Ser Pro Thr Val Ala Tyr Ser Val
1160 1165 1170

Leu Val Val Ala Lys Val Glu Lys Gly Lys Ser Lys Lys Leu Lys
1175 1180 1185

Ser Val Lys Glu Leu Leu Gly Ile Thr Ile Met Glu Arg Ser Ser
1190 1195 1200

Phe Glu Lys Asn Pro Ile Asp Phe Leu Glu Ala Lys Gly Tyr Lys
1205 1210 1215

Glu Val Lys Lys Asp Leu Ile Ile Lys Leu Pro Lys Tyr Ser Leu
1220 1225 1230

Phe Glu Leu Glu Asn Gly Arg Lys Arg Met Leu Ala Ser Ala Gly
1235 1240 1245

Glu Leu Gln Lys Gly Asn Glu Leu Ala Leu Pro Ser Lys Tyr Val
1250 1255 1260

Asn Phe Leu Tyr Leu Ala Ser His Tyr Glu Lys Leu Lys Gly Ser
1265 1270 1275

Pro Glu Asp Asn Glu Gln Lys Gln Leu Phe Val Glu Gln His Lys
1280 1285 1290

His Tyr Leu Asp Glu Ile Ile Glu Gln Ile Ser Glu Phe Ser Lys
1295 1300 1305

Arg Val Ile Leu Ala Asp Ala Asn Leu Asp Lys Val Leu Ser Ala
1310 1315 1320

Tyr Asn Lys His Arg Asp Lys Pro Ile Arg Glu Gln Ala Glu Asn
1325 1330 1335

Ile Ile His Leu Phe Thr Leu Thr Asn Leu Gly Ala Pro Ala Ala
1340 1345 1350

Phe Lys Tyr Phe Asp Thr Thr Ile Asp Arg Lys Arg Tyr Thr Ser
1355 1360 1365

Thr Lys Glu Val Leu Asp Ala Thr Leu Ile His Gln Ser Ile Thr
1370 1375 1380

Gly Leu Tyr Glu Thr Arg Ile Asp Leu Ser Gln Leu Gly Gly Asp
1385 1390 1395

Ser Arg Ala Asp Pro Lys Lys Lys Arg Lys Val Glu Phe Tyr Pro
1400 1405 1410

Tyr Asp Val Pro Asp Tyr Ala
1415 1420

<210> SEQ ID NO 26
<211> LENGTH: 36
<212> TYPE: PRT
<213> ORGANISM: Artificial Sequence
<220> FEATURE:
<223> OTHER INFORMATION: penetrating peptide; R9-HE10

<400> SEQUENCE: 26

Arg Arg Arg Arg Arg Arg Arg Arg Arg Ala Ser Gly Gly Gly Gly Gly
1 5 10 15

His Glu His Glu His Glu His Glu His Glu His Glu His Glu His Glu
20 25 30

His Glu His Glu
35

<210> SEQ ID NO 27
<211> LENGTH: 1445
<212> TYPE: PRT
<213> ORGANISM: Artificial Sequence
<220> FEATURE:
<223> OTHER INFORMATION: penetrating peptide-linkage-Cas protein; R9-HE10-Cas9

<400> SEQUENCE: 27

Arg Arg Arg Arg Arg Arg Arg Arg Arg Ala Ser Gly Gly Gly Gly Gly
1 5 10 15

```
His Glu His Glu His Glu His Glu His Glu His Glu His Glu His Glu
            20                  25                  30

His Glu His Glu Leu Asp Ser Thr Ala Pro Lys Lys Lys Arg Lys Val
        35                  40                  45

Gly Ile His Gly Val Pro Ala Ala Asp Lys Lys Tyr Ser Ile Gly Leu
    50                  55                  60

Asp Ile Gly Thr Asn Ser Val Gly Trp Ala Val Ile Thr Asp Glu Tyr
65                  70                  75                  80

Lys Val Pro Ser Lys Lys Phe Lys Val Leu Gly Asn Thr Asp Arg His
                85                  90                  95

Ser Ile Lys Lys Asn Leu Ile Gly Ala Leu Leu Phe Asp Ser Gly Glu
            100                 105                 110

Thr Ala Glu Ala Thr Arg Leu Lys Arg Thr Ala Arg Arg Arg Tyr Thr
        115                 120                 125

Arg Arg Lys Asn Arg Ile Cys Tyr Leu Gln Glu Ile Phe Ser Asn Glu
    130                 135                 140

Met Ala Lys Val Asp Asp Ser Phe Phe His Arg Leu Glu Glu Ser Phe
145                 150                 155                 160

Leu Val Glu Glu Asp Lys Lys His Glu Arg His Pro Ile Phe Gly Asn
                165                 170                 175

Ile Val Asp Glu Val Ala Tyr His Glu Lys Tyr Pro Thr Ile Tyr His
            180                 185                 190

Leu Arg Lys Lys Leu Val Asp Ser Thr Asp Lys Ala Asp Leu Arg Leu
        195                 200                 205

Ile Tyr Leu Ala Leu Ala His Met Ile Lys Phe Arg Gly His Phe Leu
    210                 215                 220

Ile Glu Gly Asp Leu Asn Pro Asp Asn Ser Asp Val Asp Lys Leu Phe
225                 230                 235                 240

Ile Gln Leu Val Gln Thr Tyr Asn Gln Leu Phe Glu Glu Asn Pro Ile
                245                 250                 255

Asn Ala Ser Gly Val Asp Ala Lys Ala Ile Leu Ser Ala Arg Leu Ser
            260                 265                 270

Lys Ser Arg Arg Leu Glu Asn Leu Ile Ala Gln Leu Pro Gly Glu Lys
        275                 280                 285

Lys Asn Gly Leu Phe Gly Asn Leu Ile Ala Leu Ser Leu Gly Leu Thr
    290                 295                 300

Pro Asn Phe Lys Ser Asn Phe Asp Leu Ala Glu Asp Ala Lys Leu Gln
305                 310                 315                 320

Leu Ser Lys Asp Thr Tyr Asp Asp Asp Leu Asp Asn Leu Leu Ala Gln
                325                 330                 335

Ile Gly Asp Gln Tyr Ala Asp Leu Phe Leu Ala Ala Lys Asn Leu Ser
            340                 345                 350

Asp Ala Ile Leu Leu Ser Asp Ile Leu Arg Val Asn Thr Glu Ile Thr
        355                 360                 365

Lys Ala Pro Leu Ser Ala Ser Met Ile Lys Arg Tyr Asp Glu His His
    370                 375                 380

Gln Asp Leu Thr Leu Leu Lys Ala Leu Val Arg Gln Gln Leu Pro Glu
385                 390                 395                 400

Lys Tyr Lys Glu Ile Phe Phe Asp Gln Ser Lys Asn Gly Tyr Ala Gly
                405                 410                 415

Tyr Ile Asp Gly Gly Ala Ser Gln Glu Glu Phe Tyr Lys Phe Ile Lys
            420                 425                 430

Pro Ile Leu Glu Lys Met Asp Gly Thr Glu Glu Leu Leu Val Lys Leu
```

```
        435                 440                 445

Asn Arg Glu Asp Leu Leu Arg Lys Gln Arg Thr Phe Asp Asn Gly Ser
    450                 455                 460

Ile Pro His Gln Ile His Leu Gly Glu Leu His Ala Ile Leu Arg Arg
465                 470                 475                 480

Gln Glu Asp Phe Tyr Pro Phe Leu Lys Asp Asn Arg Glu Lys Ile Glu
                485                 490                 495

Lys Ile Leu Thr Phe Arg Ile Pro Tyr Tyr Val Gly Pro Leu Ala Arg
            500                 505                 510

Gly Asn Ser Arg Phe Ala Trp Met Thr Arg Lys Ser Glu Glu Thr Ile
        515                 520                 525

Thr Pro Trp Asn Phe Glu Glu Val Val Asp Lys Gly Ala Ser Ala Gln
    530                 535                 540

Ser Phe Ile Glu Arg Met Thr Asn Phe Asp Lys Asn Leu Pro Asn Glu
545                 550                 555                 560

Lys Val Leu Pro Lys His Ser Leu Leu Tyr Glu Tyr Phe Thr Val Tyr
                565                 570                 575

Asn Glu Leu Thr Lys Val Lys Tyr Val Thr Glu Gly Met Arg Lys Pro
            580                 585                 590

Ala Phe Leu Ser Gly Glu Gln Lys Lys Ala Ile Val Asp Leu Leu Phe
        595                 600                 605

Lys Thr Asn Arg Lys Val Thr Val Lys Gln Leu Lys Glu Asp Tyr Phe
    610                 615                 620

Lys Lys Ile Glu Cys Phe Asp Ser Val Glu Ile Ser Gly Val Glu Asp
625                 630                 635                 640

Arg Phe Asn Ala Ser Leu Gly Thr Tyr His Asp Leu Leu Lys Ile Ile
                645                 650                 655

Lys Asp Lys Asp Phe Leu Asp Asn Glu Glu Asn Glu Asp Ile Leu Glu
            660                 665                 670

Asp Ile Val Leu Thr Leu Thr Leu Phe Glu Asp Arg Glu Met Ile Glu
        675                 680                 685

Glu Arg Leu Lys Thr Tyr Ala His Leu Phe Asp Asp Lys Val Met Lys
    690                 695                 700

Gln Leu Lys Arg Arg Arg Tyr Thr Gly Trp Gly Arg Leu Ser Arg Lys
705                 710                 715                 720

Leu Ile Asn Gly Ile Arg Asp Lys Gln Ser Gly Lys Thr Ile Leu Asp
                725                 730                 735

Phe Leu Lys Ser Asp Gly Phe Ala Asn Arg Asn Phe Met Gln Leu Ile
            740                 745                 750

His Asp Asp Ser Leu Thr Phe Lys Glu Asp Ile Gln Lys Ala Gln Val
        755                 760                 765

Ser Gly Gln Gly Asp Ser Leu His Glu His Ile Ala Asn Leu Ala Gly
    770                 775                 780

Ser Pro Ala Ile Lys Lys Gly Ile Leu Gln Thr Val Lys Val Val Asp
785                 790                 795                 800

Glu Leu Val Lys Val Met Gly Arg His Lys Pro Glu Asn Ile Val Ile
                805                 810                 815

Glu Met Ala Arg Glu Asn Gln Thr Thr Gln Lys Gly Gln Lys Asn Ser
            820                 825                 830

Arg Glu Arg Met Lys Arg Ile Glu Glu Gly Ile Lys Glu Leu Gly Ser
        835                 840                 845

Gln Ile Leu Lys Glu His Pro Val Glu Asn Thr Gln Leu Gln Asn Glu
    850                 855                 860
```

```
Lys Leu Tyr Leu Tyr Tyr Leu Gln Asn Gly Arg Asp Met Tyr Val Asp
865                 870                 875                 880

Gln Glu Leu Asp Ile Asn Arg Leu Ser Asp Tyr Asp Val Asp His Ile
                885                 890                 895

Val Pro Gln Ser Phe Leu Lys Asp Asp Ser Ile Asp Asn Lys Val Leu
            900                 905                 910

Thr Arg Ser Asp Lys Asn Arg Gly Lys Ser Asp Asn Val Pro Ser Glu
        915                 920                 925

Glu Val Val Lys Lys Met Lys Asn Tyr Trp Arg Gln Leu Leu Asn Ala
    930                 935                 940

Lys Leu Ile Thr Gln Arg Lys Phe Asp Asn Leu Thr Lys Ala Glu Arg
945                 950                 955                 960

Gly Gly Leu Ser Glu Leu Asp Lys Ala Gly Phe Ile Lys Arg Gln Leu
                965                 970                 975

Val Glu Thr Arg Gln Ile Thr Lys His Val Ala Gln Ile Leu Asp Ser
            980                 985                 990

Arg Met Asn Thr Lys Tyr Asp Glu  Asn Asp Lys Leu Ile  Arg Glu Val
        995                 1000                1005

Lys Val  Ile Thr Leu Lys Ser  Lys Leu Val Ser Asp  Phe Arg Lys
    1010                1015                1020

Asp Phe  Gln Phe Tyr Lys Val  Arg Glu Ile Asn Asn  Tyr His His
    1025                1030                1035

Ala His  Asp Ala Tyr Leu Asn  Ala Val Val Gly Thr  Ala Leu Ile
    1040                1045                1050

Lys Lys  Tyr Pro Lys Leu Glu  Ser Glu Phe Val Tyr  Gly Asp Tyr
    1055                1060                1065

Lys Val  Tyr Asp Val Arg Lys  Met Ile Ala Lys Ser  Glu Gln Glu
    1070                1075                1080

Ile Gly  Lys Ala Thr Ala Lys  Tyr Phe Phe Tyr Ser  Asn Ile Met
    1085                1090                1095

Asn Phe  Phe Lys Thr Glu Ile  Thr Leu Ala Asn Gly  Glu Ile Arg
    1100                1105                1110

Lys Arg  Pro Leu Ile Glu Thr  Asn Gly Glu Thr Gly  Glu Ile Val
    1115                1120                1125

Trp Asp  Lys Gly Arg Asp Phe  Ala Thr Val Arg Lys  Val Leu Ser
    1130                1135                1140

Met Pro  Gln Val Asn Ile Val  Lys Lys Thr Glu Val  Gln Thr Gly
    1145                1150                1155

Gly Phe  Ser Lys Glu Ser Ile  Leu Pro Lys Arg Asn  Ser Asp Lys
    1160                1165                1170

Leu Ile  Ala Arg Lys Lys Asp  Trp Asp Pro Lys Lys  Tyr Gly Gly
    1175                1180                1185

Phe Asp  Ser Pro Thr Val Ala  Tyr Ser Val Leu Val  Val Ala Lys
    1190                1195                1200

Val Glu  Lys Gly Lys Ser Lys  Lys Leu Lys Ser Val  Lys Glu Leu
    1205                1210                1215

Leu Gly  Ile Thr Ile Met Glu  Arg Ser Ser Phe Glu  Lys Asn Pro
    1220                1225                1230

Ile Asp  Phe Leu Glu Ala Lys  Gly Tyr Lys Glu Val  Lys Lys Asp
    1235                1240                1245

Leu Ile  Ile Lys Leu Pro Lys  Tyr Ser Leu Phe Glu  Leu Glu Asn
    1250                1255                1260
```

```
Gly Arg  Lys Arg Met Leu Ala  Ser Ala Gly Glu Leu  Gln Lys Gly
    1265                 1270                 1275

Asn Glu  Leu Ala Leu Pro Ser  Lys Tyr Val Asn Phe  Leu Tyr Leu
    1280                 1285                 1290

Ala Ser  His Tyr Glu Lys Leu  Lys Gly Ser Pro Glu  Asp Asn Glu
    1295                 1300                 1305

Gln Lys  Gln Leu Phe Val Glu  Gln His Lys His Tyr  Leu Asp Glu
    1310                 1315                 1320

Ile Ile  Glu Gln Ile Ser Glu  Phe Ser Lys Arg Val  Ile Leu Ala
    1325                 1330                 1335

Asp Ala  Asn Leu Asp Lys Val  Leu Ser Ala Tyr Asn  Lys His Arg
    1340                 1345                 1350

Asp Lys  Pro Ile Arg Glu Gln  Ala Glu Asn Ile Ile  His Leu Phe
    1355                 1360                 1365

Thr Leu  Thr Asn Leu Gly Ala  Pro Ala Ala Phe Lys  Tyr Phe Asp
    1370                 1375                 1380

Thr Thr  Ile Asp Arg Lys Arg  Tyr Thr Ser Thr Lys  Glu Val Leu
    1385                 1390                 1395

Asp Ala  Thr Leu Ile His Gln  Ser Ile Thr Gly Leu  Tyr Glu Thr
    1400                 1405                 1410

Arg Ile  Asp Leu Ser Gln Leu  Gly Gly Asp Ser Arg  Ala Asp Pro
    1415                 1420                 1425

Lys Lys  Lys Arg Lys Val Glu  Phe Tyr Pro Tyr Asp  Val Pro Asp
    1430                 1435                 1440

Tyr Ala
    1445
```

<210> SEQ ID NO 28
<211> LENGTH: 11
<212> TYPE: PRT
<213> ORGANISM: Artificial Sequence
<220> FEATURE:
<223> OTHER INFORMATION: penetrating peptide; TAT

<400> SEQUENCE: 28

```
Tyr Gly Arg Lys Lys Arg Arg Gln Arg Arg Arg
1               5                   10
```

<210> SEQ ID NO 29
<211> LENGTH: 1422
<212> TYPE: PRT
<213> ORGANISM: Artificial Sequence
<220> FEATURE:
<223> OTHER INFORMATION: penetrating peptide-linkage-Cas protein; TAT-Cas9

<400> SEQUENCE: 29

```
Tyr Gly Arg Lys Lys Arg Arg Gln Arg Arg Arg Ala Ser Leu Asp Ser
1               5                   10                  15

Thr Ala Pro Lys Lys Lys Arg Lys Val Gly Ile His Gly Val Pro Ala
            20                  25                  30

Ala Asp Lys Lys Tyr Ser Ile Gly Leu Asp Ile Gly Thr Asn Ser Val
        35                  40                  45

Gly Trp Ala Val Ile Thr Asp Glu Tyr Lys Val Pro Ser Lys Lys Phe
    50                  55                  60

Lys Val Leu Gly Asn Thr Asp Arg His Ser Ile Lys Lys Asn Leu Ile
65                  70                  75                  80

Gly Ala Leu Leu Phe Asp Ser Gly Glu Thr Ala Glu Ala Thr Arg Leu
```

```
                85                  90                  95

Lys Arg Thr Ala Arg Arg Arg Tyr Thr Arg Arg Lys Asn Arg Ile Cys
            100                 105                 110

Tyr Leu Gln Glu Ile Phe Ser Asn Glu Met Ala Lys Val Asp Asp Ser
        115                 120                 125

Phe Phe His Arg Leu Glu Glu Ser Phe Leu Val Glu Glu Asp Lys Lys
    130                 135                 140

His Glu Arg His Pro Ile Phe Gly Asn Ile Val Asp Glu Val Ala Tyr
145                 150                 155                 160

His Glu Lys Tyr Pro Thr Ile Tyr His Leu Arg Lys Lys Leu Val Asp
                165                 170                 175

Ser Thr Asp Lys Ala Asp Leu Arg Leu Ile Tyr Leu Ala Leu Ala His
            180                 185                 190

Met Ile Lys Phe Arg Gly His Phe Leu Ile Glu Gly Asp Leu Asn Pro
        195                 200                 205

Asp Asn Ser Asp Val Asp Lys Leu Phe Ile Gln Leu Val Gln Thr Tyr
    210                 215                 220

Asn Gln Leu Phe Glu Glu Asn Pro Ile Asn Ala Ser Gly Val Asp Ala
225                 230                 235                 240

Lys Ala Ile Leu Ser Ala Arg Leu Ser Lys Ser Arg Arg Leu Glu Asn
                245                 250                 255

Leu Ile Ala Gln Leu Pro Gly Glu Lys Lys Asn Gly Leu Phe Gly Asn
            260                 265                 270

Leu Ile Ala Leu Ser Leu Gly Leu Thr Pro Asn Phe Lys Ser Asn Phe
        275                 280                 285

Asp Leu Ala Glu Asp Ala Lys Leu Gln Leu Ser Lys Asp Thr Tyr Asp
    290                 295                 300

Asp Asp Leu Asp Asn Leu Leu Ala Gln Ile Gly Asp Gln Tyr Ala Asp
305                 310                 315                 320

Leu Phe Leu Ala Ala Lys Asn Leu Ser Asp Ala Ile Leu Leu Ser Asp
                325                 330                 335

Ile Leu Arg Val Asn Thr Glu Ile Thr Lys Ala Pro Leu Ser Ala Ser
            340                 345                 350

Met Ile Lys Arg Tyr Asp Glu His His Gln Asp Leu Thr Leu Leu Lys
        355                 360                 365

Ala Leu Val Arg Gln Gln Leu Pro Glu Lys Tyr Lys Glu Ile Phe Phe
    370                 375                 380

Asp Gln Ser Lys Asn Gly Tyr Ala Gly Tyr Ile Asp Gly Gly Ala Ser
385                 390                 395                 400

Gln Glu Glu Phe Tyr Lys Phe Ile Lys Pro Ile Leu Glu Lys Met Asp
                405                 410                 415

Gly Thr Glu Glu Leu Leu Val Lys Leu Asn Arg Glu Asp Leu Leu Arg
            420                 425                 430

Lys Gln Arg Thr Phe Asp Asn Gly Ser Ile Pro His Gln Ile His Leu
        435                 440                 445

Gly Glu Leu His Ala Ile Leu Arg Arg Gln Glu Asp Phe Tyr Pro Phe
    450                 455                 460

Leu Lys Asp Asn Arg Glu Lys Ile Glu Lys Ile Leu Thr Phe Arg Ile
465                 470                 475                 480

Pro Tyr Tyr Val Gly Pro Leu Ala Arg Gly Asn Ser Arg Phe Ala Trp
                485                 490                 495

Met Thr Arg Lys Ser Glu Glu Thr Ile Thr Pro Trp Asn Phe Glu Glu
            500                 505                 510
```

```
Val Val Asp Lys Gly Ala Ser Ala Gln Ser Phe Ile Glu Arg Met Thr
        515                 520                 525

Asn Phe Asp Lys Asn Leu Pro Asn Glu Lys Val Leu Pro Lys His Ser
    530                 535                 540

Leu Leu Tyr Glu Tyr Phe Thr Val Tyr Asn Glu Leu Thr Lys Val Lys
545                 550                 555                 560

Tyr Val Thr Glu Gly Met Arg Lys Pro Ala Phe Leu Ser Gly Glu Gln
                565                 570                 575

Lys Lys Ala Ile Val Asp Leu Leu Phe Lys Thr Asn Arg Lys Val Thr
            580                 585                 590

Val Lys Gln Leu Lys Glu Asp Tyr Phe Lys Lys Ile Glu Cys Phe Asp
        595                 600                 605

Ser Val Glu Ile Ser Gly Val Glu Asp Arg Phe Asn Ala Ser Leu Gly
    610                 615                 620

Thr Tyr His Asp Leu Leu Lys Ile Ile Lys Asp Lys Asp Phe Leu Asp
625                 630                 635                 640

Asn Glu Glu Asn Glu Asp Ile Leu Glu Asp Ile Val Leu Thr Leu Thr
                645                 650                 655

Leu Phe Glu Asp Arg Glu Met Ile Glu Glu Arg Leu Lys Thr Tyr Ala
            660                 665                 670

His Leu Phe Asp Asp Lys Val Met Lys Gln Leu Lys Arg Arg Arg Tyr
        675                 680                 685

Thr Gly Trp Gly Arg Leu Ser Arg Lys Leu Ile Asn Gly Ile Arg Asp
    690                 695                 700

Lys Gln Ser Gly Lys Thr Ile Leu Asp Phe Leu Lys Ser Asp Gly Phe
705                 710                 715                 720

Ala Asn Arg Asn Phe Met Gln Leu Ile His Asp Asp Ser Leu Thr Phe
                725                 730                 735

Lys Glu Asp Ile Gln Lys Ala Gln Val Ser Gly Gln Gly Asp Ser Leu
            740                 745                 750

His Glu His Ile Ala Asn Leu Ala Gly Ser Pro Ala Ile Lys Lys Gly
        755                 760                 765

Ile Leu Gln Thr Val Lys Val Val Asp Glu Leu Val Lys Val Met Gly
    770                 775                 780

Arg His Lys Pro Glu Asn Ile Val Ile Glu Met Ala Arg Glu Asn Gln
785                 790                 795                 800

Thr Thr Gln Lys Gly Gln Lys Asn Ser Arg Glu Arg Met Lys Arg Ile
                805                 810                 815

Glu Glu Gly Ile Lys Glu Leu Gly Ser Gln Ile Leu Lys Glu His Pro
            820                 825                 830

Val Glu Asn Thr Gln Leu Gln Asn Glu Lys Leu Tyr Leu Tyr Tyr Leu
        835                 840                 845

Gln Asn Gly Arg Asp Met Tyr Val Asp Gln Glu Leu Asp Ile Asn Arg
    850                 855                 860

Leu Ser Asp Tyr Asp Val Asp His Ile Val Pro Gln Ser Phe Leu Lys
865                 870                 875                 880

Asp Asp Ser Ile Asp Asn Lys Val Leu Thr Arg Ser Asp Lys Asn Arg
                885                 890                 895

Gly Lys Ser Asp Asn Val Pro Ser Glu Glu Val Val Lys Lys Met Lys
            900                 905                 910

Asn Tyr Trp Arg Gln Leu Leu Asn Ala Lys Leu Ile Thr Gln Arg Lys
        915                 920                 925
```

```
Phe Asp Asn Leu Thr Lys Ala Glu Arg Gly Gly Leu Ser Glu Leu Asp
    930                 935                 940

Lys Ala Gly Phe Ile Lys Arg Gln Leu Val Glu Thr Arg Gln Ile Thr
945                 950                 955                 960

Lys His Val Ala Gln Ile Leu Asp Ser Arg Met Asn Thr Lys Tyr Asp
                965                 970                 975

Glu Asn Asp Lys Leu Ile Arg Glu Val Lys Val Ile Thr Leu Lys Ser
            980                 985                 990

Lys Leu Val Ser Asp Phe Arg Lys  Asp Phe Gln Phe Tyr  Lys Val Arg
        995                 1000                1005

Glu Ile  Asn Asn Tyr His His  Ala His Asp Ala Tyr  Leu Asn Ala
    1010                 1015                 1020

Val Val  Gly Thr Ala Leu Ile  Lys Lys Tyr Pro Lys  Leu Glu Ser
    1025                 1030                 1035

Glu Phe  Val Tyr Gly Asp Tyr  Lys Val Tyr Asp Val  Arg Lys Met
    1040                 1045                 1050

Ile Ala  Lys Ser Glu Gln Glu  Ile Gly Lys Ala Thr  Ala Lys Tyr
    1055                 1060                 1065

Phe Phe  Tyr Ser Asn Ile Met  Asn Phe Phe Lys Thr  Glu Ile Thr
    1070                 1075                 1080

Leu Ala  Asn Gly Glu Ile Arg  Lys Arg Pro Leu Ile  Glu Thr Asn
    1085                 1090                 1095

Gly Glu  Thr Gly Glu Ile Val  Trp Asp Lys Gly Arg  Asp Phe Ala
    1100                 1105                 1110

Thr Val  Arg Lys Val Leu Ser  Met Pro Gln Val Asn  Ile Val Lys
    1115                 1120                 1125

Lys Thr  Glu Val Gln Thr Gly  Gly Phe Ser Lys Glu  Ser Ile Leu
    1130                 1135                 1140

Pro Lys  Arg Asn Ser Asp Lys  Leu Ile Ala Arg Lys  Lys Asp Trp
    1145                 1150                 1155

Asp Pro  Lys Lys Tyr Gly Gly  Phe Asp Ser Pro Thr  Val Ala Tyr
    1160                 1165                 1170

Ser Val  Leu Val Val Ala Lys  Val Glu Lys Gly Lys  Ser Lys Lys
    1175                 1180                 1185

Leu Lys  Ser Val Lys Glu Leu  Leu Gly Ile Thr Ile  Met Glu Arg
    1190                 1195                 1200

Ser Ser  Phe Glu Lys Asn Pro  Ile Asp Phe Leu Glu  Ala Lys Gly
    1205                 1210                 1215

Tyr Lys  Glu Val Lys Lys Asp  Leu Ile Ile Lys Leu  Pro Lys Tyr
    1220                 1225                 1230

Ser Leu  Phe Glu Leu Glu Asn  Gly Arg Lys Arg Met  Leu Ala Ser
    1235                 1240                 1245

Ala Gly  Glu Leu Gln Lys Gly  Asn Glu Leu Ala Leu  Pro Ser Lys
    1250                 1255                 1260

Tyr Val  Asn Phe Leu Tyr Leu  Ala Ser His Tyr Glu  Lys Leu Lys
    1265                 1270                 1275

Gly Ser  Pro Glu Asp Asn Glu  Gln Lys Gln Leu Phe  Val Glu Gln
    1280                 1285                 1290

His Lys  His Tyr Leu Asp Glu  Ile Ile Glu Gln Ile  Ser Glu Phe
    1295                 1300                 1305

Ser Lys  Arg Val Ile Leu Ala  Asp Ala Asn Leu Asp  Lys Val Leu
    1310                 1315                 1320

Ser Ala  Tyr Asn Lys His Arg  Asp Lys Pro Ile Arg  Glu Gln Ala
```

```
    1325                1330                1335

Glu Asn  Ile Ile His Leu Phe  Thr Leu Thr Asn Leu  Gly Ala Pro
    1340                1345                1350

Ala Ala  Phe Lys Tyr Phe Asp  Thr Thr Ile Asp Arg  Lys Arg Tyr
    1355                1360                1365

Thr Ser  Thr Lys Glu Val Leu  Asp Ala Thr Leu Ile  His Gln Ser
    1370                1375                1380

Ile Thr  Gly Leu Tyr Glu Thr  Arg Ile Asp Leu Ser  Gln Leu Gly
    1385                1390                1395

Gly Asp  Ser Arg Ala Asp Pro  Lys Lys Lys Arg Lys  Val Glu Phe
    1400                1405                1410

Tyr Pro  Tyr Asp Val Pro Asp  Tyr Ala
    1415                1420


<210> SEQ ID NO 30
<211> LENGTH: 38
<212> TYPE: PRT
<213> ORGANISM: Artificial Sequence
<220> FEATURE:
<223> OTHER INFORMATION: penetrating peptide; TAT-HE10

<400> SEQUENCE: 30

Tyr Gly Arg Lys Lys Arg Arg Gln Arg Arg Arg Ala Ser Gly Gly Gly
1               5                   10                  15

Gly Gly His Glu His Glu His Glu His Glu His Glu His Glu His Glu
            20                  25                  30

His Glu His Glu His Glu
        35


<210> SEQ ID NO 31
<211> LENGTH: 1447
<212> TYPE: PRT
<213> ORGANISM: Artificial Sequence
<220> FEATURE:
<223> OTHER INFORMATION: penetrating peptide-linkage-Cas protein;
      TAT-HE-Cas9

<400> SEQUENCE: 31

Tyr Gly Arg Lys Lys Arg Arg Gln Arg Arg Arg Ala Ser Gly Gly Gly
1               5                   10                  15

Gly Gly His Glu His Glu His Glu His Glu His Glu His Glu His Glu
            20                  25                  30

His Glu His Glu His Glu Leu Asp Ser Thr Ala Pro Lys Lys Lys Arg
        35                  40                  45

Lys Val Gly Ile His Gly Val Pro Ala Ala Asp Lys Lys Tyr Ser Ile
    50                  55                  60

Gly Leu Asp Ile Gly Thr Asn Ser Val Gly Trp Ala Val Ile Thr Asp
65                  70                  75                  80

Glu Tyr Lys Val Pro Ser Lys Lys Phe Lys Val Leu Gly Asn Thr Asp
                85                  90                  95

Arg His Ser Ile Lys Lys Asn Leu Ile Gly Ala Leu Leu Phe Asp Ser
            100                 105                 110

Gly Glu Thr Ala Glu Ala Thr Arg Leu Lys Arg Thr Ala Arg Arg Arg
        115                 120                 125

Tyr Thr Arg Arg Lys Asn Arg Ile Cys Tyr Leu Gln Glu Ile Phe Ser
    130                 135                 140

Asn Glu Met Ala Lys Val Asp Asp Ser Phe Phe His Arg Leu Glu Glu
145                 150                 155                 160
```

```
Ser Phe Leu Val Glu Glu Asp Lys Lys His Glu Arg His Pro Ile Phe
                165                 170                 175

Gly Asn Ile Val Asp Glu Val Ala Tyr His Glu Lys Tyr Pro Thr Ile
            180                 185                 190

Tyr His Leu Arg Lys Lys Leu Val Asp Ser Thr Asp Lys Ala Asp Leu
        195                 200                 205

Arg Leu Ile Tyr Leu Ala Leu Ala His Met Ile Lys Phe Arg Gly His
    210                 215                 220

Phe Leu Ile Glu Gly Asp Leu Asn Pro Asp Asn Ser Asp Val Asp Lys
225                 230                 235                 240

Leu Phe Ile Gln Leu Val Gln Thr Tyr Asn Gln Leu Phe Glu Glu Asn
                245                 250                 255

Pro Ile Asn Ala Ser Gly Val Asp Ala Lys Ala Ile Leu Ser Ala Arg
            260                 265                 270

Leu Ser Lys Ser Arg Arg Leu Glu Asn Leu Ile Ala Gln Leu Pro Gly
        275                 280                 285

Glu Lys Lys Asn Gly Leu Phe Gly Asn Leu Ile Ala Leu Ser Leu Gly
    290                 295                 300

Leu Thr Pro Asn Phe Lys Ser Asn Phe Asp Leu Ala Glu Asp Ala Lys
305                 310                 315                 320

Leu Gln Leu Ser Lys Asp Thr Tyr Asp Asp Asp Leu Asp Asn Leu Leu
                325                 330                 335

Ala Gln Ile Gly Asp Gln Tyr Ala Asp Leu Phe Leu Ala Ala Lys Asn
            340                 345                 350

Leu Ser Asp Ala Ile Leu Leu Ser Asp Ile Leu Arg Val Asn Thr Glu
        355                 360                 365

Ile Thr Lys Ala Pro Leu Ser Ala Ser Met Ile Lys Arg Tyr Asp Glu
    370                 375                 380

His His Gln Asp Leu Thr Leu Leu Lys Ala Leu Val Arg Gln Gln Leu
385                 390                 395                 400

Pro Glu Lys Tyr Lys Glu Ile Phe Phe Asp Gln Ser Lys Asn Gly Tyr
                405                 410                 415

Ala Gly Tyr Ile Asp Gly Gly Ala Ser Gln Glu Glu Phe Tyr Lys Phe
            420                 425                 430

Ile Lys Pro Ile Leu Glu Lys Met Asp Gly Thr Glu Glu Leu Leu Val
        435                 440                 445

Lys Leu Asn Arg Glu Asp Leu Leu Arg Lys Gln Arg Thr Phe Asp Asn
    450                 455                 460

Gly Ser Ile Pro His Gln Ile His Leu Gly Glu Leu His Ala Ile Leu
465                 470                 475                 480

Arg Arg Gln Glu Asp Phe Tyr Pro Phe Leu Lys Asp Asn Arg Glu Lys
                485                 490                 495

Ile Glu Lys Ile Leu Thr Phe Arg Ile Pro Tyr Tyr Val Gly Pro Leu
            500                 505                 510

Ala Arg Gly Asn Ser Arg Phe Ala Trp Met Thr Arg Lys Ser Glu Glu
        515                 520                 525

Thr Ile Thr Pro Trp Asn Phe Glu Glu Val Val Asp Lys Gly Ala Ser
    530                 535                 540

Ala Gln Ser Phe Ile Glu Arg Met Thr Asn Phe Asp Lys Asn Leu Pro
545                 550                 555                 560

Asn Glu Lys Val Leu Pro Lys His Ser Leu Leu Tyr Glu Tyr Phe Thr
                565                 570                 575
```

```
Val Tyr Asn Glu Leu Thr Lys Val Lys Tyr Val Thr Glu Gly Met Arg
            580                 585                 590

Lys Pro Ala Phe Leu Ser Gly Glu Gln Lys Lys Ala Ile Val Asp Leu
        595                 600                 605

Leu Phe Lys Thr Asn Arg Lys Val Thr Val Lys Gln Leu Lys Glu Asp
    610                 615                 620

Tyr Phe Lys Lys Ile Glu Cys Phe Asp Ser Val Glu Ile Ser Gly Val
625                 630                 635                 640

Glu Asp Arg Phe Asn Ala Ser Leu Gly Thr Tyr His Asp Leu Leu Lys
                645                 650                 655

Ile Ile Lys Asp Lys Asp Phe Leu Asp Asn Glu Glu Asn Glu Asp Ile
            660                 665                 670

Leu Glu Asp Ile Val Leu Thr Leu Thr Leu Phe Glu Asp Arg Glu Met
        675                 680                 685

Ile Glu Glu Arg Leu Lys Thr Tyr Ala His Leu Phe Asp Asp Lys Val
    690                 695                 700

Met Lys Gln Leu Lys Arg Arg Arg Tyr Thr Gly Trp Gly Arg Leu Ser
705                 710                 715                 720

Arg Lys Leu Ile Asn Gly Ile Arg Asp Lys Gln Ser Gly Lys Thr Ile
                725                 730                 735

Leu Asp Phe Leu Lys Ser Asp Gly Phe Ala Asn Arg Asn Phe Met Gln
            740                 745                 750

Leu Ile His Asp Asp Ser Leu Thr Phe Lys Glu Asp Ile Gln Lys Ala
        755                 760                 765

Gln Val Ser Gly Gln Gly Asp Ser Leu His Glu His Ile Ala Asn Leu
    770                 775                 780

Ala Gly Ser Pro Ala Ile Lys Lys Gly Ile Leu Gln Thr Val Lys Val
785                 790                 795                 800

Val Asp Glu Leu Val Lys Val Met Gly Arg His Lys Pro Glu Asn Ile
                805                 810                 815

Val Ile Glu Met Ala Arg Glu Asn Gln Thr Thr Gln Lys Gly Gln Lys
            820                 825                 830

Asn Ser Arg Glu Arg Met Lys Arg Ile Glu Glu Gly Ile Lys Glu Leu
        835                 840                 845

Gly Ser Gln Ile Leu Lys Glu His Pro Val Glu Asn Thr Gln Leu Gln
    850                 855                 860

Asn Glu Lys Leu Tyr Leu Tyr Tyr Leu Gln Asn Gly Arg Asp Met Tyr
865                 870                 875                 880

Val Asp Gln Glu Leu Asp Ile Asn Arg Leu Ser Asp Tyr Asp Val Asp
                885                 890                 895

His Ile Val Pro Gln Ser Phe Leu Lys Asp Asp Ser Ile Asp Asn Lys
            900                 905                 910

Val Leu Thr Arg Ser Asp Lys Asn Arg Gly Lys Ser Asp Asn Val Pro
        915                 920                 925

Ser Glu Glu Val Val Lys Lys Met Lys Asn Tyr Trp Arg Gln Leu Leu
    930                 935                 940

Asn Ala Lys Leu Ile Thr Gln Arg Lys Phe Asp Asn Leu Thr Lys Ala
945                 950                 955                 960

Glu Arg Gly Gly Leu Ser Glu Leu Asp Lys Ala Gly Phe Ile Lys Arg
                965                 970                 975

Gln Leu Val Glu Thr Arg Gln Ile Thr Lys His Val Ala Gln Ile Leu
            980                 985                 990

Asp Ser Arg Met Asn Thr Lys Tyr  Asp Glu Asn Asp Lys  Leu Ile Arg
```

-continued

```
        995                 1000                1005

Glu Val  Lys Val Ile Thr Leu  Lys Ser Lys Leu Val  Ser Asp Phe
    1010                 1015                 1020

Arg Lys  Asp Phe Gln Phe Tyr  Lys Val Arg Glu Ile  Asn Asn Tyr
    1025                 1030                 1035

His His  Ala His Asp Ala Tyr  Leu Asn Ala Val Val  Gly Thr Ala
    1040                 1045                 1050

Leu Ile  Lys Lys Tyr Pro Lys  Leu Glu Ser Glu Phe  Val Tyr Gly
    1055                 1060                 1065

Asp Tyr  Lys Val Tyr Asp Val  Arg Lys Met Ile Ala  Lys Ser Glu
    1070                 1075                 1080

Gln Glu  Ile Gly Lys Ala Thr  Ala Lys Tyr Phe Phe  Tyr Ser Asn
    1085                 1090                 1095

Ile Met  Asn Phe Phe Lys Thr  Glu Ile Thr Leu Ala  Asn Gly Glu
    1100                 1105                 1110

Ile Arg  Lys Arg Pro Leu Ile  Glu Thr Asn Gly Glu  Thr Gly Glu
    1115                 1120                 1125

Ile Val  Trp Asp Lys Gly Arg  Asp Phe Ala Thr Val  Arg Lys Val
    1130                 1135                 1140

Leu Ser  Met Pro Gln Val Asn  Ile Val Lys Lys Thr  Glu Val Gln
    1145                 1150                 1155

Thr Gly  Gly Phe Ser Lys Glu  Ser Ile Leu Pro Lys  Arg Asn Ser
    1160                 1165                 1170

Asp Lys  Leu Ile Ala Arg Lys  Lys Asp Trp Asp Pro  Lys Lys Tyr
    1175                 1180                 1185

Gly Gly  Phe Asp Ser Pro Thr  Val Ala Tyr Ser Val  Leu Val Val
    1190                 1195                 1200

Ala Lys  Val Glu Lys Gly Lys  Ser Lys Lys Leu Lys  Ser Val Lys
    1205                 1210                 1215

Glu Leu  Leu Gly Ile Thr Ile  Met Glu Arg Ser Ser  Phe Glu Lys
    1220                 1225                 1230

Asn Pro  Ile Asp Phe Leu Glu  Ala Lys Gly Tyr Lys  Glu Val Lys
    1235                 1240                 1245

Lys Asp  Leu Ile Ile Lys Leu  Pro Lys Tyr Ser Leu  Phe Glu Leu
    1250                 1255                 1260

Glu Asn  Gly Arg Lys Arg Met  Leu Ala Ser Ala Gly  Glu Leu Gln
    1265                 1270                 1275

Lys Gly  Asn Glu Leu Ala Leu  Pro Ser Lys Tyr Val  Asn Phe Leu
    1280                 1285                 1290

Tyr Leu  Ala Ser His Tyr Glu  Lys Leu Lys Gly Ser  Pro Glu Asp
    1295                 1300                 1305

Asn Glu  Gln Lys Gln Leu Phe  Val Glu Gln His Lys  His Tyr Leu
    1310                 1315                 1320

Asp Glu  Ile Ile Glu Gln Ile  Ser Glu Phe Ser Lys  Arg Val Ile
    1325                 1330                 1335

Leu Ala  Asp Ala Asn Leu Asp  Lys Val Leu Ser Ala  Tyr Asn Lys
    1340                 1345                 1350

His Arg  Asp Lys Pro Ile Arg  Glu Gln Ala Glu Asn  Ile Ile His
    1355                 1360                 1365

Leu Phe  Thr Leu Thr Asn Leu  Gly Ala Pro Ala Ala  Phe Lys Tyr
    1370                 1375                 1380

Phe Asp  Thr Thr Ile Asp Arg  Lys Arg Tyr Thr Ser  Thr Lys Glu
    1385                 1390                 1395
```

```
Val Leu  Asp Ala Thr Leu Ile  His Gln Ser Ile Thr  Gly Leu Tyr
    1400                 1405                 1410

Glu Thr  Arg Ile Asp Leu Ser  Gln Leu Gly Gly Asp  Ser Arg Ala
    1415                 1420                 1425

Asp Pro  Lys Lys Lys Arg Lys  Val Glu Phe Tyr Pro  Tyr Asp Val
    1430                 1435                 1440

Pro Asp  Tyr Ala
    1445
```

<210> SEQ ID NO 32
<211> LENGTH: 120
<212> TYPE: DNA
<213> ORGANISM: Artificial Sequence
<220> FEATURE:
<223> OTHER INFORMATION: gene sequence of penetrating peptide; AP-HE5

<400> SEQUENCE: 32

```
atgggcggtt ctcatcatca tcatcatcat ggtatggcct cccgccggcg ctggtgcaaa     60

cgccgccggg gttctggtgg tggtggaggt cacgagcatg agcacgaaca cgaacacgaa    120
```

<210> SEQ ID NO 33
<211> LENGTH: 126
<212> TYPE: DNA
<213> ORGANISM: Artificial Sequence
<220> FEATURE:
<223> OTHER INFORMATION: gene sequence of penetrating peptide; AP-HE6

<400> SEQUENCE: 33

```
atgggcggtt ctcatcatca tcatcatcat ggtatggcct cccgccggcg ctggtgcaaa     60

cgccgccggg gttctggtgg tggtggaggt cacgagcacg agcatgagca cgaacacgaa    120

cacgaa                                                               126
```

<210> SEQ ID NO 34
<211> LENGTH: 132
<212> TYPE: DNA
<213> ORGANISM: Artificial Sequence
<220> FEATURE:
<223> OTHER INFORMATION: gene sequence of penetrating peptide; AP-HE7

<400> SEQUENCE: 34

```
atgggcggtt ctcatcatca tcatcatcat ggtatggcct cccgccggcg ctggtgcaaa     60

cgccgccggg gttctggtgg tggtggaggt catgaacacg agcacgagca tgagcacgaa    120

cacgaacacg aa                                                        132
```

<210> SEQ ID NO 35
<211> LENGTH: 138
<212> TYPE: DNA
<213> ORGANISM: Artificial Sequence
<220> FEATURE:
<223> OTHER INFORMATION: gene sequence of penetrating peptide; AP-HE8

<400> SEQUENCE: 35

```
atgggcggtt ctcatcatca tcatcatcat ggtatggcct cccgccggcg ctggtgcaaa     60

cgccgccggg gttctggtgg tggtggaggt catgaacatg aacacgagca cgagcatgag    120

cacgaacacg aacacgaa                                                  138
```

<210> SEQ ID NO 36
<211> LENGTH: 144
<212> TYPE: DNA

<213> ORGANISM: Artificial Sequence
<220> FEATURE:
<223> OTHER INFORMATION: gene sequence of penetrating peptide; AP-HE9

<400> SEQUENCE: 36
atgggcggtt ctcatcatca tcatcatcat ggtatggcct cccgccggcg ctggtgcaaa 60
cgccgccggg gttctggtgg tggtggaggt catgaacatg aacatgaaca cgagcacgag 120
catgagcacg aacacgaaca cgaa 144

<210> SEQ ID NO 37
<211> LENGTH: 150
<212> TYPE: DNA
<213> ORGANISM: Artificial Sequence
<220> FEATURE:
<223> OTHER INFORMATION: gene sequence of penetrating peptide; AP-HE10

<400> SEQUENCE: 37
atgggcggtt ctcatcatca tcatcatcat ggtatggcct cccgccggcg ctggtgcaaa 60
cgccgccggg gttctggtgg tggtggaggt cacgaacatg aacatgaaca tgaacacgag 120
cacgagcatg agcacgaaca cgaacacgaa 150

<210> SEQ ID NO 38
<211> LENGTH: 156
<212> TYPE: DNA
<213> ORGANISM: Artificial Sequence
<220> FEATURE:
<223> OTHER INFORMATION: gene sequence of penetrating peptide; AP-HE11

<400> SEQUENCE: 38
atgggcggtt ctcatcatca tcatcatcat ggtatggcct cccgccggcg ctggtgcaaa 60
cgccgccggg gttctggtgg tggtggaggt catgaacacg aacatgaaca tgaacatgaa 120
cacgagcacg agcatgagca cgaacacgaa cacgaa 156

<210> SEQ ID NO 39
<211> LENGTH: 162
<212> TYPE: DNA
<213> ORGANISM: Artificial Sequence
<220> FEATURE:
<223> OTHER INFORMATION: gene sequence of penetrating peptide; AP-HE12

<400> SEQUENCE: 39
atgggcggtt ctcatcatca tcatcatcat ggtatggcct cccgccggcg ctggtgcaaa 60
cgccgccggg gttctggtgg tggtggaggt cacgaacatg aacacgaaca tgaacatgaa 120
catgaacacg agcacgagca tgagcacgaa cacgaacacg aa 162

<210> SEQ ID NO 40
<211> LENGTH: 4230
<212> TYPE: DNA
<213> ORGANISM: Artificial Sequence
<220> FEATURE:
<223> OTHER INFORMATION: gene sequence of Cas9

<400> SEQUENCE: 40
agcctggaca gcaccgctcc caaaaagaaa aggaaggtgg gcattcacgg cgtgcctgcg 60
gccgacaaaa agtacagcat cggccttgat atcggcacca atagcgtggg ctgggccgtt 120
atcacagacg aatacaaggt acccagcaag aagttcaagg tgctggggaa tacagacagg 180
cactctatca agaaaaacct tatcggggct ctgctgtttg actcaggcga gaccgccgag 240
gccaccaggt tgaagaggac cgcaaggcga aggtacaccc ggaggaagaa caggatctgc 300

```
tatctgcagg agatcttcag caacgagatg gccaaggtgg acgacagctt cttccacagg    360
ctggaggaga gcttccttgt cgaggaggat aagaagcacg aacgacaccc catcttcggc    420
aacatagtcg acgaggtcgc ttatcacgag aagtacccca ccatctacca cctgcgaaag    480
aaattggtgg atagcaccga taaagccgac ttgcgactta tctacttggc tctggcgcac    540
atgattaagt tcaggggcca cttcctgatc gagggcgacc ttaaccccga caacagtgac    600
gtagacaaat tgttcatcca gcttgtacag acctataacc agctgttcga ggaaaaccct    660
attaacgcca gcggggtgga tgcgaaggcc atacttagcg ccaggctgag caaaagcagg    720
cgcttggaga acctgatagc ccagctgccc ggtgaaaaga agaacggcct cttcggtaat    780
ctgattgccc tgagcctggg cctgaccccc aacttcaaga gcaacttcga cctggcagaa    840
gatgccaagc tgcagttgag taaggacacc tatgacgacg acttggacaa tctgctcgcc    900
caaatcggcg accagtacgc tgacctgttc ctcgccgcca agaacctttc tgacgcaatc    960
ctgcttagcg atatccttag ggtgaacaca gagatcacca aggccccct gagcgccagc   1020
atgatcaaga ggtacgacga gcaccatcag gacctgaccc ttctgaaggc cctggtgagg   1080
cagcaactgc ccgagaagta caaggagatc tttttcgacc agagcaagaa cggctacgcc   1140
ggctacatcg acggcggagc cagccaagag gagttctaca agttcatcaa gcccatcctg   1200
gagaagatgg atggcaccga ggagctgctg gtgaagctga acagggaaga tttgctccgg   1260
aagcagagga cctttgacaa cggtagcatc cccaccaga tccacctggg cgagctgcac   1320
gcaatactga ggcgacagga ggatttctac cccttcctca aggacaatag ggagaaaatc   1380
gaaaagattc tgaccttcag gatcccctac tacgtgggcc ctcttgccag gggcaacagc   1440
cgattcgctt ggatgacaag aaagagcgag gagaccatca cccccctggaa cttcgaggaa   1500
gtggtggaca aaggagcaag cgcgcagtct ttcatcgaac ggatgaccaa tttcgacaaa   1560
aacctgccta acgagaaggt gctgcccaag cacagcctgc tttacgagta cttcaccgtg   1620
tacaacgagc tcaccaaggt gaaatatgtg accgagggca tgcgaaaacc cgctttcctg   1680
agcggcgagc agaagaaggc catcgtggac ctgctgttca agaccaacag gaaggtgacc   1740
gtgaagcagc tgaaggagga ctacttcaag aagatcgagt gctttgatag cgtggaaata   1800
agcggcgtgg aggacaggtt caacgccagc ctgggcacct accacgactt gttgaagata   1860
atcaaagaca aggatttcct ggataatgag gagaacgagg atatactcga ggacatcgtg   1920
ctgactttga ccctgtttga ggaccgagag atgattgaag aaaggctcaa aacctacgcc   1980
cacctgttcg acgacaaagt gatgaaacaa ctgaagagac gaagatacac cggctggggc   2040
agactgtcca ggaagctcat caacggcatt agggacaagc agagcggcaa gaccatcctg   2100
gatttcctga agtccgacgg cttcgccaac cgaaacttca tgcagctgat tcacgatgac   2160
agcttgacct tcaaggagga catccagaag gcccaggtta gcggccaggg cgactccctg   2220
cacgaacata ttgcaaacct ggcaggctcc cctgcgatca agaagggcat actgcagacc   2280
gttaaggttg tggacgaatt ggtcaaggtc atgggcaggc acaagcccga aaacatagtt   2340
atagagatgg ccagagagaa ccagaccacc caaaagggcc agaagaacag ccgggagcgc   2400
atgaaaagga tcgaggaggg tatcaaggaa ctcggaagcc agatcctcaa agagcacccc   2460
gtggagaata cccagctcca gaacgagaag ctgtacctgt actacctgca gaacggcagg   2520
gacatgtacg ttgaccagga gttggacatc aacaggcttt cagactatga cgtggatcac   2580
atagtgcccc agagctttct taaagacgat agcatcgaca acaaggtcct gacccgctcc   2640
```

```
gacaaaaaca ggggcaaaag cgacaacgtg ccaagcgaag aggtggttaa aaagatgaag   2700
aactactgga ggcaactgct caacgcgaaa ttgatcaccc agagaaagtt cgataacctg   2760
accaaggccg agaggggcgg actctccgaa cttgacaaag cgggcttcat aaagaggcag   2820
ctggtcgaga cccgacagat cacgaagcac gtggcccaaa tcctcgacag cagaatgaat   2880
accaagtacg atgagaatga caaactcatc agggaagtga aagtgattac cctgaagagc   2940
aagttggtgt ccgactttcg caaagatttc cagttctaca aggtgaggga gatcaacaac   3000
taccaccatg cccacgacgc atacctgaac gccgtggtcg gcaccgccct gattaagaag   3060
tatccaaagc tggagtccga atttgtctac ggcgactaca aagtttacga tgtgaggaag   3120
atgatcgcta agagcgaaca ggagatcggc aaggccaccg ctaagtattt cttctacagc   3180
aacatcatga actttttcaa gaccgagatc acacttgcca acggcgaaat caggaagagg   3240
ccgcttatcg agaccaacgg tgagaccggc gagatcgtgt gggacaaggg cagggacttc   3300
gccaccgtga ggaaagtcct gagcatgccc caggtgaata ttgtgaaaaa aactgaggtg   3360
cagacaggcg gctttagcaa ggaatccatc ctgcccaaga ggaacagcga caagctgatc   3420
gcccggaaga aggactggga ccctaagaag tatggaggct tcgacagccc caccgtagcc   3480
tacagcgtgc tggtggtcgc gaaggtagag aaggggaaga gcaagaaact gaagagcgtg   3540
aaggagctgc tcggcataac catcatggag aggtccagct ttgagaagaa ccccattgac   3600
tttttggaag ccaagggcta caaagaggtc aaaaaggacc tgatcatcaa actccccaag   3660
tactccctgt ttgaattgga gaacggcaga aagaggatgc tggcgagcgc tggggaactg   3720
caaaagggca acgaactggc gctgcccagc aagtacgtga attttctgta cctggcgtcc   3780
cactacgaaa agctgaaagg cagccccgag gacaacgagc agaagcagct gttcgtggag   3840
cagcacaagc attacctgga cgagataatc gagcaaatca gcgagttcag caagagggtg   3900
attctggccg acgcgaacct ggataaggtc ctcagcgcct acaacaagca ccgagacaaa   3960
cccatcaggg agcaggccga gaatatcata cacctgttca ccctgacaaa tctgggcgca   4020
cctgcggcat tcaaatactt cgataccacc atcgacagga aaaggtacac tagcactaag   4080
gaggtgctgg atgccacctt gatccaccag tccattaccg gcctgtatga gaccaggatc   4140
gacctgagcc agcttggagg cgactctagg gcggacccaa aaaagaaaag gaaggtggaa   4200
ttctacccat acgatgttcc agattacgct                                    4230
```

<210> SEQ ID NO 41
<211> LENGTH: 4353
<212> TYPE: DNA
<213> ORGANISM: Artificial Sequence
<220> FEATURE:
<223> OTHER INFORMATION: gene sequence of penetrating peptide-linkage-
Cas protein; AP-HE5-Cas9

<400> SEQUENCE: 41

```
atgggcggtt ctcatcatca tcatcatcat ggtatggcct cccgccggcg ctggtgcaaa     60
cgccgccggg gttctggtgg tggtggaggt cacgagcatg agcacgaaca cgaacacgaa    120
gctagcctgg acagcaccgc tcccaaaaag aaaaggaagg tgggcattca cggcgtgcct    180
gcggccgaca aaaagtacag catcggcctt gatatcggca ccaatagcgt gggctgggcc    240
gttatcacag acgaatacaa ggtacccagc aagaagttca aggtgctggg gaatacagac    300
aggcactcta tcaagaaaaa ccttatcggg gctctgctgt ttgactcagg cgagaccgcc    360
gaggccacca ggttgaagag gaccgcaagg cgaaggtaca cccggaggaa gaacaggatc    420
```

```
tgctatctgc aggagatctt cagcaacgag atggccaagg tggacgacag cttcttccac    480
aggctggagg agagcttcct tgtcgaggag gataagaagc acgaacgaca ccccatcttc    540
ggcaacatag tcgacgaggt cgcttatcac gagaagtacc ccaccatcta ccacctgcga    600
aagaaattgg tggatagcac cgataaagcc gacttgcgac ttatctactt ggctctggcg    660
cacatgatta agttcagggg ccacttcctg atcgagggcg accttaaccc cgacaacagt    720
gacgtagaca aattgttcat ccagcttgta cagacctata accagctgtt cgaggaaaac    780
cctattaacg ccagcggggt ggatgcgaag gccatactta gcgccaggct gagcaaaagc    840
aggcgcttgg agaacctgat agcccagctg cccggtgaaa agaagaacgg cctcttcggt    900
aatctgattg ccctgagcct gggcctgacc cccaacttca agagcaactt cgacctggca    960
gaagatgcca agctgcagtt gagtaaggac acctatgacg acgacttgga caatctgctc   1020
gcccaaatcg gcgaccagta cgctgacctg ttcctcgccg ccaagaacct ttctgacgca   1080
atcctgctta gcgatatcct tagggtgaac acagagatca ccaaggcccc cctgagcgcc   1140
agcatgatca agaggtacga cgagcaccat caggacctga cccttctgaa ggccctggtg   1200
aggcagcaac tgcccgagaa gtacaaggag atcttttttcg accagagcaa gaacggctac   1260
gccggctaca tcgacggcgg agccagccaa gaggagttct acaagttcat caagcccatc   1320
ctggagaaga tggatggcac cgaggagctg ctggtgaagc tgaacaggga agatttgctc   1380
cggaagcaga ggacctttga caacggtagc atcccccacc agatccacct gggcgagctg   1440
cacgcaatac tgaggcgaca ggaggatttc tacccctttcc tcaaggacaa tagggagaaa   1500
atcgaaaaga ttctgacctt caggatcccc tactacgtgg gccctcttgc caggggcaac   1560
agccgattcg cttggatgac aagaaagagc gaggagacca tcaccccctg gaacttcgag   1620
gaagtggtgg acaaaggagc aagcgcgcag tctttcatcg aacggatgac caatttcgac   1680
aaaaacctgc ctaacgagaa ggtgctgccc aagcacagcc tgctttacga gtacttcacc   1740
gtgtacaacg agctcaccaa ggtgaaatat gtgaccgagg gcatgcgaaa acccgctttc   1800
ctgagcggcg agcagaagaa ggccatcgtg gacctgctgt tcaagaccaa caggaaggtg   1860
accgtgaagc agctgaagga ggactacttc aagaagatcg agtgctttga tagcgtggaa   1920
ataagcggcg tggaggacag gttcaacgcc agcctgggca cctaccacga cttgttgaag   1980
ataatcaaag acaaggattt cctggataat gaggagaacg aggatatact cgaggacatc   2040
gtgctgactt tgaccctgtt tgaggaccga gagatgattg aagaaaggct caaaacctac   2100
gcccacctgt tcgacgacaa agtgatgaaa caactgaaga gacgaagata caccggctgg   2160
ggcagactgt ccaggaagct catcaacggc attagggaca agcagagcgg caagaccatc   2220
ctggatttcc tgaagtccga cggcttcgcc aaccgaaact tcatgcagct gattcacgat   2280
gacagcttga ccttcaagga ggacatccag aaggcccagg ttagcggcca gggcgactcc   2340
ctgcacgaac atattgcaaa cctggcaggc tcccctgcga tcaagaaggg catactgcag   2400
accgttaagg ttgtggacga attggtcaag gtcatgggca ggcacaagcc cgaaaacata   2460
gttatagaga tggccagaga gaaccagacc acccaaaagg gccagaagaa cagccgggag   2520
cgcatgaaaa ggatcgagga gggtatcaag gaactcggaa gccagatcct caaagagcac   2580
cccgtggaga atacccagct ccagaacgag aagctgtacc tgtactacct gcagaacggc   2640
agggacatgt acgttgacca ggagttggac atcaacaggc tttcagacta tgacgtggat   2700
cacatagtgc cccagagctt tcttaaagac gatagcatcg acaacaaggt cctgacccgc   2760
tccgacaaaa acaggggcaa aagcgacaac gtgccaagcg aagaggtggt taaaaagatg   2820
```

aagaactact ggaggcaact gctcaacgcg aaattgatca cccagagaaa gttcgataac 2880
ctgaccaagg ccgagagggg cggactctcc gaacttgaca aagcgggctt cataaagagg 2940
cagctggtcg agacccgaca gatcacgaag cacgtggccc aaatcctcga cagcagaatg 3000
aataccaagt acgatgagaa tgacaaactc atcagggaag tgaaagtgat taccctgaag 3060
agcaagttgg tgtccgactt tcgcaaagat ttccagttct acaaggtgag ggagatcaac 3120
aactaccacc atgcccacga cgcatacctg aacgccgtgg tcggcaccgc cctgattaag 3180
aagtatccaa agctggagtc cgaatttgtc tacggcgact acaaagttta cgatgtgagg 3240
aagatgatcg ctaagagcga acaggagatc ggcaaggcca ccgctaagta tttcttctac 3300
agcaacatca tgaacttttt caagaccgag atcacacttg ccaacggcga aatcaggaag 3360
aggccgctta tcgagaccaa cggtgagacc ggcgagatcg tgtgggacaa gggcagggac 3420
ttcgccaccg tgaggaaagt cctgagcatg ccccaggtga atattgtgaa aaaaactgag 3480
gtgcagacag gcggctttag caaggaatcc atcctgccca agaggaacag cgacaagctg 3540
atcgcccgga agaaggactg ggaccctaag aagtatggag gcttcgacag ccccaccgta 3600
gcctacagcg tgctggtggt cgcgaaggta gagaagggga agagcaagaa actgaagagc 3660
gtgaaggagc tgctcggcat aaccatcatg gagaggtcca gctttgagaa gaaccccatt 3720
gactttttgg aagccaaggg ctacaaagag gtcaaaaagg acctgatcat caaactcccc 3780
aagtactccc tgtttgaatt ggagaacggc agaaagagga tgctggcgag cgctggggaa 3840
ctgcaaaagg gcaacgaact ggcgctgccc agcaagtacg tgaattttct gtacctggcg 3900
tcccactacg aaaagctgaa aggcagcccc gaggacaacg agcagaagca gctgttcgtg 3960
gagcagcaca agcattacct ggacgagata atcgagcaaa tcagcgagtt cagcaagagg 4020
gtgattctgg ccgacgcgaa cctggataag gtcctcagcg cctacaacaa gcaccgagac 4080
aaacccatca gggagcaggc cgagaatatc atacacctgt tcaccctgac aaatctgggc 4140
gcacctgcgg cattcaaata cttcgatacc accatcgaca ggaaaaggta cactagcact 4200
aaggaggtgc tggatgccac cttgatccac cagtccatta ccggcctgta tgagaccagg 4260
atcgacctga gccagcttgg aggcgactct agggcggacc caaaaaagaa aaggaaggtg 4320
gaattctacc catacgatgt tccagattac gct 4353

<210> SEQ ID NO 42
<211> LENGTH: 4359
<212> TYPE: DNA
<213> ORGANISM: Artificial Sequence
<220> FEATURE:
<223> OTHER INFORMATION: gene sequence of penetrating peptide-linkage-
Cas protein; AP-HE6-Cas9

<400> SEQUENCE: 42
atgggcggtt ctcatcatca tcatcatcat ggtatggcct cccgccggcg ctggtgcaaa 60
cgccgccggg gttctggtgg tggtggaggt cacgagcacg agcatgagca cgaacacgaa 120
cacgaagcta gcctggacag caccgctccc aaaaagaaaa ggaaggtggg cattcacggc 180
gtgcctgcgg ccgacaaaaa gtacagcatc ggccttgata tcggcaccaa tagcgtgggc 240
tgggccgtta tcacagacga atacaaggta cccagcaaga agttcaaggt gctggggaat 300
acagacaggc actctatcaa gaaaaacctt atcggggctc tgctgtttga ctcaggcgag 360
accgccgagg ccaccaggtt gaagaggacc gcaaggcgaa ggtacacccg gaggaagaac 420
aggatctgct atctgcagga gatcttcagc aacgagatgg ccaaggtgga cgacagcttc 480
ttccacaggc tggaggagag cttccttgtc gaggaggata agaagcacga acgacacccc 540
atcttcggca acatagtcga cgaggtcgct tatcacgaga agtaccccac catctaccac 600
ctgcgaaaga aattggtgga tagcaccgat aaagccgact tgcgacttat ctacttggct 660
ctggcgcaca tgattaagtt caggggccac ttcctgatcg agggcgacct taaccccgac 720
aacagtgacg tagacaaatt gttcatccag cttgtacaga cctataacca gctgttcgag 780
gaaaacccta ttaacgccag cggggtggat gcgaaggcca tacttagcgc caggctgagc 840
aaaagcaggc gcttggagaa cctgatagcc cagctgcccg gtgaaaagaa gaacggcctc 900
ttcggtaatc tgattgccct gagcctgggc ctgaccccca acttcaagag caacttcgac 960
ctggcagaag atgccaagct gcagttgagt aaggacacct atgacgacga cttggacaat 1020
ctgctcgccc aaatcggcga ccagtacgct gacctgttcc tcgccgccaa gaacctttct 1080
gacgcaatcc tgcttagcga tatccttagg gtgaacacag agatcaccaa ggcccccctg 1140
agcgccagca tgatcaagag gtacgacgag caccatcagg acctgaccct tctgaaggcc 1200
ctggtgaggc agcaactgcc cgagaagtac aaggagatct ttttcgacca gagcaagaac 1260
ggctacgccg gctacatcga cggcggagcc agccaagagg agttctacaa gttcatcaag 1320
cccatcctgg agaagatgga tggcaccgag gagctgctgg tgaagctgaa cagggaagat 1380
ttgctccgga agcagaggac ctttgacaac ggtagcatcc cccaccagat ccacctgggc 1440
gagctgcacg caatactgag gcgacaggag gatttctacc ccttcctcaa ggacaatagg 1500
gagaaaatcg aaaagattct gaccttcagg atcccctact acgtgggccc tcttgccagg 1560
ggcaacagcc gattcgcttg gatgacaaga aagagcgagg agaccatcac cccctggaac 1620
ttcgaggaag tggtggacaa aggagcaagc gcgcagtctt tcatcgaacg gatgaccaat 1680
ttcgacaaaa acctgcctaa cgagaaggtg ctgcccaagc acagcctgct ttacgagtac 1740
ttcaccgtgt acaacgagct caccaaggtg aaatatgtga ccgagggcat gcgaaaaccc 1800
gctttcctga gcggcgagca gaagaaggcc atcgtggacc tgctgttcaa gaccaacagg 1860
aaggtgaccg tgaagcagct gaaggaggac tacttcaaga agatcgagtg ctttgatagc 1920
gtggaaataa gcggcgtgga ggacaggttc aacgccagcc tgggcaccta ccacgacttg 1980
ttgaagataa tcaaagacaa ggatttcctg gataatgagg agaacgagga tatactcgag 2040
gacatcgtgc tgactttgac cctgtttgag gaccgagaga tgattgaaga aaggctcaaa 2100
acctacgccc acctgttcga cgacaaagtg atgaaacaac tgaagagacg aagatacacc 2160
ggctggggca gactgtccag gaagctcatc aacggcatta gggacaagca gagcggcaag 2220
accatcctgg atttcctgaa gtccgacggc ttcgccaacc gaaacttcat gcagctgatt 2280
cacgatgaca gcttgacctt caaggaggac atccagaagg cccaggttag cggccagggc 2340
gactccctgc acgaacatat tgcaaacctg gcaggctccc ctgcgatcaa gaagggcata 2400
ctgcagaccg ttaaggttgt ggacgaattg gtcaaggtca tgggcaggca caagcccgaa 2460
aacatagtta tagagatggc cagagagaac cagaccaccc aaaagggcca gaagaacagc 2520
cgggagcgca tgaaaaggat cgaggagggt atcaaggaac tcggaagcca gatcctcaaa 2580
gagcaccccg tggagaatac ccagctccag aacgagaagc tgtacctgta ctacctgcag 2640
aacggcaggg acatgtacgt tgaccaggag ttggacatca acaggctttc agactatgac 2700
gtggatcaca tagtgcccca gagctttctt aaagacgata gcatcgacaa caaggtcctg 2760
acccgctccg acaaaaacag ggcaaaagc gacaacgtgc caagcgaaga ggtggttaaa 2820

```
aagatgaaga actactggag gcaactgctc aacgcgaaat tgatcaccca gagaaagttc   2880

gataacctga ccaaggccga gaggggcgga ctctccgaac ttgacaaagc gggcttcata   2940

aagaggcagc tggtcgagac ccgacagatc acgaagcacg tggcccaaat cctcgacagc   3000

agaatgaata ccaagtacga tgagaatgac aaactcatca gggaagtgaa agtgattacc   3060

ctgaagagca agttggtgtc cgactttcgc aaagatttcc agttctacaa ggtgagggag   3120

atcaacaact accaccatgc ccacgacgca tacctgaacg ccgtggtcgg caccgccctg   3180

attaagaagt atccaaagct ggagtccgaa tttgtctacg gcgactacaa agtttacgat   3240

gtgaggaaga tgatcgctaa gagcgaacag gagatcggca aggccaccgc taagtatttc   3300

ttctacagca acatcatgaa ctttttcaag accgagatca cacttgccaa cggcgaaatc   3360

aggaagaggc cgcttatcga gaccaacggt gagaccggcg agatcgtgtg ggacaagggc   3420

agggacttcg ccaccgtgag gaaagtcctg agcatgcccc aggtgaatat tgtgaaaaaa   3480

actgaggtgc agacaggcgg ctttagcaag gaatccatcc tgcccaagag gaacagcgac   3540

aagctgatcg cccggaagaa ggactgggac cctaagaagt atggaggctt cgacagcccc   3600

accgtagcct acagcgtgct ggtggtcgcg aaggtagaga aggggaagag caagaaactg   3660

aagagcgtga aggagctgct cggcataacc atcatggaga ggtccagctt tgagaagaac   3720

cccattgact tttggaagc caagggctac aaagaggtca aaaaggacct gatcatcaaa   3780

ctccccaagt actccctgtt tgaattggag aacggcagaa agaggatgct ggcgagcgct   3840

ggggaactgc aaaagggcaa cgaactggcg ctgcccagca agtacgtgaa ttttctgtac   3900

ctggcgtccc actacgaaaa gctgaaaggc agccccgagg acaacgagca gaagcagctg   3960

ttcgtggagc agcacaagca ttacctggac gagataatcg agcaaatcag cgagttcagc   4020

aagagggtga ttctggccga cgcgaacctg gataaggtcc tcagcgccta caacaagcac   4080

cgagacaaac ccatcaggga gcaggccgag aatatcatac acctgttcac cctgacaaat   4140

ctgggcgcac ctgcggcatt caaatacttc gataccacca tcgacaggaa aaggtacact   4200

agcactaagg aggtgctgga tgccaccttg atccaccagt ccattaccgg cctgtatgag   4260

accaggatcg acctgagcca gcttggaggc gactctaggg cggacccaaa aaagaaaagg   4320

aaggtggaat tctacccata cgatgttcca gattacgct                          4359
```

<210> SEQ ID NO 43
<211> LENGTH: 4365
<212> TYPE: DNA
<213> ORGANISM: Artificial Sequence
<220> FEATURE:
<223> OTHER INFORMATION: gene sequence of penetrating peptide-linkage-
Cas protein; AP-HE7-Cas9

<400> SEQUENCE: 43

```
atgggcggtt ctcatcatca tcatcatcat ggtatggcct cccgccggcg ctggtgcaaa     60

cgccgccggg gttctggtgg tggtggaggt catgaacacg agcacgagca tgagcacgaa    120

cacgaacacg aagctagcct ggacagcacc gctcccaaaa agaaaaggaa ggtgggcatt    180

cacggcgtgc ctgcggccga caaaaagtac agcatcggcc ttgatatcgg caccaatagc    240

gtgggctggg ccgttatcac agacgaatac aaggtaccca gcaagaagtt caaggtgctg    300

gggaatacag acaggcactc tatcaagaaa aaccttatcg gggctctgct gtttgactca    360

ggcgagaccg ccgaggccac caggttgaag aggaccgcaa ggcgaaggta cacccggagg    420

aagaacagga tctgctatct gcaggagatc ttcagcaacg agatggccaa ggtggacgac    480
```

```
agcttcttcc acaggctgga ggagagcttc cttgtcgagg aggataagaa gcacgaacga    540
caccccatct tcggcaacat agtcgacgag gtcgcttatc acgagaagta ccccaccatc    600
taccacctgc gaaagaaatt ggtggatagc accgataaag ccgacttgcg acttatctac    660
ttggctctgg cgcacatgat taagttcagg ggccacttcc tgatcgaggg cgaccttaac    720
cccgacaaca gtgacgtaga caaattgttc atccagcttg tacagaccta taaccagctg    780
ttcgaggaaa accctattaa cgccagcggg gtggatgcga aggccatact tagcgccagg    840
ctgagcaaaa gcaggcgctt ggagaacctg atagcccagc tgcccggtga aaagaagaac    900
ggcctcttcg gtaatctgat tgccctgagc ctgggcctga cccccaactt caagagcaac    960
ttcgacctgg cagaagatgc caagctgcag ttgagtaagg acacctatga cgacgacttg   1020
gacaatctgc tcgcccaaat cggcgaccag tacgctgacc tgttcctcgc cgccaagaac   1080
ctttctgacg caatcctgct tagcgatatc cttagggtga acacagagat caccaaggcc   1140
cccctgagcg ccagcatgat caagaggtac gacgagcacc atcaggacct gacccttctg   1200
aaggccctgg tgaggcagca actgcccgag aagtacaagg agatcttttt cgaccagagc   1260
aagaacggct acgccggcta catcgacggc ggagccagcc aagaggagtt ctacaagttc   1320
atcaagccca tcctggagaa gatggatggc accgaggagc tgctggtgaa gctgaacagg   1380
gaagatttgc tccggaagca gaggaccttt gacaacggta gcatccccca ccagatccac   1440
ctgggcgagc tgcacgcaat actgaggcga caggaggatt tctacccctt cctcaaggac   1500
aatagggaga aaatcgaaaa gattctgacc ttcaggatcc cctactacgt gggccctctt   1560
gccaggggca acagccgatt cgcttggatg acaagaaaga gcgaggagac catcaccccc   1620
tggaacttcg aggaagtggt ggacaaagga gcaagcgcgc agtctttcat cgaacggatg   1680
accaatttcg acaaaaacct gcctaacgag aaggtgctgc ccaagcacag cctgctttac   1740
gagtacttca ccgtgtacaa cgagctcacc aaggtgaaat atgtgaccga gggcatgcga   1800
aaacccgctt tcctgagcgg cgagcagaag aaggccatcg tggacctgct gttcaagacc   1860
aacaggaagg tgaccgtgaa gcagctgaag gaggactact tcaagaagat cgagtgcttt   1920
gatagcgtgg aaataagcgg cgtggaggac aggttcaacg ccagcctggg cacctaccac   1980
gacttgttga agataatcaa agacaaggat ttcctggata atgaggagaa cgaggatata   2040
ctcgaggaca tcgtgctgac tttgaccctg tttgaggacc gagagatgat tgaagaaagg   2100
ctcaaaacct acgcccacct gttcgacgac aaagtgatga aacaactgaa gagacgaaga   2160
tacaccggct ggggcagact gtccaggaag ctcatcaacg gcattaggga caagcagagc   2220
ggcaagacca tcctggattt cctgaagtcc gacggcttcg ccaaccgaaa cttcatgcag   2280
ctgattcacg atgacagctt gaccttcaag gaggacatcc agaaggccca ggttagcggc   2340
cagggcgact ccctgcacga acatattgca aacctggcag gctcccctgc gatcaagaag   2400
ggcatactgc agaccgttaa ggttgtggac gaattggtca aggtcatggg caggcacaag   2460
cccgaaaaca tagttataga gatggccaga gagaaccaga ccacccaaaa gggccagaag   2520
aacagccggg agcgcatgaa aaggatcgag gagggtatca aggaactcgg aagccagatc   2580
ctcaaagagc accccgtgga gaatacccag ctccagaacg agaagctgta cctgtactac   2640
ctgcagaacg gcagggacat gtacgttgac caggagttgg acatcaacag gctttcagac   2700
tatgacgtgg atcacatagt gccccagagc tttcttaaag acgatagcat cgacaacaag   2760
gtcctgaccc gctccgacaa aaacaggggc aaaagcgaca acgtgccaag cgaagaggtg   2820
gttaaaaaga tgaagaacta ctggaggcaa ctgctcaacg cgaaattgat cacccagaga   2880
```

aagttcgata acctgaccaa ggccgagagg ggcggactct ccgaacttga caaagcgggc 2940
ttcataaaga ggcagctggt cgagacccga cagatcacga agcacgtggc ccaaatcctc 3000
gacagcagaa tgaataccaa gtacgatgag aatgacaaac tcatcaggga agtgaaagtg 3060
attaccctga agagcaagtt ggtgtccgac tttcgcaaag atttccagtt ctacaaggtg 3120
agggagatca acaactacca ccatgcccac gacgcatacc tgaacgccgt ggtcggcacc 3180
gccctgatta agaagtatcc aaagctggag tccgaatttg tctacggcga ctacaaagtt 3240
tacgatgtga ggaagatgat cgctaagagc gaacaggaga tcggcaaggc caccgctaag 3300
tatttcttct acagcaacat catgaacttt ttcaagaccg agatcacact tgccaacggc 3360
gaaatcagga agaggccgct tatcgagacc aacggtgaga ccggcgagat cgtgtgggac 3420
aagggcaggg acttcgccac cgtgaggaaa gtcctgagca tgccccaggt gaatattgtg 3480
aaaaaaactg aggtgcagac aggcggcttt agcaaggaat ccatcctgcc caagaggaac 3540
agcgacaagc tgatcgcccg gaagaaggac tgggacccta agaagtatgg aggcttcgac 3600
agccccaccg tagcctacag cgtgctggtg gtcgcgaagg tagagaaggg gaagagcaag 3660
aaactgaaga gcgtgaagga gctgctcggc ataaccatca tggagaggtc cagctttgag 3720
aagaacccca ttgacttttt ggaagccaag ggctacaaag aggtcaaaaa ggacctgatc 3780
atcaaactcc ccaagtactc cctgtttgaa ttggagaacg gcagaaagag gatgctggcg 3840
agcgctgggg aactgcaaaa gggcaacgaa ctggcgctgc ccagcaagta cgtgaatttt 3900
ctgtacctgg cgtcccacta cgaaaagctg aaaggcagcc ccgaggacaa cgagcagaag 3960
cagctgttcg tggagcagca caagcattac ctggacgaga taatcgagca aatcagcgag 4020
ttcagcaaga gggtgattct ggccgacgcg aacctggata aggtcctcag cgcctacaac 4080
aagcaccgag acaaacccat cagggagcag gccgagaata tcatacacct gttcaccctg 4140
acaaatctgg gcgcacctgc ggcattcaaa tacttcgata ccaccatcga caggaaaagg 4200
tacactagca ctaaggaggt gctggatgcc accttgatcc accagtccat taccggcctg 4260
tatgagacca ggatcgacct gagccagctt ggaggcgact ctagggcgga cccaaaaaag 4320
aaaaggaagg tggaattcta cccatacgat gttccagatt acgct 4365

<210> SEQ ID NO 44
<211> LENGTH: 4371
<212> TYPE: DNA
<213> ORGANISM: Artificial Sequence
<220> FEATURE:
<223> OTHER INFORMATION: gene sequence of penetrating peptide-linkage-
Cas protein; AP-HE8-Cas9

<400> SEQUENCE: 44
atgggcggtt ctcatcatca tcatcatcat ggtatggcct cccgccggcg ctggtgcaaa 60
cgccgccggg gttctggtgg tggtggaggt catgaacatg aacacgagca cgagcatgag 120
cacgaacacg aacacgaagc tagcctggac agcaccgctc ccaaaaagaa aaggaaggtg 180
ggcattcacg gcgtgcctgc ggccgacaaa aagtacagca tcggccttga tatcggcacc 240
aatagcgtgg gctgggccgt tatcacagac gaatacaagg tacccagcaa gaagttcaag 300
gtgctgggga atacagacag gcactctatc aagaaaaacc ttatcggggc tctgctgttt 360
gactcaggcg agaccgccga ggccaccagg ttgaagagga ccgcaaggcg aaggtacacc 420
cggaggaaga acaggatctg ctatctgcag gagatcttca gcaacgagat ggccaaggtg 480
gacgacagct tcttccacag gctggaggag agcttccttg tcgaggagga taagaagcac 540

```
gaacgacacc ccatcttcgg caacatagtc gacgaggtcg cttatcacga gaagtacccc    600
accatctacc acctgcgaaa gaaattggtg gatagcaccg ataaagccga cttgcgactt    660
atctacttgg ctctggcgca catgattaag ttcaggggcc acttcctgat cgagggcgac    720
cttaaccccg acaacagtga cgtagacaaa ttgttcatcc agcttgtaca gacctataac    780
cagctgttcg aggaaaaccc tattaacgcc agcggggtgg atgcgaaggc catacttagc    840
gccaggctga gcaaaagcag gcgcttggag aacctgatag cccagctgcc cggtgaaaag    900
aagaacggcc tcttcggtaa tctgattgcc ctgagcctgg gcctgacccc caacttcaag    960
agcaacttcg acctggcaga agatgccaag ctgcagttga gtaaggacac ctatgacgac   1020
gacttggaca atctgctcgc ccaaatcggc gaccagtacg ctgacctgtt cctcgccgcc   1080
aagaaccttt ctgacgcaat cctgcttagc gatatcctta gggtgaacac agagatcacc   1140
aaggcccccc tgagcgccag catgatcaag aggtacgacg agcaccatca ggacctgacc   1200
cttctgaagg ccctggtgag gcagcaactg cccgagaagt acaaggagat ctttttcgac   1260
cagagcaaga acggctacgc cggctacatc gacggcggag ccagccaaga ggagttctac   1320
aagttcatca agcccatcct ggagaagatg gatggcaccg aggagctgct ggtgaagctg   1380
aacagggaag atttgctccg gaagcagagg acctttgaca acggtagcat cccccaccag   1440
atccacctgg gcgagctgca cgcaatactg aggcgacagg aggatttcta ccccttcctc   1500
aaggacaata gggagaaaat cgaaaagatt ctgaccttca ggatccccta ctacgtgggc   1560
cctcttgcca ggggcaacag ccgattcgct tggatgacaa gaaagagcga ggagaccatc   1620
acccccctgga acttcgagga agtggtggac aaaggagcaa gcgcgcagtc tttcatcgaa  1680
cggatgacca atttcgacaa aaacctgcct aacgagaagg tgctgcccaa gcacagcctg   1740
ctttacgagt acttcaccgt gtacaacgag ctcaccaagg tgaaatatgt gaccgagggc   1800
atgcgaaaac ccgctttcct gagcggcgag cagaagaagg ccatcgtgga cctgctgttc   1860
aagaccaaca ggaaggtgac cgtgaagcag ctgaaggagg actacttcaa gaagatcgag   1920
tgctttgata gcgtggaaat aagcggcgtg gaggacaggt tcaacgccag cctgggcacc   1980
taccacgact tgttgaagat aatcaaagac aaggatttcc tggataatga ggagaacgag   2040
gatatactcg aggacatcgt gctgactttg accctgtttg aggaccgaga gatgattgaa   2100
gaaaggctca aaacctacgc ccacctgttc gacgacaaag tgatgaaaca actgaagaga   2160
cgaagataca ccggctgggg cagactgtcc aggaagctca tcaacggcat tagggacaag   2220
cagagcggca agaccatcct ggatttcctg aagtccgacg gcttcgccaa ccgaaacttc   2280
atgcagctga ttcacgatga cagcttgacc ttcaaggagg acatccagaa ggcccaggtt   2340
agcggccagg gcgactccct gcacgaacat attgcaaacc tggcaggctc ccctgcgatc   2400
aagaagggca tactgcagac cgttaaggtt gtggacgaat tggtcaaggt catgggcagg   2460
cacaagcccg aaaacatagt tatagagatg gccagagaga accagaccac ccaaaagggc   2520
cagaagaaca gccgggagcg catgaaaagg atcgaggagg gtatcaagga actcggaagc   2580
cagatcctca aagagcaccc cgtggagaat acccagctcc agaacgagaa gctgtacctg   2640
tactacctgc agaacggcag ggacatgtac gttgaccagg agttggacat caacaggctt   2700
tcagactatg acgtggatca catagtgccc cagagctttc ttaaagacga tagcatcgac   2760
aacaaggtcc tgacccgctc cgacaaaaac aggggcaaaa gcgacaacgt gccaagcgaa   2820
gaggtggtta aaaagatgaa gaactactgg aggcaactgc tcaacgcgaa attgatcacc   2880
```

cagagaaagt tcgataacct gaccaaggcc gagaggggcg gactctccga acttgacaaa 2940
gcgggcttca taaagaggca gctggtcgag acccgacaga tcacgaagca cgtggcccaa 3000
atcctcgaca gcagaatgaa taccaagtac gatgagaatg acaaactcat cagggaagtg 3060
aaagtgatta ccctgaagag caagttggtg tccgactttc gcaaagattt ccagttctac 3120
aaggtgaggg agatcaacaa ctaccaccat gcccacgacg catacctgaa cgccgtggtc 3180
ggcaccgccc tgattaagaa gtatccaaag ctggagtccg aatttgtcta cggcgactac 3240
aaagtttacg atgtgaggaa gatgatcgct aagagcgaac aggagatcgg caaggccacc 3300
gctaagtatt tcttctacag caacatcatg aacttttca agaccgagat cacacttgcc 3360
aacggcgaaa tcaggaagag gccgcttatc gagaccaacg gtgagaccgg cgagatcgtg 3420
tgggacaagg gcagggactt cgccaccgtg aggaaagtcc tgagcatgcc ccaggtgaat 3480
attgtgaaaa aaactgaggt gcagacaggc ggctttagca aggaatccat cctgcccaag 3540
aggaacagcg acaagctgat cgcccggaag aaggactggg accctaagaa gtatggaggc 3600
ttcgacagcc ccaccgtagc ctacagcgtg ctggtggtcg cgaaggtaga gaaggggaag 3660
agcaagaaac tgaagagcgt gaaggagctg ctcggcataa ccatcatgga gaggtccagc 3720
tttgagaaga accccattga ctttttggaa gccaagggct acaaagaggt caaaaaggac 3780
ctgatcatca aactccccaa gtactccctg tttgaattgg agaacggcag aaagaggatg 3840
ctggcgagcg ctggggaact gcaaaagggc aacgaactgg cgctgcccag caagtacgtg 3900
aattttctgt acctggcgtc ccactacgaa aagctgaaag gcagccccga ggacaacgag 3960
cagaagcagc tgttcgtgga gcagcacaag cattacctgg acgagataat cgagcaaatc 4020
agcgagttca gcaagagggt gattctggcc gacgcgaacc tggataaggt cctcagcgcc 4080
tacaacaagc accgagacaa acccatcagg gagcaggccg agaatatcat acacctgttc 4140
accctgacaa atctgggcgc acctgcggca ttcaaatact tcgataccac catcgacagg 4200
aaaaggtaca ctagcactaa ggaggtgctg gatgccacct tgatccacca gtccattacc 4260
ggcctgtatg agaccaggat cgacctgagc cagcttggag gcgactctag ggcggaccca 4320
aaaaagaaaa ggaaggtgga attctaccca tacgatgttc cagattacgc t 4371

<210> SEQ ID NO 45
<211> LENGTH: 4377
<212> TYPE: DNA
<213> ORGANISM: Artificial Sequence
<220> FEATURE:
<223> OTHER INFORMATION: gene sequence of penetrating peptide-linkage-
Cas protein; AP-HE9-Cas9

<400> SEQUENCE: 45
atgggcggtt ctcatcatca tcatcatcat ggtatggcct cccgccggcg ctggtgcaaa 60
cgccgccggg gttctggtgg tggtggaggt catgaacatg aacatgaaca cgagcacgag 120
catgagcacg aacacgaaca cgaagctagc ctggacagca ccgctcccaa aaagaaaagg 180
aaggtgggca ttcacggcgt gcctgcggcc gacaaaaagt acagcatcgg ccttgatatc 240
ggcaccaata gcgtgggctg ggccgttatc acagacgaat acaaggtacc cagcaagaag 300
ttcaaggtgc tggggaatac agacaggcac tctatcaaga aaaaccttat cggggctctg 360
ctgtttgact caggcgagac cgccgaggcc accaggttga agaggaccgc aaggcgaagg 420
tacacccgga ggaagaacag gatctgctat ctgcaggaga tcttcagcaa cgagatggcc 480
aaggtggacg acagcttctt ccacaggctg gaggagagct tccttgtcga ggaggataag 540

```
aagcacgaac gacaccccat cttcggcaac atagtcgacg aggtcgctta tcacgagaag    600
taccccacca tctaccacct gcgaaagaaa ttggtggata gcaccgataa agccgacttg    660
cgacttatct acttggctct ggcgcacatg attaagttca ggggccactt cctgatcgag    720
ggcgacctta accccgacaa cagtgacgta gacaaattgt tcatccagct tgtacagacc    780
tataaccagc tgttcgagga aaaccctatt aacgccagcg ggtggatgc gaaggccata     840
cttagcgcca ggctgagcaa aagcaggcgc ttggagaacc tgatagccca gctgcccggt    900
gaaaagaaga acggcctctt cggtaatctg attgccctga gcctgggcct gacccccaac    960
ttcaagagca acttcgacct ggcagaagat gccaagctgc agttgagtaa ggacacctat   1020
gacgacgact tggacaatct gctcgcccaa atcggcgacc agtacgctga cctgttcctc   1080
gccgccaaga acctttctga cgcaatcctg cttagcgata tccttagggt gaacacagag   1140
atcaccaagg cccccctgag cgccagcatg atcaagaggt acgacgagca ccatcaggac   1200
ctgacccttc tgaaggccct ggtgaggcag caactgcccg agaagtacaa ggagatcttt   1260
ttcgaccaga gcaagaacgg ctacgccggc tacatcgacg gcggagccag ccaagaggag   1320
ttctacaagt tcatcaagcc catcctggag aagatggatg gcaccgagga gctgctggtg   1380
aagctgaaca gggaagattt gctccggaag cagaggacct ttgacaacgg tagcatcccc   1440
caccagatcc acctgggcga gctgcacgca atactgaggc gacaggagga tttctacccc   1500
ttcctcaagg acaataggga gaaaatcgaa aagattctga ccttcaggat cccctactac   1560
gtgggccctc ttgccagggg caacagccga ttcgcttgga tgacaagaaa gagcgaggag   1620
accatcaccc cctggaactt cgaggaagtg gtggacaaag gagcaagcgc gcagtctttc   1680
atcgaacgga tgaccaattt cgacaaaaac ctgcctaacg agaaggtgct gcccaagcac   1740
agcctgcttt acgagtactt caccgtgtac aacgagctca ccaaggtgaa atatgtgacc   1800
gagggcatgc gaaaacccgc tttcctgagc ggcgagcaga agaaggccat cgtggacctg   1860
ctgttcaaga ccaacaggaa ggtgaccgtg aagcagctga aggaggacta cttcaagaag   1920
atcgagtgct ttgatagcgt ggaaataagc ggcgtggagg acaggttcaa cgccagcctg   1980
ggcacctacc acgacttgtt gaagataatc aaagacaagg atttcctgga taatgaggag   2040
aacgaggata tactcgagga catcgtgctg actttgaccc tgtttgagga ccgagagatg   2100
attgaagaaa ggctcaaaac ctacgcccac ctgttcgacg acaaagtgat gaaacaactg   2160
aagagacgaa gatacaccgg ctggggcaga ctgtccagga agctcatcaa cggcattagg   2220
gacaagcaga gcggcaagac catcctggat ttcctgaagt ccgacggctt cgccaaccga   2280
aacttcatgc agctgattca cgatgacagc ttgaccttca aggaggacat ccagaaggcc   2340
caggttagcg gccagggcga ctccctgcac gaacatattg caaacctggc aggctcccct   2400
gcgatcaaga agggcatact gcagaccgtt aaggttgtgg acgaattggt caaggtcatg   2460
ggcaggcaca agcccgaaaa catagttata gagatggcca gagagaacca gaccacccaa   2520
aagggccaga agaacagccg ggagcgcatg aaaaggatcg aggagggtat caaggaactc   2580
ggaagccaga tcctcaaaga gcaccccgtg gagaataccc agctccagaa cgagaagctg   2640
tacctgtact acctgcagaa cggcagggac atgtacgttg accaggagtt ggacatcaac   2700
aggctttcag actatgacgt ggatcacata gtgccccaga gctttcttaa agacgatagc   2760
atcgacaaca aggtcctgac ccgctccgac aaaaacaggg gcaaaagcga caacgtgcca   2820
agcgaagagg tggttaaaaa gatgaagaac tactggaggc aactgctcaa cgcgaaattg   2880
atcacccaga gaaagttcga taacctgacc aaggccgaga ggggcggact ctccgaactt   2940
```

gacaaagcgg gcttcataaa gaggcagctg gtcgagaccc gacagatcac gaagcacgtg 3000
gcccaaatcc tcgacagcag aatgaatacc aagtacgatg agaatgacaa actcatcagg 3060
gaagtgaaag tgattaccct gaagagcaag ttggtgtccg actttcgcaa agatttccag 3120
ttctacaagg tgagggagat caacaactac caccatgccc acgacgcata cctgaacgcc 3180
gtggtcggca ccgccctgat taagaagtat ccaaagctgg agtccgaatt tgtctacggc 3240
gactacaaag tttacgatgt gaggaagatg atcgctaaga gcgaacagga gatcggcaag 3300
gccaccgcta agtatttctt ctacagcaac atcatgaact tttcaagac cgagatcaca 3360 cttgccaacg gcgaaatcag gaagaggccg cttatcgaga ccaacggtga gaccggcgag 3420
atcgtgtggg acaagggcag ggacttcgcc accgtgagga aagtcctgag catgccccag 3480
gtgaatattg tgaaaaaaac tgaggtgcag acaggcggct ttagcaagga atccatcctg 3540
cccaagagga acagcgacaa gctgatcgcc cggaagaagg actgggaccc taagaagtat 3600
ggaggcttcg acagccccac cgtagcctac agcgtgctgg tggtcgcgaa ggtagagaag 3660
gggaagagca agaaactgaa gagcgtgaag gagctgctcg gcataaccat catggagagg 3720
tccagctttg agaagaaccc cattgacttt ttggaagcca agggctacaa agaggtcaaa 3780
aaggacctga tcatcaaact ccccaagtac tccctgtttg aattggagaa cggcagaaag 3840
aggatgctgg cgagcgctgg ggaactgcaa aagggcaacg aactggcgct gcccagcaag 3900
tacgtgaatt ttctgtacct ggcgtcccac tacgaaaagc tgaaaggcag ccccgaggac 3960
aacgagcaga agcagctgtt cgtggagcag cacaagcatt acctggacga gataatcgag 4020
caaatcagcg agttcagcaa gagggtgatt ctggccgacg cgaacctgga taaggtcctc 4080
agcgcctaca acaagcaccg agacaaaccc atcagggagc aggccgagaa tatcatacac 4140
ctgttcaccc tgacaaatct gggcgcacct gcggcattca aatacttcga taccaccatc 4200
gacaggaaaa ggtacactag cactaaggag gtgctggatg ccaccttgat ccaccagtcc 4260
attaccggcc tgtatgagac caggatcgac ctgagccagc ttggaggcga ctctagggcg 4320
gacccaaaaa agaaaaggaa ggtggaattc tacccatacg atgttccaga ttacgct 4377

<210> SEQ ID NO 46
<211> LENGTH: 4383
<212> TYPE: DNA
<213> ORGANISM: Artificial Sequence
<220> FEATURE:
<223> OTHER INFORMATION: gene sequence of penetrating peptide-linkage-
Cas protein; AP-HE10-Cas9

<400> SEQUENCE: 46
atgggcggtt ctcatcatca tcatcatcat ggtatggcct cccgccggcg ctggtgcaaa 60
cgccgccggg gttctggtgg tggtggaggt cacgaacatg aacatgaaca tgaacacgag 120
cacgagcatg agcacgaaca cgaacacgaa gctagcctgg acagcaccgc tcccaaaaag 180
aaaaggaagg tgggcattca cggcgtgcct gcggccgaca aaaagtacag catcggcctt 240
gatatcggca ccaatagcgt gggctgggcc gttatcacag acgaatacaa ggtacccagc 300
aagaagttca aggtgctggg gaatacagac aggcactcta tcaagaaaaa ccttatcggg 360
gctctgctgt ttgactcagg cgagaccgcc gaggccacca ggttgaagag gaccgcaagg 420
cgaaggtaca cccggaggaa gaacaggatc tgctatctgc aggagatctt cagcaacgag 480
atggccaagg tggacgacag cttcttccac aggctggagg agagcttcct tgtcgaggag 540
gataagaagc acgaacgaca ccccatcttc ggcaacatag tcgacgaggt cgcttatcac 600
gagaagtacc ccaccatcta ccacctgcga aagaaattgg tggatagcac cgataaagcc 660
gacttgcgac ttatctactt ggctctggcg cacatgatta agttcagggg ccacttcctg 720
atcgagggcg accttaaccc cgacaacagt gacgtagaca aattgttcat ccagcttgta 780
cagacctata accagctgtt cgaggaaaac cctattaacg ccagcggggt ggatgcgaag 840
gccatactta gcgccaggct gagcaaaagc aggcgcttgg agaacctgat agcccagctg 900
cccggtgaaa agaagaacgg cctcttcggt aatctgattg ccctgagcct gggcctgacc 960
cccaacttca agagcaactt cgacctggca gaagatgcca agctgcagtt gagtaaggac 1020
acctatgacg acgacttgga caatctgctc gcccaaatcg gcgaccagta cgctgacctg 1080
ttcctcgccg ccaagaacct ttctgacgca atcctgctta gcgatatcct tagggtgaac 1140
acagagatca ccaaggcccc cctgagcgcc agcatgatca agaggtacga cgagcaccat 1200
caggacctga cccttctgaa ggccctggtg aggcagcaac tgcccgagaa gtacaaggag 1260
atcttttcg accagagcaa gaacggctac gccggctaca tcgacggcgg agccagccaa 1320
gaggagttct acaagttcat caagcccatc ctggagaaga tggatggcac cgaggagctg 1380
ctggtgaagc tgaacaggga agatttgctc cggaagcaga ggacctttga caacggtagc 1440
atcccccacc agatccacct gggcgagctg cacgcaatac tgaggcgaca ggaggatttc 1500
taccccttcc tcaaggacaa tagggagaaa atcgaaaaga ttctgacctt caggatcccc 1560
tactacgtgg gccctcttgc caggggcaac agccgattcg cttggatgac aagaaagagc 1620
gaggagacca tcaccccctg gaacttcgag gaagtggtgg acaaaggagc aagcgcgcag 1680
tctttcatcg aacggatgac caatttcgac aaaaacctgc ctaacgagaa ggtgctgccc 1740
aagcacagcc tgctttacga gtacttcacc gtgtacaacg agctcaccaa ggtgaaatat 1800
gtgaccgagg gcatgcgaaa acccgctttc ctgagcggcg agcagaagaa ggccatcgtg 1860
gacctgctgt tcaagaccaa caggaaggtg accgtgaagc agctgaagga ggactacttc 1920
aagaagatcg agtgctttga tagcgtggaa ataagcggcg tggaggacag gttcaacgcc 1980
agcctgggca cctaccacga cttgttgaag ataatcaaag acaaggattt cctggataat 2040
gaggagaacg aggatatact cgaggacatc gtgctgactt tgaccctgtt tgaggaccga 2100
gagatgattg aagaaaggct caaaacctac gcccacctgt tcgacgacaa agtgatgaaa 2160
caactgaaga gacgaagata caccggctgg ggcagactgt ccaggaagct catcaacggc 2220
attagggaca agcagagcgg caagaccatc ctggatttcc tgaagtccga cggcttcgcc 2280
aaccgaaact tcatgcagct gattcacgat gacagcttga ccttcaagga ggacatccag 2340
aaggcccagg ttagcggcca gggcgactcc ctgcacgaac atattgcaaa cctggcaggc 2400
tcccctgcga tcaagaaggg catactgcag accgttaagg ttgtggacga attggtcaag 2460
gtcatgggca ggcacaagcc cgaaaacata gttatagaga tggccagaga gaaccagacc 2520
acccaaaagg gccagaagaa cagccgggag cgcatgaaaa ggatcgagga gggtatcaag 2580
gaactcggaa gccagatcct caaagagcac cccgtggaga atacccagct ccagaacgag 2640
aagctgtacc tgtactacct gcagaacggc agggacatgt acgttgacca ggagttggac 2700
atcaacaggc tttcagacta tgacgtggat cacatagtgc cccagagctt tcttaaagac 2760
gatagcatcg acaacaaggt cctgacccgc tccgacaaaa acaggggcaa aagcgacaac 2820
gtgccaagcg aagaggtggt taaaaagatg aagaactact ggaggcaact gctcaacgcg 2880
aaattgatca cccagagaaa gttcgataac ctgaccaagg ccgagagggg cggactctcc 2940

```
gaacttgaca aagcgggctt cataaagagg cagctggtcg agacccgaca gatcacgaag   3000

cacgtggccc aaatcctcga cagcagaatg aataccaagt acgatgagaa tgacaaactc   3060

atcagggaag tgaaagtgat taccctgaag agcaagttgg tgtccgactt tcgcaaagat   3120

ttccagttct acaaggtgag ggagatcaac aactaccacc atgcccacga cgcatacctg   3180

aacgccgtgg tcggcaccgc cctgattaag aagtatccaa agctggagtc cgaatttgtc   3240

tacggcgact acaaagttta cgatgtgagg aagatgatcg ctaagagcga acaggagatc   3300

ggcaaggcca ccgctaagta tttcttctac agcaacatca tgaacttttt caagaccgag   3360

atcacacttg ccaacggcga aatcaggaag aggccgctta tcgagaccaa cggtgagacc   3420

ggcgagatcg tgtgggacaa gggcagggac ttcgccaccg tgaggaaagt cctgagcatg   3480

ccccaggtga atattgtgaa aaaaactgag gtgcagacag gcggctttag caaggaatcc   3540

atcctgccca agaggaacag cgacaagctg atcgcccgga agaaggactg ggaccctaag   3600

aagtatggag gcttcgacag ccccaccgta gcctacagcg tgctggtggt cgcgaaggta   3660

gagaagggga agagcaagaa actgaagagc gtgaaggagc tgctcggcat aaccatcatg   3720

gagaggtcca gctttgagaa gaaccccatt gactttttgg aagccaaggg ctacaaagag   3780

gtcaaaaagg acctgatcat caaactcccc aagtactccc tgtttgaatt ggagaacggc   3840

agaaagagga tgctggcgag cgctggggaa ctgcaaaagg gcaacgaact ggcgctgccc   3900

agcaagtacg tgaatttttct gtacctggcg tcccactacg aaaagctgaa aggcagcccc   3960

gaggacaacg agcagaagca gctgttcgtg gagcagcaca agcattacct ggacgagata   4020

atcgagcaaa tcagcgagtt cagcaagagg gtgattctgg ccgacgcgaa cctggataag   4080

gtcctcagcg cctacaacaa gcaccgagac aaacccatca gggagcaggc cgagaatatc   4140

atacacctgt tcaccctgac aaatctgggc gcacctgcgg cattcaaata cttcgatacc   4200

accatcgaca ggaaaaggta cactagcact aaggaggtgc tggatgccac cttgatccac   4260

cagtccatta ccggcctgta tgagaccagg atcgacctga gccagcttgg aggcgactct   4320

agggcggacc caaaaaagaa aaggaaggtg gaattctacc catacgatgt tccagattac   4380

gct                                                                 4383
```

<210> SEQ ID NO 47
<211> LENGTH: 4389
<212> TYPE: DNA
<213> ORGANISM: Artificial Sequence
<220> FEATURE:
<223> OTHER INFORMATION: gene sequence of penetrating peptide-linkage-
Cas protein; AP-HE11-Cas9

<400> SEQUENCE: 47

```
atgggcggtt ctcatcatca tcatcatcat ggtatggcct cccgccggcg ctggtgcaaa     60

cgccgccggg gttctggtgg tggtggaggt catgaacacg aacatgaaca tgaacatgaa    120

cacgagcacg agcatgagca cgaacacgaa cacgaagcta gcctggacag caccgctccc    180

aaaaagaaaa ggaaggtggg cattcacggc gtgcctgcgg ccgacaaaaa gtacagcatc    240

ggccttgata tcggcaccaa tagcgtgggc tgggccgtta tcacagacga atacaaggta    300

cccagcaaga agttcaaggt gctggggaat acagacaggc actctatcaa gaaaaacctt    360

atcggggctc tgctgtttga ctcaggcgag accgccgagg ccaccaggtt gaagaggacc    420

gcaaggcgaa ggtacacccg gaggaagaac aggatctgct atctgcagga gatcttcagc    480

aacgagatgg ccaaggtgga cgacagcttc ttccacaggc tggaggagag cttccttgtc    540
```

```
gaggaggata agaagcacga acgacacccc atcttcggca acatagtcga cgaggtcgct    600
tatcacgaga agtaccccac catctaccac ctgcgaaaga aattggtgga tagcaccgat    660
aaagccgact tgcgacttat ctacttggct ctggcgcaca tgattaagtt caggggccac    720
ttcctgatcg agggcgacct taaccccgac aacagtgacg tagacaaatt gttcatccag    780
cttgtacaga cctataacca gctgttcgag gaaaacccta ttaacgccag cggggtggat    840
gcgaaggcca tacttagcgc caggctgagc aaaagcaggc gcttggagaa cctgatagcc    900
cagctgcccg gtgaaaagaa gaacggcctc ttcggtaatc tgattgccct gagcctgggc    960
ctgaccccca acttcaagag caacttcgac ctggcagaag atgccaagct gcagttgagt   1020
aaggacacct atgacgacga cttggacaat ctgctcgccc aaatcggcga ccagtacgct   1080
gacctgttcc tcgccgccaa gaacctttct gacgcaatcc tgcttagcga tatccttagg   1140
gtgaacacag agatcaccaa ggcccccctg agcgccagca tgatcaagag gtacgacgag   1200
caccatcagg acctgaccct tctgaaggcc ctggtgaggc agcaactgcc cgagaagtac   1260
aaggagatct tttcgacca gagcaagaac ggctacgccg gctacatcga cggcggagcc    1320
agccaagagg agttctacaa gttcatcaag cccatcctgg agaagatgga tggcaccgag   1380
gagctgctgg tgaagctgaa cagggaagat ttgctccgga agcagaggac ctttgacaac   1440
ggtagcatcc cccaccagat ccacctgggc gagctgcacg caatactgag gcgacaggag   1500
gatttctacc ccttcctcaa ggacaatagg gagaaaatcg aaaagattct gaccttcagg   1560
atcccctact acgtgggccc tcttgccagg ggcaacagcc gattcgcttg gatgacaaga   1620
aagagcgagg agaccatcac cccctggaac ttcgaggaag tggtggacaa aggagcaagc   1680
gcgcagtctt tcatcgaacg gatgaccaat ttcgacaaaa acctgcctaa cgagaaggtg   1740
ctgcccaagc acagcctgct ttacgagtac ttcaccgtgt acaacgagct caccaaggtg   1800
aaatatgtga ccgagggcat gcgaaaaccc gctttcctga gcggcgagca gaagaaggcc   1860
atcgtggacc tgctgttcaa gaccaacagg aaggtgaccg tgaagcagct gaaggaggac   1920
tacttcaaga agatcgagtg ctttgatagc gtggaaataa gcggcgtgga ggacaggttc   1980
aacgccagcc tgggcaccta ccacgacttg ttgaagataa tcaaagacaa ggatttcctg   2040
gataatgagg agaacgagga tatactcgag gacatcgtgc tgactttgac cctgtttgag   2100
gaccgagaga tgattgaaga aaggctcaaa acctacgccc acctgttcga cgacaaagtg   2160
atgaaacaac tgaagagacg aagatacacc ggctggggca gactgtccag gaagctcatc   2220
aacggcatta gggacaagca gagcggcaag accatcctgg atttcctgaa gtccgacggc   2280
ttcgccaacc gaaacttcat gcagctgatt cacgatgaca gcttgacctt caaggaggac   2340
atccagaagg cccaggttag cggccagggc gactccctgc acgaacatat tgcaaacctg   2400
gcaggctccc ctgcgatcaa gaagggcata ctgcagaccg ttaaggttgt ggacgaattg   2460
gtcaaggtca tgggcaggca caagcccgaa aacatagtta tagagatggc cagagagaac   2520
cagaccaccc aaaagggcca gaagaacagc cgggagcgca tgaaaaggat cgaggagggt   2580
atcaaggaac tcggaagcca gatcctcaaa gagcaccccg tggagaatac ccagctccag   2640
aacgagaagc tgtacctgta ctacctgcag aacggcaggg acatgtacgt tgaccaggag   2700
ttggacatca acaggctttc agactatgac gtggatcaca tagtgcccca gagctttctt   2760
aaagacgata gcatcgacaa caaggtcctg acccgctccg acaaaaacag ggcaaaagc    2820
gacaacgtgc caagcgaaga ggtggttaaa aagatgaaga actactggag gcaactgctc   2880
aacgcgaaat tgatcaccca gagaaagttc gataacctga ccaaggccga gaggggcgga   2940
```

```
ctctccgaac ttgacaaagc gggcttcata aagaggcagc tggtcgagac ccgacagatc   3000

acgaagcacg tggcccaaat cctcgacagc agaatgaata ccaagtacga tgagaatgac   3060

aaactcatca gggaagtgaa agtgattacc ctgaagagca agttggtgtc cgactttcgc   3120

aaagatttcc agttctacaa ggtgagggag atcaacaact accaccatgc ccacgacgca   3180

tacctgaacg ccgtggtcgg caccgccctg attaagaagt atccaaagct ggagtccgaa   3240

tttgtctacg gcgactacaa agtttacgat gtgaggaaga tgatcgctaa gagcgaacag   3300

gagatcggca aggccaccgc taagtatttc ttctacagca acatcatgaa ctttttcaag   3360

accgagatca cacttgccaa cggcgaaatc aggaagaggc cgcttatcga gaccaacggt   3420

gagaccggcg agatcgtgtg ggacaagggc agggacttcg ccaccgtgag gaaagtcctg   3480

agcatgcccc aggtgaatat tgtgaaaaaa actgaggtgc agacaggcgg ctttagcaag   3540

gaatccatcc tgcccaagag gaacagcgac aagctgatcg cccggaagaa ggactgggac   3600

cctaagaagt atggaggctt cgacagcccc accgtagcct acagcgtgct ggtggtcgcg   3660

aaggtagaga aggggaagag caagaaactg aagagcgtga aggagctgct cggcataacc   3720

atcatggaga ggtccagctt tgagaagaac cccattgact ttttggaagc caagggctac   3780

aaagaggtca aaaaggacct gatcatcaaa ctccccaagt actccctgtt tgaattggag   3840

aacggcagaa agaggatgct ggcgagcgct ggggaactgc aaaagggcaa cgaactggcg   3900

ctgcccagca agtacgtgaa ttttctgtac ctggcgtccc actacgaaaa gctgaaaggc   3960

agccccgagg acaacgagca gaagcagctg ttcgtggagc agcacaagca ttacctggac   4020

gagataatcg agcaaatcag cgagttcagc aagagggtga ttctggccga cgcgaacctg   4080

gataaggtcc tcagcgccta caacaagcac cgagacaaac ccatcaggga gcaggccgag   4140

aatatcatac acctgttcac cctgacaaat ctgggcgcac ctgcggcatt caaatacttc   4200

gataccacca tcgacaggaa aaggtacact agcactaagg aggtgctgga tgccaccttg   4260

atccaccagt ccattaccgg cctgtatgag accaggatcg acctgagcca gcttggaggc   4320

gactctaggg cggacccaaa aaagaaaagg aaggtggaat tctacccata cgatgttcca   4380

gattacgct                                                           4389
```

<210> SEQ ID NO 48
<211> LENGTH: 4395
<212> TYPE: DNA
<213> ORGANISM: Artificial Sequence
<220> FEATURE:
<223> OTHER INFORMATION: gene sequence of penetrating peptide-linkage-
      Cas protein; AP-HE12-Cas9

<400> SEQUENCE: 48

```
atgggcggtt ctcatcatca tcatcatcat ggtatggcct cccgccggcg ctggtgcaaa     60

cgccgccggg gttctggtgg tggtggaggt cacgaacatg aacacgaaca tgaacatgaa    120

catgaacacg agcacgagca tgagcacgaa cacgaacacg aagctagcct ggacagcacc    180

gctcccaaaa agaaaaggaa ggtgggcatt cacggcgtgc ctgcggccga caaaaagtac    240

agcatcggcc ttgatatcgg caccaatagc gtgggctggg ccgttatcac agacgaatac    300

aaggtaccca gcaagaagtt caaggtgctg gggaatacag acaggcactc tatcaagaaa    360

aaccttatcg gggctctgct gtttgactca ggcgagaccg ccgaggccac caggttgaag    420

aggaccgcaa ggcgaaggta cacccggagg aagaacagga tctgctatct gcaggagatc    480

ttcagcaacg agatggccaa ggtggacgac agcttcttcc acaggctgga ggagagcttc    540
```

```
cttgtcgagg aggataagaa gcacgaacga caccccatct tcggcaacat agtcgacgag    600
gtcgcttatc acgagaagta ccccaccatc taccacctgc gaaagaaatt ggtggatagc    660
accgataaag ccgacttgcg acttatctac ttggctctgg cgcacatgat taagttcagg    720
ggccacttcc tgatcgaggg cgaccttaac cccgacaaca gtgacgtaga caaattgttc    780
atccagcttg tacagaccta taaccagctg ttcgaggaaa accctattaa cgccagcggg    840
gtggatgcga aggccatact tagcgccagg ctgagcaaaa gcaggcgctt ggagaacctg    900
atagcccagc tgcccggtga aaagaagaac ggcctcttcg gtaatctgat tgccctgagc    960
ctgggcctga cccccaactt caagagcaac ttcgacctgg cagaagatgc caagctgcag   1020
ttgagtaagg acacctatga cgacgacttg gacaatctgc tcgcccaaat cggcgaccag   1080
tacgctgacc tgttcctcgc cgccaagaac ctttctgacg caatcctgct tagcgatatc   1140
cttagggtga acacagagat caccaaggcc cccctgagcg ccagcatgat caagaggtac   1200
gacgagcacc atcaggacct gacccttctg aaggccctgg tgaggcagca actgcccgag   1260
aagtacaagg agatcttttt cgaccagagc aagaacggct acgccggcta catcgacggc   1320
ggagccagcc aagaggagtt ctacaagttc atcaagccca tcctggagaa gatggatggc   1380
accgaggagc tgctggtgaa gctgaacagg gaagatttgc tccggaagca gaggaccttt   1440
gacaacggta gcatccccca ccagatccac ctgggcgagc tgcacgcaat actgaggcga   1500
caggaggatt tctacccctt cctcaaggac aatagggaga aaatcgaaaa gattctgacc   1560
ttcaggatcc cctactacgt gggccctctt gccaggggca acagccgatt cgcttggatg   1620
acaagaaaga gcgaggagac catcaccccc tggaacttcg aggaagtggt ggacaaagga   1680
gcaagcgcgc agtctttcat cgaacggatg accaatttcg acaaaaacct gcctaacgag   1740
aaggtgctgc ccaagcacag cctgctttac gagtacttca ccgtgtacaa cgagctcacc   1800
aaggtgaaat atgtgaccga gggcatgcga aaacccgctt tcctgagcgg cgagcagaag   1860
aaggccatcg tggacctgct gttcaagacc aacaggaagg tgaccgtgaa gcagctgaag   1920
gaggactact tcaagaagat cgagtgcttt gatagcgtgg aaataagcgg cgtggaggac   1980
aggttcaacg ccagcctggg cacctaccac gacttgttga agataatcaa agacaaggat   2040
ttcctggata atgaggagaa cgaggatata ctcgaggaca tcgtgctgac tttgaccctg   2100
tttgaggacc gagagatgat tgaagaaagg ctcaaaacct acgcccacct gttcgacgac   2160
aaagtgatga aacaactgaa gagacgaaga tacaccggct ggggcagact gtccaggaag   2220
ctcatcaacg gcattaggga caagcagagc ggcaagacca tcctggattt cctgaagtcc   2280
gacggcttcg ccaaccgaaa cttcatgcag ctgattcacg atgacagctt gaccttcaag   2340
gaggacatcc agaaggccca ggttagcggc cagggcgact ccctgcacga acatattgca   2400
aacctggcag gctcccctgc gatcaagaag ggcatactgc agaccgttaa ggttgtggac   2460
gaattggtca aggtcatggg caggcacaag cccgaaaaca tagttataga gatggccaga   2520
gagaaccaga ccacccaaaa gggccagaag aacagccggg agcgcatgaa aaggatcgag   2580
gagggtatca aggaactcgg aagccagatc ctcaaagagc accccgtgga gaatacccag   2640
ctccagaacg agaagctgta cctgtactac ctgcagaacg gcagggacat gtacgttgac   2700
caggagttgg acatcaacag gctttcagac tatgacgtgg atcacatagt gccccagagc   2760
tttcttaaag acgatagcat cgacaacaag gtcctgaccc gctccgacaa aaacaggggc   2820
aaaagcgaca acgtgccaag cgaagaggtg gttaaaaaga tgaagaacta ctggaggcaa   2880
```

```
ctgctcaacg cgaaattgat cacccagaga aagttcgata acctgaccaa ggccgagagg   2940

ggcggactct ccgaacttga caaagcgggc ttcataaaga ggcagctggt cgagacccga   3000

cagatcacga agcacgtggc ccaaatcctc gacagcagaa tgaataccaa gtacgatgag   3060

aatgacaaac tcatcaggga agtgaaagtg attaccctga agagcaagtt ggtgtccgac   3120

tttcgcaaag atttccagtt ctacaaggtg agggagatca acaactacca ccatgcccac   3180

gacgcatacc tgaacgccgt ggtcggcacc gccctgatta agaagtatcc aaagctggag   3240

tccgaatttg tctacggcga ctacaaagtt tacgatgtga ggaagatgat cgctaagagc   3300

gaacaggaga tcggcaaggc caccgctaag tatttcttct acagcaacat catgaacttt   3360

ttcaagaccg agatcacact tgccaacggc gaaatcagga agaggccgct tatcgagacc   3420

aacggtgaga ccggcgagat cgtgtgggac aagggcaggg acttcgccac cgtgaggaaa   3480

gtcctgagca tgccccaggt gaatattgtg aaaaaaactg aggtgcagac aggcggcttt   3540

agcaaggaat ccatcctgcc caagaggaac agcgacaagc tgatcgcccg gaagaaggac   3600

tgggacccta agaagtatgg aggcttcgac agccccaccg tagcctacag cgtgctggtg   3660

gtcgcgaagg tagagaaggg gaagagcaag aaactgaaga gcgtgaagga gctgctcggc   3720

ataaccatca tggagaggtc cagctttgag aagaacccca ttgacttttt ggaagccaag   3780

ggctacaaag aggtcaaaaa ggacctgatc atcaaactcc ccaagtactc cctgtttgaa   3840

ttggagaacg gcagaaagag gatgctggcg agcgctgggg aactgcaaaa gggcaacgaa   3900

ctggcgctgc ccagcaagta cgtgaatttt ctgtacctgg cgtcccacta cgaaaagctg   3960

aaaggcagcc ccgaggacaa cgagcagaag cagctgttcg tggagcagca caagcattac   4020

ctggacgaga taatcgagca aatcagcgag ttcagcaaga gggtgattct ggccgacgcg   4080

aacctggata aggtcctcag cgcctacaac aagcaccgag acaaacccat cagggagcag   4140

gccgagaata tcatacacct gttcaccctg acaaatctgg gcgcacctgc ggcattcaaa   4200

tacttcgata ccaccatcga caggaaaagg tacactagca ctaaggaggt gctggatgcc   4260

accttgatcc accagtccat taccggcctg tatgagacca ggatcgacct gagccagctt   4320

ggaggcgact ctagggcgga cccaaaaaag aaaaggaagg tggaattcta cccatacgat   4380

gttccagatt acgct                                                    4395
```

<210> SEQ ID NO 49
<211> LENGTH: 90
<212> TYPE: DNA
<213> ORGANISM: Artificial Sequence
<220> FEATURE:
<223> OTHER INFORMATION: gene sequence of penetrating peptide;AP

<400> SEQUENCE: 49

```
atgggcagca gccatcatca tcatcatcac agcagcggcc tggtgccgcg cggcagccat     60

atgcgccggc gctggtgcaa acgccgccgg                                      90
```

<210> SEQ ID NO 50
<211> LENGTH: 4404
<212> TYPE: DNA
<213> ORGANISM: Artificial Sequence
<220> FEATURE:
<223> OTHER INFORMATION: gene sequence of penetrating peptide-linkage-
Cas protein; AP-Cas9

<400> SEQUENCE: 50

```
atgggcagca gccatcatca tcatcatcac agcagcggcc tggtgccgcg cggcagccat     60
```

-continued

```
atgcgccggc gctggtgcaa acgccgccgg ggttctggtg gtggtggagg tcacgaacat    120
gaacatgaac atgaacacga gcacgagcat gagcacgaac acgaacacga agctagcctg    180
gacagcaccg ctcccaaaaa gaaaaggaag gtgggcattc acggcgtgcc tgcggccgac    240
aaaaagtaca gcatcggcct tgatatcggc accaatagcg tgggctgggc cgttatcaca    300
gacgaataca aggtacccag caagaagttc aaggtgctgg ggaatacaga caggcactct    360
atcaagaaaa accttatcgg ggctctgctg tttgactcag gcgagaccgc cgaggccacc    420
aggttgaaga ggaccgcaag gcgaaggtac acccggagga agaacaggat ctgctatctg    480
caggagatct tcagcaacga gatggccaag gtggacgaca gcttcttcca caggctggag    540
gagagcttcc ttgtcgagga ggataagaag cacgaacgac accccatctt cggcaacata    600
gtcgacgagg tcgcttatca cgagaagtac cccaccatct accacctgcg aaagaaattg    660
gtggatagca ccgataaagc cgacttgcga cttatctact tggctctggc gcacatgatt    720
aagttcaggg gccacttcct gatcgagggc gaccttaacc ccgacaacag tgacgtagac    780
aaattgttca tccagcttgt acagacctat aaccagctgt tcgaggaaaa ccctattaac    840
gccagcgggg tggatgcgaa ggccatactt agcgccaggc tgagcaaaag caggcgcttg    900
gagaacctga tagcccagct gcccggtgaa aagaagaacg gcctcttcgg taatctgatt    960
gccctgagcc tgggcctgac ccccaacttc aagagcaact tcgacctggc agaagatgcc   1020
aagctgcagt tgagtaagga cacctatgac gacgacttgg acaatctgct cgcccaaatc   1080
ggcgaccagt acgctgacct gttcctcgcc gccaagaacc tttctgacgc aatcctgctt   1140
agcgatatcc ttagggtgaa cacagagatc accaaggccc ccctgagcgc cagcatgatc   1200
aagaggtacg acgagcacca tcaggacctg acccttctga aggccctggt gaggcagcaa   1260
ctgcccgaga agtacaagga gatctttttc gaccagagca agaacggcta cgccggctac   1320
atcgacggcg gagccagcca agaggagttc tacaagttca tcaagcccat cctggagaag   1380
atggatggca ccgaggagct gctggtgaag ctgaacaggg aagatttgct ccggaagcag   1440
aggacctttg acaacggtag catcccccac cagatccacc tgggcgagct gcacgcaata   1500
ctgaggcgac aggaggattt ctacccccttc ctcaaggaca atagggagaa aatcgaaaag   1560
attctgacct tcaggatccc ctactacgtg ggccctcttg ccaggggcaa cagccgattc   1620
gcttggatga caagaaagag cgaggagacc atcacccccct ggaacttcga ggaagtggtg   1680
gacaaaggag caagcgcgca gtctttcatc gaacggatga ccaatttcga caaaaacctg   1740
cctaacgaga aggtgctgcc caagcacagc ctgctttacg agtacttcac cgtgtacaac   1800
gagctcacca aggtgaaata tgtgaccgag ggcatgcgaa aacccgcttt cctgagcggc   1860
gagcagaaga aggccatcgt ggacctgctg ttcaagacca acaggaaggt gaccgtgaag   1920
cagctgaagg aggactactt caagaagatc gagtgctttg atagcgtgga aataagcggc   1980
gtggaggaca ggttcaacgc cagcctgggc acctaccacg acttgttgaa gataatcaaa   2040
gacaaggatt tcctggataa tgaggagaac gaggatatac tcgaggacat cgtgctgact   2100
ttgaccctgt ttgaggaccg agagatgatt gaagaaaggc tcaaaaccta cgcccacctg   2160
ttcgacgaca aagtgatgaa acaactgaag agacgaagat acaccggctg gggcagactg   2220
tccaggaagc tcatcaacgg cattagggac aagcagagcg gcaagaccat cctggatttc   2280
ctgaagtccg acggcttcgc caaccgaaac ttcatgcagc tgattcacga tgacagcttg   2340
accttcaagg aggacatcca gaaggcccag gttagcggcc agggcgactc cctgcacgaa   2400
catattgcaa acctggcagg ctcccctgcg atcaagaagg gcatactgca gaccgttaag   2460
```

```
gttgtggacg aattggtcaa ggtcatgggc aggcacaagc ccgaaaacat agttatagag   2520

atggccagag agaaccagac cacccaaaag ggccagaaga acagccggga gcgcatgaaa   2580

aggatcgagg agggtatcaa ggaactcgga agccagatcc tcaaagagca ccccgtggag   2640

aatacccagc tccagaacga gaagctgtac ctgtactacc tgcagaacgg cagggacatg   2700

tacgttgacc aggagttgga catcaacagg ctttcagact atgacgtgga tcacatagtg   2760

ccccagagct ttcttaaaga cgatagcatc gacaacaagg tcctgacccg ctccgacaaa   2820

aacaggggca aaagcgacaa cgtgccaagc gaagaggtgg ttaaaaagat gaagaactac   2880

tggaggcaac tgctcaacgc gaaattgatc acccagagaa agttcgataa cctgaccaag   2940

gccgagaggg gcggactctc cgaacttgac aaagcgggct tcataaagag gcagctggtc   3000

gagacccgac agatcacgaa gcacgtggcc caaatcctcg acagcagaat gaataccaag   3060

tacgatgaga atgacaaact catcagggaa gtgaaagtga ttaccctgaa gagcaagttg   3120

gtgtccgact ttcgcaaaga tttccagttc tacaaggtga gggagatcaa caactaccac   3180

catgcccacg acgcatacct gaacgccgtg gtcggcaccg ccctgattaa gaagtatcca   3240

aagctggagt ccgaatttgt ctacggcgac tacaaagttt acgatgtgag gaagatgatc   3300

gctaagagcg aacaggagat cggcaaggcc accgctaagt atttcttcta cagcaacatc   3360

atgaactttt tcaagaccga gatcacactt gccaacggcg aaatcaggaa gaggccgctt   3420

atcgagacca acggtgagac cggcgagatc gtgtgggaca agggcaggga cttcgccacc   3480

gtgaggaaag tcctgagcat gccccaggtg aatattgtga aaaaaactga ggtgcagaca   3540

ggcggcttta gcaaggaatc catcctgccc aagaggaaca gcgacaagct gatcgcccgg   3600

aagaaggact gggaccctaa gaagtatgga ggcttcgaca gccccaccgt agcctacagc   3660

gtgctggtgg tcgcgaaggt agagaagggg aagagcaaga aactgaagag cgtgaaggag   3720

ctgctcggca taaccatcat ggagaggtcc agctttgaga agaaccccat tgactttttg   3780

gaagccaagg gctacaaaga ggtcaaaaag gacctgatca tcaaactccc caagtactcc   3840

ctgtttgaat tggagaacgg cagaaagagg atgctggcga gcgctgggga actgcaaaag   3900

ggcaacgaac tggcgctgcc cagcaagtac gtgaattttc tgtacctggc gtcccactac   3960

gaaaagctga aaggcagccc cgaggacaac gagcagaagc agctgttcgt ggagcagcac   4020

aagcattacc tggacgagat aatcgagcaa atcagcgagt tcagcaagag ggtgattctg   4080

gccgacgcga acctggataa ggtcctcagc gcctacaaca agcaccgaga caaacccatc   4140

agggagcagg ccgagaatat catacacctg ttcaccctga caaatctggg cgcacctgcg   4200

gcattcaaat acttcgatac caccatcgac aggaaaaggt acactagcac taaggaggtg   4260

ctggatgcca ccttgatcca ccagtccatt accggcctgt atgagaccag gatcgacctg   4320

agccagcttg gaggcgactc tagggcggac ccaaaaaaga aaaggaaggt ggaattctac   4380

ccatacgatg ttccagatta cgct                                          4404
```

<210> SEQ ID NO 51
<211> LENGTH: 135
<212> TYPE: DNA
<213> ORGANISM: Artificial Sequence
<220> FEATURE:
<223> OTHER INFORMATION: gene sequence of penetrating peptide; dNP2

<400> SEQUENCE: 51

```
atgggcagca gccatcatca tcatcatcac agcagcggcc tggtgccgcg cggcagccat     60
```

atgaagatca agaaggttaa aaaaaagggt cgcaagggct ctaaaattaa aaaagtcaag 120
aagaaaggaa gaaaa 135

<210> SEQ ID NO 52
<211> LENGTH: 4368
<212> TYPE: DNA
<213> ORGANISM: Artificial Sequence
<220> FEATURE:
<223> OTHER INFORMATION: gene sequence of penetrating peptide-linkage-
Cas protein; dNP2-Cas9

<400> SEQUENCE: 52
atgggcagca gccatcatca tcatcatcac agcagcggcc tggtgccgcg cggcagccat 60
atgaagatca agaaggttaa aaaaaagggt cgcaagggct ctaaaattaa aaaagtcaag 120
aagaaaggaa gaaaagctag cctggacagc accgctccca aaaagaaaag gaaggtgggc 180
attcacggcg tgcctgcggc cgacaaaaag tacagcatcg gccttgatat cggcaccaat 240
agcgtgggct gggccgttat cacagacgaa tacaaggtac ccagcaagaa gttcaaggtg 300
ctggggaata cagacaggca ctctatcaag aaaaacctta tcggggctct gctgtttgac 360
tcaggcgaga ccgccgaggc caccaggttg aagaggaccg caaggcgaag gtacacccgg 420
aggaagaaca ggatctgcta tctgcaggag atcttcagca acgagatggc caaggtggac 480
gacagcttct tccacaggct ggaggagagc ttccttgtcg aggaggataa gaagcacgaa 540
cgacacccca tcttcggcaa catagtcgac gaggtcgctt atcacgagaa gtaccccacc 600
atctaccacc tgcgaaagaa attggtggat agcaccgata aagccgactt gcgacttatc 660
tacttggctc tggcgcacat gattaagttc aggggccact tcctgatcga gggcgacctt 720
aaccccgaca acagtgacgt agacaaattg ttcatccagc ttgtacagac ctataaccag 780
ctgttcgagg aaaaccctat taacgccagc ggggtggatg cgaaggccat acttagcgcc 840
aggctgagca aaagcaggcg cttggagaac ctgatagccc agctgcccgg tgaaaagaag 900
aacggcctct tcggtaatct gattgccctg agcctgggcc tgacccccaa cttcaagagc 960
aacttcgacc tggcagaaga tgccaagctg cagttgagta aggacaccta tgacgacgac 1020
ttggacaatc tgctcgccca aatcggcgac cagtacgctg acctgttcct cgccgccaag 1080
aacctttctg acgcaatcct gcttagcgat atccttaggg tgaacacaga gatcaccaag 1140 gccccccctga gcgccagcat gatcaagagg tacgacgagc accatcagga cctgaccctt 1200
ctgaaggccc tggtgaggca gcaactgccc gagaagtaca aggagatctt tttcgaccag 1260
agcaagaacg gctacgccgg ctacatcgac ggcggagcca gccaagagga gttctacaag 1320
ttcatcaagc ccatcctgga gaagatggat ggcaccgagg agctgctggt gaagctgaac 1380
agggaagatt tgctccggaa gcagaggacc tttgacaacg gtagcatccc ccaccagatc 1440
cacctgggcg agctgcacgc aatactgagg cgacaggagg atttctaccc cttcctcaag 1500
gacaataggg agaaaatcga aaagattctg accttcagga tcccctacta cgtgggccct 1560
cttgccaggg gcaacagccg attcgcttgg atgacaagaa agagcgagga gaccatcacc 1620
ccctggaact tcgaggaagt ggtggacaaa ggagcaagcg cgcagtcttt catcgaacgg 1680
atgaccaatt tcgacaaaaa cctgcctaac gagaaggtgc tgcccaagca cagcctgctt 1740
tacgagtact tcaccgtgta caacgagctc accaaggtga aatatgtgac cgagggcatg 1800
cgaaaacccg ctttcctgag cggcgagcag aagaaggcca tcgtggacct gctgttcaag 1860
accaacagga aggtgaccgt gaagcagctg aaggaggact acttcaagaa gatcgagtgc 1920

```
tttgatagcg tggaaataag cggcgtggag gacaggttca acgccagcct gggcacctac   1980
cacgacttgt tgaagataat caaagacaag gatttcctgg ataatgagga gaacgaggat   2040
atactcgagg acatcgtgct gactttgacc ctgtttgagg accgagagat gattgaagaa   2100
aggctcaaaa cctacgccca cctgttcgac gacaaagtga tgaaacaact gaagagacga   2160
agatacaccg gctggggcag actgtccagg aagctcatca acggcattag ggacaagcag   2220
agcggcaaga ccatcctgga tttcctgaag tccgacggct tcgccaaccg aaacttcatg   2280
cagctgattc acgatgacag cttgaccttc aaggaggaca tccagaaggc ccaggttagc   2340
ggccagggcg actccctgca cgaacatatt gcaaacctgg caggctcccc tgcgatcaag   2400
aagggcatac tgcagaccgt taaggttgtg gacgaattgg tcaaggtcat gggcaggcac   2460
aagcccgaaa acatagttat agagatggcc agagagaacc agaccaccca aaagggccag   2520
aagaacagcc gggagcgcat gaaaaggatc gaggagggta tcaaggaact cggaagccag   2580
atcctcaaag agcaccccgt ggagaatacc cagctccaga acgagaagct gtacctgtac   2640
tacctgcaga acggcaggga catgtacgtt gaccaggagt tggacatcaa caggctttca   2700
gactatgacg tggatcacat agtgccccag agctttctta aagacgatag catcgacaac   2760
aaggtcctga cccgctccga caaaaacagg ggcaaaagcg acaacgtgcc aagcgaagag   2820
gtggttaaaa agatgaagaa ctactggagg caactgctca acgcgaaatt gatcacccag   2880
agaaagttcg ataacctgac caaggccgag aggggcggac tctccgaact tgacaaagcg   2940
ggcttcataa agaggcagct ggtcgagacc cgacagatca cgaagcacgt ggcccaaatc   3000
ctcgacagca gaatgaatac caagtacgat gagaatgaca aactcatcag ggaagtgaaa   3060
gtgattaccc tgaagagcaa gttggtgtcc gactttcgca aagatttcca gttctacaag   3120
gtgagggaga tcaacaacta ccaccatgcc cacgacgcat acctgaacgc cgtggtcggc   3180
accgccctga ttaagaagta tccaaagctg gagtccgaat ttgtctacgg cgactacaaa   3240
gtttacgatg tgaggaagat gatcgctaag agcgaacagg agatcggcaa ggccaccgct   3300
aagtatttct tctacagcaa catcatgaac tttttcaaga ccgagatcac acttgccaac   3360
ggcgaaatca ggaagaggcc gcttatcgag accaacggtg agaccggcga gatcgtgtgg   3420
gacaagggca gggacttcgc caccgtgagg aaagtcctga gcatgcccca ggtgaatatt   3480
gtgaaaaaaa ctgaggtgca gacaggcggc tttagcaagg aatccatcct gcccaagagg   3540
aacagcgaca agctgatcgc ccggaagaag gactgggacc ctaagaagta tggaggcttc   3600
gacagcccca ccgtagccta cagcgtgctg gtggtcgcga aggtagagaa ggggaagagc   3660
aagaaactga agagcgtgaa ggagctgctc ggcataacca tcatggagag gtccagcttt   3720
gagaagaacc ccattgactt tttggaagcc aagggctaca aagaggtcaa aaaggacctg   3780
atcatcaaac tccccaagta ctccctgttt gaattggaga acggcagaaa gaggatgctg   3840
gcgagcgctg gggaactgca aaagggcaac gaactggcgc tgcccagcaa gtacgtgaat   3900
ttctgtacc tggcgtccca ctacgaaaag ctgaaaggca gccccgagga caacgagcag   3960
aagcagctgt tcgtggagca gcacaagcat tacctggacg agataatcga gcaaatcagc   4020
gagttcagca agagggtgat tctggccgac gcgaacctgg ataaggtcct cagcgcctac   4080
aacaagcacc gagacaaacc catcagggag caggccgaga atatcataca cctgttcacc   4140
ctgacaaatc tgggcgcacc tgcggcattc aaatacttcg ataccaccat cgacaggaaa   4200
aggtacacta gcactaagga ggtgctggat gccaccttga tccaccagtc cattaccggc   4260
ctgtatgaga ccaggatcga cctgagccag cttggaggcg actctagggc ggacccaaaa   4320
```

aagaaaagga aggtggaatt ctacccatac gatgttccag attacgct 4368

<210> SEQ ID NO 53
<211> LENGTH: 189
<212> TYPE: DNA
<213> ORGANISM: Artificial Sequence
<220> FEATURE:
<223> OTHER INFORMATION: gene sequence of penetrating peptide; dNP2-HE10

<400> SEQUENCE: 53
atgggcggtt ctcatcatca tcatcatcat catatgaaga tcaagaaggt taaaaaaaag 60
ggtcgcaagg gctctaaaat taaaaaagtc aagaagaaag gaagaaaagc tagcggtggt 120
ggtggaggtc acgaacatga acatgaacat gaacacgagc acgagcatga gcacgaacac 180
gaacacgaa 189

<210> SEQ ID NO 54
<211> LENGTH: 4416
<212> TYPE: DNA
<213> ORGANISM: Artificial Sequence
<220> FEATURE:
<223> OTHER INFORMATION: gene sequence of penetrating peptide-linkage-
Cas protein; dNP2-HE10-Cas9

<400> SEQUENCE: 54
atgggcggtt ctcatcatca tcatcatcat catatgaaga tcaagaaggt taaaaaaaag 60
ggtcgcaagg gctctaaaat taaaaaagtc aagaagaaag gaagaaaagc tagcggtggt 120
ggtggaggtc acgaacatga acatgaacat gaacacgagc acgagcatga gcacgaacac 180
gaacacgaac tggacagcac cgctcccaaa aagaaaagga aggtgggcat tcacggcgtg 240
cctgcggccg acaaaaagta cagcatcggc cttgatatcg gcaccaatag cgtgggctgg 300
gccgttatca cagacgaata caaggtaccc agcaagaagt tcaaggtgct ggggaataca 360
gacaggcact ctatcaagaa aaaccttatc ggggctctgc tgtttgactc aggcgagacc 420
gccgaggcca ccaggttgaa gaggaccgca aggcgaaggt acacccggag gaagaacagg 480
atctgctatc tgcaggagat cttcagcaac gagatggcca aggtggacga cagcttcttc 540
cacaggctgg aggagagctt ccttgtcgag gaggataaga agcacgaacg acaccccatc 600
ttcggcaaca tagtcgacga ggtcgcttat cacgagaagt accccaccat ctaccacctg 660
cgaaagaaat tggtggatag caccgataaa gccgacttgc gacttatcta cttggctctg 720
gcgcacatga ttaagttcag gggccacttc ctgatcgagg gcgaccttaa ccccgacaac 780
agtgacgtag acaaattgtt catccagctt gtacagacct ataaccagct gttcgaggaa 840
aaccctatta acgccagcgg ggtggatgcg aaggccatac ttagcgccag gctgagcaaa 900
agcaggcgct tggagaacct gatagcccag ctgcccggtg aaaagaagaa cggcctcttc 960
ggtaatctga ttgccctgag cctgggcctg acccccaact tcaagagcaa cttcgacctg 1020
gcagaagatg ccaagctgca gttgagtaag gacacctatg acgacgactt ggacaatctg 1080
ctcgcccaaa tcggcgacca gtacgctgac ctgttcctcg ccgccaagaa cctttctgac 1140
gcaatcctgc ttagcgatat ccttagggtg aacacagaga tcaccaaggc ccccctgagc 1200
gccagcatga tcaagaggta cgacgagcac catcaggacc tgacccttct gaaggccctg 1260
gtgaggcagc aactgcccga gaagtacaag gagatctttt tcgaccagag caagaacggc 1320
tacgccggct acatcgacgg cggagccagc caagaggagt tctacaagtt catcaagccc 1380
atcctggaga agatggatgg caccgaggag ctgctggtga agctgaacag ggaagatttg 1440
ctccggaagc agaggacctt tgacaacggt agcatccccc accagatcca cctgggcgag 1500
ctgcacgcaa tactgaggcg acaggaggat ttctacccct tcctcaagga caatagggag 1560
aaaatcgaaa agattctgac cttcaggatc ccctactacg tgggccctct tgccaggggc 1620
aacagccgat tcgcttggat gacaagaaag agcgaggaga ccatcacccc ctggaacttc 1680
gaggaagtgg tggacaaagg agcaagcgcg cagtctttca tcgaacggat gaccaatttc 1740
gacaaaaacc tgcctaacga gaaggtgctg cccaagcaca gcctgcttta cgagtacttc 1800
accgtgtaca acgagctcac caaggtgaaa tatgtgaccg agggcatgcg aaaacccgct 1860
ttcctgagcg gcgagcagaa gaaggccatc gtggacctgc tgttcaagac caacaggaag 1920
gtgaccgtga agcagctgaa ggaggactac ttcaagaaga tcgagtgctt tgatagcgtg 1980
gaaataagcg gcgtggagga caggttcaac gccagcctgg gcacctacca cgacttgttg 2040
aagataatca aagacaagga tttcctggat aatgaggaga acgaggatat actcgaggac 2100
atcgtgctga ctttgaccct gtttgaggac cgagagatga ttgaagaaag gctcaaaacc 2160
tacgcccacc tgttcgacga caaagtgatg aaacaactga agagacgaag atacaccggc 2220
tggggcagac tgtccaggaa gctcatcaac ggcattaggg acaagcagag cggcaagacc 2280
atcctggatt tcctgaagtc cgacggcttc gccaaccgaa acttcatgca gctgattcac 2340
gatgacagct tgaccttcaa ggaggacatc cagaaggccc aggttagcgg ccagggcgac 2400
tccctgcacg aacatattgc aaacctggca ggctcccctg cgatcaagaa gggcatactg 2460
cagaccgtta aggttgtgga cgaattggtc aaggtcatgg gcaggcacaa gcccgaaaac 2520
atagttatag agatggccag agagaaccag accacccaaa agggccagaa gaacagccgg 2580
gagcgcatga aaaggatcga ggagggtatc aaggaactcg gaagccagat cctcaaagag 2640
caccccgtgg agaataccca gctccagaac gagaagctgt acctgtacta cctgcagaac 2700
ggcagggaca tgtacgttga ccaggagttg gacatcaaca ggctttcaga ctatgacgtg 2760
gatcacatag tgccccagag ctttcttaaa gacgatagca tcgacaacaa ggtcctgacc 2820
cgctccgaca aaaacagggg caaaagcgac aacgtgccaa gcgaagaggt ggttaaaaag 2880
atgaagaact actggaggca actgctcaac gcgaaattga tcacccagag aaagttcgat 2940
aacctgacca aggccgagag gggcggactc tccgaacttg acaaagcggg cttcataaag 3000
aggcagctgg tcgagacccg acagatcacg aagcacgtgg cccaaatcct cgacagcaga 3060
atgaatacca agtacgatga gaatgacaaa ctcatcaggg aagtgaaagt gattaccctg 3120
aagagcaagt tggtgtccga ctttcgcaaa gatttccagt tctacaaggt gagggagatc 3180
aacaactacc accatgccca cgacgcatac ctgaacgccg tggtcggcac cgccctgatt 3240
aagaagtatc caaagctgga gtccgaattt gtctacggcg actacaaagt ttacgatgtg 3300
aggaagatga tcgctaagag cgaacaggag atcggcaagg ccaccgctaa gtatttcttc 3360
tacagcaaca tcatgaactt tttcaagacc gagatcacac ttgccaacgg cgaaatcagg 3420
aagaggccgc ttatcgagac caacggtgag accggcgaga tcgtgtggga caagggcagg 3480
gacttcgcca ccgtgaggaa agtcctgagc atgccccagg tgaatattgt gaaaaaaact 3540
gaggtgcaga caggcggctt tagcaaggaa tccatcctgc ccaagaggaa cagcgacaag 3600
ctgatcgccc ggaagaagga ctgggaccct aagaagtatg gaggcttcga cagccccacc 3660
gtagcctaca gcgtgctggt ggtcgcgaag gtagagaagg ggaagagcaa gaaactgaag 3720
agcgtgaagg agctgctcgg cataaccatc atggagaggt ccagctttga gaagaacccc 3780
attgactttt tggaagccaa gggctacaaa gaggtcaaaa aggacctgat catcaaactc 3840
cccaagtact ccctgtttga attggagaac ggcagaaaga ggatgctggc gagcgctggg 3900
gaactgcaaa agggcaacga actggcgctg cccagcaagt acgtgaattt tctgtacctg 3960
gcgtcccact acgaaaagct gaaaggcagc cccgaggaca acgagcagaa gcagctgttc 4020
gtggagcagc acaagcatta cctggacgag ataatcgagc aaatcagcga gttcagcaag 4080
agggtgattc tggccgacgc gaacctggat aaggtcctca gcgcctacaa caagcaccga 4140
gacaaaccca tcagggagca ggccgagaat atcatacacc tgttcaccct gacaaatctg 4200
ggcgcacctg cggcattcaa atacttcgat accaccatcg acaggaaaag gtacactagc 4260
actaaggagg tgctggatgc caccttgatc caccagtcca ttaccggcct gtatgagacc 4320
aggatcgacc tgagccagct tggaggcgac tctagggcgg acccaaaaaa gaaaaggaag 4380
gtggaattct acccatacga tgttccagat tacgct 4416

<210> SEQ ID NO 55
<211> LENGTH: 90
<212> TYPE: DNA
<213> ORGANISM: Artificial Sequence
<220> FEATURE:
<223> OTHER INFORMATION: gene sequence of penetrating peptide; R9

<400> SEQUENCE: 55
atgggcagca gccatcatca tcatcatcac agcagcggcc tggtgccgcg cggcagccat 60
atgagacgaa gacgaagacg tagacgtaga 90

<210> SEQ ID NO 56
<211> LENGTH: 4323
<212> TYPE: DNA
<213> ORGANISM: Artificial Sequence
<220> FEATURE:
<223> OTHER INFORMATION: gene sequence of penetrating peptide-linkage-
Cas protein; R9-Cas9

<400> SEQUENCE: 56
atgggcagca gccatcatca tcatcatcac agcagcggcc tggtgccgcg cggcagccat 60
atgagacgaa gacgaagacg tagacgtaga gctagcctgg acagcaccgc tcccaaaaag 120
aaaaggaagg tgggcattca cggcgtgcct gcggccgaca aaaagtacag catcggcctt 180
gatatcggca ccaatagcgt gggctgggcc gttatcacag acgaatacaa ggtacccagc 240
aagaagttca aggtgctggg gaatacagac aggcactcta tcaagaaaaa ccttatcggg 300
gctctgctgt ttgactcagg cgagaccgcc gaggccacca ggttgaagag gaccgcaagg 360
cgaaggtaca cccggaggaa gaacaggatc tgctatctgc aggagatctt cagcaacgag 420
atggccaagg tggacgacag cttcttccac aggctggagg agagcttcct tgtcgaggag 480
gataagaagc acgaacgaca ccccatcttc ggcaacatag tcgacgaggt cgcttatcac 540
gagaagtacc ccaccatcta ccacctgcga aagaaattgg tggatagcac cgataaagcc 600
gacttgcgac ttatctactt ggctctggcg cacatgatta agttcagggg ccacttcctg 660
atcgagggcg accttaaccc cgacaacagt gacgtagaca aattgttcat ccagcttgta 720
cagacctata accagctgtt cgaggaaaac cctattaacg ccagcggggt ggatgcgaag 780
gccatactta gcgccaggct gagcaaaagc aggcgcttgg agaacctgat agcccagctg 840
cccggtgaaa agaagaacgg cctcttcggt aatctgattg ccctgagcct gggcctgacc 900
cccaacttca agagcaactt cgacctggca gaagatgcca agctgcagtt gagtaaggac 960
acctatgacg acgacttgga caatctgctc gcccaaatcg gcgaccagta cgctgacctg 1020
ttcctcgccg ccaagaacct ttctgacgca atcctgctta gcgatatcct tagggtgaac 1080
acagagatca ccaaggcccc cctgagcgcc agcatgatca agaggtacga cgagcaccat 1140
caggacctga cccttctgaa ggccctggtg aggcagcaac tgcccgagaa gtacaaggag 1200
atcttttcg accagagcaa gaacggctac gccggctaca tcgacggcgg agccagccaa 1260
gaggagttct acaagttcat caagcccatc ctggagaaga tggatggcac cgaggagctg 1320
ctggtgaagc tgaacaggga agatttgctc cggaagcaga ggacctttga caacggtagc 1380
atcccccacc agatccacct gggcgagctg cacgcaatac tgaggcgaca ggaggatttc 1440
taccccttcc tcaaggacaa tagggagaaa atcgaaaaga ttctgacctt caggatcccc 1500
tactacgtgg gccctcttgc caggggcaac agccgattcg cttggatgac aagaaagagc 1560
gaggagacca tcaccccctg gaacttcgag gaagtggtgg acaaaggagc aagcgcgcag 1620
tctttcatcg aacggatgac caatttcgac aaaaacctgc ctaacgagaa ggtgctgccc 1680
aagcacagcc tgctttacga gtacttcacc gtgtacaacg agctcaccaa ggtgaaatat 1740
gtgaccgagg gcatgcgaaa acccgctttc ctgagcggcg agcagaagaa ggccatcgtg 1800
gacctgctgt tcaagaccaa caggaaggtg accgtgaagc agctgaagga ggactacttc 1860
aagaagatcg agtgctttga tagcgtggaa ataagcggcg tggaggacag gttcaacgcc 1920
agcctgggca cctaccacga cttgttgaag ataatcaaag acaaggattt cctggataat 1980
gaggagaacg aggatatact cgaggacatc gtgctgactt tgaccctgtt tgaggaccga 2040
gagatgattg aagaaaggct caaaacctac gcccacctgt tcgacgacaa agtgatgaaa 2100
caactgaaga gacgaagata caccggctgg ggcagactgt ccaggaagct catcaacggc 2160
attagggaca agcagagcgg caagaccatc ctggatttcc tgaagtccga cggcttcgcc 2220
aaccgaaact tcatgcagct gattcacgat gacagcttga ccttcaagga ggacatccag 2280
aaggcccagg ttagcggcca gggcgactcc ctgcacgaac atattgcaaa cctggcaggc 2340
tcccctgcga tcaagaaggg catactgcag accgttaagg ttgtggacga attggtcaag 2400
gtcatgggca ggcacaagcc cgaaaacata gttatagaga tggccagaga gaaccagacc 2460
acccaaaagg gccagaagaa cagccgggag cgcatgaaaa ggatcgagga gggtatcaag 2520
gaactcggaa gccagatcct caaagagcac cccgtggaga atacccagct ccagaacgag 2580
aagctgtacc tgtactacct gcagaacggc agggacatgt acgttgacca ggagttggac 2640
atcaacaggc tttcagacta tgacgtggat cacatagtgc cccagagctt tcttaaagac 2700
gatagcatcg acaacaaggt cctgacccgc tccgacaaaa acaggggcaa aagcgacaac 2760
gtgccaagcg aagaggtggt taaaaagatg aagaactact ggaggcaact gctcaacgcg 2820
aaattgatca cccagagaaa gttcgataac ctgaccaagg ccgagagggg cggactctcc 2880
gaacttgaca aagcgggctt cataaagagg cagctggtcg agacccgaca gatcacgaag 2940
cacgtggccc aaatcctcga cagcagaatg aataccaagt acgatgagaa tgacaaactc 3000
atcagggaag tgaaagtgat taccctgaag agcaagttgg tgtccgactt tcgcaaagat 3060
ttccagttct acaaggtgag ggagatcaac aactaccacc atgcccacga cgcatacctg 3120
aacgccgtgg tcggcaccgc cctgattaag aagtatccaa agctggagtc cgaatttgtc 3180
tacggcgact acaaagttta cgatgtgagg aagatgatcg ctaagagcga acaggagatc 3240
ggcaaggcca ccgctaagta tttcttctac agcaacatca tgaacttttt caagaccgag 3300
atcacacttg ccaacggcga aatcaggaag aggccgctta tcgagaccaa cggtgagacc 3360

```
ggcgagatcg tgtgggacaa gggcagggac ttcgccaccg tgaggaaagt cctgagcatg   3420

ccccaggtga atattgtgaa aaaaactgag gtgcagacag gcggctttag caaggaatcc   3480

atcctgccca agaggaacag cgacaagctg atcgcccgga agaaggactg ggaccctaag   3540

aagtatggag gcttcgacag ccccaccgta gcctacagcg tgctggtggt cgcgaaggta   3600

gagaagggga agagcaagaa actgaagagc gtgaaggagc tgctcggcat aaccatcatg   3660

gagaggtcca gctttgagaa gaaccccatt gactttttgg aagccaaggg ctacaaagag   3720

gtcaaaaagg acctgatcat caaactcccc aagtactccc tgtttgaatt ggagaacggc   3780

agaaagagga tgctggcgag cgctggggaa ctgcaaaagg gcaacgaact ggcgctgccc   3840

agcaagtacg tgaattttct gtacctggcg tcccactacg aaaagctgaa aggcagcccc   3900

gaggacaacg agcagaagca gctgttcgtg gagcagcaca agcattacct ggacgagata   3960

atcgagcaaa tcagcgagtt cagcaagagg gtgattctgg ccgacgcgaa cctggataag   4020

gtcctcagcg cctacaacaa gcaccgagac aaacccatca gggagcaggc cgagaatatc   4080

atacacctgt tcaccctgac aaatctgggc gcacctgcgg cattcaaata cttcgatacc   4140

accatcgaca ggaaaaggta cactagcact aaggaggtgc tggatgccac cttgatccac   4200

cagtccatta ccggcctgta tgagaccagg atcgacctga gccagcttgg aggcgactct   4260

agggcggacc caaaaaagaa aaggaaggtg gaattctacc catacgatgt tccagattac   4320

gct                                                                 4323
```

```
<210> SEQ ID NO 57
<211> LENGTH: 144
<212> TYPE: DNA
<213> ORGANISM: Artificial Sequence
<220> FEATURE:
<223> OTHER INFORMATION: gene sequence of penetrating peptide; R9-HE10

<400> SEQUENCE: 57

atgggcggtt ctcatcatca tcatcatcat catatgagac gaagacgaag acgtagacgt     60

agagctagcg gtggtggtgg aggtcacgaa catgaacatg aacatgaaca cgagcacgag    120

catgagcacg aacacgaaca cgaa                                           144
```

```
<210> SEQ ID NO 58
<211> LENGTH: 4371
<212> TYPE: DNA
<213> ORGANISM: Artificial Sequence
<220> FEATURE:
<223> OTHER INFORMATION: gene sequence of penetrating peptide-linkage-
      Cas protein; R9-HE10-Cas9

<400> SEQUENCE: 58

atgggcggtt ctcatcatca tcatcatcat catatgagac gaagacgaag acgtagacgt     60

agagctagcg gtggtggtgg aggtcacgaa catgaacatg aacatgaaca cgagcacgag    120

catgagcacg aacacgaaca cgaactggac agcaccgctc ccaaaaagaa aaggaaggtg    180

ggcattcacg gcgtgcctgc ggccgacaaa aagtacagca tcggccttga tatcggcacc    240

aatagcgtgg gctgggccgt tatcacagac gaatacaagg tacccagcaa gaagttcaag    300

gtgctgggga atacagacag gcactctatc aagaaaaacc ttatcggggc tctgctgttt    360

gactcaggcg agaccgccga ggccaccagg ttgaagagga ccgcaaggcg aaggtacacc    420

cggaggaaga acaggatctg ctatctgcag gagatcttca gcaacgagat ggccaaggtg    480

gacgacagct tcttccacag gctggaggag agcttccttg tcgaggagga taagaagcac    540
```

gaacgacacc ccatcttcgg caacatagtc gacgaggtcg cttatcacga gaagtacccc 600
accatctacc acctgcgaaa gaaattggtg gatagcaccg ataaagccga cttgcgactt 660
atctacttgg ctctggcgca catgattaag ttcaggggcc acttcctgat cgagggcgac 720
cttaaccccg acaacagtga cgtagacaaa ttgttcatcc agcttgtaca gacctataac 780
cagctgttcg aggaaaaccc tattaacgcc agcggggtgg atgcgaaggc catacttagc 840
gccaggctga gcaaaagcag gcgcttggag aacctgatag cccagctgcc cggtgaaaag 900
aagaacggcc tcttcggtaa tctgattgcc ctgagcctgg gcctgacccc caacttcaag 960
agcaacttcg acctggcaga agatgccaag ctgcagttga gtaaggacac ctatgacgac 1020
gacttggaca atctgctcgc ccaaatcggc gaccagtacg ctgacctgtt cctcgccgcc 1080
aagaaccttt ctgacgcaat cctgcttagc gatatcctta gggtgaacac agagatcacc 1140
aaggcccccc tgagcgccag catgatcaag aggtacgacg agcaccatca ggacctgacc 1200
cttctgaagg ccctggtgag gcagcaactg cccgagaagt acaaggagat ctttttcgac 1260
cagagcaaga acggctacgc cggctacatc gacggcggag ccagccaaga ggagttctac 1320
aagttcatca agcccatcct ggagaagatg gatggcaccg aggagctgct ggtgaagctg 1380
aacagggaag atttgctccg gaagcagagg acctttgaca acggtagcat cccccaccag 1440
atccacctgg gcgagctgca cgcaatactg aggcgacagg aggatttcta ccccttcctc 1500
aaggacaata gggagaaaat cgaaaagatt ctgaccttca ggatccccta ctacgtgggc 1560
cctcttgcca ggggcaacag ccgattcgct tggatgacaa gaaagagcga ggagaccatc 1620 acccccctgga acttcgagga agtggtggac aaaggagcaa gcgcgcagtc tttcatcgaa 1680
cggatgacca atttcgacaa aaacctgcct aacgagaagg tgctgcccaa gcacagcctg 1740
ctttacgagt acttcaccgt gtacaacgag ctcaccaagg tgaaatatgt gaccgagggc 1800
atgcgaaaac ccgctttcct gagcggcgag cagaagaagg ccatcgtgga cctgctgttc 1860
aagaccaaca ggaaggtgac cgtgaagcag ctgaaggagg actacttcaa gaagatcgag 1920
tgctttgata gcgtggaaat aagcggcgtg gaggacaggt tcaacgccag cctgggcacc 1980
taccacgact tgttgaagat aatcaaagac aaggatttcc tggataatga ggagaacgag 2040
gatatactcg aggacatcgt gctgactttg accctgtttg aggaccgaga gatgattgaa 2100
gaaaggctca aaacctacgc ccacctgttc gacgacaaag tgatgaaaca actgaagaga 2160
cgaagataca ccggctgggg cagactgtcc aggaagctca tcaacggcat tagggacaag 2220
cagagcggca agaccatcct ggatttcctg aagtccgacg gcttcgccaa ccgaaacttc 2280
atgcagctga ttcacgatga cagcttgacc ttcaaggagg acatccagaa ggcccaggtt 2340
agcggccagg gcgactccct gcacgaacat attgcaaacc tggcaggctc ccctgcgatc 2400
aagaagggca tactgcagac cgttaaggtt gtggacgaat tggtcaaggt catgggcagg 2460
cacaagcccg aaaacatagt tatagagatg gccagagaga accagaccac ccaaaagggc 2520
cagaagaaca gccgggagcg catgaaaagg atcgaggagg gtatcaagga actcggaagc 2580
cagatcctca aagagcaccc cgtggagaat acccagctcc agaacgagaa gctgtacctg 2640
tactacctgc agaacggcag ggacatgtac gttgaccagg agttggacat caacaggctt 2700
tcagactatg acgtggatca catagtgccc cagagctttc ttaaagacga tagcatcgac 2760
aacaaggtcc tgacccgctc cgacaaaaac aggggcaaaa gcgacaacgt gccaagcgaa 2820
gaggtggtta aaaagatgaa gaactactgg aggcaactgc tcaacgcgaa attgatcacc 2880
cagagaaagt tcgataacct gaccaaggcc gagaggggcg gactctccga acttgacaaa 2940
gcgggcttca taaagaggca gctggtcgag acccgacaga tcacgaagca cgtggcccaa 3000
atcctcgaca gcagaatgaa taccaagtac gatgagaatg acaaactcat cagggaagtg 3060
aaagtgatta ccctgaagag caagttggtg tccgactttc gcaaagattt ccagttctac 3120
aaggtgaggg agatcaacaa ctaccaccat gcccacgacg catacctgaa cgccgtggtc 3180
ggcaccgccc tgattaagaa gtatccaaag ctggagtccg aatttgtcta cggcgactac 3240
aaagtttacg atgtgaggaa gatgatcgct aagagcgaac aggagatcgg caaggccacc 3300
gctaagtatt tcttctacag caacatcatg aacttttca agaccgagat cacacttgcc 3360
aacggcgaaa tcaggaagag gccgcttatc gagaccaacg gtgagaccgg cgagatcgtg 3420
tgggacaagg gcagggactt cgccaccgtg aggaaagtcc tgagcatgcc ccaggtgaat 3480
attgtgaaaa aaactgaggt gcagacaggc ggctttagca aggaatccat cctgcccaag 3540
aggaacagcg acaagctgat cgcccggaag aaggactggg accctaagaa gtatggaggc 3600
ttcgacagcc ccaccgtagc ctacagcgtg ctggtggtcg cgaaggtaga gaaggggaag 3660
agcaagaaac tgaagagcgt gaaggagctg ctcggcataa ccatcatgga gaggtccagc 3720
tttgagaaga accccattga ctttttggaa gccaagggct acaaagaggt caaaaaggac 3780
ctgatcatca aactccccaa gtactccctg tttgaattgg agaacggcag aaagaggatg 3840
ctggcgagcg ctggggaact gcaaaagggc aacgaactgg cgctgcccag caagtacgtg 3900
aattttctgt acctggcgtc ccactacgaa aagctgaaag gcagccccga ggacaacgag 3960
cagaagcagc tgttcgtgga gcagcacaag cattacctgg acgagataat cgagcaaatc 4020
agcgagttca gcaagagggt gattctggcc gacgcgaacc tggataaggt cctcagcgcc 4080
tacaacaagc accgagacaa acccatcagg gagcaggccg agaatatcat acacctgttc 4140
accctgacaa atctgggcgc acctgcggca ttcaaatact tcgataccac catcgacagg 4200
aaaaggtaca ctagcactaa ggaggtgctg gatgccacct tgatccacca gtccattacc 4260
ggcctgtatg agaccaggat cgacctgagc cagcttggag gcgactctag ggcggaccca 4320
aaaaagaaaa ggaaggtgga attctaccca tacgatgttc cagattacgc t 4371

<210> SEQ ID NO 59
<211> LENGTH: 96
<212> TYPE: DNA
<213> ORGANISM: Artificial Sequence
<220> FEATURE:
<223> OTHER INFORMATION: gene sequence of penetrating peptide; TAT

<400> SEQUENCE: 59
atgggcagca gccatcatca tcatcatcac agcagcggcc tggtgccgcg cggcagccat 60
atgtatggac gcaagaagcg ccgccagcgc cgccgc 96

<210> SEQ ID NO 60
<211> LENGTH: 4329
<212> TYPE: DNA
<213> ORGANISM: Artificial Sequence
<220> FEATURE:
<223> OTHER INFORMATION: gene sequence of penetrating peptide-linkage-
Cas protein; TAT-Cas9

<400> SEQUENCE: 60
atgggcagca gccatcatca tcatcatcac agcagcggcc tggtgccgcg cggcagccat 60
atgtatggac gcaagaagcg ccgccagcgc cgccgcgcta gcctggacag caccgctccc 120

-continued

```
aaaaagaaaa ggaaggtggg cattcacggc gtgcctgcgg ccgacaaaaa gtacagcatc    180
ggccttgata tcggcaccaa tagcgtgggc tgggccgtta tcacagacga atacaaggta    240
cccagcaaga agttcaaggt gctggggaat acagacaggc actctatcaa gaaaaacctt    300
atcggggctc tgctgtttga ctcaggcgag accgccgagg ccaccaggtt gaagaggacc    360
gcaaggcgaa ggtacacccg gaggaagaac aggatctgct atctgcagga gatcttcagc    420
aacgagatgg ccaaggtgga cgacagcttc ttccacaggc tggaggagag cttccttgtc    480
gaggaggata agaagcacga acgacacccc atcttcggca acatagtcga cgaggtcgct    540
tatcacgaga agtaccccac catctaccac ctgcgaaaga aattggtgga tagcaccgat    600
aaagccgact tgcgacttat ctacttggct ctggcgcaca tgattaagtt caggggccac    660
ttcctgatcg agggcgacct taaccccgac aacagtgacg tagacaaatt gttcatccag    720
cttgtacaga cctataacca gctgttcgag gaaaacccta ttaacgccag cggggtggat    780
gcgaaggcca tacttagcgc caggctgagc aaaagcaggc gcttggagaa cctgatagcc    840
cagctgcccg gtgaaaagaa gaacggcctc ttcggtaatc tgattgccct gagcctgggc    900
ctgaccccca acttcaagag caacttcgac ctggcagaag atgccaagct gcagttgagt    960
aaggacacct atgacgacga cttggacaat ctgctcgccc aaatcggcga ccagtacgct   1020
gacctgttcc tcgccgccaa gaacctttct gacgcaatcc tgcttagcga tatccttagg   1080
gtgaacacag agatcaccaa ggcccccctg agcgccagca tgatcaagag gtacgacgag   1140
caccatcagg acctgaccct tctgaaggcc ctggtgaggc agcaactgcc cgagaagtac   1200
aaggagatct tttcgacca gagcaagaac ggctacgccg gctacatcga cggcggagcc   1260
agccaagagg agttctacaa gttcatcaag cccatcctgg agaagatgga tggcaccgag   1320
gagctgctgg tgaagctgaa cagggaagat ttgctccgga agcagaggac ctttgacaac   1380
ggtagcatcc cccaccagat ccacctgggc gagctgcacg caatactgag gcgacaggag   1440
gatttctacc ccttcctcaa ggacaatagg gagaaaatcg aaaagattct gaccttcagg   1500
atcccctact acgtgggccc tcttgccagg ggcaacagcc gattcgcttg gatgacaaga   1560
aagagcgagg agaccatcac cccctggaac ttcgaggaag tggtggacaa aggagcaagc   1620
gcgcagtctt tcatcgaacg gatgaccaat ttcgacaaaa acctgcctaa cgagaaggtg   1680
ctgcccaagc acagcctgct ttacgagtac ttcaccgtgt acaacgagct caccaaggtg   1740
aaatatgtga ccgagggcat gcgaaaaccc gctttcctga gcggcgagca gaagaaggcc   1800
atcgtggacc tgctgttcaa gaccaacagg aaggtgaccg tgaagcagct gaaggaggac   1860
tacttcaaga agatcgagtg ctttgatagc gtggaaataa gcggcgtgga ggacaggttc   1920
aacgccagcc tgggcaccta ccacgacttg ttgaagataa tcaaagacaa ggatttcctg   1980
gataatgagg agaacgagga tatactcgag gacatcgtgc tgactttgac cctgtttgag   2040
gaccgagaga tgattgaaga aaggctcaaa acctacgccc acctgttcga cgacaaagtg   2100
atgaaacaac tgaagagacg aagatacacc ggctggggca gactgtccag gaagctcatc   2160
aacggcatta gggacaagca gagcggcaag accatcctgg atttcctgaa gtccgacggc   2220
ttcgccaacc gaaacttcat gcagctgatt cacgatgaca gcttgacctt caaggaggac   2280
atccagaagg cccaggttag cggccagggc gactccctgc acgaacatat tgcaaacctg   2340
gcaggctccc ctgcgatcaa gaagggcata ctgcagaccg ttaaggttgt ggacgaattg   2400
gtcaaggtca tgggcaggca caagcccgaa aacatagtta tagagatggc cagagagaac   2460
cagaccaccc aaaagggcca gaagaacagc cgggagcgca tgaaaaggat cgaggagggt   2520
```

atcaaggaac tcggaagcca gatcctcaaa gagcaccccg tggagaatac ccagctccag 2580
aacgagaagc tgtacctgta ctacctgcag aacggcaggg acatgtacgt tgaccaggag 2640
ttggacatca acaggctttc agactatgac gtggatcaca tagtgcccca gagctttctt 2700
aaagacgata gcatcgacaa caaggtcctg acccgctccg acaaaaacag ggcaaaagc 2760 gacaacgtgc caagcgaaga ggtggttaaa aagatgaaga actactggag gcaactgctc 2820
aacgcgaaat tgatcaccca gagaaagttc gataacctga ccaaggccga gaggggcgga 2880
ctctccgaac ttgacaaagc gggcttcata aagaggcagc tggtcgagac ccgacagatc 2940
acgaagcacg tggcccaaat cctcgacagc agaatgaata ccaagtacga tgagaatgac 3000
aaactcatca gggaagtgaa agtgattacc ctgaagagca agttggtgtc cgactttcgc 3060
aaagatttcc agttctacaa ggtgagggag atcaacaact accaccatgc ccacgacgca 3120
tacctgaacg ccgtggtcgg caccgccctg attaagaagt atccaaagct ggagtccgaa 3180
tttgtctacg gcgactacaa agtttacgat gtgaggaaga tgatcgctaa gagcgaacag 3240
gagatcggca aggccaccgc taagtatttc ttctacagca acatcatgaa ctttttcaag 3300
accgagatca cacttgccaa cggcgaaatc aggaagaggc cgcttatcga gaccaacggt 3360
gagaccggcg agatcgtgtg ggacaagggc agggacttcg ccaccgtgag gaaagtcctg 3420
agcatgcccc aggtgaatat tgtgaaaaaa actgaggtgc agacaggcgg ctttagcaag 3480
gaatccatcc tgcccaagag gaacagcgac aagctgatcg cccggaagaa ggactgggac 3540
cctaagaagt atggaggctt cgacagcccc accgtagcct acagcgtgct ggtggtcgcg 3600
aaggtagaga aggggaagag caagaaactg aagagcgtga aggagctgct cggcataacc 3660
atcatggaga ggtccagctt tgagaagaac cccattgact tttggaagc caagggctac 3720 aaagaggtca aaaaggacct gatcatcaaa ctccccaagt actccctgtt tgaattggag 3780
aacggcagaa agaggatgct ggcgagcgct ggggaactgc aaaagggcaa cgaactggcg 3840
ctgcccagca agtacgtgaa ttttctgtac ctggcgtccc actacgaaaa gctgaaaggc 3900
agccccgagg acaacgagca gaagcagctg ttcgtggagc agcacaagca ttacctggac 3960
gagataatcg agcaaatcag cgagttcagc aagagggtga ttctggccga cgcgaacctg 4020
gataaggtcc tcagcgccta caacaagcac cgagacaaac ccatcaggga gcaggccgag 4080
aatatcatac acctgttcac cctgacaaat ctgggcgcac ctgcggcatt caaatacttc 4140
gataccacca tcgacaggaa aaggtacact agcactaagg aggtgctgga tgccaccttg 4200
atccaccagt ccattaccgg cctgtatgag accaggatcg acctgagcca gcttggaggc 4260
gactctaggg cggacccaaa aaagaaaagg aaggtggaat tctacccata cgatgttcca 4320
gattacgct 4329

<210> SEQ ID NO 61
<211> LENGTH: 150
<212> TYPE: DNA
<213> ORGANISM: Artificial Sequence
<220> FEATURE:
<223> OTHER INFORMATION: gene sequence of penetrating peptide; TAT-HE10

<400> SEQUENCE: 61
atgggcggtt ctcatcatca tcatcatcat catatgtatg gacgcaagaa gcgccgccag 60
cgccgccgcg ctagcggtgg tggtggaggt cacgaacatg aacatgaaca tgaacacgag 120
cacgagcatg agcacgaaca cgaacacgaa 150

<210> SEQ ID NO 62
<211> LENGTH: 4377
<212> TYPE: DNA
<213> ORGANISM: Artificial Sequence
<220> FEATURE:
<223> OTHER INFORMATION: gene sequence of penetrating peptide-linkage-
      Cas protein; TAT-HE10-Cas9

<400> SEQUENCE: 62

```
atgggcggtt ctcatcatca tcatcatcat catatgtatg gacgcaagaa gcgccgccag     60
cgccgccgcg ctagcggtgg tggtggaggt cacgaacatg aacatgaaca tgaacacgag    120
cacgagcatg agcacgaaca cgaacacgaa ctggacagca ccgctcccaa aaagaaaagg    180
aaggtgggca ttcacggcgt gcctgcggcc gacaaaaagt acagcatcgg ccttgatatc    240
ggcaccaata gcgtgggctg ggccgttatc acagacgaat acaaggtacc cagcaagaag    300
ttcaaggtgc tggggaatac agacaggcac tctatcaaga aaaaccttat cggggctctg    360
ctgtttgact caggcgagac cgccgaggcc accaggttga agaggaccgc aaggcgaagg    420
tacacccgga ggaagaacag gatctgctat ctgcaggaga tcttcagcaa cgagatggcc    480
aaggtggacg acagcttctt ccacaggctg gaggagagct tccttgtcga ggaggataag    540
aagcacgaac gacaccccat cttcggcaac atagtcgacg aggtcgctta tcacgagaag    600
taccccacca tctaccacct gcgaaagaaa ttggtggata gcaccgataa agccgacttg    660
cgacttatct acttggctct ggcgcacatg attaagttca ggggccactt cctgatcgag    720
ggcgacctta accccgacaa cagtgacgta gacaaattgt tcatccagct tgtacagacc    780
tataaccagc tgttcgagga aaaccctatt aacgccagcg gggtggatgc gaaggccata    840
cttagcgcca ggctgagcaa aagcaggcgc ttggagaacc tgatagccca gctgcccggt    900
gaaaagaaga acggcctctt cggtaatctg attgccctga gcctgggcct gacccccaac    960
ttcaagagca acttcgacct ggcagaagat gccaagctgc agttgagtaa ggacacctat   1020
gacgacgact tggacaatct gctcgcccaa atcggcgacc agtacgctga cctgttcctc   1080
gccgccaaga acctttctga cgcaatcctg cttagcgata tccttagggt gaacacagag   1140
atcaccaagg cccccctgag cgccagcatg atcaagaggt acgacgagca ccatcaggac   1200
ctgacccttc tgaaggccct ggtgaggcag caactgcccg agaagtacaa ggagatcttt   1260
ttcgaccaga gcaagaacgg ctacgccggc tacatcgacg gcggagccag ccaagaggag   1320
ttctacaagt tcatcaagcc catcctggag aagatggatg gcaccgagga gctgctggtg   1380
aagctgaaca gggaagattt gctccggaag cagaggacct ttgacaacgg tagcatcccc   1440
caccagatcc acctgggcga gctgcacgca atactgaggc gacaggagga tttctacccc   1500
ttcctcaagg acaataggga gaaaatcgaa aagattctga ccttcaggat cccctactac   1560
gtgggccctc ttgccagggg caacagccga ttcgcttgga tgacaagaaa gagcgaggag   1620
accatcaccc cctggaactt cgaggaagtg gtggacaaag gagcaagcgc gcagtctttc   1680
atcgaacgga tgaccaattt cgacaaaaac ctgcctaacg agaaggtgct gcccaagcac   1740
agcctgcttt acgagtactt caccgtgtac aacgagctca ccaaggtgaa atatgtgacc   1800
gagggcatgc gaaaacccgc tttcctgagc ggcgagcaga agaaggccat cgtggacctg   1860
ctgttcaaga ccaacaggaa ggtgaccgtg aagcagctga aggaggacta cttcaagaag   1920
atcgagtgct ttgatagcgt ggaaataagc ggcgtggagg acaggttcaa cgccagcctg   1980
ggcacctacc acgacttgtt gaagataatc aaagacaagg atttcctgga taatgaggag   2040
```

```
aacgaggata tactcgagga catcgtgctg actttgaccc tgtttgagga ccgagagatg   2100
attgaagaaa ggctcaaaac ctacgcccac ctgttcgacg acaaagtgat gaaacaactg   2160
aagagacgaa gatacaccgg ctggggcaga ctgtccagga agctcatcaa cggcattagg   2220
gacaagcaga gcggcaagac catcctggat ttcctgaagt ccgacggctt cgccaaccga   2280
aacttcatgc agctgattca cgatgacagc ttgaccttca aggaggacat ccagaaggcc   2340
caggttagcg gccagggcga ctccctgcac gaacatattg caaacctggc aggctcccct   2400
gcgatcaaga agggcatact gcagaccgtt aaggttgtgg acgaattggt caaggtcatg   2460
ggcaggcaca agcccgaaaa catagttata gagatggcca gagagaacca gaccacccaa   2520
aagggccaga agaacagccg ggagcgcatg aaaaggatcg aggagggtat caaggaactc   2580
ggaagccaga tcctcaaaga gcaccccgtg gagaataccc agctccagaa cgagaagctg   2640
tacctgtact acctgcagaa cggcagggac atgtacgttg accaggagtt ggacatcaac   2700
aggctttcag actatgacgt ggatcacata gtgccccaga gctttcttaa agacgatagc   2760
atcgacaaca aggtcctgac ccgctccgac aaaaacaggg gcaaaagcga caacgtgcca   2820
agcgaagagg tggttaaaaa gatgaagaac tactggaggc aactgctcaa cgcgaaattg   2880
atcacccaga gaaagttcga taacctgacc aaggccgaga ggggcggact ctccgaactt   2940
gacaaagcgg gcttcataaa gaggcagctg gtcgagaccc gacagatcac gaagcacgtg   3000
gcccaaatcc tcgacagcag aatgaatacc aagtacgatg agaatgacaa actcatcagg   3060
gaagtgaaag tgattaccct gaagagcaag ttggtgtccg actttcgcaa agatttccag   3120
ttctacaagg tgagggagat caacaactac caccatgccc acgacgcata cctgaacgcc   3180
gtggtcggca ccgccctgat taagaagtat ccaaagctgg agtccgaatt tgtctacggc   3240
gactacaaag tttacgatgt gaggaagatg atcgctaaga gcgaacagga gatcggcaag   3300
gccaccgcta agtatttctt ctacagcaac atcatgaact tttcaagac cgagatcaca   3360
cttgccaacg gcgaaatcag gaagaggccg cttatcgaga ccaacggtga gaccggcgag   3420
atcgtgtggg acaagggcag ggacttcgcc accgtgagga aagtcctgag catgccccag   3480
gtgaatattg tgaaaaaaac tgaggtgcag acaggcggct ttagcaagga atccatcctg   3540
cccaagagga acagcgacaa gctgatcgcc cggaagaagg actgggaccc taagaagtat   3600
ggaggcttcg acagccccac cgtagcctac agcgtgctgg tggtcgcgaa ggtagagaag   3660
gggaagagca agaaactgaa gagcgtgaag gagctgctcg gcataaccat catggagagg   3720
tccagctttg agaagaaccc cattgacttt ttggaagcca agggctacaa agaggtcaaa   3780
aaggacctga tcatcaaact ccccaagtac tccctgtttg aattggagaa cggcagaaag   3840
aggatgctgg cgagcgctgg ggaactgcaa aagggcaacg aactggcgct gcccagcaag   3900
tacgtgaatt ttctgtacct ggcgtcccac tacgaaaagc tgaaaggcag ccccgaggac   3960
aacgagcaga agcagctgtt cgtggagcag cacaagcatt acctggacga gataatcgag   4020
caaatcagcg agttcagcaa gagggtgatt ctggccgacg cgaacctgga taaggtcctc   4080
agcgcctaca acaagcaccg agacaaaccc atcagggagc aggccgagaa tatcatacac   4140
ctgttcaccc tgacaaatct gggcgcacct gcggcattca aatacttcga taccaccatc   4200
gacaggaaaa ggtacactag cactaaggag gtgctggatg ccaccttgat ccaccagtcc   4260
attaccggcc tgtatgagac caggatcgac ctgagccagc ttggaggcga ctctagggcg   4320
gacccaaaaa agaaaaggaa ggtggaattc tacccatacg atgttccaga ttacgct      4377
```

<210> SEQ ID NO 63
<211> LENGTH: 4050
<212> TYPE: DNA
<213> ORGANISM: Artificial Sequence
<220> FEATURE:
<223> OTHER INFORMATION: gene sequence of AsCas12a

<400> SEQUENCE: 63
atgggcagca gccatcatca tcatcatcac agcagcggcc tggtgccgcg cggcagccat 60
atggctgctg ctgctagcac acagttcgag ggctttacca acctgtatca ggtgagcaag 120
acactgcggt ttgagctgat cccacagggc aagaccctga agcacatcca ggagcagggc 180
ttcatcgagg aggacaaggc ccgcaatgat cactacaagg agctgaagcc catcatcgat 240
cggatctaca agacctatgc cgaccagtgc ctgcagctgg tgcagctgga ttgggagaac 300
ctgagcgccg ccatcgactc ctatagaaag gagaaaaccg aggagacaag gaacgccctg 360
atcgaggagc aggccacata tcgcaatgcc atccacgact acttcatcgg ccggacagac 420
aacctgaccg atgccatcaa taagagacac gccgagatct acaagggcct gttcaaggcc 480
gagctgttta atggcaaggt gctgaagcag ctgggcaccg tgaccacaac cgagcacgag 540
aacgccctgc tgcggagctt cgacaagttt acaacctact tctccggctt ttatgagaac 600
aggaagaacg tgttcagcgc cgaggatatc agcacagcca tcccacaccg catcgtgcag 660
gacaacttcc ccaagtttaa ggagaattgt cacatcttca cacgcctgat caccgccgtg 720
cccagcctgc gggagcactt tgagaacgtg aagaaggcca tcggcatctt cgtgagcacc 780
tccatcgagg aggtgttttc cttccctttt tataaccagc tgctgacaca gacccagatc 840
gacctgtata accagctgct gggaggaatc tctcgggagg caggcaccga gaagatcaag 900
ggcctgaacg aggtgctgaa tctggccatc cagaagaatg atgagacagc ccacatcatc 960
gcctccctgc cacacagatt catccccctg tttaagcaga tcctgtccga taggaacacc 1020
ctgtctttca tcctggagga gtttaagagc gacgaggaag tgatccagtc cttctgcaag 1080
tacaagacac tgctgagaaa cgagaacgtg ctggagacag ccgaggccct gtttaacgag 1140
ctgaacagca tcgacctgac acacatcttc atcagccaca agaagctgga gacaatcagc 1200
agcgccctgt gcgaccactg ggatacactg aggaatgccc tgtatgagcg gagaatctcc 1260
gagctgacag gcaagatcac caagtctgcc aaggagaagg tgcagcgcag cctgaagcac 1320
gaggatatca acctgcagga gatcatctct gccgcaggca aggagctgag cgaggccttc 1380
aagcagaaaa ccagcgagat cctgtcccac gcacacgccg ccctggatca gccactgcct 1440
acaaccctga agaagcagga ggagaaggag atcctgaagt ctcagctgga cagcctgctg 1500
ggcctgtacc acctgctgga ctggtttgcc gtggatgagt ccaacgaggt ggaccccgag 1560
ttctctgccc ggctgaccgg catcaagctg gagatggagc cttctctgag cttctacaac 1620
aaggccagaa attatgccac caagaagccc tactccgtgg agaagttcaa gctgaacttt 1680
cagatgccta cactggcctc tggctgggac gtgaataagg agaagaacaa tggcgccatc 1740
ctgtttgtga agaacggcct gtactatctg ggcatcatgc caaagcagaa gggcaggtat 1800
aaggccctga gcttcgagcc cacagagaaa accagcgagg gctttgataa gatgtactat 1860
gactacttcc ctgatgccgc caagatgatc ccaaagtgca gcacccagct gaaggccgtg 1920
acagcccact ttcagaccca cacaaccccc atcctgctgt ccaacaattt catcgagcct 1980
ctggagatca caaaggagat ctacgacctg aacaatcctg agaaggagcc aaagaagttt 2040
cagacagcct acgccaagaa aaccggcgac cagaagggct acagagaggc cctgtgcaag 2100
tggatcgact tcacaaggga ttttctgtcc aagtatacca agacaacctc tatcgatctg 2160
tctagcctgc ggccatcctc tcagtataag gacctgggcg agtactatgc cgagctgaat 2220
cccctgctgt accacatcag cttccagaga atcgccgaga aggagatcat ggatgccgtg 2280
gagacaggca agctgtacct gttccagatc tataacaagg actttgccaa gggccaccac 2340
ggcaagccta atctgcacac actgtattgg accggcctgt tttctccaga gaacctggcc 2400
aagacaagca tcaagctgaa tggccaggcc gagctgttct accgccctaa gtccaggatg 2460
aagaggatgg cacaccggct gggagagaag atgctgaaca agaagctgaa ggatcagaaa 2520
accccaatcc ccgacaccct gtaccaggag ctgtacgact atgtgaatca cagactgtcc 2580
cacgacctgt ctgatgaggc cagggccctg ctgcccaacg tgatcaccaa ggaggtgtct 2640
cacgagatca tcaaggatag gcgctttacc agcgacaagt tctttttcca cgtgcctatc 2700
acactgaact atcaggccgc caattcccca tctaagttca accagagggt gaatgcctac 2760
ctgaaggagc accccgagac acctatcatc ggcatcgatc ggggcgagag aaacctgatc 2820
tatatcacag tgatcgactc caccggcaag atcctggagc agcggagcct gaacaccatc 2880
cagcagtttg attaccagaa gaagctggac aacagggaga aggagagggt ggcagcaagg 2940
caggcctggt ctgtggtggg cacaatcaag gatctgaagc agggctatct gagccaggtc 3000
atccacgaga tcgtggacct gatgatccac taccaggccg tggtggtgct ggagaacctg 3060
aatttcggct ttaagagcaa gaggaccggc atcgccgaga aggccgtgta ccagcagttc 3120
gagaagatgc tgatcgataa gctgaattgc ctggtgctga aggactatcc agcagagaaa 3180
gtgggaggcg tgctgaaccc ataccagctg acagaccagt tcacctcctt tgccaagatg 3240
ggcacccagt ctggcttcct gttttacgtg cctgccccat atacatctaa gatcgatccc 3300
ctgaccggct tcgtggaccc cttcgtgtgg aaaaccatca agaatcacga gagccgcaag 3360
cacttcctgg agggcttcga ctttctgcac tacgacgtga aaaccggcga cttcatcctg 3420
cactttaaga tgaacagaaa tctgtccttc cagaggggcc tgcccggctt tatgcctgca 3480
tgggatatcg tgttcgagaa gaacgagaca cagtttgacg ccaagggcac ccctttcatc 3540
gccggcaaga gaatcgtgcc agtgatcgag aatcacagat tcaccggcag ataccgggac 3600
ctgtatcctg ccaacgagct gatcgccctg ctggaggaga agggcatcgt gttcagggat 3660
ggctccaaca tcctgccaaa gctgctggag aatgacgatt ctcacgccat cgacaccatg 3720
gtggccctga tccgcagcgt gctgcagatg cggaactcca atgccgccac aggcgaggac 3780
tatatcaaca gccccgtgcg cgatctgaat ggcgtgtgct tcgactcccg gtttcagaac 3840
ccagagtggc ccatggacgc cgatgccaat ggcgcctacc acatcgccct gaagggccag 3900
ctgctgctga atcacctgaa ggagagcaag gatctgaagc tgcagaacgg catctccaat 3960
caggactggc tggcctacat ccaggagctg cgcaacaaaa ggccggcggc cacgaaaaag 4020
gccggccagg caaaaaagaa aaaggaattc 4050

<210> SEQ ID NO 64
<211> LENGTH: 3813
<212> TYPE: DNA
<213> ORGANISM: Artificial Sequence
<220> FEATURE:
<223> OTHER INFORMATION: gene sequence of LbCas12a

<400> SEQUENCE: 64
atgggcagca gccatcatca tcatcatcac agcagcggcc tggtgccgcg cggcagccat 60
atggctgctg ctgctagcag caagctggag aagtttacaa actgctactc cctgtctaag 120

```
accctgaggt tcaaggccat ccctgtgggc aagacccagg agaacatcga caataagcgg    180
ctgctggtgg aggacgagaa gagagccgag gattataagg gcgtgaagaa gctgctggat    240
cgctactatc tgtcttttat caacgacgtg ctgcacagca tcaagctgaa gaatctgaac    300
aattacatca gcctgttccg gaagaaaacc agaaccgaga aggagaataa ggagctggag    360
aacctggaga tcaatctgcg gaaggagatc gccaaggcct tcaagggcaa cgagggctac    420
aagtccctgt ttaagaagga tatcatcgag acaatcctgc cagagttcct ggacgataag    480
gacgagatcg ccctggtgaa cagcttcaat ggctttacca cagccttcac cggcttcttt    540
gataacagag agaatatgtt ttccgaggag gccaagagca catccatcgc cttcaggtgt    600
atcaacgaga atctgacccg ctacatctct aatatggaca tcttcgagaa ggtggacgcc    660
atctttgata agcacgaggt gcaggagatc aaggagaaga tcctgaacag cgactatgat    720
gtggaggatt tctttgaggg cgagttcttt aactttgtgc tgacacagga gggcatcgac    780
gtgtataacg ccatcatcgg cggcttcgtg accgagagcg gcgagaagat caagggcctg    840
aacgagtaca tcaacctgta taatcagaaa accaagcaga agctgcctaa gtttaagcca    900
ctgtataagc aggtgctgag cgatcgggag tctctgagct tctacggcga gggctataca    960
tccgatgagg aggtgctgga ggtgtttaga aacaccctga acaagaacag cgagatcttc   1020
agctccatca agaagctgga gaagctgttc aagaattttg acgagtactc tagcgccggc   1080
atctttgtga agaacggccc cgccatcagc acaatctcca aggatatctt cggcgagtgg   1140
aacgtgatcc gggacaagtg gaatgccgag tatgacgata tccacctgaa gaagaaggcc   1200
gtggtgaccg agaagtacga ggacgatcgg agaaagtcct tcaagaagat cggctccttt   1260
tctctggagc agctgcagga gtacgccgac gccgatctgt ctgtggtgga gaagctgaag   1320
gagatcatca tccagaaggt ggatgagatc tacaaggtgt atggctcctc tgagaagctg   1380
ttcgacgccg attttgtgct ggagaagagc ctgaagaaga acgacgccgt ggtggccatc   1440
atgaaggacc tgctggattc tgtgaagagc ttcgagaatt acatcaaggc cttctttggc   1500
gagggcaagg agacaaacag ggacgagtcc ttctatggcg attttgtgct ggcctacgac   1560
atcctgctga aggtggacca catctacgat gccatccgca attatgtgac ccagaagccc   1620
tactctaagg ataagttcaa gctgtatttt cagaaccctc agttcatggg cggctgggac   1680
aaggataagg agacagacta tcgggccacc atcctgagat acggctccaa gtactatctg   1740
gccatcatgg ataagaagta cgccaagtgc ctgcagaaga tcgacaagga cgatgtgaac   1800
ggcaattacg agaagatcaa ctataagctg ctgcccggcc ctaataagat gctgccaaag   1860
gtgttctttt ctaagaagtg gatggcctac tataacccca gcgaggacat ccagaagatc   1920
tacaagaatg gcacattcaa gaagggcgat atgtttaacc tgaatgactg tcacaagctg   1980
atcgacttct ttaaggatag catctcccgg tatccaaagt ggtccaatgc ctacgatttc   2040
aacttttctg agacagagaa gtataaggac atcgccggct tttacagaga ggtggaggag   2100
cagggctata aggtgagctt cgagtctgcc agcaagaagg aggtggataa gctggtggag   2160
gagggcaagc tgtatatgtt ccagatctat aacaaggact tttccgataa gtctcacggc   2220
acacccaatc tgcacaccat gtacttcaag ctgctgtttg acgagaacaa tcacggacag   2280
atcaggctga gcggaggagc agagctgttc atgaggcgcg cctccctgaa gaaggaggag   2340
ctggtggtgc acccagccaa ctcccctatc gccaacaaga atccagataa tcccaagaaa   2400
accacaaccc tgtcctacga cgtgtataag gataagaggt tttctgagga ccagtacgag   2460
```

```
ctgcacatcc caatcgccat caataagtgc cccaagaaca tcttcaagat caatacagag   2520
gtgcgcgtgc tgctgaagca cgacgataac ccctatgtga tcggcatcga taggggcgag   2580
cgcaatctgc tgtatatcgt ggtggtggac ggcaagggca acatcgtgga gcagtattcc   2640
ctgaacgaga tcatcaacaa cttcaacggc atcaggatca agacagatta ccactctctg   2700
ctggacaaga aggagaagga gaggttcgag gcccgccaga actggacctc catcgagaat   2760
atcaaggagc tgaaggccgg ctatatctct caggtggtgc acaagatctg cgagctggtg   2820
gagaagtacg atgccgtgat cgccctggag gacctgaact ctggctttaa gaatagccgc   2880
gtgaaggtgg agaagcaggt gtatcagaag ttcgagaaga tgctgatcga taagctgaac   2940
tacatggtgg acaagaagtc taatccttgt gcaacaggcg gcgccctgaa gggctatcag   3000
atcaccaata agttcgagag ctttaagtcc atgtctaccc agaacggctt catcttttac   3060
atccctgcct ggctgacatc caagatcgat ccatctaccg gctttgtgaa cctgctgaaa   3120
accaagtata ccagcatcgc cgattccaag aagttcatca gctcctttga caggatcatg   3180
tacgtgcccg aggaggatct gttcgagttt gccctggact ataagaactt ctctcgcaca   3240
gacgccgatt acatcaagaa gtggaagctg tactcctacg gcaaccggat cagaatcttc   3300
cggaatccta agaagaacaa cgtgttcgac tgggaggagg tgtgcctgac cagcgcctat   3360
aaggagctgt tcaacaagta cggcatcaat tatcagcagg gcgatatcag agccctgctg   3420
tgcgagcagt ccgacaaggc cttctactct agctttatgg ccctgatgag cctgatgctg   3480
cagatgcgga acagcatcac aggccgcacc gacgtggatt ttctgatcag ccctgtgaag   3540
aactccgacg gcatcttcta cgatagccgg aactatgagg cccaggagaa tgccatcctg   3600
ccaaagaacg ccgacgccaa tggcgcctat aacatcgcca gaaaggtgct gtgggccatc   3660
ggccagttca agaaggccga ggacgagaag ctggataagg tgaagatcgc catctctaac   3720
aaggagtggc tggagtacgc ccagaccagc gtgaagcaca aaaggccggc ggccacgaaa   3780
aaggccggcc aggcaaaaaa gaaaaaggaa ttc                                3813
```

<210> SEQ ID NO 65
<211> LENGTH: 4305
<212> TYPE: DNA
<213> ORGANISM: Artificial Sequence
<220> FEATURE:
<223> OTHER INFORMATION: gene sequence of SpCas9

<400> SEQUENCE: 65

```
atgggcagca gccatcatca tcatcatcac agcagcggcc tggtgccgcg cggcagccat     60
atggctgctg ctgctagcct ggacagcacc gctcccaaaa agaaaaggaa ggtgggcatt    120
cacggcgtgc ctgcggccga caaaaagtac agcatcggcc ttgatatcgg caccaatagc    180
gtgggctggg ccgttatcac agacgaatac aaggtaccca gcaagaagtt caaggtgctg    240
gggaatacag acaggcactc tatcaagaaa aaccttatcg gggctctgct gtttgactca    300
ggcgagaccg ccgaggccac caggttgaag aggaccgcaa ggcgaaggta cacccggagg    360
aagaacagga tctgctatct gcaggagatc ttcagcaacg agatggccaa ggtggacgac    420
agcttcttcc acaggctgga ggagagcttc cttgtcgagg aggataagaa gcacgaacga    480
caccccatct tcggcaacat agtcgacgag gtcgcttatc acgagaagta ccccaccatc    540
taccacctgc gaaagaaatt ggtggatagc accgataaag ccgacttgcg acttatctac    600
ttggctctgg cgcacatgat taagttcagg ggccacttcc tgatcgaggg cgaccttaac    660
cccgacaaca gtgacgtaga caaattgttc atccagcttg tacagaccta taaccagctg    720
```

```
ttcgaggaaa accctattaa cgccagcggg gtggatgcga aggccatact tagcgccagg    780
ctgagcaaaa gcaggcgctt ggagaacctg atagcccagc tgcccggtga aaagaagaac    840
ggcctcttcg gtaatctgat tgccctgagc ctgggcctga cccccaactt caagagcaac    900
ttcgacctgg cagaagatgc caagctgcag ttgagtaagg acacctatga cgacgacttg    960
gacaatctgc tcgcccaaat cggcgaccag tacgctgacc tgttcctcgc cgccaagaac   1020
ctttctgacg caatcctgct tagcgatatc cttagggtga acacagagat caccaaggcc   1080
cccctgagcg ccagcatgat caagaggtac gacgagcacc atcaggacct gacccttctg   1140
aaggccctgg tgaggcagca actgcccgag aagtacaagg agatcttttt cgaccagagc   1200
aagaacggct acgccggcta catcgacggc ggagccagcc aagaggagtt ctacaagttc   1260
atcaagccca tcctggagaa gatggatggc accgaggagc tgctggtgaa gctgaacagg   1320
gaagatttgc tccggaagca gaggaccttt gacaacggta gcatcccccca ccagatccac   1380
ctgggcgagc tgcacgcaat actgaggcga caggaggatt tctacccctt cctcaaggac   1440
aatagggaga aaatcgaaaa gattctgacc ttcaggatcc cctactacgt gggccctctt   1500
gccaggggca acagccgatt cgcttggatg acaagaaaga gcgaggagac catcaccccc   1560
tggaacttcg aggaagtggt ggacaaagga gcaagcgcgc agtctttcat cgaacggatg   1620
accaatttcg acaaaaacct gcctaacgag aaggtgctgc ccaagcacag cctgctttac   1680
gagtacttca ccgtgtacaa cgagctcacc aaggtgaaat atgtgaccga gggcatgcga   1740
aaacccgctt tcctgagcgg cgagcagaag aaggccatcg tggacctgct gttcaagacc   1800
aacaggaagg tgaccgtgaa gcagctgaag gaggactact tcaagaagat cgagtgcttt   1860
gatagcgtgg aaataagcgg cgtggaggac aggttcaacg ccagcctggg cacctaccac   1920
gacttgttga agataatcaa agacaaggat ttcctggata atgaggagaa cgaggatata   1980
ctcgaggaca tcgtgctgac tttgaccctg tttgaggacc gagagatgat tgaagaaagg   2040
ctcaaaacct acgcccacct gttcgacgac aaagtgatga aacaactgaa gagacgaaga   2100
tacaccggct ggggcagact gtccaggaag ctcatcaacg gcattaggga caagcagagc   2160
ggcaagacca tcctggattt cctgaagtcc gacggcttcg ccaaccgaaa cttcatgcag   2220
ctgattcacg atgacagctt gaccttcaag gaggacatcc agaaggccca ggttagcggc   2280
cagggcgact ccctgcacga acatattgca aacctggcag gctcccctgc gatcaagaag   2340
ggcatactgc agaccgttaa ggttgtggac gaattggtca aggtcatggg caggcacaag   2400
cccgaaaaca tagttataga gatggccaga gagaaccaga ccacccaaaa gggccagaag   2460
aacagccggg agcgcatgaa aaggatcgag gagggtatca aggaactcgg aagccagatc   2520
ctcaaagagc accccgtgga gaatacccag ctccagaacg agaagctgta cctgtactac   2580
ctgcagaacg gcagggacat gtacgttgac caggagttgg acatcaacag gctttcagac   2640
tatgacgtgg atcacatagt gccccagagc tttcttaaag acgatagcat cgacaacaag   2700
gtcctgaccc gctccgacaa aaacaggggc aaaagcgaca acgtgccaag cgaagaggtg   2760
gttaaaaaga tgaagaacta ctggaggcaa ctgctcaacg cgaaattgat cacccagaga   2820
aagttcgata acctgaccaa ggccgagagg ggcggactct ccgaacttga caaagcgggc   2880
ttcataaaga ggcagctggt cgagacccga cagatcacga agcacgtggc ccaaatcctc   2940
gacagcagaa tgaataccaa gtacgatgag aatgacaaac tcatcaggga agtgaaagtg   3000
attaccctga agagcaagtt ggtgtccgac tttcgcaaag atttccagtt ctacaaggtg   3060
```

```
agggagatca acaactacca ccatgcccac gacgcatacc tgaacgccgt ggtcggcacc   3120

gccctgatta agaagtatcc aaagctggag tccgaatttg tctacggcga ctacaaagtt   3180

tacgatgtga ggaagatgat cgctaagagc gaacaggaga tcggcaaggc caccgctaag   3240

tatttcttct acagcaacat catgaacttt ttcaagaccg agatcacact tgccaacggc   3300

gaaatcagga agaggccgct tatcgagacc aacggtgaga ccggcgagat cgtgtgggac   3360

aagggcaggg acttcgccac cgtgaggaaa gtcctgagca tgccccaggt gaatattgtg   3420

aaaaaaactg aggtgcagac aggcggcttt agcaaggaat ccatcctgcc caagaggaac   3480

agcgacaagc tgatcgcccg gaagaaggac tgggacccta agaagtatgg aggcttcgac   3540

agccccaccg tagcctacag cgtgctggtg gtcgcgaagg tagagaaggg gaagagcaag   3600

aaactgaaga gcgtgaagga gctgctcggc ataaccatca tggagaggtc cagctttgag   3660

aagaacccca ttgacttttt ggaagccaag ggctacaaag aggtcaaaaa ggacctgatc   3720

atcaaactcc ccaagtactc cctgtttgaa ttggagaacg gcagaaagag gatgctggcg   3780

agcgctgggg aactgcaaaa gggcaacgaa ctggcgctgc ccagcaagta cgtgaatttt   3840

ctgtacctgg cgtcccacta cgaaaagctg aaaggcagcc ccgaggacaa cgagcagaag   3900

cagctgttcg tggagcagca caagcattac ctggacgaga taatcgagca aatcagcgag   3960

ttcagcaaga gggtgattct ggccgacgcg aacctggata aggtcctcag cgcctacaac   4020

aagcaccgag acaaacccat cagggagcag gccgagaata tcatacacct gttcaccctg   4080

acaaatctgg gcgcacctgc ggcattcaaa tacttcgata ccaccatcga caggaaaagg   4140

tacactagca ctaaggaggt gctggatgcc accttgatcc accagtccat taccggcctg   4200

tatgagacca ggatcgacct gagccagctt ggaggcgact ctagggcgga cccaaaaaag   4260

aaaaggaagg tggaattcta cccatacgat gttccagatt acgct                   4305
```

<210> SEQ ID NO 66
<211> LENGTH: 1350
<212> TYPE: PRT
<213> ORGANISM: Artificial Sequence
<220> FEATURE:
<223> OTHER INFORMATION: Synthetic amino acid sequence; AsCas12a

<400> SEQUENCE: 66

```
Met Gly Ser Ser His His His His His His Ser Ser Gly Leu Val Pro
1               5                   10                  15

Arg Gly Ser His Met Ala Ala Ala Ala Ser Thr Gln Phe Glu Gly Phe
            20                  25                  30

Thr Asn Leu Tyr Gln Val Ser Lys Thr Leu Arg Phe Glu Leu Ile Pro
        35                  40                  45

Gln Gly Lys Thr Leu Lys His Ile Gln Glu Gln Gly Phe Ile Glu Glu
    50                  55                  60

Asp Lys Ala Arg Asn Asp His Tyr Lys Glu Leu Lys Pro Ile Ile Asp
65                  70                  75                  80

Arg Ile Tyr Lys Thr Tyr Ala Asp Gln Cys Leu Gln Leu Val Gln Leu
                85                  90                  95

Asp Trp Glu Asn Leu Ser Ala Ala Ile Asp Ser Tyr Arg Lys Glu Lys
            100                 105                 110

Thr Glu Glu Thr Arg Asn Ala Leu Ile Glu Glu Gln Ala Thr Tyr Arg
        115                 120                 125

Asn Ala Ile His Asp Tyr Phe Ile Gly Arg Thr Asp Asn Leu Thr Asp
    130                 135                 140
```

```
Ala Ile Asn Lys Arg His Ala Glu Ile Tyr Lys Gly Leu Phe Lys Ala
145                 150                 155                 160

Glu Leu Phe Asn Gly Lys Val Leu Lys Gln Leu Gly Thr Val Thr Thr
                165                 170                 175

Thr Glu His Glu Asn Ala Leu Leu Arg Ser Phe Asp Lys Phe Thr Thr
            180                 185                 190

Tyr Phe Ser Gly Phe Tyr Glu Asn Arg Lys Asn Val Phe Ser Ala Glu
        195                 200                 205

Asp Ile Ser Thr Ala Ile Pro His Arg Ile Val Gln Asp Asn Phe Pro
    210                 215                 220

Lys Phe Lys Glu Asn Cys His Ile Phe Thr Arg Leu Ile Thr Ala Val
225                 230                 235                 240

Pro Ser Leu Arg Glu His Phe Glu Asn Val Lys Lys Ala Ile Gly Ile
                245                 250                 255

Phe Val Ser Thr Ser Ile Glu Glu Val Phe Ser Phe Pro Phe Tyr Asn
            260                 265                 270

Gln Leu Leu Thr Gln Thr Gln Ile Asp Leu Tyr Asn Gln Leu Leu Gly
        275                 280                 285

Gly Ile Ser Arg Glu Ala Gly Thr Glu Lys Ile Lys Gly Leu Asn Glu
    290                 295                 300

Val Leu Asn Leu Ala Ile Gln Lys Asn Asp Glu Thr Ala His Ile Ile
305                 310                 315                 320

Ala Ser Leu Pro His Arg Phe Ile Pro Leu Phe Lys Gln Ile Leu Ser
                325                 330                 335

Asp Arg Asn Thr Leu Ser Phe Ile Leu Glu Glu Phe Lys Ser Asp Glu
            340                 345                 350

Glu Val Ile Gln Ser Phe Cys Lys Tyr Lys Thr Leu Leu Arg Asn Glu
        355                 360                 365

Asn Val Leu Glu Thr Ala Glu Ala Leu Phe Asn Glu Leu Asn Ser Ile
    370                 375                 380

Asp Leu Thr His Ile Phe Ile Ser His Lys Lys Leu Glu Thr Ile Ser
385                 390                 395                 400

Ser Ala Leu Cys Asp His Trp Asp Thr Leu Arg Asn Ala Leu Tyr Glu
                405                 410                 415

Arg Arg Ile Ser Glu Leu Thr Gly Lys Ile Thr Lys Ser Ala Lys Glu
            420                 425                 430

Lys Val Gln Arg Ser Leu Lys His Glu Asp Ile Asn Leu Gln Glu Ile
        435                 440                 445

Ile Ser Ala Ala Gly Lys Glu Leu Ser Glu Ala Phe Lys Gln Lys Thr
    450                 455                 460

Ser Glu Ile Leu Ser His Ala His Ala Ala Leu Asp Gln Pro Leu Pro
465                 470                 475                 480

Thr Thr Leu Lys Lys Gln Glu Glu Lys Glu Ile Leu Lys Ser Gln Leu
                485                 490                 495

Asp Ser Leu Leu Gly Leu Tyr His Leu Leu Asp Trp Phe Ala Val Asp
            500                 505                 510

Glu Ser Asn Glu Val Asp Pro Glu Phe Ser Ala Arg Leu Thr Gly Ile
        515                 520                 525

Lys Leu Glu Met Glu Pro Ser Leu Ser Phe Tyr Asn Lys Ala Arg Asn
    530                 535                 540

Tyr Ala Thr Lys Lys Pro Tyr Ser Val Glu Lys Phe Lys Leu Asn Phe
545                 550                 555                 560

Gln Met Pro Thr Leu Ala Ser Gly Trp Asp Val Asn Lys Glu Lys Asn
```

```
                565                 570                 575

Asn Gly Ala Ile Leu Phe Val Lys Asn Gly Leu Tyr Tyr Leu Gly Ile
            580                 585                 590

Met Pro Lys Gln Lys Gly Arg Tyr Lys Ala Leu Ser Phe Glu Pro Thr
        595                 600                 605

Glu Lys Thr Ser Glu Gly Phe Asp Lys Met Tyr Tyr Asp Tyr Phe Pro
    610                 615                 620

Asp Ala Ala Lys Met Ile Pro Lys Cys Ser Thr Gln Leu Lys Ala Val
625                 630                 635                 640

Thr Ala His Phe Gln Thr His Thr Thr Pro Ile Leu Leu Ser Asn Asn
                645                 650                 655

Phe Ile Glu Pro Leu Glu Ile Thr Lys Glu Ile Tyr Asp Leu Asn Asn
            660                 665                 670

Pro Glu Lys Glu Pro Lys Lys Phe Gln Thr Ala Tyr Ala Lys Lys Thr
        675                 680                 685

Gly Asp Gln Lys Gly Tyr Arg Glu Ala Leu Cys Lys Trp Ile Asp Phe
    690                 695                 700

Thr Arg Asp Phe Leu Ser Lys Tyr Thr Lys Thr Thr Ser Ile Asp Leu
705                 710                 715                 720

Ser Ser Leu Arg Pro Ser Ser Gln Tyr Lys Asp Leu Gly Glu Tyr Tyr
                725                 730                 735

Ala Glu Leu Asn Pro Leu Leu Tyr His Ile Ser Phe Gln Arg Ile Ala
            740                 745                 750

Glu Lys Glu Ile Met Asp Ala Val Glu Thr Gly Lys Leu Tyr Leu Phe
        755                 760                 765

Gln Ile Tyr Asn Lys Asp Phe Ala Lys Gly His His Gly Lys Pro Asn
    770                 775                 780

Leu His Thr Leu Tyr Trp Thr Gly Leu Phe Ser Pro Glu Asn Leu Ala
785                 790                 795                 800

Lys Thr Ser Ile Lys Leu Asn Gly Gln Ala Glu Leu Phe Tyr Arg Pro
                805                 810                 815

Lys Ser Arg Met Lys Arg Met Ala His Arg Leu Gly Glu Lys Met Leu
            820                 825                 830

Asn Lys Lys Leu Lys Asp Gln Lys Thr Pro Ile Pro Asp Thr Leu Tyr
        835                 840                 845

Gln Glu Leu Tyr Asp Tyr Val Asn His Arg Leu Ser His Asp Leu Ser
    850                 855                 860

Asp Glu Ala Arg Ala Leu Leu Pro Asn Val Ile Thr Lys Glu Val Ser
865                 870                 875                 880

His Glu Ile Ile Lys Asp Arg Arg Phe Thr Ser Asp Lys Phe Phe Phe
                885                 890                 895

His Val Pro Ile Thr Leu Asn Tyr Gln Ala Ala Asn Ser Pro Ser Lys
            900                 905                 910

Phe Asn Gln Arg Val Asn Ala Tyr Leu Lys Glu His Pro Glu Thr Pro
        915                 920                 925

Ile Ile Gly Ile Asp Arg Gly Glu Arg Asn Leu Ile Tyr Ile Thr Val
    930                 935                 940

Ile Asp Ser Thr Gly Lys Ile Leu Glu Gln Arg Ser Leu Asn Thr Ile
945                 950                 955                 960

Gln Gln Phe Asp Tyr Gln Lys Lys Leu Asp Asn Arg Glu Lys Glu Arg
                965                 970                 975

Val Ala Ala Arg Gln Ala Trp Ser Val Val Gly Thr Ile Lys Asp Leu
            980                 985                 990
```

```
Lys Gln Gly Tyr Leu Ser Gln Val  Ile His Glu Ile Val  Asp Leu Met
     995                 1000                 1005

Ile His  Tyr Gln Ala Val Val  Val Leu Glu Asn Leu  Asn Phe Gly
    1010                 1015                 1020

Phe Lys  Ser Lys Arg Thr Gly  Ile Ala Glu Lys Ala  Val Tyr Gln
    1025                 1030                 1035

Gln Phe  Glu Lys Met Leu Ile  Asp Lys Leu Asn Cys  Leu Val Leu
    1040                 1045                 1050

Lys Asp  Tyr Pro Ala Glu Lys  Val Gly Gly Val Leu  Asn Pro Tyr
    1055                 1060                 1065

Gln Leu  Thr Asp Gln Phe Thr  Ser Phe Ala Lys Met  Gly Thr Gln
    1070                 1075                 1080

Ser Gly  Phe Leu Phe Tyr Val  Pro Ala Pro Tyr Thr  Ser Lys Ile
    1085                 1090                 1095

Asp Pro  Leu Thr Gly Phe Val  Asp Pro Phe Val Trp  Lys Thr Ile
    1100                 1105                 1110

Lys Asn  His Glu Ser Arg Lys  His Phe Leu Glu Gly  Phe Asp Phe
    1115                 1120                 1125

Leu His  Tyr Asp Val Lys Thr  Gly Asp Phe Ile Leu  His Phe Lys
    1130                 1135                 1140

Met Asn  Arg Asn Leu Ser Phe  Gln Arg Gly Leu Pro  Gly Phe Met
    1145                 1150                 1155

Pro Ala  Trp Asp Ile Val Phe  Glu Lys Asn Glu Thr  Gln Phe Asp
    1160                 1165                 1170

Ala Lys  Gly Thr Pro Phe Ile  Ala Gly Lys Arg Ile  Val Pro Val
    1175                 1180                 1185

Ile Glu  Asn His Arg Phe Thr  Gly Arg Tyr Arg Asp  Leu Tyr Pro
    1190                 1195                 1200

Ala Asn  Glu Leu Ile Ala Leu  Leu Glu Glu Lys Gly  Ile Val Phe
    1205                 1210                 1215

Arg Asp  Gly Ser Asn Ile Leu  Pro Lys Leu Leu Glu  Asn Asp Asp
    1220                 1225                 1230

Ser His  Ala Ile Asp Thr Met  Val Ala Leu Ile Arg  Ser Val Leu
    1235                 1240                 1245

Gln Met  Arg Asn Ser Asn Ala  Ala Thr Gly Glu Asp  Tyr Ile Asn
    1250                 1255                 1260

Ser Pro  Val Arg Asp Leu Asn  Gly Val Cys Phe Asp  Ser Arg Phe
    1265                 1270                 1275

Gln Asn  Pro Glu Trp Pro Met  Asp Ala Asp Ala Asn  Gly Ala Tyr
    1280                 1285                 1290

His Ile  Ala Leu Lys Gly Gln  Leu Leu Leu Asn His  Leu Lys Glu
    1295                 1300                 1305

Ser Lys  Asp Leu Lys Leu Gln  Asn Gly Ile Ser Asn  Gln Asp Trp
    1310                 1315                 1320

Leu Ala  Tyr Ile Gln Glu Leu  Arg Asn Lys Arg Pro  Ala Ala Thr
    1325                 1330                 1335

Lys Lys  Ala Gly Gln Ala Lys  Lys Lys Lys Glu Phe
    1340                 1345                 1350
```

<210> SEQ ID NO 67
<211> LENGTH: 1271
<212> TYPE: PRT
<213> ORGANISM: Artificial Sequence
<220> FEATURE:

<223> OTHER INFORMATION: Synthetic amino acid sequence; LbCas12a

<400> SEQUENCE: 67

```
Met Gly Ser Ser His His His His His His Ser Ser Gly Leu Val Pro
1               5                   10                  15

Arg Gly Ser His Met Ala Ala Ala Ala Ser Ser Lys Leu Glu Lys Phe
            20                  25                  30

Thr Asn Cys Tyr Ser Leu Ser Lys Thr Leu Arg Phe Lys Ala Ile Pro
        35                  40                  45

Val Gly Lys Thr Gln Glu Asn Ile Asp Asn Lys Arg Leu Leu Val Glu
    50                  55                  60

Asp Glu Lys Arg Ala Glu Asp Tyr Lys Gly Val Lys Lys Leu Leu Asp
65                  70                  75                  80

Arg Tyr Tyr Leu Ser Phe Ile Asn Asp Val Leu His Ser Ile Lys Leu
                85                  90                  95

Lys Asn Leu Asn Asn Tyr Ile Ser Leu Phe Arg Lys Lys Thr Arg Thr
            100                 105                 110

Glu Lys Glu Asn Lys Glu Leu Glu Asn Leu Glu Ile Asn Leu Arg Lys
        115                 120                 125

Glu Ile Ala Lys Ala Phe Lys Gly Asn Glu Gly Tyr Lys Ser Leu Phe
    130                 135                 140

Lys Lys Asp Ile Ile Glu Thr Ile Leu Pro Glu Phe Leu Asp Asp Lys
145                 150                 155                 160

Asp Glu Ile Ala Leu Val Asn Ser Phe Asn Gly Phe Thr Thr Ala Phe
                165                 170                 175

Thr Gly Phe Phe Asp Asn Arg Glu Asn Met Phe Ser Glu Glu Ala Lys
            180                 185                 190

Ser Thr Ser Ile Ala Phe Arg Cys Ile Asn Glu Asn Leu Thr Arg Tyr
        195                 200                 205

Ile Ser Asn Met Asp Ile Phe Glu Lys Val Asp Ala Ile Phe Asp Lys
    210                 215                 220

His Glu Val Gln Glu Ile Lys Glu Lys Ile Leu Asn Ser Asp Tyr Asp
225                 230                 235                 240

Val Glu Asp Phe Phe Glu Gly Glu Phe Phe Asn Phe Val Leu Thr Gln
                245                 250                 255

Glu Gly Ile Asp Val Tyr Asn Ala Ile Ile Gly Gly Phe Val Thr Glu
            260                 265                 270

Ser Gly Glu Lys Ile Lys Gly Leu Asn Glu Tyr Ile Asn Leu Tyr Asn
        275                 280                 285

Gln Lys Thr Lys Gln Lys Leu Pro Lys Phe Lys Pro Leu Tyr Lys Gln
    290                 295                 300

Val Leu Ser Asp Arg Glu Ser Leu Ser Phe Tyr Gly Glu Gly Tyr Thr
305                 310                 315                 320

Ser Asp Glu Glu Val Leu Glu Val Phe Arg Asn Thr Leu Asn Lys Asn
                325                 330                 335

Ser Glu Ile Phe Ser Ser Ile Lys Lys Leu Glu Lys Leu Phe Lys Asn
            340                 345                 350

Phe Asp Glu Tyr Ser Ser Ala Gly Ile Phe Val Lys Asn Gly Pro Ala
        355                 360                 365

Ile Ser Thr Ile Ser Lys Asp Ile Phe Gly Glu Trp Asn Val Ile Arg
    370                 375                 380

Asp Lys Trp Asn Ala Glu Tyr Asp Asp Ile His Leu Lys Lys Lys Ala
385                 390                 395                 400
```

Val Val Thr Glu Lys Tyr Glu Asp Asp Arg Arg Lys Ser Phe Lys Lys
405 410 415

Ile Gly Ser Phe Ser Leu Glu Gln Leu Gln Glu Tyr Ala Asp Ala Asp
420 425 430

Leu Ser Val Val Glu Lys Leu Lys Glu Ile Ile Ile Gln Lys Val Asp
435 440 445

Glu Ile Tyr Lys Val Tyr Gly Ser Ser Glu Lys Leu Phe Asp Ala Asp
450 455 460

Phe Val Leu Glu Lys Ser Leu Lys Lys Asn Asp Ala Val Val Ala Ile
465 470 475 480

Met Lys Asp Leu Leu Asp Ser Val Lys Ser Phe Glu Asn Tyr Ile Lys
485 490 495

Ala Phe Phe Gly Glu Gly Lys Glu Thr Asn Arg Asp Glu Ser Phe Tyr
500 505 510

Gly Asp Phe Val Leu Ala Tyr Asp Ile Leu Leu Lys Val Asp His Ile
515 520 525

Tyr Asp Ala Ile Arg Asn Tyr Val Thr Gln Lys Pro Tyr Ser Lys Asp
530 535 540

Lys Phe Lys Leu Tyr Phe Gln Asn Pro Gln Phe Met Gly Gly Trp Asp
545 550 555 560

Lys Asp Lys Glu Thr Asp Tyr Arg Ala Thr Ile Leu Arg Tyr Gly Ser
565 570 575

Lys Tyr Tyr Leu Ala Ile Met Asp Lys Lys Tyr Ala Lys Cys Leu Gln
580 585 590

Lys Ile Asp Lys Asp Asp Val Asn Gly Asn Tyr Glu Lys Ile Asn Tyr
595 600 605

Lys Leu Leu Pro Gly Pro Asn Lys Met Leu Pro Lys Val Phe Phe Ser
610 615 620

Lys Lys Trp Met Ala Tyr Tyr Asn Pro Ser Glu Asp Ile Gln Lys Ile
625 630 635 640

Tyr Lys Asn Gly Thr Phe Lys Lys Gly Asp Met Phe Asn Leu Asn Asp
645 650 655

Cys His Lys Leu Ile Asp Phe Phe Lys Asp Ser Ile Ser Arg Tyr Pro
660 665 670

Lys Trp Ser Asn Ala Tyr Asp Phe Asn Phe Ser Glu Thr Glu Lys Tyr
675 680 685

Lys Asp Ile Ala Gly Phe Tyr Arg Glu Val Glu Glu Gln Gly Tyr Lys
690 695 700

Val Ser Phe Glu Ser Ala Ser Lys Lys Glu Val Asp Lys Leu Val Glu
705 710 715 720

Glu Gly Lys Leu Tyr Met Phe Gln Ile Tyr Asn Lys Asp Phe Ser Asp
725 730 735

Lys Ser His Gly Thr Pro Asn Leu His Thr Met Tyr Phe Lys Leu Leu
740 745 750

Phe Asp Glu Asn Asn His Gly Gln Ile Arg Leu Ser Gly Gly Ala Glu
755 760 765

Leu Phe Met Arg Arg Ala Ser Leu Lys Lys Glu Glu Leu Val Val His
770 775 780

Pro Ala Asn Ser Pro Ile Ala Asn Lys Asn Pro Asp Asn Pro Lys Lys
785 790 795 800

Thr Thr Thr Leu Ser Tyr Asp Val Tyr Lys Asp Lys Arg Phe Ser Glu
805 810 815

Asp Gln Tyr Glu Leu His Ile Pro Ile Ala Ile Asn Lys Cys Pro Lys

```
            820                 825                 830

Asn Ile Phe Lys Ile Asn Thr Glu Val Arg Val Leu Leu Lys His Asp
        835                 840                 845

Asp Asn Pro Tyr Val Ile Gly Ile Asp Arg Gly Glu Arg Asn Leu Leu
    850                 855                 860

Tyr Ile Val Val Val Asp Gly Lys Gly Asn Ile Val Glu Gln Tyr Ser
865                 870                 875                 880

Leu Asn Glu Ile Ile Asn Asn Phe Asn Gly Ile Arg Ile Lys Thr Asp
                885                 890                 895

Tyr His Ser Leu Leu Asp Lys Lys Glu Lys Glu Arg Phe Glu Ala Arg
            900                 905                 910

Gln Asn Trp Thr Ser Ile Glu Asn Ile Lys Glu Leu Lys Ala Gly Tyr
        915                 920                 925

Ile Ser Gln Val Val His Lys Ile Cys Glu Leu Val Glu Lys Tyr Asp
    930                 935                 940

Ala Val Ile Ala Leu Glu Asp Leu Asn Ser Gly Phe Lys Asn Ser Arg
945                 950                 955                 960

Val Lys Val Glu Lys Gln Val Tyr Gln Lys Phe Glu Lys Met Leu Ile
                965                 970                 975

Asp Lys Leu Asn Tyr Met Val Asp Lys Lys Ser Asn Pro Cys Ala Thr
            980                 985                 990

Gly Gly Ala Leu Lys Gly Tyr Gln  Ile Thr Asn Lys Phe  Glu Ser Phe
        995                 1000                 1005

Lys Ser  Met Ser Thr Gln Asn  Gly Phe Ile Phe Tyr  Ile Pro Ala
    1010                 1015                 1020

Trp Leu  Thr Ser Lys Ile Asp  Pro Ser Thr Gly Phe  Val Asn Leu
    1025                 1030                 1035

Leu Lys  Thr Lys Tyr Thr Ser  Ile Ala Asp Ser Lys  Lys Phe Ile
    1040                 1045                 1050

Ser Ser  Phe Asp Arg Ile Met  Tyr Val Pro Glu Glu  Asp Leu Phe
    1055                 1060                 1065

Glu Phe  Ala Leu Asp Tyr Lys  Asn Phe Ser Arg Thr  Asp Ala Asp
    1070                 1075                 1080

Tyr Ile  Lys Lys Trp Lys Leu  Tyr Ser Tyr Gly Asn  Arg Ile Arg
    1085                 1090                 1095

Ile Phe  Arg Asn Pro Lys Lys  Asn Asn Val Phe Asp  Trp Glu Glu
    1100                 1105                 1110

Val Cys  Leu Thr Ser Ala Tyr  Lys Glu Leu Phe Asn  Lys Tyr Gly
    1115                 1120                 1125

Ile Asn  Tyr Gln Gln Gly Asp  Ile Arg Ala Leu Leu  Cys Glu Gln
    1130                 1135                 1140

Ser Asp  Lys Ala Phe Tyr Ser  Ser Phe Met Ala Leu  Met Ser Leu
    1145                 1150                 1155

Met Leu  Gln Met Arg Asn Ser  Ile Thr Gly Arg Thr  Asp Val Asp
    1160                 1165                 1170

Phe Leu  Ile Ser Pro Val Lys  Asn Ser Asp Gly Ile  Phe Tyr Asp
    1175                 1180                 1185

Ser Arg  Asn Tyr Glu Ala Gln  Glu Asn Ala Ile Leu  Pro Lys Asn
    1190                 1195                 1200

Ala Asp  Ala Asn Gly Ala Tyr  Asn Ile Ala Arg Lys  Val Leu Trp
    1205                 1210                 1215

Ala Ile  Gly Gln Phe Lys Lys  Ala Glu Asp Glu Lys  Leu Asp Lys
    1220                 1225                 1230
```

Val Lys Ile Ala Ile Ser Asn Lys Glu Trp Leu Glu Tyr Ala Gln
1235 1240 1245

Thr Ser Val Lys His Lys Arg Pro Ala Ala Thr Lys Lys Ala Gly
1250 1255 1260

Gln Ala Lys Lys Lys Lys Glu Phe
1265 1270

<210> SEQ ID NO 68
<211> LENGTH: 1435
<212> TYPE: PRT
<213> ORGANISM: Artificial Sequence
<220> FEATURE:
<223> OTHER INFORMATION: Synthetic amino acid sequence; SpCas9

<400> SEQUENCE: 68

Met Gly Ser Ser His His His His His His Ser Ser Gly Leu Val Pro
1 5 10 15

Arg Gly Ser His Met Ala Ala Ala Ala Ser Leu Asp Ser Thr Ala Pro
20 25 30

Lys Lys Lys Arg Lys Val Gly Ile His Gly Val Pro Ala Ala Asp Lys
35 40 45

Lys Tyr Ser Ile Gly Leu Asp Ile Gly Thr Asn Ser Val Gly Trp Ala
50 55 60

Val Ile Thr Asp Glu Tyr Lys Val Pro Ser Lys Lys Phe Lys Val Leu
65 70 75 80

Gly Asn Thr Asp Arg His Ser Ile Lys Lys Asn Leu Ile Gly Ala Leu
85 90 95

Leu Phe Asp Ser Gly Glu Thr Ala Glu Ala Thr Arg Leu Lys Arg Thr
100 105 110

Ala Arg Arg Arg Tyr Thr Arg Arg Lys Asn Arg Ile Cys Tyr Leu Gln
115 120 125

Glu Ile Phe Ser Asn Glu Met Ala Lys Val Asp Asp Ser Phe Phe His
130 135 140

Arg Leu Glu Glu Ser Phe Leu Val Glu Glu Asp Lys Lys His Glu Arg
145 150 155 160

His Pro Ile Phe Gly Asn Ile Val Asp Glu Val Ala Tyr His Glu Lys
165 170 175

Tyr Pro Thr Ile Tyr His Leu Arg Lys Lys Leu Val Asp Ser Thr Asp
180 185 190

Lys Ala Asp Leu Arg Leu Ile Tyr Leu Ala Leu Ala His Met Ile Lys
195 200 205

Phe Arg Gly His Phe Leu Ile Glu Gly Asp Leu Asn Pro Asp Asn Ser
210 215 220

Asp Val Asp Lys Leu Phe Ile Gln Leu Val Gln Thr Tyr Asn Gln Leu
225 230 235 240

Phe Glu Glu Asn Pro Ile Asn Ala Ser Gly Val Asp Ala Lys Ala Ile
245 250 255

Leu Ser Ala Arg Leu Ser Lys Ser Arg Arg Leu Glu Asn Leu Ile Ala
260 265 270

Gln Leu Pro Gly Glu Lys Lys Asn Gly Leu Phe Gly Asn Leu Ile Ala
275 280 285

Leu Ser Leu Gly Leu Thr Pro Asn Phe Lys Ser Asn Phe Asp Leu Ala
290 295 300

Glu Asp Ala Lys Leu Gln Leu Ser Lys Asp Thr Tyr Asp Asp Asp Leu
305 310 315 320

```
Asp Asn Leu Leu Ala Gln Ile Gly Asp Gln Tyr Ala Asp Leu Phe Leu
                325                 330                 335

Ala Ala Lys Asn Leu Ser Asp Ala Ile Leu Leu Ser Asp Ile Leu Arg
            340                 345                 350

Val Asn Thr Glu Ile Thr Lys Ala Pro Leu Ser Ala Ser Met Ile Lys
        355                 360                 365

Arg Tyr Asp Glu His His Gln Asp Leu Thr Leu Leu Lys Ala Leu Val
    370                 375                 380

Arg Gln Gln Leu Pro Glu Lys Tyr Lys Glu Ile Phe Phe Asp Gln Ser
385                 390                 395                 400

Lys Asn Gly Tyr Ala Gly Tyr Ile Asp Gly Gly Ala Ser Gln Glu Glu
                405                 410                 415

Phe Tyr Lys Phe Ile Lys Pro Ile Leu Glu Lys Met Asp Gly Thr Glu
            420                 425                 430

Glu Leu Leu Val Lys Leu Asn Arg Glu Asp Leu Leu Arg Lys Gln Arg
        435                 440                 445

Thr Phe Asp Asn Gly Ser Ile Pro His Gln Ile His Leu Gly Glu Leu
    450                 455                 460

His Ala Ile Leu Arg Arg Gln Glu Asp Phe Tyr Pro Phe Leu Lys Asp
465                 470                 475                 480

Asn Arg Glu Lys Ile Glu Lys Ile Leu Thr Phe Arg Ile Pro Tyr Tyr
                485                 490                 495

Val Gly Pro Leu Ala Arg Gly Asn Ser Arg Phe Ala Trp Met Thr Arg
            500                 505                 510

Lys Ser Glu Glu Thr Ile Thr Pro Trp Asn Phe Glu Glu Val Val Asp
        515                 520                 525

Lys Gly Ala Ser Ala Gln Ser Phe Ile Glu Arg Met Thr Asn Phe Asp
    530                 535                 540

Lys Asn Leu Pro Asn Glu Lys Val Leu Pro Lys His Ser Leu Leu Tyr
545                 550                 555                 560

Glu Tyr Phe Thr Val Tyr Asn Glu Leu Thr Lys Val Lys Tyr Val Thr
                565                 570                 575

Glu Gly Met Arg Lys Pro Ala Phe Leu Ser Gly Glu Gln Lys Lys Ala
            580                 585                 590

Ile Val Asp Leu Leu Phe Lys Thr Asn Arg Lys Val Thr Val Lys Gln
        595                 600                 605

Leu Lys Glu Asp Tyr Phe Lys Lys Ile Glu Cys Phe Asp Ser Val Glu
    610                 615                 620

Ile Ser Gly Val Glu Asp Arg Phe Asn Ala Ser Leu Gly Thr Tyr His
625                 630                 635                 640

Asp Leu Leu Lys Ile Ile Lys Asp Lys Asp Phe Leu Asp Asn Glu Glu
                645                 650                 655

Asn Glu Asp Ile Leu Glu Asp Ile Val Leu Thr Leu Thr Leu Phe Glu
            660                 665                 670

Asp Arg Glu Met Ile Glu Glu Arg Leu Lys Thr Tyr Ala His Leu Phe
        675                 680                 685

Asp Asp Lys Val Met Lys Gln Leu Lys Arg Arg Arg Tyr Thr Gly Trp
    690                 695                 700

Gly Arg Leu Ser Arg Lys Leu Ile Asn Gly Ile Arg Asp Lys Gln Ser
705                 710                 715                 720

Gly Lys Thr Ile Leu Asp Phe Leu Lys Ser Asp Gly Phe Ala Asn Arg
                725                 730                 735
```

```
Asn Phe Met Gln Leu Ile His Asp Asp Ser Leu Thr Phe Lys Glu Asp
            740                 745                 750

Ile Gln Lys Ala Gln Val Ser Gly Gln Gly Asp Ser Leu His Glu His
        755                 760                 765

Ile Ala Asn Leu Ala Gly Ser Pro Ala Ile Lys Lys Gly Ile Leu Gln
    770                 775                 780

Thr Val Lys Val Val Asp Glu Leu Val Lys Val Met Gly Arg His Lys
785                 790                 795                 800

Pro Glu Asn Ile Val Ile Glu Met Ala Arg Glu Asn Gln Thr Thr Gln
                805                 810                 815

Lys Gly Gln Lys Asn Ser Arg Glu Arg Met Lys Arg Ile Glu Glu Gly
            820                 825                 830

Ile Lys Glu Leu Gly Ser Gln Ile Leu Lys Glu His Pro Val Glu Asn
        835                 840                 845

Thr Gln Leu Gln Asn Glu Lys Leu Tyr Leu Tyr Tyr Leu Gln Asn Gly
    850                 855                 860

Arg Asp Met Tyr Val Asp Gln Glu Leu Asp Ile Asn Arg Leu Ser Asp
865                 870                 875                 880

Tyr Asp Val Asp His Ile Val Pro Gln Ser Phe Leu Lys Asp Asp Ser
                885                 890                 895

Ile Asp Asn Lys Val Leu Thr Arg Ser Asp Lys Asn Arg Gly Lys Ser
            900                 905                 910

Asp Asn Val Pro Ser Glu Glu Val Val Lys Lys Met Lys Asn Tyr Trp
        915                 920                 925

Arg Gln Leu Leu Asn Ala Lys Leu Ile Thr Gln Arg Lys Phe Asp Asn
    930                 935                 940

Leu Thr Lys Ala Glu Arg Gly Gly Leu Ser Glu Leu Asp Lys Ala Gly
945                 950                 955                 960

Phe Ile Lys Arg Gln Leu Val Glu Thr Arg Gln Ile Thr Lys His Val
                965                 970                 975

Ala Gln Ile Leu Asp Ser Arg Met Asn Thr Lys Tyr Asp Glu Asn Asp
            980                 985                 990

Lys Leu Ile Arg Glu Val Lys Val  Ile Thr Leu Lys Ser  Lys Leu Val
        995                 1000                1005

Ser Asp  Phe Arg Lys Asp Phe  Gln Phe Tyr Lys Val  Arg Glu Ile
    1010                1015                1020

Asn Asn  Tyr His His Ala His  Asp Ala Tyr Leu Asn  Ala Val Val
    1025                1030                1035

Gly Thr  Ala Leu Ile Lys Lys  Tyr Pro Lys Leu Glu  Ser Glu Phe
    1040                1045                1050

Val Tyr  Gly Asp Tyr Lys Val  Tyr Asp Val Arg Lys  Met Ile Ala
    1055                1060                1065

Lys Ser  Glu Gln Glu Ile Gly  Lys Ala Thr Ala Lys  Tyr Phe Phe
    1070                1075                1080

Tyr Ser  Asn Ile Met Asn Phe  Phe Lys Thr Glu Ile  Thr Leu Ala
    1085                1090                1095

Asn Gly  Glu Ile Arg Lys Arg  Pro Leu Ile Glu Thr  Asn Gly Glu
    1100                1105                1110

Thr Gly  Glu Ile Val Trp Asp  Lys Gly Arg Asp Phe  Ala Thr Val
    1115                1120                1125

Arg Lys  Val Leu Ser Met Pro  Gln Val Asn Ile Val  Lys Lys Thr
    1130                1135                1140

Glu Val  Gln Thr Gly Gly Phe  Ser Lys Glu Ser Ile  Leu Pro Lys
```

```
    1145                1150                1155

Arg Asn  Ser Asp Lys Leu Ile  Ala Arg Lys Lys Asp  Trp Asp Pro
    1160                1165                1170

Lys Lys  Tyr Gly Gly Phe Asp  Ser Pro Thr Val Ala  Tyr Ser Val
    1175                1180                1185

Leu Val  Val Ala Lys Val Glu  Lys Gly Lys Ser Lys  Lys Leu Lys
    1190                1195                1200

Ser Val  Lys Glu Leu Leu Gly  Ile Thr Ile Met Glu  Arg Ser Ser
    1205                1210                1215

Phe Glu  Lys Asn Pro Ile Asp  Phe Leu Glu Ala Lys  Gly Tyr Lys
    1220                1225                1230

Glu Val  Lys Lys Asp Leu Ile  Ile Lys Leu Pro Lys  Tyr Ser Leu
    1235                1240                1245

Phe Glu  Leu Glu Asn Gly Arg  Lys Arg Met Leu Ala  Ser Ala Gly
    1250                1255                1260

Glu Leu  Gln Lys Gly Asn Glu  Leu Ala Leu Pro Ser  Lys Tyr Val
    1265                1270                1275

Asn Phe  Leu Tyr Leu Ala Ser  His Tyr Glu Lys Leu  Lys Gly Ser
    1280                1285                1290

Pro Glu  Asp Asn Glu Gln Lys  Gln Leu Phe Val Glu  Gln His Lys
    1295                1300                1305

His Tyr  Leu Asp Glu Ile Ile  Glu Gln Ile Ser Glu  Phe Ser Lys
    1310                1315                1320

Arg Val  Ile Leu Ala Asp Ala  Asn Leu Asp Lys Val  Leu Ser Ala
    1325                1330                1335

Tyr Asn  Lys His Arg Asp Lys  Pro Ile Arg Glu Gln  Ala Glu Asn
    1340                1345                1350

Ile Ile  His Leu Phe Thr Leu  Thr Asn Leu Gly Ala  Pro Ala Ala
    1355                1360                1365

Phe Lys  Tyr Phe Asp Thr Thr  Ile Asp Arg Lys Arg  Tyr Thr Ser
    1370                1375                1380

Thr Lys  Glu Val Leu Asp Ala  Thr Leu Ile His Gln  Ser Ile Thr
    1385                1390                1395

Gly Leu  Tyr Glu Thr Arg Ile  Asp Leu Ser Gln Leu  Gly Gly Asp
    1400                1405                1410

Ser Arg  Ala Asp Pro Lys Lys  Lys Arg Lys Val Glu  Phe Tyr Pro
    1415                1420                1425

Tyr Asp  Val Pro Asp Tyr Ala
    1430                1435
```

<210> SEQ ID NO 69
<211> LENGTH: 1356
<212> TYPE: PRT
<213> ORGANISM: Artificial Sequence
<220> FEATURE:
<223> OTHER INFORMATION: Synthetic amino acid sequence; AP-AsCas12a

<400> SEQUENCE: 69

```
Met Gly Ser Ser His His His His His His Ser Ser Gly Leu Val Pro
1               5                   10                  15

Arg Gly Ser His Met Arg Arg Arg Trp Cys Lys Arg Arg Arg Ala Ser
            20                  25                  30

Thr Gln Phe Glu Gly Phe Thr Asn Leu Tyr Gln Val Ser Lys Thr Leu
        35                  40                  45

Arg Phe Glu Leu Ile Pro Gln Gly Lys Thr Leu Lys His Ile Gln Glu
```

```
    50                  55                  60

Gln Gly Phe Ile Glu Glu Asp Lys Ala Arg Asn Asp His Tyr Lys Glu
65                  70                  75                  80

Leu Lys Pro Ile Ile Asp Arg Ile Tyr Lys Thr Tyr Ala Asp Gln Cys
                85                  90                  95

Leu Gln Leu Val Gln Leu Asp Trp Glu Asn Leu Ser Ala Ala Ile Asp
            100                 105                 110

Ser Tyr Arg Lys Glu Lys Thr Glu Glu Thr Arg Asn Ala Leu Ile Glu
        115                 120                 125

Glu Gln Ala Thr Tyr Arg Asn Ala Ile His Asp Tyr Phe Ile Gly Arg
    130                 135                 140

Thr Asp Asn Leu Thr Asp Ala Ile Asn Lys Arg His Ala Glu Ile Tyr
145                 150                 155                 160

Lys Gly Leu Phe Lys Ala Glu Leu Phe Asn Gly Lys Val Leu Lys Gln
                165                 170                 175

Leu Gly Thr Val Thr Thr Thr Glu His Glu Asn Ala Leu Leu Arg Ser
            180                 185                 190

Phe Asp Lys Phe Thr Thr Tyr Phe Ser Gly Phe Tyr Glu Asn Arg Lys
        195                 200                 205

Asn Val Phe Ser Ala Glu Asp Ile Ser Thr Ala Ile Pro His Arg Ile
    210                 215                 220

Val Gln Asp Asn Phe Pro Lys Phe Lys Glu Asn Cys His Ile Phe Thr
225                 230                 235                 240

Arg Leu Ile Thr Ala Val Pro Ser Leu Arg Glu His Phe Glu Asn Val
                245                 250                 255

Lys Lys Ala Ile Gly Ile Phe Val Ser Thr Ser Ile Glu Glu Val Phe
            260                 265                 270

Ser Phe Pro Phe Tyr Asn Gln Leu Leu Thr Gln Thr Gln Ile Asp Leu
        275                 280                 285

Tyr Asn Gln Leu Leu Gly Gly Ile Ser Arg Glu Ala Gly Thr Glu Lys
    290                 295                 300

Ile Lys Gly Leu Asn Glu Val Leu Asn Leu Ala Ile Gln Lys Asn Asp
305                 310                 315                 320

Glu Thr Ala His Ile Ile Ala Ser Leu Pro His Arg Phe Ile Pro Leu
                325                 330                 335

Phe Lys Gln Ile Leu Ser Asp Arg Asn Thr Leu Ser Phe Ile Leu Glu
            340                 345                 350

Glu Phe Lys Ser Asp Glu Glu Val Ile Gln Ser Phe Cys Lys Tyr Lys
        355                 360                 365

Thr Leu Leu Arg Asn Glu Asn Val Leu Glu Thr Ala Glu Ala Leu Phe
    370                 375                 380

Asn Glu Leu Asn Ser Ile Asp Leu Thr His Ile Phe Ile Ser His Lys
385                 390                 395                 400

Lys Leu Glu Thr Ile Ser Ser Ala Leu Cys Asp His Trp Asp Thr Leu
                405                 410                 415

Arg Asn Ala Leu Tyr Glu Arg Arg Ile Ser Glu Leu Thr Gly Lys Ile
            420                 425                 430

Thr Lys Ser Ala Lys Glu Lys Val Gln Arg Ser Leu Lys His Glu Asp
        435                 440                 445

Ile Asn Leu Gln Glu Ile Ile Ser Ala Ala Gly Lys Glu Leu Ser Glu
    450                 455                 460

Ala Phe Lys Gln Lys Thr Ser Glu Ile Leu Ser His Ala His Ala Ala
465                 470                 475                 480
```

```
Leu Asp Gln Pro Leu Pro Thr Thr Leu Lys Lys Gln Glu Glu Lys Glu
                485                 490                 495

Ile Leu Lys Ser Gln Leu Asp Ser Leu Leu Gly Leu Tyr His Leu Leu
            500                 505                 510

Asp Trp Phe Ala Val Asp Glu Ser Asn Glu Val Asp Pro Glu Phe Ser
        515                 520                 525

Ala Arg Leu Thr Gly Ile Lys Leu Glu Met Glu Pro Ser Leu Ser Phe
    530                 535                 540

Tyr Asn Lys Ala Arg Asn Tyr Ala Thr Lys Lys Pro Tyr Ser Val Glu
545                 550                 555                 560

Lys Phe Lys Leu Asn Phe Gln Met Pro Thr Leu Ala Ser Gly Trp Asp
                565                 570                 575

Val Asn Lys Glu Lys Asn Asn Gly Ala Ile Leu Phe Val Lys Asn Gly
            580                 585                 590

Leu Tyr Tyr Leu Gly Ile Met Pro Lys Gln Lys Gly Arg Tyr Lys Ala
        595                 600                 605

Leu Ser Phe Glu Pro Thr Glu Lys Thr Ser Glu Gly Phe Asp Lys Met
    610                 615                 620

Tyr Tyr Asp Tyr Phe Pro Asp Ala Ala Lys Met Ile Pro Lys Cys Ser
625                 630                 635                 640

Thr Gln Leu Lys Ala Val Thr Ala His Phe Gln Thr His Thr Thr Pro
                645                 650                 655

Ile Leu Leu Ser Asn Asn Phe Ile Glu Pro Leu Glu Ile Thr Lys Glu
            660                 665                 670

Ile Tyr Asp Leu Asn Asn Pro Glu Lys Glu Pro Lys Lys Phe Gln Thr
        675                 680                 685

Ala Tyr Ala Lys Lys Thr Gly Asp Gln Lys Gly Tyr Arg Glu Ala Leu
    690                 695                 700

Cys Lys Trp Ile Asp Phe Thr Arg Asp Phe Leu Ser Lys Tyr Thr Lys
705                 710                 715                 720

Thr Thr Ser Ile Asp Leu Ser Ser Leu Arg Pro Ser Ser Gln Tyr Lys
                725                 730                 735

Asp Leu Gly Glu Tyr Tyr Ala Glu Leu Asn Pro Leu Leu Tyr His Ile
            740                 745                 750

Ser Phe Gln Arg Ile Ala Glu Lys Glu Ile Met Asp Ala Val Glu Thr
        755                 760                 765

Gly Lys Leu Tyr Leu Phe Gln Ile Tyr Asn Lys Asp Phe Ala Lys Gly
    770                 775                 780

His His Gly Lys Pro Asn Leu His Thr Leu Tyr Trp Thr Gly Leu Phe
785                 790                 795                 800

Ser Pro Glu Asn Leu Ala Lys Thr Ser Ile Lys Leu Asn Gly Gln Ala
                805                 810                 815

Glu Leu Phe Tyr Arg Pro Lys Ser Arg Met Lys Arg Met Ala His Arg
            820                 825                 830

Leu Gly Glu Lys Met Leu Asn Lys Lys Leu Lys Asp Gln Lys Thr Pro
        835                 840                 845

Ile Pro Asp Thr Leu Tyr Gln Glu Leu Tyr Asp Tyr Val Asn His Arg
    850                 855                 860

Leu Ser His Asp Leu Ser Asp Glu Ala Arg Ala Leu Leu Pro Asn Val
865                 870                 875                 880

Ile Thr Lys Glu Val Ser His Glu Ile Ile Lys Asp Arg Arg Phe Thr
                885                 890                 895
```

```
Ser Asp Lys Phe Phe Phe His Val Pro Ile Thr Leu Asn Tyr Gln Ala
            900                 905                 910

Ala Asn Ser Pro Ser Lys Phe Asn Gln Arg Val Asn Ala Tyr Leu Lys
        915                 920                 925

Glu His Pro Glu Thr Pro Ile Ile Gly Ile Asp Arg Gly Glu Arg Asn
    930                 935                 940

Leu Ile Tyr Ile Thr Val Ile Asp Ser Thr Gly Lys Ile Leu Glu Gln
945                 950                 955                 960

Arg Ser Leu Asn Thr Ile Gln Gln Phe Asp Tyr Gln Lys Lys Leu Asp
                965                 970                 975

Asn Arg Glu Lys Glu Arg Val Ala Ala Arg Gln Ala Trp Ser Val Val
            980                 985                 990

Gly Thr Ile Lys Asp Leu Lys Gln  Gly Tyr Leu Ser Gln  Val Ile His
        995                 1000                1005

Glu Ile  Val Asp Leu Met Ile  His Tyr Gln Ala Val  Val Val Leu
    1010                1015                1020

Glu Asn  Leu Asn Phe Gly Phe  Lys Ser Lys Arg Thr  Gly Ile Ala
    1025                1030                1035

Glu Lys  Ala Val Tyr Gln Gln  Phe Glu Lys Met Leu  Ile Asp Lys
    1040                1045                1050

Leu Asn  Cys Leu Val Leu Lys  Asp Tyr Pro Ala Glu  Lys Val Gly
    1055                1060                1065

Gly Val  Leu Asn Pro Tyr Gln  Leu Thr Asp Gln Phe  Thr Ser Phe
    1070                1075                1080

Ala Lys  Met Gly Thr Gln Ser  Gly Phe Leu Phe Tyr  Val Pro Ala
    1085                1090                1095

Pro Tyr  Thr Ser Lys Ile Asp  Pro Leu Thr Gly Phe  Val Asp Pro
    1100                1105                1110

Phe Val  Trp Lys Thr Ile Lys  Asn His Glu Ser Arg  Lys His Phe
    1115                1120                1125

Leu Glu  Gly Phe Asp Phe Leu  His Tyr Asp Val Lys  Thr Gly Asp
    1130                1135                1140

Phe Ile  Leu His Phe Lys Met  Asn Arg Asn Leu Ser  Phe Gln Arg
    1145                1150                1155

Gly Leu  Pro Gly Phe Met Pro  Ala Trp Asp Ile Val  Phe Glu Lys
    1160                1165                1170

Asn Glu  Thr Gln Phe Asp Ala  Lys Gly Thr Pro Phe  Ile Ala Gly
    1175                1180                1185

Lys Arg  Ile Val Pro Val Ile  Glu Asn His Arg Phe  Thr Gly Arg
    1190                1195                1200

Tyr Arg  Asp Leu Tyr Pro Ala  Asn Glu Leu Ile Ala  Leu Leu Glu
    1205                1210                1215

Glu Lys  Gly Ile Val Phe Arg  Asp Gly Ser Asn Ile  Leu Pro Lys
    1220                1225                1230

Leu Leu  Glu Asn Asp Asp Ser  His Ala Ile Asp Thr  Met Val Ala
    1235                1240                1245

Leu Ile  Arg Ser Val Leu Gln  Met Arg Asn Ser Asn  Ala Ala Thr
    1250                1255                1260

Gly Glu  Asp Tyr Ile Asn Ser  Pro Val Arg Asp Leu  Asn Gly Val
    1265                1270                1275

Cys Phe  Asp Ser Arg Phe Gln  Asn Pro Glu Trp Pro  Met Asp Ala
    1280                1285                1290

Asp Ala  Asn Gly Ala Tyr His  Ile Ala Leu Lys Gly  Gln Leu Leu
```

1295 1300 1305

Leu Asn His Leu Lys Glu Ser Lys Asp Leu Lys Leu Gln Asn Gly
1310 1315 1320

Ile Ser Asn Gln Asp Trp Leu Ala Tyr Ile Gln Glu Leu Arg Asn
1325 1330 1335

Lys Arg Pro Ala Ala Thr Lys Lys Ala Gly Gln Ala Lys Lys Lys
1340 1345 1350

Lys Glu Phe
1355

<210> SEQ ID NO 70
<211> LENGTH: 1371
<212> TYPE: PRT
<213> ORGANISM: Artificial Sequence
<220> FEATURE:
<223> OTHER INFORMATION: Synthetic amino acid sequence; dNP2-AsCas12a

<400> SEQUENCE: 70

Met Gly Ser Ser His His His His His His Ser Ser Gly Leu Val Pro
1 5 10 15

Arg Gly Ser His Met Lys Ile Lys Lys Val Lys Lys Lys Gly Arg Lys
20 25 30

Gly Ser Lys Ile Lys Lys Val Lys Lys Lys Gly Arg Lys Ala Ser Thr
35 40 45

Gln Phe Glu Gly Phe Thr Asn Leu Tyr Gln Val Ser Lys Thr Leu Arg
50 55 60

Phe Glu Leu Ile Pro Gln Gly Lys Thr Leu Lys His Ile Gln Glu Gln
65 70 75 80

Gly Phe Ile Glu Glu Asp Lys Ala Arg Asn Asp His Tyr Lys Glu Leu
85 90 95

Lys Pro Ile Ile Asp Arg Ile Tyr Lys Thr Tyr Ala Asp Gln Cys Leu
100 105 110

Gln Leu Val Gln Leu Asp Trp Glu Asn Leu Ser Ala Ala Ile Asp Ser
115 120 125

Tyr Arg Lys Glu Lys Thr Glu Glu Thr Arg Asn Ala Leu Ile Glu Glu
130 135 140

Gln Ala Thr Tyr Arg Asn Ala Ile His Asp Tyr Phe Ile Gly Arg Thr
145 150 155 160

Asp Asn Leu Thr Asp Ala Ile Asn Lys Arg His Ala Glu Ile Tyr Lys
165 170 175

Gly Leu Phe Lys Ala Glu Leu Phe Asn Gly Lys Val Leu Lys Gln Leu
180 185 190

Gly Thr Val Thr Thr Thr Glu His Glu Asn Ala Leu Leu Arg Ser Phe
195 200 205

Asp Lys Phe Thr Thr Tyr Phe Ser Gly Phe Tyr Glu Asn Arg Lys Asn
210 215 220

Val Phe Ser Ala Glu Asp Ile Ser Thr Ala Ile Pro His Arg Ile Val
225 230 235 240

Gln Asp Asn Phe Pro Lys Phe Lys Glu Asn Cys His Ile Phe Thr Arg
245 250 255

Leu Ile Thr Ala Val Pro Ser Leu Arg Glu His Phe Glu Asn Val Lys
260 265 270

Lys Ala Ile Gly Ile Phe Val Ser Thr Ser Ile Glu Glu Val Phe Ser
275 280 285

Phe Pro Phe Tyr Asn Gln Leu Leu Thr Gln Thr Gln Ile Asp Leu Tyr

```
    290                 295                 300

Asn Gln Leu Leu Gly Gly Ile Ser Arg Glu Ala Gly Thr Glu Lys Ile
305                 310                 315                 320

Lys Gly Leu Asn Glu Val Leu Asn Leu Ala Ile Gln Lys Asn Asp Glu
                325                 330                 335

Thr Ala His Ile Ile Ala Ser Leu Pro His Arg Phe Ile Pro Leu Phe
            340                 345                 350

Lys Gln Ile Leu Ser Asp Arg Asn Thr Leu Ser Phe Ile Leu Glu Glu
        355                 360                 365

Phe Lys Ser Asp Glu Glu Val Ile Gln Ser Phe Cys Lys Tyr Lys Thr
    370                 375                 380

Leu Leu Arg Asn Glu Asn Val Leu Glu Thr Ala Glu Ala Leu Phe Asn
385                 390                 395                 400

Glu Leu Asn Ser Ile Asp Leu Thr His Ile Phe Ile Ser His Lys Lys
                405                 410                 415

Leu Glu Thr Ile Ser Ser Ala Leu Cys Asp His Trp Asp Thr Leu Arg
            420                 425                 430

Asn Ala Leu Tyr Glu Arg Arg Ile Ser Glu Leu Thr Gly Lys Ile Thr
        435                 440                 445

Lys Ser Ala Lys Glu Lys Val Gln Arg Ser Leu Lys His Glu Asp Ile
    450                 455                 460

Asn Leu Gln Glu Ile Ile Ser Ala Ala Gly Lys Glu Leu Ser Glu Ala
465                 470                 475                 480

Phe Lys Gln Lys Thr Ser Glu Ile Leu Ser His Ala His Ala Ala Leu
                485                 490                 495

Asp Gln Pro Leu Pro Thr Thr Leu Lys Lys Gln Glu Glu Lys Glu Ile
            500                 505                 510

Leu Lys Ser Gln Leu Asp Ser Leu Leu Gly Leu Tyr His Leu Leu Asp
        515                 520                 525

Trp Phe Ala Val Asp Glu Ser Asn Glu Val Asp Pro Glu Phe Ser Ala
    530                 535                 540

Arg Leu Thr Gly Ile Lys Leu Glu Met Glu Pro Ser Leu Ser Phe Tyr
545                 550                 555                 560

Asn Lys Ala Arg Asn Tyr Ala Thr Lys Lys Pro Tyr Ser Val Glu Lys
                565                 570                 575

Phe Lys Leu Asn Phe Gln Met Pro Thr Leu Ala Ser Gly Trp Asp Val
            580                 585                 590

Asn Lys Glu Lys Asn Asn Gly Ala Ile Leu Phe Val Lys Asn Gly Leu
        595                 600                 605

Tyr Tyr Leu Gly Ile Met Pro Lys Gln Lys Gly Arg Tyr Lys Ala Leu
    610                 615                 620

Ser Phe Glu Pro Thr Glu Lys Thr Ser Glu Gly Phe Asp Lys Met Tyr
625                 630                 635                 640

Tyr Asp Tyr Phe Pro Asp Ala Ala Lys Met Ile Pro Lys Cys Ser Thr
                645                 650                 655

Gln Leu Lys Ala Val Thr Ala His Phe Gln Thr His Thr Thr Pro Ile
            660                 665                 670

Leu Leu Ser Asn Asn Phe Ile Glu Pro Leu Glu Ile Thr Lys Glu Ile
        675                 680                 685

Tyr Asp Leu Asn Asn Pro Glu Lys Glu Pro Lys Lys Phe Gln Thr Ala
    690                 695                 700

Tyr Ala Lys Lys Thr Gly Asp Gln Lys Gly Tyr Arg Glu Ala Leu Cys
705                 710                 715                 720
```

```
Lys Trp Ile Asp Phe Thr Arg Asp Phe Leu Ser Lys Tyr Thr Lys Thr
                725                 730                 735

Thr Ser Ile Asp Leu Ser Ser Leu Arg Pro Ser Ser Gln Tyr Lys Asp
            740                 745                 750

Leu Gly Glu Tyr Tyr Ala Glu Leu Asn Pro Leu Leu Tyr His Ile Ser
        755                 760                 765

Phe Gln Arg Ile Ala Glu Lys Glu Ile Met Asp Ala Val Glu Thr Gly
    770                 775                 780

Lys Leu Tyr Leu Phe Gln Ile Tyr Asn Lys Asp Phe Ala Lys Gly His
785                 790                 795                 800

His Gly Lys Pro Asn Leu His Thr Leu Tyr Trp Thr Gly Leu Phe Ser
                805                 810                 815

Pro Glu Asn Leu Ala Lys Thr Ser Ile Lys Leu Asn Gly Gln Ala Glu
            820                 825                 830

Leu Phe Tyr Arg Pro Lys Ser Arg Met Lys Arg Met Ala His Arg Leu
        835                 840                 845

Gly Glu Lys Met Leu Asn Lys Lys Leu Lys Asp Gln Lys Thr Pro Ile
    850                 855                 860

Pro Asp Thr Leu Tyr Gln Glu Leu Tyr Asp Tyr Val Asn His Arg Leu
865                 870                 875                 880

Ser His Asp Leu Ser Asp Glu Ala Arg Ala Leu Leu Pro Asn Val Ile
                885                 890                 895

Thr Lys Glu Val Ser His Glu Ile Ile Lys Asp Arg Arg Phe Thr Ser
            900                 905                 910

Asp Lys Phe Phe Phe His Val Pro Ile Thr Leu Asn Tyr Gln Ala Ala
        915                 920                 925

Asn Ser Pro Ser Lys Phe Asn Gln Arg Val Asn Ala Tyr Leu Lys Glu
    930                 935                 940

His Pro Glu Thr Pro Ile Ile Gly Ile Asp Arg Gly Glu Arg Asn Leu
945                 950                 955                 960

Ile Tyr Ile Thr Val Ile Asp Ser Thr Gly Lys Ile Leu Glu Gln Arg
                965                 970                 975

Ser Leu Asn Thr Ile Gln Gln Phe Asp Tyr Gln Lys Lys Leu Asp Asn
            980                 985                 990

Arg Glu Lys Glu Arg Val Ala Ala  Arg Gln Ala Trp Ser  Val Val Gly
        995                 1000                 1005

Thr Ile  Lys Asp Leu Lys Gln  Gly Tyr Leu Ser Gln  Val Ile His
    1010                 1015                 1020

Glu Ile  Val Asp Leu Met Ile  His Tyr Gln Ala Val  Val Val Leu
    1025                 1030                 1035

Glu Asn  Leu Asn Phe Gly Phe  Lys Ser Lys Arg Thr  Gly Ile Ala
    1040                 1045                 1050

Glu Lys  Ala Val Tyr Gln Gln  Phe Glu Lys Met Leu  Ile Asp Lys
    1055                 1060                 1065

Leu Asn  Cys Leu Val Leu Lys  Asp Tyr Pro Ala Glu  Lys Val Gly
    1070                 1075                 1080

Gly Val  Leu Asn Pro Tyr Gln  Leu Thr Asp Gln Phe  Thr Ser Phe
    1085                 1090                 1095

Ala Lys  Met Gly Thr Gln Ser  Gly Phe Leu Phe Tyr  Val Pro Ala
    1100                 1105                 1110

Pro Tyr  Thr Ser Lys Ile Asp  Pro Leu Thr Gly Phe  Val Asp Pro
    1115                 1120                 1125
```

```
Phe Val  Trp Lys Thr Ile Lys  Asn His Glu Ser Arg  Lys His Phe
    1130                1135                1140

Leu Glu  Gly Phe Asp Phe Leu  His Tyr Asp Val Lys  Thr Gly Asp
    1145                1150                1155

Phe Ile  Leu His Phe Lys Met  Asn Arg Asn Leu Ser  Phe Gln Arg
    1160                1165                1170

Gly Leu  Pro Gly Phe Met Pro  Ala Trp Asp Ile Val  Phe Glu Lys
    1175                1180                1185

Asn Glu  Thr Gln Phe Asp Ala  Lys Gly Thr Pro Phe  Ile Ala Gly
    1190                1195                1200

Lys Arg  Ile Val Pro Val Ile  Glu Asn His Arg Phe  Thr Gly Arg
    1205                1210                1215

Tyr Arg  Asp Leu Tyr Pro Ala  Asn Glu Leu Ile Ala  Leu Leu Glu
    1220                1225                1230

Glu Lys  Gly Ile Val Phe Arg  Asp Gly Ser Asn Ile  Leu Pro Lys
    1235                1240                1245

Leu Leu  Glu Asn Asp Asp Ser  His Ala Ile Asp Thr  Met Val Ala
    1250                1255                1260

Leu Ile  Arg Ser Val Leu Gln  Met Arg Asn Ser Asn  Ala Ala Thr
    1265                1270                1275

Gly Glu  Asp Tyr Ile Asn Ser  Pro Val Arg Asp Leu  Asn Gly Val
    1280                1285                1290

Cys Phe  Asp Ser Arg Phe Gln  Asn Pro Glu Trp Pro  Met Asp Ala
    1295                1300                1305

Asp Ala  Asn Gly Ala Tyr His  Ile Ala Leu Lys Gly  Gln Leu Leu
    1310                1315                1320

Leu Asn  His Leu Lys Glu Ser  Lys Asp Leu Lys Leu  Gln Asn Gly
    1325                1330                1335

Ile Ser  Asn Gln Asp Trp Leu  Ala Tyr Ile Gln Glu  Leu Arg Asn
    1340                1345                1350

Lys Arg  Pro Ala Ala Thr Lys  Lys Ala Gly Gln Ala  Lys Lys Lys
    1355                1360                1365

Lys Glu  Phe
    1370


<210> SEQ ID NO 71
<211> LENGTH: 1356
<212> TYPE: PRT
<213> ORGANISM: Artificial Sequence
<220> FEATURE:
<223> OTHER INFORMATION: Synthetic amino acid sequence; R9-AsCas12a

<400> SEQUENCE: 71

Met Gly Ser Ser His His His His His His Ser Ser Gly Leu Val Pro
1               5                   10                  15

Arg Gly Ser His Met Arg Arg Arg Arg Arg Arg Arg Arg Arg Ala Ser
            20                  25                  30

Thr Gln Phe Glu Gly Phe Thr Asn Leu Tyr Gln Val Ser Lys Thr Leu
        35                  40                  45

Arg Phe Glu Leu Ile Pro Gln Gly Lys Thr Leu Lys His Ile Gln Glu
    50                  55                  60

Gln Gly Phe Ile Glu Glu Asp Lys Ala Arg Asn Asp His Tyr Lys Glu
65                  70                  75                  80

Leu Lys Pro Ile Ile Asp Arg Ile Tyr Lys Thr Tyr Ala Asp Gln Cys
                85                  90                  95
```

```
Leu Gln Leu Val Gln Leu Asp Trp Glu Asn Leu Ser Ala Ala Ile Asp
            100                 105                 110

Ser Tyr Arg Lys Glu Lys Thr Glu Glu Thr Arg Asn Ala Leu Ile Glu
        115                 120                 125

Glu Gln Ala Thr Tyr Arg Asn Ala Ile His Asp Tyr Phe Ile Gly Arg
    130                 135                 140

Thr Asp Asn Leu Thr Asp Ala Ile Asn Lys Arg His Ala Glu Ile Tyr
145                 150                 155                 160

Lys Gly Leu Phe Lys Ala Glu Leu Phe Asn Gly Lys Val Leu Lys Gln
                165                 170                 175

Leu Gly Thr Val Thr Thr Thr Glu His Glu Asn Ala Leu Leu Arg Ser
            180                 185                 190

Phe Asp Lys Phe Thr Thr Tyr Phe Ser Gly Phe Tyr Glu Asn Arg Lys
        195                 200                 205

Asn Val Phe Ser Ala Glu Asp Ile Ser Thr Ala Ile Pro His Arg Ile
    210                 215                 220

Val Gln Asp Asn Phe Pro Lys Phe Lys Glu Asn Cys His Ile Phe Thr
225                 230                 235                 240

Arg Leu Ile Thr Ala Val Pro Ser Leu Arg Glu His Phe Glu Asn Val
                245                 250                 255

Lys Lys Ala Ile Gly Ile Phe Val Ser Thr Ser Ile Glu Glu Val Phe
            260                 265                 270

Ser Phe Pro Phe Tyr Asn Gln Leu Leu Thr Gln Thr Gln Ile Asp Leu
        275                 280                 285

Tyr Asn Gln Leu Leu Gly Gly Ile Ser Arg Glu Ala Gly Thr Glu Lys
    290                 295                 300

Ile Lys Gly Leu Asn Glu Val Leu Asn Leu Ala Ile Gln Lys Asn Asp
305                 310                 315                 320

Glu Thr Ala His Ile Ile Ala Ser Leu Pro His Arg Phe Ile Pro Leu
                325                 330                 335

Phe Lys Gln Ile Leu Ser Asp Arg Asn Thr Leu Ser Phe Ile Leu Glu
            340                 345                 350

Glu Phe Lys Ser Asp Glu Glu Val Ile Gln Ser Phe Cys Lys Tyr Lys
        355                 360                 365

Thr Leu Leu Arg Asn Glu Asn Val Leu Glu Thr Ala Glu Ala Leu Phe
    370                 375                 380

Asn Glu Leu Asn Ser Ile Asp Leu Thr His Ile Phe Ile Ser His Lys
385                 390                 395                 400

Lys Leu Glu Thr Ile Ser Ser Ala Leu Cys Asp His Trp Asp Thr Leu
                405                 410                 415

Arg Asn Ala Leu Tyr Glu Arg Arg Ile Ser Glu Leu Thr Gly Lys Ile
            420                 425                 430

Thr Lys Ser Ala Lys Glu Lys Val Gln Arg Ser Leu Lys His Glu Asp
        435                 440                 445

Ile Asn Leu Gln Glu Ile Ile Ser Ala Ala Gly Lys Glu Leu Ser Glu
    450                 455                 460

Ala Phe Lys Gln Lys Thr Ser Glu Ile Leu Ser His Ala His Ala Ala
465                 470                 475                 480

Leu Asp Gln Pro Leu Pro Thr Thr Leu Lys Lys Gln Glu Glu Lys Glu
                485                 490                 495

Ile Leu Lys Ser Gln Leu Asp Ser Leu Leu Gly Leu Tyr His Leu Leu
            500                 505                 510

Asp Trp Phe Ala Val Asp Glu Ser Asn Glu Val Asp Pro Glu Phe Ser
```

```
        515                 520                 525

Ala Arg Leu Thr Gly Ile Lys Leu Glu Met Glu Pro Ser Leu Ser Phe
    530                 535                 540

Tyr Asn Lys Ala Arg Asn Tyr Ala Thr Lys Lys Pro Tyr Ser Val Glu
545                 550                 555                 560

Lys Phe Lys Leu Asn Phe Gln Met Pro Thr Leu Ala Ser Gly Trp Asp
                565                 570                 575

Val Asn Lys Glu Lys Asn Asn Gly Ala Ile Leu Phe Val Lys Asn Gly
            580                 585                 590

Leu Tyr Tyr Leu Gly Ile Met Pro Lys Gln Lys Gly Arg Tyr Lys Ala
        595                 600                 605

Leu Ser Phe Glu Pro Thr Glu Lys Thr Ser Glu Gly Phe Asp Lys Met
    610                 615                 620

Tyr Tyr Asp Tyr Phe Pro Asp Ala Ala Lys Met Ile Pro Lys Cys Ser
625                 630                 635                 640

Thr Gln Leu Lys Ala Val Thr Ala His Phe Gln Thr His Thr Thr Pro
                645                 650                 655

Ile Leu Leu Ser Asn Asn Phe Ile Glu Pro Leu Glu Ile Thr Lys Glu
            660                 665                 670

Ile Tyr Asp Leu Asn Asn Pro Glu Lys Glu Pro Lys Lys Phe Gln Thr
        675                 680                 685

Ala Tyr Ala Lys Lys Thr Gly Asp Gln Lys Gly Tyr Arg Glu Ala Leu
    690                 695                 700

Cys Lys Trp Ile Asp Phe Thr Arg Asp Phe Leu Ser Lys Tyr Thr Lys
705                 710                 715                 720

Thr Thr Ser Ile Asp Leu Ser Ser Leu Arg Pro Ser Ser Gln Tyr Lys
                725                 730                 735

Asp Leu Gly Glu Tyr Tyr Ala Glu Leu Asn Pro Leu Leu Tyr His Ile
            740                 745                 750

Ser Phe Gln Arg Ile Ala Glu Lys Glu Ile Met Asp Ala Val Glu Thr
        755                 760                 765

Gly Lys Leu Tyr Leu Phe Gln Ile Tyr Asn Lys Asp Phe Ala Lys Gly
    770                 775                 780

His His Gly Lys Pro Asn Leu His Thr Leu Tyr Trp Thr Gly Leu Phe
785                 790                 795                 800

Ser Pro Glu Asn Leu Ala Lys Thr Ser Ile Lys Leu Asn Gly Gln Ala
                805                 810                 815

Glu Leu Phe Tyr Arg Pro Lys Ser Arg Met Lys Arg Met Ala His Arg
            820                 825                 830

Leu Gly Glu Lys Met Leu Asn Lys Lys Leu Lys Asp Gln Lys Thr Pro
        835                 840                 845

Ile Pro Asp Thr Leu Tyr Gln Glu Leu Tyr Asp Tyr Val Asn His Arg
    850                 855                 860

Leu Ser His Asp Leu Ser Asp Glu Ala Arg Ala Leu Leu Pro Asn Val
865                 870                 875                 880

Ile Thr Lys Glu Val Ser His Glu Ile Ile Lys Asp Arg Arg Phe Thr
                885                 890                 895

Ser Asp Lys Phe Phe Phe His Val Pro Ile Thr Leu Asn Tyr Gln Ala
            900                 905                 910

Ala Asn Ser Pro Ser Lys Phe Asn Gln Arg Val Asn Ala Tyr Leu Lys
        915                 920                 925

Glu His Pro Glu Thr Pro Ile Ile Gly Ile Asp Arg Gly Glu Arg Asn
    930                 935                 940
```

```
Leu Ile Tyr Ile Thr Val Ile Asp Ser Thr Gly Lys Ile Leu Glu Gln
945                 950                 955                 960

Arg Ser Leu Asn Thr Ile Gln Gln Phe Asp Tyr Gln Lys Lys Leu Asp
                965                 970                 975

Asn Arg Glu Lys Glu Arg Val Ala Ala Arg Gln Ala Trp Ser Val Val
            980                 985                 990

Gly Thr Ile Lys Asp Leu Lys Gln  Gly Tyr Leu Ser Gln  Val Ile His
        995                 1000                1005

Glu Ile  Val Asp Leu Met Ile  His Tyr Gln Ala Val  Val Val Leu
    1010                1015                1020

Glu Asn  Leu Asn Phe Gly Phe  Lys Ser Lys Arg Thr  Gly Ile Ala
    1025                1030                1035

Glu Lys  Ala Val Tyr Gln Gln  Phe Glu Lys Met Leu  Ile Asp Lys
    1040                1045                1050

Leu Asn  Cys Leu Val Leu Lys  Asp Tyr Pro Ala Glu  Lys Val Gly
    1055                1060                1065

Gly Val  Leu Asn Pro Tyr Gln  Leu Thr Asp Gln Phe  Thr Ser Phe
    1070                1075                1080

Ala Lys  Met Gly Thr Gln Ser  Gly Phe Leu Phe Tyr  Val Pro Ala
    1085                1090                1095

Pro Tyr  Thr Ser Lys Ile Asp  Pro Leu Thr Gly Phe  Val Asp Pro
    1100                1105                1110

Phe Val  Trp Lys Thr Ile Lys  Asn His Glu Ser Arg  Lys His Phe
    1115                1120                1125

Leu Glu  Gly Phe Asp Phe Leu  His Tyr Asp Val Lys  Thr Gly Asp
    1130                1135                1140

Phe Ile  Leu His Phe Lys Met  Asn Arg Asn Leu Ser  Phe Gln Arg
    1145                1150                1155

Gly Leu  Pro Gly Phe Met Pro  Ala Trp Asp Ile Val  Phe Glu Lys
    1160                1165                1170

Asn Glu  Thr Gln Phe Asp Ala  Lys Gly Thr Pro Phe  Ile Ala Gly
    1175                1180                1185

Lys Arg  Ile Val Pro Val Ile  Glu Asn His Arg Phe  Thr Gly Arg
    1190                1195                1200

Tyr Arg  Asp Leu Tyr Pro Ala  Asn Glu Leu Ile Ala  Leu Leu Glu
    1205                1210                1215

Glu Lys  Gly Ile Val Phe Arg  Asp Gly Ser Asn Ile  Leu Pro Lys
    1220                1225                1230

Leu Leu  Glu Asn Asp Asp Ser  His Ala Ile Asp Thr  Met Val Ala
    1235                1240                1245

Leu Ile  Arg Ser Val Leu Gln  Met Arg Asn Ser Asn  Ala Ala Thr
    1250                1255                1260

Gly Glu  Asp Tyr Ile Asn Ser  Pro Val Arg Asp Leu  Asn Gly Val
    1265                1270                1275

Cys Phe  Asp Ser Arg Phe Gln  Asn Pro Glu Trp Pro  Met Asp Ala
    1280                1285                1290

Asp Ala  Asn Gly Ala Tyr His  Ile Ala Leu Lys Gly  Gln Leu Leu
    1295                1300                1305

Leu Asn  His Leu Lys Glu Ser  Lys Asp Leu Lys Leu  Gln Asn Gly
    1310                1315                1320

Ile Ser  Asn Gln Asp Trp Leu  Ala Tyr Ile Gln Glu  Leu Arg Asn
    1325                1330                1335
```

```
Lys Arg  Pro Ala Ala Thr Lys  Lys Ala Gly Gln Ala  Lys Lys Lys
    1340                1345                1350

Lys Glu  Phe
    1355


<210> SEQ ID NO 72
<211> LENGTH: 1358
<212> TYPE: PRT
<213> ORGANISM: Artificial Sequence
<220> FEATURE:
<223> OTHER INFORMATION: Synthetic amino acid sequence; TAT-AsCas12a

<400> SEQUENCE: 72

Met Gly Ser Ser His His His His His His Ser Ser Gly Leu Val Pro
1               5                   10                  15

Arg Gly Ser His Met Tyr Gly Arg Lys Lys Arg Arg Gln Arg Arg Arg
            20                  25                  30

Ala Ser Thr Gln Phe Glu Gly Phe Thr Asn Leu Tyr Gln Val Ser Lys
        35                  40                  45

Thr Leu Arg Phe Glu Leu Ile Pro Gln Gly Lys Thr Leu Lys His Ile
    50                  55                  60

Gln Glu Gln Gly Phe Ile Glu Glu Asp Lys Ala Arg Asn Asp His Tyr
65                  70                  75                  80

Lys Glu Leu Lys Pro Ile Ile Asp Arg Ile Tyr Lys Thr Tyr Ala Asp
                85                  90                  95

Gln Cys Leu Gln Leu Val Gln Leu Asp Trp Glu Asn Leu Ser Ala Ala
            100                 105                 110

Ile Asp Ser Tyr Arg Lys Glu Lys Thr Glu Glu Thr Arg Asn Ala Leu
        115                 120                 125

Ile Glu Glu Gln Ala Thr Tyr Arg Asn Ala Ile His Asp Tyr Phe Ile
    130                 135                 140

Gly Arg Thr Asp Asn Leu Thr Asp Ala Ile Asn Lys Arg His Ala Glu
145                 150                 155                 160

Ile Tyr Lys Gly Leu Phe Lys Ala Glu Leu Phe Asn Gly Lys Val Leu
                165                 170                 175

Lys Gln Leu Gly Thr Val Thr Thr Thr Glu His Glu Asn Ala Leu Leu
            180                 185                 190

Arg Ser Phe Asp Lys Phe Thr Thr Tyr Phe Ser Gly Phe Tyr Glu Asn
        195                 200                 205

Arg Lys Asn Val Phe Ser Ala Glu Asp Ile Ser Thr Ala Ile Pro His
    210                 215                 220

Arg Ile Val Gln Asp Asn Phe Pro Lys Phe Lys Glu Asn Cys His Ile
225                 230                 235                 240

Phe Thr Arg Leu Ile Thr Ala Val Pro Ser Leu Arg Glu His Phe Glu
                245                 250                 255

Asn Val Lys Lys Ala Ile Gly Ile Phe Val Ser Thr Ser Ile Glu Glu
            260                 265                 270

Val Phe Ser Phe Pro Phe Tyr Asn Gln Leu Leu Thr Gln Thr Gln Ile
        275                 280                 285

Asp Leu Tyr Asn Gln Leu Leu Gly Gly Ile Ser Arg Glu Ala Gly Thr
    290                 295                 300

Glu Lys Ile Lys Gly Leu Asn Glu Val Leu Asn Leu Ala Ile Gln Lys
305                 310                 315                 320

Asn Asp Glu Thr Ala His Ile Ile Ala Ser Leu Pro His Arg Phe Ile
                325                 330                 335
```

-continued

Pro Leu Phe Lys Gln Ile Leu Ser Asp Arg Asn Thr Leu Ser Phe Ile
340 345 350

Leu Glu Glu Phe Lys Ser Asp Glu Glu Val Ile Gln Ser Phe Cys Lys
355 360 365

Tyr Lys Thr Leu Leu Arg Asn Glu Asn Val Leu Glu Thr Ala Glu Ala
370 375 380

Leu Phe Asn Glu Leu Asn Ser Ile Asp Leu Thr His Ile Phe Ile Ser
385 390 395 400

His Lys Lys Leu Glu Thr Ile Ser Ser Ala Leu Cys Asp His Trp Asp
405 410 415

Thr Leu Arg Asn Ala Leu Tyr Glu Arg Arg Ile Ser Glu Leu Thr Gly
420 425 430

Lys Ile Thr Lys Ser Ala Lys Glu Lys Val Gln Arg Ser Leu Lys His
435 440 445

Glu Asp Ile Asn Leu Gln Glu Ile Ile Ser Ala Ala Gly Lys Glu Leu
450 455 460

Ser Glu Ala Phe Lys Gln Lys Thr Ser Glu Ile Leu Ser His Ala His
465 470 475 480

Ala Ala Leu Asp Gln Pro Leu Pro Thr Thr Leu Lys Lys Gln Glu Glu
485 490 495

Lys Glu Ile Leu Lys Ser Gln Leu Asp Ser Leu Leu Gly Leu Tyr His
500 505 510

Leu Leu Asp Trp Phe Ala Val Asp Glu Ser Asn Glu Val Asp Pro Glu
515 520 525

Phe Ser Ala Arg Leu Thr Gly Ile Lys Leu Glu Met Glu Pro Ser Leu
530 535 540

Ser Phe Tyr Asn Lys Ala Arg Asn Tyr Ala Thr Lys Lys Pro Tyr Ser
545 550 555 560

Val Glu Lys Phe Lys Leu Asn Phe Gln Met Pro Thr Leu Ala Ser Gly
565 570 575

Trp Asp Val Asn Lys Glu Lys Asn Asn Gly Ala Ile Leu Phe Val Lys
580 585 590

Asn Gly Leu Tyr Tyr Leu Gly Ile Met Pro Lys Gln Lys Gly Arg Tyr
595 600 605

Lys Ala Leu Ser Phe Glu Pro Thr Glu Lys Thr Ser Glu Gly Phe Asp
610 615 620

Lys Met Tyr Tyr Asp Tyr Phe Pro Asp Ala Ala Lys Met Ile Pro Lys
625 630 635 640

Cys Ser Thr Gln Leu Lys Ala Val Thr Ala His Phe Gln Thr His Thr
645 650 655

Thr Pro Ile Leu Leu Ser Asn Asn Phe Ile Glu Pro Leu Glu Ile Thr
660 665 670

Lys Glu Ile Tyr Asp Leu Asn Asn Pro Glu Lys Glu Pro Lys Lys Phe
675 680 685

Gln Thr Ala Tyr Ala Lys Lys Thr Gly Asp Gln Lys Gly Tyr Arg Glu
690 695 700

Ala Leu Cys Lys Trp Ile Asp Phe Thr Arg Asp Phe Leu Ser Lys Tyr
705 710 715 720

Thr Lys Thr Thr Ser Ile Asp Leu Ser Ser Leu Arg Pro Ser Ser Gln
725 730 735

Tyr Lys Asp Leu Gly Glu Tyr Tyr Ala Glu Leu Asn Pro Leu Leu Tyr
740 745 750

His Ile Ser Phe Gln Arg Ile Ala Glu Lys Glu Ile Met Asp Ala Val

```
        755                 760                 765

Glu Thr Gly Lys Leu Tyr Leu Phe Gln Ile Tyr Asn Lys Asp Phe Ala
    770                 775                 780

Lys Gly His His Gly Lys Pro Asn Leu His Thr Leu Tyr Trp Thr Gly
785                 790                 795                 800

Leu Phe Ser Pro Glu Asn Leu Ala Lys Thr Ser Ile Lys Leu Asn Gly
                805                 810                 815

Gln Ala Glu Leu Phe Tyr Arg Pro Lys Ser Arg Met Lys Arg Met Ala
            820                 825                 830

His Arg Leu Gly Glu Lys Met Leu Asn Lys Lys Leu Lys Asp Gln Lys
        835                 840                 845

Thr Pro Ile Pro Asp Thr Leu Tyr Gln Glu Leu Tyr Asp Tyr Val Asn
    850                 855                 860

His Arg Leu Ser His Asp Leu Ser Asp Glu Ala Arg Ala Leu Leu Pro
865                 870                 875                 880

Asn Val Ile Thr Lys Glu Val Ser His Glu Ile Ile Lys Asp Arg Arg
                885                 890                 895

Phe Thr Ser Asp Lys Phe Phe Phe His Val Pro Ile Thr Leu Asn Tyr
            900                 905                 910

Gln Ala Ala Asn Ser Pro Ser Lys Phe Asn Gln Arg Val Asn Ala Tyr
        915                 920                 925

Leu Lys Glu His Pro Glu Thr Pro Ile Ile Gly Ile Asp Arg Gly Glu
    930                 935                 940

Arg Asn Leu Ile Tyr Ile Thr Val Ile Asp Ser Thr Gly Lys Ile Leu
945                 950                 955                 960

Glu Gln Arg Ser Leu Asn Thr Ile Gln Gln Phe Asp Tyr Gln Lys Lys
                965                 970                 975

Leu Asp Asn Arg Glu Lys Glu Arg Val Ala Ala Arg Gln Ala Trp Ser
            980                 985                 990

Val Val Gly Thr Ile Lys Asp Leu  Lys Gln Gly Tyr Leu  Ser Gln Val
        995                 1000                 1005

Ile His  Glu Ile Val Asp Leu  Met Ile His Tyr Gln  Ala Val Val
    1010                 1015                 1020

Val Leu  Glu Asn Leu Asn Phe  Gly Phe Lys Ser Lys  Arg Thr Gly
    1025                 1030                 1035

Ile Ala  Glu Lys Ala Val Tyr  Gln Gln Phe Glu Lys  Met Leu Ile
    1040                 1045                 1050

Asp Lys  Leu Asn Cys Leu Val  Leu Lys Asp Tyr Pro  Ala Glu Lys
    1055                 1060                 1065

Val Gly  Gly Val Leu Asn Pro  Tyr Gln Leu Thr Asp  Gln Phe Thr
    1070                 1075                 1080

Ser Phe  Ala Lys Met Gly Thr  Gln Ser Gly Phe Leu  Phe Tyr Val
    1085                 1090                 1095

Pro Ala  Pro Tyr Thr Ser Lys  Ile Asp Pro Leu Thr  Gly Phe Val
    1100                 1105                 1110

Asp Pro  Phe Val Trp Lys Thr  Ile Lys Asn His Glu  Ser Arg Lys
    1115                 1120                 1125

His Phe  Leu Glu Gly Phe Asp  Phe Leu His Tyr Asp  Val Lys Thr
    1130                 1135                 1140

Gly Asp  Phe Ile Leu His Phe  Lys Met Asn Arg Asn  Leu Ser Phe
    1145                 1150                 1155

Gln Arg  Gly Leu Pro Gly Phe  Met Pro Ala Trp Asp  Ile Val Phe
    1160                 1165                 1170
```

Glu Lys Asn Glu Thr Gln Phe Asp Ala Lys Gly Thr Pro Phe Ile
1175 1180 1185

Ala Gly Lys Arg Ile Val Pro Val Ile Glu Asn His Arg Phe Thr
1190 1195 1200

Gly Arg Tyr Arg Asp Leu Tyr Pro Ala Asn Glu Leu Ile Ala Leu
1205 1210 1215

Leu Glu Glu Lys Gly Ile Val Phe Arg Asp Gly Ser Asn Ile Leu
1220 1225 1230

Pro Lys Leu Leu Glu Asn Asp Asp Ser His Ala Ile Asp Thr Met
1235 1240 1245

Val Ala Leu Ile Arg Ser Val Leu Gln Met Arg Asn Ser Asn Ala
1250 1255 1260

Ala Thr Gly Glu Asp Tyr Ile Asn Ser Pro Val Arg Asp Leu Asn
1265 1270 1275

Gly Val Cys Phe Asp Ser Arg Phe Gln Asn Pro Glu Trp Pro Met
1280 1285 1290

Asp Ala Asp Ala Asn Gly Ala Tyr His Ile Ala Leu Lys Gly Gln
1295 1300 1305

Leu Leu Leu Asn His Leu Lys Glu Ser Lys Asp Leu Lys Leu Gln
1310 1315 1320

Asn Gly Ile Ser Asn Gln Asp Trp Leu Ala Tyr Ile Gln Glu Leu
1325 1330 1335

Arg Asn Lys Arg Pro Ala Ala Thr Lys Lys Ala Gly Gln Ala Lys
1340 1345 1350

Lys Lys Lys Glu Phe
1355

<210> SEQ ID NO 73
<211> LENGTH: 1277
<212> TYPE: PRT
<213> ORGANISM: Artificial Sequence
<220> FEATURE:
<223> OTHER INFORMATION: Synthetic amino acid sequence; AP-LbCas12a

<400> SEQUENCE: 73

Met Gly Ser Ser His His His His His His Ser Ser Gly Leu Val Pro
1 5 10 15

Arg Gly Ser His Met Arg Arg Arg Trp Cys Lys Arg Arg Arg Ala Ser
20 25 30

Ser Lys Leu Glu Lys Phe Thr Asn Cys Tyr Ser Leu Ser Lys Thr Leu
35 40 45

Arg Phe Lys Ala Ile Pro Val Gly Lys Thr Gln Glu Asn Ile Asp Asn
50 55 60

Lys Arg Leu Leu Val Glu Asp Glu Lys Arg Ala Glu Asp Tyr Lys Gly
65 70 75 80

Val Lys Lys Leu Leu Asp Arg Tyr Tyr Leu Ser Phe Ile Asn Asp Val
85 90 95

Leu His Ser Ile Lys Leu Lys Asn Leu Asn Asn Tyr Ile Ser Leu Phe
100 105 110

Arg Lys Lys Thr Arg Thr Glu Lys Glu Asn Lys Glu Leu Glu Asn Leu
115 120 125

Glu Ile Asn Leu Arg Lys Glu Ile Ala Lys Ala Phe Lys Gly Asn Glu
130 135 140

Gly Tyr Lys Ser Leu Phe Lys Lys Asp Ile Ile Glu Thr Ile Leu Pro
145 150 155 160

```
Glu Phe Leu Asp Asp Lys Asp Glu Ile Ala Leu Val Asn Ser Phe Asn
                165                 170                 175

Gly Phe Thr Thr Ala Phe Thr Gly Phe Phe Asp Asn Arg Glu Asn Met
            180                 185                 190

Phe Ser Glu Glu Ala Lys Ser Thr Ser Ile Ala Phe Arg Cys Ile Asn
        195                 200                 205

Glu Asn Leu Thr Arg Tyr Ile Ser Asn Met Asp Ile Phe Glu Lys Val
    210                 215                 220

Asp Ala Ile Phe Asp Lys His Glu Val Gln Glu Ile Lys Glu Lys Ile
225                 230                 235                 240

Leu Asn Ser Asp Tyr Asp Val Glu Asp Phe Phe Glu Gly Glu Phe Phe
                245                 250                 255

Asn Phe Val Leu Thr Gln Glu Gly Ile Asp Val Tyr Asn Ala Ile Ile
            260                 265                 270

Gly Gly Phe Val Thr Glu Ser Gly Glu Lys Ile Lys Gly Leu Asn Glu
        275                 280                 285

Tyr Ile Asn Leu Tyr Asn Gln Lys Thr Lys Gln Lys Leu Pro Lys Phe
    290                 295                 300

Lys Pro Leu Tyr Lys Gln Val Leu Ser Asp Arg Glu Ser Leu Ser Phe
305                 310                 315                 320

Tyr Gly Glu Gly Tyr Thr Ser Asp Glu Glu Val Leu Glu Val Phe Arg
                325                 330                 335

Asn Thr Leu Asn Lys Asn Ser Glu Ile Phe Ser Ser Ile Lys Lys Leu
            340                 345                 350

Glu Lys Leu Phe Lys Asn Phe Asp Glu Tyr Ser Ser Ala Gly Ile Phe
        355                 360                 365

Val Lys Asn Gly Pro Ala Ile Ser Thr Ile Ser Lys Asp Ile Phe Gly
    370                 375                 380

Glu Trp Asn Val Ile Arg Asp Lys Trp Asn Ala Glu Tyr Asp Asp Ile
385                 390                 395                 400

His Leu Lys Lys Lys Ala Val Val Thr Glu Lys Tyr Glu Asp Asp Arg
                405                 410                 415

Arg Lys Ser Phe Lys Lys Ile Gly Ser Phe Ser Leu Glu Gln Leu Gln
            420                 425                 430

Glu Tyr Ala Asp Ala Asp Leu Ser Val Val Glu Lys Leu Lys Glu Ile
        435                 440                 445

Ile Ile Gln Lys Val Asp Glu Ile Tyr Lys Val Tyr Gly Ser Ser Glu
    450                 455                 460

Lys Leu Phe Asp Ala Asp Phe Val Leu Glu Lys Ser Leu Lys Lys Asn
465                 470                 475                 480

Asp Ala Val Val Ala Ile Met Lys Asp Leu Leu Asp Ser Val Lys Ser
                485                 490                 495

Phe Glu Asn Tyr Ile Lys Ala Phe Phe Gly Glu Gly Lys Glu Thr Asn
            500                 505                 510

Arg Asp Glu Ser Phe Tyr Gly Asp Phe Val Leu Ala Tyr Asp Ile Leu
        515                 520                 525

Leu Lys Val Asp His Ile Tyr Asp Ala Ile Arg Asn Tyr Val Thr Gln
    530                 535                 540

Lys Pro Tyr Ser Lys Asp Lys Phe Lys Leu Tyr Phe Gln Asn Pro Gln
545                 550                 555                 560

Phe Met Gly Gly Trp Asp Lys Asp Lys Glu Thr Asp Tyr Arg Ala Thr
                565                 570                 575
```

Ile Leu Arg Tyr Gly Ser Lys Tyr Tyr Leu Ala Ile Met Asp Lys Lys
580 585 590

Tyr Ala Lys Cys Leu Gln Lys Ile Asp Lys Asp Asp Val Asn Gly Asn
595 600 605

Tyr Glu Lys Ile Asn Tyr Lys Leu Leu Pro Gly Pro Asn Lys Met Leu
610 615 620

Pro Lys Val Phe Phe Ser Lys Lys Trp Met Ala Tyr Tyr Asn Pro Ser
625 630 635 640

Glu Asp Ile Gln Lys Ile Tyr Lys Asn Gly Thr Phe Lys Lys Gly Asp
645 650 655

Met Phe Asn Leu Asn Asp Cys His Lys Leu Ile Asp Phe Phe Lys Asp
660 665 670

Ser Ile Ser Arg Tyr Pro Lys Trp Ser Asn Ala Tyr Asp Phe Asn Phe
675 680 685

Ser Glu Thr Glu Lys Tyr Lys Asp Ile Ala Gly Phe Tyr Arg Glu Val
690 695 700

Glu Glu Gln Gly Tyr Lys Val Ser Phe Glu Ser Ala Ser Lys Lys Glu
705 710 715 720

Val Asp Lys Leu Val Glu Glu Gly Lys Leu Tyr Met Phe Gln Ile Tyr
725 730 735

Asn Lys Asp Phe Ser Asp Lys Ser His Gly Thr Pro Asn Leu His Thr
740 745 750

Met Tyr Phe Lys Leu Leu Phe Asp Glu Asn Asn His Gly Gln Ile Arg
755 760 765

Leu Ser Gly Gly Ala Glu Leu Phe Met Arg Arg Ala Ser Leu Lys Lys
770 775 780

Glu Glu Leu Val Val His Pro Ala Asn Ser Pro Ile Ala Asn Lys Asn
785 790 795 800

Pro Asp Asn Pro Lys Lys Thr Thr Thr Leu Ser Tyr Asp Val Tyr Lys
805 810 815

Asp Lys Arg Phe Ser Glu Asp Gln Tyr Glu Leu His Ile Pro Ile Ala
820 825 830

Ile Asn Lys Cys Pro Lys Asn Ile Phe Lys Ile Asn Thr Glu Val Arg
835 840 845

Val Leu Leu Lys His Asp Asp Asn Pro Tyr Val Ile Gly Ile Asp Arg
850 855 860

Gly Glu Arg Asn Leu Leu Tyr Ile Val Val Val Asp Gly Lys Gly Asn
865 870 875 880

Ile Val Glu Gln Tyr Ser Leu Asn Glu Ile Ile Asn Asn Phe Asn Gly
885 890 895

Ile Arg Ile Lys Thr Asp Tyr His Ser Leu Leu Asp Lys Lys Glu Lys
900 905 910

Glu Arg Phe Glu Ala Arg Gln Asn Trp Thr Ser Ile Glu Asn Ile Lys
915 920 925

Glu Leu Lys Ala Gly Tyr Ile Ser Gln Val Val His Lys Ile Cys Glu
930 935 940

Leu Val Glu Lys Tyr Asp Ala Val Ile Ala Leu Glu Asp Leu Asn Ser
945 950 955 960

Gly Phe Lys Asn Ser Arg Val Lys Val Glu Lys Gln Val Tyr Gln Lys
965 970 975

Phe Glu Lys Met Leu Ile Asp Lys Leu Asn Tyr Met Val Asp Lys Lys
980 985 990

Ser Asn Pro Cys Ala Thr Gly Gly Ala Leu Lys Gly Tyr Gln Ile Thr 995 1000 1005

Asn Lys Phe Glu Ser Phe Lys Ser Met Ser Thr Gln Asn Gly Phe
1010 1015 1020

Ile Phe Tyr Ile Pro Ala Trp Leu Thr Ser Lys Ile Asp Pro Ser
1025 1030 1035

Thr Gly Phe Val Asn Leu Leu Lys Thr Lys Tyr Thr Ser Ile Ala
1040 1045 1050

Asp Ser Lys Lys Phe Ile Ser Ser Phe Asp Arg Ile Met Tyr Val
1055 1060 1065

Pro Glu Glu Asp Leu Phe Glu Phe Ala Leu Asp Tyr Lys Asn Phe
1070 1075 1080

Ser Arg Thr Asp Ala Asp Tyr Ile Lys Lys Trp Lys Leu Tyr Ser
1085 1090 1095

Tyr Gly Asn Arg Ile Arg Ile Phe Arg Asn Pro Lys Lys Asn Asn
1100 1105 1110

Val Phe Asp Trp Glu Glu Val Cys Leu Thr Ser Ala Tyr Lys Glu
1115 1120 1125

Leu Phe Asn Lys Tyr Gly Ile Asn Tyr Gln Gln Gly Asp Ile Arg
1130 1135 1140

Ala Leu Leu Cys Glu Gln Ser Asp Lys Ala Phe Tyr Ser Ser Phe
1145 1150 1155

Met Ala Leu Met Ser Leu Met Leu Gln Met Arg Asn Ser Ile Thr
1160 1165 1170

Gly Arg Thr Asp Val Asp Phe Leu Ile Ser Pro Val Lys Asn Ser
1175 1180 1185

Asp Gly Ile Phe Tyr Asp Ser Arg Asn Tyr Glu Ala Gln Glu Asn
1190 1195 1200

Ala Ile Leu Pro Lys Asn Ala Asp Ala Asn Gly Ala Tyr Asn Ile
1205 1210 1215

Ala Arg Lys Val Leu Trp Ala Ile Gly Gln Phe Lys Lys Ala Glu
1220 1225 1230

Asp Glu Lys Leu Asp Lys Val Lys Ile Ala Ile Ser Asn Lys Glu
1235 1240 1245

Trp Leu Glu Tyr Ala Gln Thr Ser Val Lys His Lys Arg Pro Ala
1250 1255 1260

Ala Thr Lys Lys Ala Gly Gln Ala Lys Lys Lys Lys Glu Phe
1265 1270 1275

<210> SEQ ID NO 74
<211> LENGTH: 1292
<212> TYPE: PRT
<213> ORGANISM: Artificial Sequence
<220> FEATURE:
<223> OTHER INFORMATION: Synthetic amino acid sequence; dNP2-LbCas12a

<400> SEQUENCE: 74

Met Gly Ser Ser His His His His His His Ser Ser Gly Leu Val Pro
1 5 10 15

Arg Gly Ser His Met Lys Ile Lys Lys Val Lys Lys Lys Gly Arg Lys
20 25 30

Gly Ser Lys Ile Lys Lys Val Lys Lys Lys Gly Arg Lys Ala Ser Ser
35 40 45

Lys Leu Glu Lys Phe Thr Asn Cys Tyr Ser Leu Ser Lys Thr Leu Arg
50 55 60

Phe Lys Ala Ile Pro Val Gly Lys Thr Gln Glu Asn Ile Asp Asn Lys

```
65                  70                  75                  80

Arg Leu Leu Val Glu Asp Glu Lys Arg Ala Glu Asp Tyr Lys Gly Val
                85                  90                  95

Lys Lys Leu Leu Asp Arg Tyr Tyr Leu Ser Phe Ile Asn Asp Val Leu
            100                 105                 110

His Ser Ile Lys Leu Lys Asn Leu Asn Asn Tyr Ile Ser Leu Phe Arg
        115                 120                 125

Lys Lys Thr Arg Thr Glu Lys Glu Asn Lys Glu Leu Glu Asn Leu Glu
    130                 135                 140

Ile Asn Leu Arg Lys Glu Ile Ala Lys Ala Phe Lys Gly Asn Glu Gly
145                 150                 155                 160

Tyr Lys Ser Leu Phe Lys Lys Asp Ile Ile Glu Thr Ile Leu Pro Glu
                165                 170                 175

Phe Leu Asp Asp Lys Asp Glu Ile Ala Leu Val Asn Ser Phe Asn Gly
            180                 185                 190

Phe Thr Thr Ala Phe Thr Gly Phe Phe Asp Asn Arg Glu Asn Met Phe
        195                 200                 205

Ser Glu Glu Ala Lys Ser Thr Ser Ile Ala Phe Arg Cys Ile Asn Glu
    210                 215                 220

Asn Leu Thr Arg Tyr Ile Ser Asn Met Asp Ile Phe Glu Lys Val Asp
225                 230                 235                 240

Ala Ile Phe Asp Lys His Glu Val Gln Glu Ile Lys Glu Lys Ile Leu
                245                 250                 255

Asn Ser Asp Tyr Asp Val Glu Asp Phe Phe Glu Gly Glu Phe Phe Asn
            260                 265                 270

Phe Val Leu Thr Gln Glu Gly Ile Asp Val Tyr Asn Ala Ile Ile Gly
        275                 280                 285

Gly Phe Val Thr Glu Ser Gly Glu Lys Ile Lys Gly Leu Asn Glu Tyr
    290                 295                 300

Ile Asn Leu Tyr Asn Gln Lys Thr Lys Gln Lys Leu Pro Lys Phe Lys
305                 310                 315                 320

Pro Leu Tyr Lys Gln Val Leu Ser Asp Arg Glu Ser Leu Ser Phe Tyr
                325                 330                 335

Gly Glu Gly Tyr Thr Ser Asp Glu Glu Val Leu Glu Val Phe Arg Asn
            340                 345                 350

Thr Leu Asn Lys Asn Ser Glu Ile Phe Ser Ser Ile Lys Lys Leu Glu
        355                 360                 365

Lys Leu Phe Lys Asn Phe Asp Glu Tyr Ser Ser Ala Gly Ile Phe Val
    370                 375                 380

Lys Asn Gly Pro Ala Ile Ser Thr Ile Ser Lys Asp Ile Phe Gly Glu
385                 390                 395                 400

Trp Asn Val Ile Arg Asp Lys Trp Asn Ala Glu Tyr Asp Asp Ile His
                405                 410                 415

Leu Lys Lys Lys Ala Val Val Thr Glu Lys Tyr Glu Asp Asp Arg Arg
            420                 425                 430

Lys Ser Phe Lys Lys Ile Gly Ser Phe Ser Leu Glu Gln Leu Gln Glu
        435                 440                 445

Tyr Ala Asp Ala Asp Leu Ser Val Val Glu Lys Leu Lys Glu Ile Ile
    450                 455                 460

Ile Gln Lys Val Asp Glu Ile Tyr Lys Val Tyr Gly Ser Ser Glu Lys
465                 470                 475                 480

Leu Phe Asp Ala Asp Phe Val Leu Glu Lys Ser Leu Lys Lys Asn Asp
                485                 490                 495
```

```
Ala Val Val Ala Ile Met Lys Asp Leu Leu Asp Ser Val Lys Ser Phe
            500                 505                 510

Glu Asn Tyr Ile Lys Ala Phe Phe Gly Glu Gly Lys Glu Thr Asn Arg
        515                 520                 525

Asp Glu Ser Phe Tyr Gly Asp Phe Val Leu Ala Tyr Asp Ile Leu Leu
    530                 535                 540

Lys Val Asp His Ile Tyr Asp Ala Ile Arg Asn Tyr Val Thr Gln Lys
545                 550                 555                 560

Pro Tyr Ser Lys Asp Lys Phe Lys Leu Tyr Phe Gln Asn Pro Gln Phe
                565                 570                 575

Met Gly Gly Trp Asp Lys Asp Lys Glu Thr Asp Tyr Arg Ala Thr Ile
            580                 585                 590

Leu Arg Tyr Gly Ser Lys Tyr Tyr Leu Ala Ile Met Asp Lys Lys Tyr
        595                 600                 605

Ala Lys Cys Leu Gln Lys Ile Asp Lys Asp Asp Val Asn Gly Asn Tyr
    610                 615                 620

Glu Lys Ile Asn Tyr Lys Leu Leu Pro Gly Pro Asn Lys Met Leu Pro
625                 630                 635                 640

Lys Val Phe Phe Ser Lys Lys Trp Met Ala Tyr Tyr Asn Pro Ser Glu
                645                 650                 655

Asp Ile Gln Lys Ile Tyr Lys Asn Gly Thr Phe Lys Lys Gly Asp Met
            660                 665                 670

Phe Asn Leu Asn Asp Cys His Lys Leu Ile Asp Phe Phe Lys Asp Ser
        675                 680                 685

Ile Ser Arg Tyr Pro Lys Trp Ser Asn Ala Tyr Asp Phe Asn Phe Ser
    690                 695                 700

Glu Thr Glu Lys Tyr Lys Asp Ile Ala Gly Phe Tyr Arg Glu Val Glu
705                 710                 715                 720

Glu Gln Gly Tyr Lys Val Ser Phe Glu Ser Ala Ser Lys Lys Glu Val
                725                 730                 735

Asp Lys Leu Val Glu Glu Gly Lys Leu Tyr Met Phe Gln Ile Tyr Asn
            740                 745                 750

Lys Asp Phe Ser Asp Lys Ser His Gly Thr Pro Asn Leu His Thr Met
        755                 760                 765

Tyr Phe Lys Leu Leu Phe Asp Glu Asn Asn His Gly Gln Ile Arg Leu
    770                 775                 780

Ser Gly Gly Ala Glu Leu Phe Met Arg Arg Ala Ser Leu Lys Lys Glu
785                 790                 795                 800

Glu Leu Val Val His Pro Ala Asn Ser Pro Ile Ala Asn Lys Asn Pro
                805                 810                 815

Asp Asn Pro Lys Lys Thr Thr Thr Leu Ser Tyr Asp Val Tyr Lys Asp
            820                 825                 830

Lys Arg Phe Ser Glu Asp Gln Tyr Glu Leu His Ile Pro Ile Ala Ile
        835                 840                 845

Asn Lys Cys Pro Lys Asn Ile Phe Lys Ile Asn Thr Glu Val Arg Val
    850                 855                 860

Leu Leu Lys His Asp Asp Asn Pro Tyr Val Ile Gly Ile Asp Arg Gly
865                 870                 875                 880

Glu Arg Asn Leu Leu Tyr Ile Val Val Val Asp Gly Lys Gly Asn Ile
                885                 890                 895

Val Glu Gln Tyr Ser Leu Asn Glu Ile Ile Asn Asn Phe Asn Gly Ile
            900                 905                 910
```

```
Arg Ile Lys Thr Asp Tyr His Ser Leu Leu Asp Lys Lys Glu Lys Glu
        915                 920                 925

Arg Phe Glu Ala Arg Gln Asn Trp Thr Ser Ile Glu Asn Ile Lys Glu
    930                 935                 940

Leu Lys Ala Gly Tyr Ile Ser Gln Val Val His Lys Ile Cys Glu Leu
945                 950                 955                 960

Val Glu Lys Tyr Asp Ala Val Ile Ala Leu Glu Asp Leu Asn Ser Gly
                965                 970                 975

Phe Lys Asn Ser Arg Val Lys Val Glu Lys Gln Val Tyr Gln Lys Phe
            980                 985                 990

Glu Lys Met Leu Ile Asp Lys Leu  Asn Tyr Met Val Asp  Lys Lys Ser
        995                 1000                1005

Asn Pro  Cys Ala Thr Gly Gly  Ala Leu Lys Gly Tyr  Gln Ile Thr
    1010                 1015                 1020

Asn Lys  Phe Glu Ser Phe Lys  Ser Met Ser Thr Gln  Asn Gly Phe
    1025                 1030                 1035

Ile Phe  Tyr Ile Pro Ala Trp  Leu Thr Ser Lys Ile  Asp Pro Ser
    1040                 1045                 1050

Thr Gly  Phe Val Asn Leu Leu  Lys Thr Lys Tyr Thr  Ser Ile Ala
    1055                 1060                 1065

Asp Ser  Lys Lys Phe Ile Ser  Ser Phe Asp Arg Ile  Met Tyr Val
    1070                 1075                 1080

Pro Glu  Glu Asp Leu Phe Glu  Phe Ala Leu Asp Tyr  Lys Asn Phe
    1085                 1090                 1095

Ser Arg  Thr Asp Ala Asp Tyr  Ile Lys Lys Trp Lys  Leu Tyr Ser
    1100                 1105                 1110

Tyr Gly  Asn Arg Ile Arg Ile  Phe Arg Asn Pro Lys  Lys Asn Asn
    1115                 1120                 1125

Val Phe  Asp Trp Glu Glu Val  Cys Leu Thr Ser Ala  Tyr Lys Glu
    1130                 1135                 1140

Leu Phe  Asn Lys Tyr Gly Ile  Asn Tyr Gln Gln Gly  Asp Ile Arg
    1145                 1150                 1155

Ala Leu  Leu Cys Glu Gln Ser  Asp Lys Ala Phe Tyr  Ser Ser Phe
    1160                 1165                 1170

Met Ala  Leu Met Ser Leu Met  Leu Gln Met Arg Asn  Ser Ile Thr
    1175                 1180                 1185

Gly Arg  Thr Asp Val Asp Phe  Leu Ile Ser Pro Val  Lys Asn Ser
    1190                 1195                 1200

Asp Gly  Ile Phe Tyr Asp Ser  Arg Asn Tyr Glu Ala  Gln Glu Asn
    1205                 1210                 1215

Ala Ile  Leu Pro Lys Asn Ala  Asp Ala Asn Gly Ala  Tyr Asn Ile
    1220                 1225                 1230

Ala Arg  Lys Val Leu Trp Ala  Ile Gly Gln Phe Lys  Lys Ala Glu
    1235                 1240                 1245

Asp Glu  Lys Leu Asp Lys Val  Lys Ile Ala Ile Ser  Asn Lys Glu
    1250                 1255                 1260

Trp Leu  Glu Tyr Ala Gln Thr  Ser Val Lys His Lys  Arg Pro Ala
    1265                 1270                 1275

Ala Thr  Lys Lys Ala Gly Gln  Ala Lys Lys Lys Lys  Glu Phe
    1280                 1285                 1290
```

<210> SEQ ID NO 75
<211> LENGTH: 1277
<212> TYPE: PRT

<213> ORGANISM: Artificial Sequence
<220> FEATURE:
<223> OTHER INFORMATION: Synthetic amino acid sequence; R9-LbCas12a

<400> SEQUENCE: 75

Met Gly Ser Ser His His His His His His Ser Ser Gly Leu Val Pro
1 5 10 15

Arg Gly Ser His Met Arg Arg Arg Arg Arg Arg Arg Arg Arg Ala Ser
20 25 30

Ser Lys Leu Glu Lys Phe Thr Asn Cys Tyr Ser Leu Ser Lys Thr Leu
35 40 45

Arg Phe Lys Ala Ile Pro Val Gly Lys Thr Gln Glu Asn Ile Asp Asn
50 55 60

Lys Arg Leu Leu Val Glu Asp Glu Lys Arg Ala Glu Asp Tyr Lys Gly
65 70 75 80

Val Lys Lys Leu Leu Asp Arg Tyr Tyr Leu Ser Phe Ile Asn Asp Val
85 90 95

Leu His Ser Ile Lys Leu Lys Asn Leu Asn Asn Tyr Ile Ser Leu Phe
100 105 110

Arg Lys Lys Thr Arg Thr Glu Lys Glu Asn Lys Glu Leu Glu Asn Leu
115 120 125

Glu Ile Asn Leu Arg Lys Glu Ile Ala Lys Ala Phe Lys Gly Asn Glu
130 135 140

Gly Tyr Lys Ser Leu Phe Lys Lys Asp Ile Ile Glu Thr Ile Leu Pro
145 150 155 160

Glu Phe Leu Asp Asp Lys Asp Glu Ile Ala Leu Val Asn Ser Phe Asn
165 170 175

Gly Phe Thr Thr Ala Phe Thr Gly Phe Phe Asp Asn Arg Glu Asn Met
180 185 190

Phe Ser Glu Glu Ala Lys Ser Thr Ser Ile Ala Phe Arg Cys Ile Asn
195 200 205

Glu Asn Leu Thr Arg Tyr Ile Ser Asn Met Asp Ile Phe Glu Lys Val
210 215 220

Asp Ala Ile Phe Asp Lys His Glu Val Gln Glu Ile Lys Glu Lys Ile
225 230 235 240

Leu Asn Ser Asp Tyr Asp Val Glu Asp Phe Phe Glu Gly Glu Phe Phe
245 250 255

Asn Phe Val Leu Thr Gln Glu Gly Ile Asp Val Tyr Asn Ala Ile Ile
260 265 270

Gly Gly Phe Val Thr Glu Ser Gly Glu Lys Ile Lys Gly Leu Asn Glu
275 280 285

Tyr Ile Asn Leu Tyr Asn Gln Lys Thr Lys Gln Lys Leu Pro Lys Phe
290 295 300

Lys Pro Leu Tyr Lys Gln Val Leu Ser Asp Arg Glu Ser Leu Ser Phe
305 310 315 320

Tyr Gly Glu Gly Tyr Thr Ser Asp Glu Glu Val Leu Glu Val Phe Arg
325 330 335

Asn Thr Leu Asn Lys Asn Ser Glu Ile Phe Ser Ser Ile Lys Lys Leu
340 345 350

Glu Lys Leu Phe Lys Asn Phe Asp Glu Tyr Ser Ser Ala Gly Ile Phe
355 360 365

Val Lys Asn Gly Pro Ala Ile Ser Thr Ile Ser Lys Asp Ile Phe Gly
370 375 380

Glu Trp Asn Val Ile Arg Asp Lys Trp Asn Ala Glu Tyr Asp Asp Ile

```
385                 390                 395                 400

His Leu Lys Lys Lys Ala Val Val Thr Glu Lys Tyr Glu Asp Asp Arg
                405                 410                 415

Arg Lys Ser Phe Lys Lys Ile Gly Ser Phe Ser Leu Glu Gln Leu Gln
            420                 425                 430

Glu Tyr Ala Asp Ala Asp Leu Ser Val Val Glu Lys Leu Lys Glu Ile
        435                 440                 445

Ile Ile Gln Lys Val Asp Glu Ile Tyr Lys Val Tyr Gly Ser Ser Glu
    450                 455                 460

Lys Leu Phe Asp Ala Asp Phe Val Leu Glu Lys Ser Leu Lys Lys Asn
465                 470                 475                 480

Asp Ala Val Val Ala Ile Met Lys Asp Leu Leu Asp Ser Val Lys Ser
                485                 490                 495

Phe Glu Asn Tyr Ile Lys Ala Phe Phe Gly Glu Gly Lys Glu Thr Asn
            500                 505                 510

Arg Asp Glu Ser Phe Tyr Gly Asp Phe Val Leu Ala Tyr Asp Ile Leu
        515                 520                 525

Leu Lys Val Asp His Ile Tyr Asp Ala Ile Arg Asn Tyr Val Thr Gln
    530                 535                 540

Lys Pro Tyr Ser Lys Asp Lys Phe Lys Leu Tyr Phe Gln Asn Pro Gln
545                 550                 555                 560

Phe Met Gly Gly Trp Asp Lys Asp Lys Glu Thr Asp Tyr Arg Ala Thr
                565                 570                 575

Ile Leu Arg Tyr Gly Ser Lys Tyr Tyr Leu Ala Ile Met Asp Lys Lys
            580                 585                 590

Tyr Ala Lys Cys Leu Gln Lys Ile Asp Lys Asp Asp Val Asn Gly Asn
        595                 600                 605

Tyr Glu Lys Ile Asn Tyr Lys Leu Leu Pro Gly Pro Asn Lys Met Leu
    610                 615                 620

Pro Lys Val Phe Phe Ser Lys Lys Trp Met Ala Tyr Tyr Asn Pro Ser
625                 630                 635                 640

Glu Asp Ile Gln Lys Ile Tyr Lys Asn Gly Thr Phe Lys Lys Gly Asp
                645                 650                 655

Met Phe Asn Leu Asn Asp Cys His Lys Leu Ile Asp Phe Phe Lys Asp
            660                 665                 670

Ser Ile Ser Arg Tyr Pro Lys Trp Ser Asn Ala Tyr Asp Phe Asn Phe
        675                 680                 685

Ser Glu Thr Glu Lys Tyr Lys Asp Ile Ala Gly Phe Tyr Arg Glu Val
    690                 695                 700

Glu Glu Gln Gly Tyr Lys Val Ser Phe Glu Ser Ala Ser Lys Lys Glu
705                 710                 715                 720

Val Asp Lys Leu Val Glu Glu Gly Lys Leu Tyr Met Phe Gln Ile Tyr
                725                 730                 735

Asn Lys Asp Phe Ser Asp Lys Ser His Gly Thr Pro Asn Leu His Thr
            740                 745                 750

Met Tyr Phe Lys Leu Leu Phe Asp Glu Asn Asn His Gly Gln Ile Arg
        755                 760                 765

Leu Ser Gly Gly Ala Glu Leu Phe Met Arg Arg Ala Ser Leu Lys Lys
    770                 775                 780

Glu Glu Leu Val Val His Pro Ala Asn Ser Pro Ile Ala Asn Lys Asn
785                 790                 795                 800

Pro Asp Asn Pro Lys Lys Thr Thr Thr Leu Ser Tyr Asp Val Tyr Lys
                805                 810                 815
```

```
Asp Lys Arg Phe Ser Glu Asp Gln Tyr Glu Leu His Ile Pro Ile Ala
            820                 825                 830

Ile Asn Lys Cys Pro Lys Asn Ile Phe Lys Ile Asn Thr Glu Val Arg
        835                 840                 845

Val Leu Leu Lys His Asp Asp Asn Pro Tyr Val Ile Gly Ile Asp Arg
    850                 855                 860

Gly Glu Arg Asn Leu Leu Tyr Ile Val Val Val Asp Gly Lys Gly Asn
865                 870                 875                 880

Ile Val Glu Gln Tyr Ser Leu Asn Glu Ile Ile Asn Asn Phe Asn Gly
                885                 890                 895

Ile Arg Ile Lys Thr Asp Tyr His Ser Leu Leu Asp Lys Lys Glu Lys
            900                 905                 910

Glu Arg Phe Glu Ala Arg Gln Asn Trp Thr Ser Ile Glu Asn Ile Lys
        915                 920                 925

Glu Leu Lys Ala Gly Tyr Ile Ser Gln Val Val His Lys Ile Cys Glu
    930                 935                 940

Leu Val Glu Lys Tyr Asp Ala Val Ile Ala Leu Glu Asp Leu Asn Ser
945                 950                 955                 960

Gly Phe Lys Asn Ser Arg Val Lys Val Glu Lys Gln Val Tyr Gln Lys
                965                 970                 975

Phe Glu Lys Met Leu Ile Asp Lys Leu Asn Tyr Met Val Asp Lys Lys
            980                 985                 990

Ser Asn Pro Cys Ala Thr Gly Gly  Ala Leu Lys Gly Tyr  Gln Ile Thr
        995                 1000                1005

Asn Lys  Phe Glu Ser Phe Lys  Ser Met Ser Thr Gln  Asn Gly Phe
    1010                1015                1020

Ile Phe  Tyr Ile Pro Ala Trp  Leu Thr Ser Lys Ile  Asp Pro Ser
    1025                1030                1035

Thr Gly  Phe Val Asn Leu Leu  Lys Thr Lys Tyr Thr  Ser Ile Ala
    1040                1045                1050

Asp Ser  Lys Lys Phe Ile Ser  Ser Phe Asp Arg Ile  Met Tyr Val
    1055                1060                1065

Pro Glu  Glu Asp Leu Phe Glu  Phe Ala Leu Asp Tyr  Lys Asn Phe
    1070                1075                1080

Ser Arg  Thr Asp Ala Asp Tyr  Ile Lys Lys Trp Lys  Leu Tyr Ser
    1085                1090                1095

Tyr Gly  Asn Arg Ile Arg Ile  Phe Arg Asn Pro Lys  Lys Asn Asn
    1100                1105                1110

Val Phe  Asp Trp Glu Glu Val  Cys Leu Thr Ser Ala  Tyr Lys Glu
    1115                1120                1125

Leu Phe  Asn Lys Tyr Gly Ile  Asn Tyr Gln Gln Gly  Asp Ile Arg
    1130                1135                1140

Ala Leu  Leu Cys Glu Gln Ser  Asp Lys Ala Phe Tyr  Ser Ser Phe
    1145                1150                1155

Met Ala  Leu Met Ser Leu Met  Leu Gln Met Arg Asn  Ser Ile Thr
    1160                1165                1170

Gly Arg  Thr Asp Val Asp Phe  Leu Ile Ser Pro Val  Lys Asn Ser
    1175                1180                1185

Asp Gly  Ile Phe Tyr Asp Ser  Arg Asn Tyr Glu Ala  Gln Glu Asn
    1190                1195                1200

Ala Ile  Leu Pro Lys Asn Ala  Asp Ala Asn Gly Ala  Tyr Asn Ile
    1205                1210                1215
```

```
Ala Arg  Lys Val Leu Trp Ala  Ile Gly Gln Phe Lys  Lys Ala Glu
    1220                 1225                 1230

Asp Glu  Lys Leu Asp Lys Val  Lys Ile Ala Ile Ser  Asn Lys Glu
    1235                 1240                 1245

Trp Leu  Glu Tyr Ala Gln Thr  Ser Val Lys His Lys  Arg Pro Ala
    1250                 1255                 1260

Ala Thr  Lys Lys Ala Gly Gln  Ala Lys Lys Lys Lys  Glu Phe
    1265                 1270                 1275


<210> SEQ ID NO 76
<211> LENGTH: 1279
<212> TYPE: PRT
<213> ORGANISM: Artificial Sequence
<220> FEATURE:
<223> OTHER INFORMATION: Synthetic amino acid sequence; TAT-LbCas12a

<400> SEQUENCE: 76

Met Gly Ser Ser His His His His His His Ser Ser Gly Leu Val Pro
1               5                   10                  15

Arg Gly Ser His Met Tyr Gly Arg Lys Lys Arg Arg Gln Arg Arg Arg
            20                  25                  30

Ala Ser Ser Lys Leu Glu Lys Phe Thr Asn Cys Tyr Ser Leu Ser Lys
        35                  40                  45

Thr Leu Arg Phe Lys Ala Ile Pro Val Gly Lys Thr Gln Glu Asn Ile
    50                  55                  60

Asp Asn Lys Arg Leu Leu Val Glu Asp Glu Lys Arg Ala Glu Asp Tyr
65                  70                  75                  80

Lys Gly Val Lys Lys Leu Leu Asp Arg Tyr Tyr Leu Ser Phe Ile Asn
                85                  90                  95

Asp Val Leu His Ser Ile Lys Leu Lys Asn Leu Asn Asn Tyr Ile Ser
            100                 105                 110

Leu Phe Arg Lys Lys Thr Arg Thr Glu Lys Glu Asn Lys Glu Leu Glu
        115                 120                 125

Asn Leu Glu Ile Asn Leu Arg Lys Glu Ile Ala Lys Ala Phe Lys Gly
    130                 135                 140

Asn Glu Gly Tyr Lys Ser Leu Phe Lys Lys Asp Ile Ile Glu Thr Ile
145                 150                 155                 160

Leu Pro Glu Phe Leu Asp Asp Lys Asp Glu Ile Ala Leu Val Asn Ser
                165                 170                 175

Phe Asn Gly Phe Thr Thr Ala Phe Thr Gly Phe Phe Asp Asn Arg Glu
            180                 185                 190

Asn Met Phe Ser Glu Glu Ala Lys Ser Thr Ser Ile Ala Phe Arg Cys
        195                 200                 205

Ile Asn Glu Asn Leu Thr Arg Tyr Ile Ser Asn Met Asp Ile Phe Glu
    210                 215                 220

Lys Val Asp Ala Ile Phe Asp Lys His Glu Val Gln Glu Ile Lys Glu
225                 230                 235                 240

Lys Ile Leu Asn Ser Asp Tyr Asp Val Glu Asp Phe Phe Glu Gly Glu
                245                 250                 255

Phe Phe Asn Phe Val Leu Thr Gln Glu Gly Ile Asp Val Tyr Asn Ala
            260                 265                 270

Ile Ile Gly Gly Phe Val Thr Glu Ser Gly Glu Lys Ile Lys Gly Leu
        275                 280                 285

Asn Glu Tyr Ile Asn Leu Tyr Asn Gln Lys Thr Lys Gln Lys Leu Pro
    290                 295                 300
```

```
Lys Phe Lys Pro Leu Tyr Lys Gln Val Leu Ser Asp Arg Glu Ser Leu
305                 310                 315                 320

Ser Phe Tyr Gly Glu Gly Tyr Thr Ser Asp Glu Glu Val Leu Glu Val
                325                 330                 335

Phe Arg Asn Thr Leu Asn Lys Asn Ser Glu Ile Phe Ser Ser Ile Lys
            340                 345                 350

Lys Leu Glu Lys Leu Phe Lys Asn Phe Asp Glu Tyr Ser Ser Ala Gly
        355                 360                 365

Ile Phe Val Lys Asn Gly Pro Ala Ile Ser Thr Ile Ser Lys Asp Ile
    370                 375                 380

Phe Gly Glu Trp Asn Val Ile Arg Asp Lys Trp Asn Ala Glu Tyr Asp
385                 390                 395                 400

Asp Ile His Leu Lys Lys Lys Ala Val Val Thr Glu Lys Tyr Glu Asp
                405                 410                 415

Asp Arg Arg Lys Ser Phe Lys Lys Ile Gly Ser Phe Ser Leu Glu Gln
            420                 425                 430

Leu Gln Glu Tyr Ala Asp Ala Asp Leu Ser Val Val Glu Lys Leu Lys
        435                 440                 445

Glu Ile Ile Ile Gln Lys Val Asp Glu Ile Tyr Lys Val Tyr Gly Ser
    450                 455                 460

Ser Glu Lys Leu Phe Asp Ala Asp Phe Val Leu Glu Lys Ser Leu Lys
465                 470                 475                 480

Lys Asn Asp Ala Val Val Ala Ile Met Lys Asp Leu Leu Asp Ser Val
                485                 490                 495

Lys Ser Phe Glu Asn Tyr Ile Lys Ala Phe Phe Gly Glu Gly Lys Glu
            500                 505                 510

Thr Asn Arg Asp Glu Ser Phe Tyr Gly Asp Phe Val Leu Ala Tyr Asp
        515                 520                 525

Ile Leu Leu Lys Val Asp His Ile Tyr Asp Ala Ile Arg Asn Tyr Val
    530                 535                 540

Thr Gln Lys Pro Tyr Ser Lys Asp Lys Phe Lys Leu Tyr Phe Gln Asn
545                 550                 555                 560

Pro Gln Phe Met Gly Gly Trp Asp Lys Asp Lys Glu Thr Asp Tyr Arg
                565                 570                 575

Ala Thr Ile Leu Arg Tyr Gly Ser Lys Tyr Tyr Leu Ala Ile Met Asp
            580                 585                 590

Lys Lys Tyr Ala Lys Cys Leu Gln Lys Ile Asp Lys Asp Asp Val Asn
        595                 600                 605

Gly Asn Tyr Glu Lys Ile Asn Tyr Lys Leu Leu Pro Gly Pro Asn Lys
    610                 615                 620

Met Leu Pro Lys Val Phe Phe Ser Lys Lys Trp Met Ala Tyr Tyr Asn
625                 630                 635                 640

Pro Ser Glu Asp Ile Gln Lys Ile Tyr Lys Asn Gly Thr Phe Lys Lys
                645                 650                 655

Gly Asp Met Phe Asn Leu Asn Asp Cys His Lys Leu Ile Asp Phe Phe
            660                 665                 670

Lys Asp Ser Ile Ser Arg Tyr Pro Lys Trp Ser Asn Ala Tyr Asp Phe
        675                 680                 685

Asn Phe Ser Glu Thr Glu Lys Tyr Lys Asp Ile Ala Gly Phe Tyr Arg
    690                 695                 700

Glu Val Glu Glu Gln Gly Tyr Lys Val Ser Phe Glu Ser Ala Ser Lys
705                 710                 715                 720

Lys Glu Val Asp Lys Leu Val Glu Glu Gly Lys Leu Tyr Met Phe Gln
```

```
                725                 730                 735

Ile Tyr Asn Lys Asp Phe Ser Asp Lys Ser His Gly Thr Pro Asn Leu
            740                 745                 750

His Thr Met Tyr Phe Lys Leu Leu Phe Asp Glu Asn Asn His Gly Gln
        755                 760                 765

Ile Arg Leu Ser Gly Gly Ala Glu Leu Phe Met Arg Arg Ala Ser Leu
    770                 775                 780

Lys Lys Glu Glu Leu Val Val His Pro Ala Asn Ser Pro Ile Ala Asn
785                 790                 795                 800

Lys Asn Pro Asp Asn Pro Lys Lys Thr Thr Thr Leu Ser Tyr Asp Val
                805                 810                 815

Tyr Lys Asp Lys Arg Phe Ser Glu Asp Gln Tyr Glu Leu His Ile Pro
            820                 825                 830

Ile Ala Ile Asn Lys Cys Pro Lys Asn Ile Phe Lys Ile Asn Thr Glu
        835                 840                 845

Val Arg Val Leu Leu Lys His Asp Asp Asn Pro Tyr Val Ile Gly Ile
    850                 855                 860

Asp Arg Gly Glu Arg Asn Leu Leu Tyr Ile Val Val Val Asp Gly Lys
865                 870                 875                 880

Gly Asn Ile Val Glu Gln Tyr Ser Leu Asn Glu Ile Ile Asn Asn Phe
                885                 890                 895

Asn Gly Ile Arg Ile Lys Thr Asp Tyr His Ser Leu Leu Asp Lys Lys
            900                 905                 910

Glu Lys Glu Arg Phe Glu Ala Arg Gln Asn Trp Thr Ser Ile Glu Asn
        915                 920                 925

Ile Lys Glu Leu Lys Ala Gly Tyr Ile Ser Gln Val Val His Lys Ile
    930                 935                 940

Cys Glu Leu Val Glu Lys Tyr Asp Ala Val Ile Ala Leu Glu Asp Leu
945                 950                 955                 960

Asn Ser Gly Phe Lys Asn Ser Arg Val Lys Val Glu Lys Gln Val Tyr
                965                 970                 975

Gln Lys Phe Glu Lys Met Leu Ile Asp Lys Leu Asn Tyr Met Val Asp
            980                 985                 990

Lys Lys Ser Asn Pro Cys Ala Thr  Gly Gly Ala Leu Lys  Gly Tyr Gln
        995                 1000                1005

Ile Thr  Asn Lys Phe Glu Ser  Phe Lys Ser Met Ser  Thr Gln Asn
    1010                1015                1020

Gly Phe  Ile Phe Tyr Ile Pro  Ala Trp Leu Thr Ser  Lys Ile Asp
    1025                1030                1035

Pro Ser  Thr Gly Phe Val Asn  Leu Leu Lys Thr Lys  Tyr Thr Ser
    1040                1045                1050

Ile Ala  Asp Ser Lys Lys Phe  Ile Ser Ser Phe Asp  Arg Ile Met
    1055                1060                1065

Tyr Val  Pro Glu Glu Asp Leu  Phe Glu Phe Ala Leu  Asp Tyr Lys
    1070                1075                1080

Asn Phe  Ser Arg Thr Asp Ala  Asp Tyr Ile Lys Lys  Trp Lys Leu
    1085                1090                1095

Tyr Ser  Tyr Gly Asn Arg Ile  Arg Ile Phe Arg Asn  Pro Lys Lys
    1100                1105                1110

Asn Asn  Val Phe Asp Trp Glu  Glu Val Cys Leu Thr  Ser Ala Tyr
    1115                1120                1125

Lys Glu  Leu Phe Asn Lys Tyr  Gly Ile Asn Tyr Gln  Gln Gly Asp
    1130                1135                1140
```

```
Ile Arg  Ala Leu Leu Cys Glu  Gln Ser Asp Lys Ala  Phe Tyr Ser
    1145                 1150                 1155

Ser Phe  Met Ala Leu Met Ser  Leu Met Leu Gln Met  Arg Asn Ser
    1160                 1165                 1170

Ile Thr  Gly Arg Thr Asp Val  Asp Phe Leu Ile Ser  Pro Val Lys
    1175                 1180                 1185

Asn Ser  Asp Gly Ile Phe Tyr  Asp Ser Arg Asn Tyr  Glu Ala Gln
    1190                 1195                 1200

Glu Asn  Ala Ile Leu Pro Lys  Asn Ala Asp Ala Asn  Gly Ala Tyr
    1205                 1210                 1215

Asn Ile  Ala Arg Lys Val Leu  Trp Ala Ile Gly Gln  Phe Lys Lys
    1220                 1225                 1230

Ala Glu  Asp Glu Lys Leu Asp  Lys Val Lys Ile Ala  Ile Ser Asn
    1235                 1240                 1245

Lys Glu  Trp Leu Glu Tyr Ala  Gln Thr Ser Val Lys  His Lys Arg
    1250                 1255                 1260

Pro Ala  Ala Thr Lys Lys Ala  Gly Gln Ala Lys Lys  Lys Lys Glu
    1265                 1270                 1275

Phe


<210> SEQ ID NO 77
<211> LENGTH: 4068
<212> TYPE: DNA
<213> ORGANISM: Artificial Sequence
<220> FEATURE:
<223> OTHER INFORMATION: Synthetic gene sequence; AP-AsCas12a

<400> SEQUENCE: 77

atgggcagca gccatcatca tcatcatcac agcagcggcc tggtgccgcg cggcagccat     60

atgcgccggc gctggtgcaa acgccgccgg gctagcacac agttcgaggg ctttaccaac    120

ctgtatcagg tgagcaagac actgcggttt gagctgatcc cacagggcaa gaccctgaag    180

cacatccagg agcagggctt catcgaggag gacaaggccc gcaatgatca ctacaaggag    240

ctgaagccca tcatcgatcg gatctacaag acctatgccg accagtgcct gcagctggtg    300

cagctggatt gggagaacct gagcgccgcc atcgactcct atagaaagga gaaaaccgag    360

gagacaagga acgccctgat cgaggagcag gccacatatc gcaatgccat ccacgactac    420

ttcatcggcc ggacagacaa cctgaccgat gccatcaata agagacacgc cgagatctac    480

aagggcctgt tcaaggccga gctgtttaat ggcaaggtgc tgaagcagct gggcaccgtg    540

accacaaccg agcacgagaa cgccctgctg cggagcttcg acaagtttac aacctacttc    600

tccggctttt atgagaacag gaagaacgtg ttcagcgccg aggatatcag cacagccatc    660

ccacaccgca tcgtgcagga caacttcccc aagtttaagg agaattgtca catcttcaca    720

cgcctgatca ccgccgtgcc cagcctgcgg gagcactttg agaacgtgaa gaaggccatc    780

ggcatcttcg tgagcacctc catcgaggag gtgttttcct tccctttta taaccagctg     840

ctgacacaga cccagatcga cctgtataac cagctgctgg gaggaatctc tcgggaggca    900

ggcaccgaga agatcaaggg cctgaacgag gtgctgaatc tggccatcca gaagaatgat    960

gagacagccc acatcatcgc ctccctgcca cacagattca tccccctgtt taagcagatc   1020

ctgtccgata ggaacaccct gtctttcatc ctggaggagt ttaagagcga cgaggaagtg   1080

atccagtcct tctgcaagta caagacactg ctgagaaacg agaacgtgct ggagacagcc   1140

gaggccctgt ttaacgagct gaacagcatc gacctgacac acatcttcat cagccacaag   1200
```

aagctggaga caatcagcag cgccctgtgc gaccactggg atacactgag gaatgccctg 1260
tatgagcgga gaatctccga gctgacaggc aagatcacca agtctgccaa ggagaaggtg 1320
cagcgcagcc tgaagcacga ggatatcaac ctgcaggaga tcatctctgc cgcaggcaag 1380
gagctgagcg aggccttcaa gcagaaaacc agcgagatcc tgtcccacgc acacgccgcc 1440
ctggatcagc cactgcctac aaccctgaag aagcaggagg agaaggagat cctgaagtct 1500
cagctggaca gcctgctggg cctgtaccac ctgctggact ggtttgccgt ggatgagtcc 1560
aacgaggtgg accccgagtt ctctgcccgg ctgaccggca tcaagctgga gatggagcct 1620
tctctgagct tctacaacaa ggccagaaat tatgccacca agaagcccta ctccgtggag 1680
aagttcaagc tgaactttca gatgcctaca ctggcctctg gctgggacgt gaataaggag 1740
aagaacaatg gcgccatcct gtttgtgaag aacggcctgt actatctggg catcatgcca 1800
aagcagaagg gcaggtataa ggccctgagc ttcgagccca cagagaaaac cagcgagggc 1860
tttgataaga tgtactatga ctacttccct gatgccgcca agatgatccc aaagtgcagc 1920
acccagctga aggccgtgac agcccacttt cagacccaca caacccccat cctgctgtcc 1980
aacaatttca tcgagcctct ggagatcaca aaggagatct acgacctgaa caatcctgag 2040
aaggagccaa agaagtttca gacagcctac gccaagaaaa ccggcgacca gaagggctac 2100
agagaggccc tgtgcaagtg gatcgacttc acaagggatt ttctgtccaa gtataccaag 2160
acaacctcta tcgatctgtc tagcctgcgg ccatcctctc agtataagga cctgggcgag 2220
tactatgccg agctgaatcc cctgctgtac cacatcagct tccagagaat cgccgagaag 2280
gagatcatgg atgccgtgga gacaggcaag ctgtacctgt tccagatcta taacaaggac 2340
tttgccaagg gccaccacgg caagcctaat ctgcacacac tgtattggac cggcctgttt 2400
tctccagaga acctggccaa gacaagcatc aagctgaatg gccaggccga gctgttctac 2460
cgccctaagt ccaggatgaa gaggatggca caccggctgg gagagaagat gctgaacaag 2520
aagctgaagg atcagaaaac cccaatcccc gacaccctgt accaggagct gtacgactat 2580
gtgaatcaca gactgtccca cgacctgtct gatgaggcca gggccctgct gcccaacgtg 2640
atcaccaagg aggtgtctca cgagatcatc aaggataggc gctttaccag cgacaagttc 2700
tttttccacg tgcctatcac actgaactat caggccgcca attccccatc taagttcaac 2760
cagagggtga atgcctacct gaaggagcac cccgagacac ctatcatcgg catcgatcgg 2820
ggcgagagaa acctgatcta tatcacagtg atcgactcca ccggcaagat cctggagcag 2880
cggagcctga acaccatcca gcagtttgat taccagaaga agctggacaa cagggagaag 2940
gagagggtgg cagcaaggca ggcctggtct gtggtgggca caatcaagga tctgaagcag 3000
ggctatctga gccaggtcat ccacgagatc gtggacctga tgatccacta ccaggccgtg 3060
gtggtgctgg agaacctgaa tttcggcttt aagagcaaga ggaccggcat cgccgagaag 3120
gccgtgtacc agcagttcga gaagatgctg atcgataagc tgaattgcct ggtgctgaag 3180
gactatccag cagagaaagt gggaggcgtg ctgaacccat accagctgac agaccagttc 3240
acctcctttg ccaagatggg cacccagtct ggcttcctgt tttacgtgcc tgccccatat 3300
acatctaaga tcgatcccct gaccggcttc gtggacccct tcgtgtggaa aaccatcaag 3360
aatcacgaga gccgcaagca cttcctggag ggcttcgact ttctgcacta cgacgtgaaa 3420
accggcgact tcatcctgca ctttaagatg aacagaaatc tgtccttcca gaggggcctg 3480
cccggcttta tgcctgcatg ggatatcgtg ttcgagaaga acgagacaca gtttgacgcc 3540
aagggcaccc ctttcatcgc cggcaagaga atcgtgccag tgatcgagaa tcacagattc 3600
accggcagat accgggacct gtatcctgcc aacgagctga tcgccctgct ggaggagaag 3660
ggcatcgtgt tcagggatgg ctccaacatc ctgccaaagc tgctggagaa tgacgattct 3720
cacgccatcg acaccatggt ggccctgatc cgcagcgtgc tgcagatgcg gaactccaat 3780
gccgccacag gcgaggacta tatcaacagc cccgtgcgcg atctgaatgg cgtgtgcttc 3840
gactcccggt ttcagaaccc agagtggccc atggacgccg atgccaatgg cgcctaccac 3900
atcgccctga agggccagct gctgctgaat cacctgaagg agagcaagga tctgaagctg 3960
cagaacggca tctccaatca ggactggctg gcctacatcc aggagctgcg caacaaaagg 4020
ccggcggcca cgaaaaaggc cggccaggca aaaaagaaaa aggaattc 4068

<210> SEQ ID NO 78
<211> LENGTH: 4113
<212> TYPE: DNA
<213> ORGANISM: Artificial Sequence
<220> FEATURE:
<223> OTHER INFORMATION: Synthetic gene sequence; dNP2-AsCas12a

<400> SEQUENCE: 78
atgggcagca gccatcatca tcatcatcac agcagcggcc tggtgccgcg cggcagccat 60
atgaagatca agaaggttaa aaaaaagggt cgcaagggct ctaaaattaa aaaagtcaag 120
aagaaaggaa gaaaagctag cacacagttc gagggcttta ccaacctgta tcaggtgagc 180
aagacactgc ggtttgagct gatcccacag ggcaagaccc tgaagcacat ccaggagcag 240
ggcttcatcg aggaggacaa ggcccgcaat gatcactaca aggagctgaa gcccatcatc 300
gatcggatct acaagaccta tgccgaccag tgcctgcagc tggtgcagct ggattgggag 360
aacctgagcg ccgccatcga ctcctataga aaggagaaaa ccgaggagac aaggaacgcc 420
ctgatcgagg agcaggccac atatcgcaat gccatccacg actacttcat cggccggaca 480
gacaacctga ccgatgccat caataagaga cacgccgaga tctacaaggg cctgttcaag 540
gccgagctgt ttaatggcaa ggtgctgaag cagctgggca ccgtgaccac aaccgagcac 600
gagaacgccc tgctgcggag cttcgacaag tttacaacct acttctccgg cttttatgag 660
aacaggaaga acgtgttcag cgccgaggat atcagcacag ccatcccaca ccgcatcgtg 720
caggacaact tccccaagtt taaggagaat tgtcacatct tcacacgcct gatcaccgcc 780
gtgcccagcc tgcgggagca ctttgagaac gtgaagaagg ccatcggcat cttcgtgagc 840
acctccatcg aggaggtgtt ttccttccct ttttataacc agctgctgac acagacccag 900
atcgacctgt ataaccagct gctgggagga atctctcggg aggcaggcac cgagaagatc 960
aagggcctga acgaggtgct gaatctggcc atccagaaga atgatgagac agcccacatc 1020
atcgcctccc tgccacacag attcatcccc ctgtttaagc agatcctgtc cgataggaac 1080
accctgtctt tcatcctgga ggagtttaag agcgacgagg aagtgatcca gtccttctgc 1140
aagtacaaga cactgctgag aaacgagaac gtgctggaga cagccgaggc cctgtttaac 1200
gagctgaaca gcatcgacct gacacacatc ttcatcagcc acaagaagct ggagacaatc 1260
agcagcgccc tgtgcgacca ctgggataca ctgaggaatg ccctgtatga gcggagaatc 1320
tccgagctga caggcaagat caccaagtct gccaaggaga aggtgcagcg cagcctgaag 1380
cacgaggata tcaacctgca ggagatcatc tctgccgcag gcaaggagct gagcgaggcc 1440
ttcaagcaga aaaccagcga gatcctgtcc cacgcacacg ccgccctgga tcagccactg 1500
cctacaaccc tgaagaagca ggaggagaag gagatcctga agtctcagct ggacagcctg 1560
ctgggcctgt accacctgct ggactggttt gccgtggatg agtccaacga ggtggacccc 1620
gagttctctg cccggctgac cggcatcaag ctggagatgg agccttctct gagcttctac 1680
aacaaggcca gaaattatgc caccaagaag ccctactccg tggagaagtt caagctgaac 1740
tttcagatgc ctacactggc ctctggctgg gacgtgaata aggagaagaa caatggcgcc 1800
atcctgtttg tgaagaacgg cctgtactat ctgggcatca tgccaaagca gaagggcagg 1860
tataaggccc tgagcttcga gcccacagag aaaaccagcg agggctttga taagatgtac 1920
tatgactact tccctgatgc cgccaagatg atcccaaagt gcagcaccca gctgaaggcc 1980
gtgacagccc actttcagac ccacacaacc cccatcctgc tgtccaacaa tttcatcgag 2040
cctctggaga tcacaaagga gatctacgac ctgaacaatc ctgagaagga gccaaagaag 2100
tttcagacag cctacgccaa gaaaaccggc gaccagaagg gctacagaga ggccctgtgc 2160
aagtggatcg acttcacaag ggattttctg tccaagtata ccaagacaac ctctatcgat 2220
ctgtctagcc tgcggccatc ctctcagtat aaggacctgg gcgagtacta tgccgagctg 2280
aatcccctgc tgtaccacat cagcttccag agaatcgccg agaaggagat catggatgcc 2340
gtggagacag gcaagctgta cctgttccag atctataaca aggactttgc caagggccac 2400
cacggcaagc ctaatctgca cacactgtat tggaccggcc tgttttctcc agagaacctg 2460
gccaagacaa gcatcaagct gaatggccag gccgagctgt tctaccgccc taagtccagg 2520
atgaagagga tggcacaccg gctgggagag aagatgctga acaagaagct gaaggatcag 2580
aaaaccccaa tccccgacac cctgtaccag gagctgtacg actatgtgaa tcacagactg 2640
tcccacgacc tgtctgatga ggccagggcc ctgctgccca acgtgatcac caaggaggtg 2700
tctcacgaga tcatcaagga taggcgcttt accagcgaca agttcttttt ccacgtgcct 2760
atcacactga actatcaggc cgccaattcc ccatctaagt tcaaccagag ggtgaatgcc 2820
tacctgaagg agcaccccga gacacctatc atcggcatcg atcggggcga gagaaacctg 2880
atctatatca cagtgatcga ctccaccggc aagatcctgg agcagcggag cctgaacacc 2940
atccagcagt ttgattacca gaagaagctg gacaacaggg agaaggagag ggtggcagca 3000
aggcaggcct ggtctgtggt gggcacaatc aaggatctga agcagggcta tctgagccag 3060
gtcatccacg agatcgtgga cctgatgatc cactaccagg ccgtggtggt gctggagaac 3120
ctgaatttcg gctttaagag caagaggacc ggcatcgccg agaaggccgt gtaccagcag 3180
ttcgagaaga tgctgatcga taagctgaat tgcctggtgc tgaaggacta tccagcagag 3240
aaagtgggag gcgtgctgaa cccataccag ctgacagacc agttcacctc ctttgccaag 3300
atgggcaccc agtctggctt cctgttttac gtgcctgccc catatacatc taagatcgat 3360
cccctgaccg gcttcgtgga ccccttcgtg tggaaaacca tcaagaatca cgagagccgc 3420
aagcacttcc tggagggctt cgactttctg cactacgacg tgaaaaccgg cgacttcatc 3480
ctgcacttta agatgaacag aaatctgtcc ttccagaggg gcctgcccgg ctttatgcct 3540
gcatgggata tcgtgttcga gaagaacgag acacagtttg acgccaaggg cacccctttc 3600
atcgccggca agagaatcgt gccagtgatc gagaatcaca gattcaccgg cagataccgg 3660
gacctgtatc ctgccaacga gctgatcgcc ctgctggagg agaagggcat cgtgttcagg 3720
gatggctcca acatcctgcc aaagctgctg gagaatgacg attctcacgc catcgacacc 3780
atggtggccc tgatccgcag cgtgctgcag atgcggaact ccaatgccgc cacaggcgag 3840
gactatatca acagccccgt gcgcgatctg aatggcgtgt gcttcgactc ccggtttcag 3900
aacccagagt ggcccatgga cgccgatgcc aatggcgcct accacatcgc cctgaagggc 3960
cagctgctgc tgaatcacct gaaggagagc aaggatctga agctgcagaa cggcatctcc 4020
aatcaggact ggctggccta catccaggag ctgcgcaaca aaaggccggc ggccacgaaa 4080
aaggccggcc aggcaaaaaa gaaaaaggaa ttc 4113

<210> SEQ ID NO 79
<211> LENGTH: 4068
<212> TYPE: DNA
<213> ORGANISM: Artificial Sequence
<220> FEATURE:
<223> OTHER INFORMATION: Synthetic gene sequence; R9-AsCas12a

<400> SEQUENCE: 79
atgggcagca gccatcatca tcatcatcac agcagcggcc tggtgccgcg cggcagccat 60
atgagacgaa gacgaagacg tagacgtaga gctagcacac agttcgaggg ctttaccaac 120
ctgtatcagg tgagcaagac actgcggttt gagctgatcc cacagggcaa gaccctgaag 180
cacatccagg agcagggctt catcgaggag gacaaggccc gcaatgatca ctacaaggag 240
ctgaagccca tcatcgatcg gatctacaag acctatgccg accagtgcct gcagctggtg 300
cagctggatt gggagaacct gagcgccgcc atcgactcct atagaaagga gaaaaccgag 360
gagacaagga acgccctgat cgaggagcag gccacatatc gcaatgccat ccacgactac 420
ttcatcggcc ggacagacaa cctgaccgat gccatcaata agagacacgc cgagatctac 480
aagggcctgt tcaaggccga gctgtttaat ggcaaggtgc tgaagcagct gggcaccgtg 540
accacaaccg agcacgagaa cgccctgctg cggagcttcg acaagtttac aacctacttc 600
tccggctttt atgagaacag gaagaacgtg ttcagcgccg aggatatcag cacagccatc 660
ccacaccgca tcgtgcagga caacttcccc aagtttaagg agaattgtca catcttcaca 720
cgcctgatca ccgccgtgcc cagcctgcgg gagcactttg agaacgtgaa gaaggccatc 780
ggcatcttcg tgagcacctc catcgaggag gtgttttcct tcccttttta taaccagctg 840
ctgacacaga cccagatcga cctgtataac cagctgctgg gaggaatctc tcgggaggca 900
ggcaccgaga agatcaaggg cctgaacgag gtgctgaatc tggccatcca gaagaatgat 960
gagacagccc acatcatcgc ctccctgcca cacagattca tcccccctgtt taagcagatc 1020 ctgtccgata ggaacaccct gtctttcatc ctggaggagt ttaagagcga cgaggaagtg 1080
atccagtcct tctgcaagta caagacactg ctgagaaacg agaacgtgct ggagacagcc 1140
gaggccctgt ttaacgagct gaacagcatc gacctgacac acatcttcat cagccacaag 1200
aagctggaga caatcagcag cgccctgtgc gaccactggg atacactgag gaatgccctg 1260
tatgagcgga gaatctccga gctgacaggc aagatcacca agtctgccaa ggagaaggtg 1320
cagcgcagcc tgaagcacga ggatatcaac ctgcaggaga tcatctctgc cgcaggcaag 1380
gagctgagcg aggccttcaa gcagaaaacc agcgagatcc tgtcccacgc acacgccgcc 1440
ctggatcagc cactgcctac aaccctgaag aagcaggagg agaaggagat cctgaagtct 1500
cagctggaca gcctgctggg cctgtaccac ctgctggact ggtttgccgt ggatgagtcc 1560
aacgaggtgg accccgagtt ctctgcccgg ctgaccggca tcaagctgga gatggagcct 1620
tctctgagct tctacaacaa ggccagaaat tatgccacca agaagcccta ctccgtggag 1680
aagttcaagc tgaactttca gatgcctaca ctggcctctg gctgggacgt gaataaggag 1740
aagaacaatg gcgccatcct gtttgtgaag aacggcctgt actatctggg catcatgcca 1800
aagcagaagg gcaggtataa ggccctgagc ttcgagccca cagagaaaac cagcgagggc 1860
tttgataaga tgtactatga ctacttccct gatgccgcca agatgatccc aaagtgcagc 1920
acccagctga aggccgtgac agcccacttt cagacccaca caaccccat cctgctgtcc 1980 aacaatttca tcgagcctct ggagatcaca aaggagatct acgacctgaa caatcctgag 2040
aaggagccaa agaagtttca gacagcctac gccaagaaaa ccggcgacca gaagggctac 2100
agagaggccc tgtgcaagtg gatcgacttc acaagggatt ttctgtccaa gtataccaag 2160
acaacctcta tcgatctgtc tagcctgcgg ccatcctctc agtataagga cctgggcgag 2220
tactatgccg agctgaatcc cctgctgtac cacatcagct tccagagaat cgccgagaag 2280
gagatcatgg atgccgtgga gacaggcaag ctgtacctgt tccagatcta taacaaggac 2340
tttgccaagg gccaccacgg caagcctaat ctgcacacac tgtattggac cggcctgttt 2400
tctccagaga acctggccaa gacaagcatc aagctgaatg gccaggccga gctgttctac 2460
cgccctaagt ccaggatgaa gaggatggca caccggctgg gagagaagat gctgaacaag 2520
aagctgaagg atcagaaaac cccaatcccc gacaccctgt accaggagct gtacgactat 2580
gtgaatcaca gactgtccca cgacctgtct gatgaggcca gggccctgct gcccaacgtg 2640
atcaccaagg aggtgtctca cgagatcatc aaggataggc gctttaccag cgacaagttc 2700
tttttccacg tgcctatcac actgaactat caggccgcca attccccatc taagttcaac 2760
cagagggtga atgcctacct gaaggagcac cccgagacac ctatcatcgg catcgatcgg 2820
ggcgagagaa acctgatcta tatcacagtg atcgactcca ccggcaagat cctggagcag 2880
cggagcctga acaccatcca gcagtttgat taccagaaga agctggacaa cagggagaag 2940
gagagggtgg cagcaaggca ggcctggtct gtggtgggca caatcaagga tctgaagcag 3000
ggctatctga gccaggtcat ccacgagatc gtggacctga tgatccacta ccaggccgtg 3060
gtggtgctgg agaacctgaa tttcggcttt aagagcaaga ggaccggcat cgccgagaag 3120
gccgtgtacc agcagttcga gaagatgctg atcgataagc tgaattgcct ggtgctgaag 3180
gactatccag cagagaaagt gggaggcgtg ctgaacccat accagctgac agaccagttc 3240
acctcctttg ccaagatggg cacccagtct ggcttcctgt tttacgtgcc tgccccatat 3300
acatctaaga tcgatcccct gaccggcttc gtggacccct tcgtgtggaa aaccatcaag 3360
aatcacgaga gccgcaagca cttcctggag ggcttcgact ttctgcacta cgacgtgaaa 3420
accggcgact tcatcctgca ctttaagatg aacagaaatc tgtccttcca gaggggcctg 3480
cccggcttta tgcctgcatg ggatatcgtg ttcgagaaga acgagacaca gtttgacgcc 3540
aagggcaccc ctttcatcgc cggcaagaga atcgtgccag tgatcgagaa tcacagattc 3600
accggcagat accgggacct gtatcctgcc aacgagctga tcgccctgct ggaggagaag 3660
ggcatcgtgt tcagggatgg ctccaacatc ctgccaaagc tgctggagaa tgacgattct 3720
cacgccatcg acaccatggt ggccctgatc cgcagcgtgc tgcagatgcg gaactccaat 3780
gccgccacag gcgaggacta tatcaacagc cccgtgcgcg atctgaatgg cgtgtgcttc 3840
gactcccggt ttcagaaccc agagtggccc atggacgccg atgccaatgg cgcctaccac 3900
atcgccctga agggccagct gctgctgaat cacctgaagg agagcaagga tctgaagctg 3960
cagaacggca tctccaatca ggactggctg gcctacatcc aggagctgcg caacaaaagg 4020
ccggcggcca cgaaaaaggc cggccaggca aaaaagaaaa aggaattc 4068

<210> SEQ ID NO 80
<211> LENGTH: 4074
<212> TYPE: DNA

<213> ORGANISM: Artificial Sequence
<220> FEATURE:
<223> OTHER INFORMATION: Synthetic gene sequence; TAT-AsCas12a

<400> SEQUENCE: 80
atgggcagca gccatcatca tcatcatcac agcagcggcc tggtgccgcg cggcagccat 60
atgtatggac gcaagaagcg ccgccagcgc cgccgcgcta gcacacagtt cgagggcttt 120
accaacctgt atcaggtgag caagacactg cggtttgagc tgatcccaca gggcaagacc 180
ctgaagcaca tccaggagca gggcttcatc gaggaggaca aggcccgcaa tgatcactac 240
aaggagctga agcccatcat cgatcggatc tacaagacct atgccgacca gtgcctgcag 300
ctggtgcagc tggattggga gaacctgagc gccgccatcg actcctatag aaaggagaaa 360
accgaggaga caaggaacgc cctgatcgag gagcaggcca catatcgcaa tgccatccac 420
gactacttca tcggccggac agacaacctg accgatgcca tcaataagag acacgccgag 480
atctacaagg gcctgttcaa ggccgagctg tttaatggca aggtgctgaa gcagctgggc 540
accgtgacca caaccgagca cgagaacgcc ctgctgcgga gcttcgacaa gtttacaacc 600
tacttctccg gcttttatga gaacaggaag aacgtgttca gcgccgagga tatcagcaca 660
gccatcccac accgcatcgt gcaggacaac ttccccaagt ttaaggagaa ttgtcacatc 720
ttcacacgcc tgatcaccgc cgtgcccagc ctgcgggagc actttgagaa cgtgaagaag 780
gccatcggca tcttcgtgag cacctccatc gaggaggtgt tttccttccc tttttataac 840
cagctgctga cacagaccca gatcgacctg tataaccagc tgctgggagg aatctctcgg 900
gaggcaggca ccgagaagat caagggcctg aacgaggtgc tgaatctggc catccagaag 960
aatgatgaga cagcccacat catcgcctcc ctgccacaca gattcatccc cctgtttaag 1020
cagatcctgt ccgataggaa caccctgtct ttcatcctgg aggagtttaa gagcgacgag 1080
gaagtgatcc agtccttctg caagtacaag acactgctga gaaacgagaa cgtgctggag 1140
acagccgagg ccctgtttaa cgagctgaac agcatcgacc tgacacacat cttcatcagc 1200
cacaagaagc tggagacaat cagcagcgcc ctgtgcgacc actgggatac actgaggaat 1260
gccctgtatg agcggagaat ctccgagctg acaggcaaga tcaccaagtc tgccaaggag 1320
aaggtgcagc gcagcctgaa gcacgaggat atcaacctgc aggagatcat ctctgccgca 1380
ggcaaggagc tgagcgaggc cttcaagcag aaaaccagcg agatcctgtc ccacgcacac 1440
gccgccctgg atcagccact gcctacaacc ctgaagaagc aggaggagaa ggagatcctg 1500
aagtctcagc tggacagcct gctgggcctg taccacctgc tggactggtt tgccgtggat 1560
gagtccaacg aggtggaccc cgagttctct gcccggctga ccggcatcaa gctggagatg 1620
gagccttctc tgagcttcta caacaaggcc agaaattatg ccaccaagaa gccctactcc 1680
gtggagaagt tcaagctgaa ctttcagatg cctacactgg cctctggctg ggacgtgaat 1740
aaggagaaga acaatggcgc catcctgttt gtgaagaacg gcctgtacta tctgggcatc 1800
atgccaaagc agaagggcag gtataaggcc ctgagcttcg agcccacaga gaaaaccagc 1860
gagggctttg ataagatgta ctatgactac ttccctgatg ccgccaagat gatcccaaag 1920
tgcagcaccc agctgaaggc cgtgacagcc cactttcaga cccacacaac cccccatcctg 1980 ctgtccaaca atttcatcga gcctctggag atcacaaagg agatctacga cctgaacaat 2040
cctgagaagg agccaaagaa gtttcagaca gcctacgcca agaaaaccgg cgaccagaag 2100
ggctacagag aggccctgtg caagtggatc gacttcacaa gggattttct gtccaagtat 2160
accaagacaa cctctatcga tctgtctagc ctgcggccat cctctcagta taaggacctg 2220

```
ggcgagtact atgccgagct gaatcccctg ctgtaccaca tcagcttcca gagaatcgcc   2280

gagaaggaga tcatggatgc cgtggagaca ggcaagctgt acctgttcca gatctataac   2340

aaggactttg ccaagggcca ccacggcaag cctaatctgc acacactgta ttggaccggc   2400

ctgttttctc cagagaacct ggccaagaca agcatcaagc tgaatggcca ggccgagctg   2460

ttctaccgcc ctaagtccag gatgaagagg atggcacacc ggctgggaga gaagatgctg   2520

aacaagaagc tgaaggatca gaaaacccca atccccgaca ccctgtacca ggagctgtac   2580

gactatgtga atcacagact gtcccacgac ctgtctgatg aggccagggc cctgctgccc   2640

aacgtgatca ccaaggaggt gtctcacgag atcatcaagg ataggcgctt taccagcgac   2700

aagttctttt tccacgtgcc tatcacactg aactatcagg ccgccaattc cccatctaag   2760

ttcaaccaga gggtgaatgc ctacctgaag gagcaccccg agacacctat catcggcatc   2820

gatcggggcg agagaaacct gatctatatc acagtgatcg actccaccgg caagatcctg   2880

gagcagcgga gcctgaacac catccagcag tttgattacc agaagaagct ggacaacagg   2940

gagaaggaga gggtggcagc aaggcaggcc tggtctgtgg tgggcacaat caaggatctg   3000

aagcagggct atctgagcca ggtcatccac gagatcgtgg acctgatgat ccactaccag   3060

gccgtggtgg tgctggagaa cctgaatttc ggctttaaga gcaagaggac cggcatcgcc   3120

gagaaggccg tgtaccagca gttcgagaag atgctgatcg ataagctgaa ttgcctggtg   3180

ctgaaggact atccagcaga gaaagtggga ggcgtgctga acccatacca gctgacagac   3240

cagttcacct cctttgccaa gatgggcacc cagtctggct tcctgtttta cgtgcctgcc   3300

ccatatacat ctaagatcga tcccctgacc ggcttcgtgg accccttcgt gtggaaaacc   3360

atcaagaatc acgagagccg caagcacttc ctggagggct tcgactttct gcactacgac   3420

gtgaaaaccg gcgacttcat cctgcacttt aagatgaaca gaaatctgtc cttccagagg   3480

ggcctgcccg gctttatgcc tgcatgggat atcgtgttcg agaagaacga gacacagttt   3540

gacgccaagg gcaccccttt catcgccggc aagagaatcg tgccagtgat cgagaatcac   3600

agattcaccg gcagataccg ggacctgtat cctgccaacg agctgatcgc cctgctggag   3660

gagaagggca tcgtgttcag ggatggctcc aacatcctgc caaagctgct ggagaatgac   3720

gattctcacg ccatcgacac catggtggcc ctgatccgca gcgtgctgca gatgcggaac   3780

tccaatgccg ccacaggcga ggactatatc aacagccccg tgcgcgatct gaatggcgtg   3840

tgcttcgact cccggtttca gaacccagag tggcccatgg acgccgatgc caatggcgcc   3900

taccacatcg ccctgaaggg ccagctgctg ctgaatcacc tgaaggagag caaggatctg   3960

aagctgcaga acggcatctc caatcaggac tggctggcct acatccagga gctgcgcaac   4020

aaaaggccgg cggccacgaa aaaggccggc caggcaaaaa agaaaaagga attc         4074
```

<210> SEQ ID NO 81
<211> LENGTH: 3831
<212> TYPE: DNA
<213> ORGANISM: Artificial Sequence
<220> FEATURE:
<223> OTHER INFORMATION: Synthetic gene sequence; AP-LbCas12a

<400> SEQUENCE: 81

```
atgggcagca gccatcatca tcatcatcac agcagcggcc tggtgccgcg cggcagccat     60

atgcgccggc gctggtgcaa acgccgccgg gctagcagca agctggagaa gtttacaaac    120

tgctactccc tgtctaagac cctgaggttc aaggccatcc ctgtgggcaa gacccaggag    180
```

```
aacatcgaca ataagcggct gctggtggag gacgagaaga gagccgagga ttataagggc    240
gtgaagaagc tgctggatcg ctactatctg tcttttatca acgacgtgct gcacagcatc    300
aagctgaaga atctgaacaa ttacatcagc ctgttccgga agaaaaccag aaccgagaag    360
gagaataagg agctggagaa cctggagatc aatctgcgga aggagatcgc caaggccttc    420
aagggcaacg agggctacaa gtccctgttt aagaaggata tcatcgagac aatcctgcca    480
gagttcctgg acgataagga cgagatcgcc ctggtgaaca gcttcaatgg ctttaccaca    540
gccttcaccg gcttctttga taacagagag aatatgtttt ccgaggaggc caagagcaca    600
tccatcgcct tcaggtgtat caacgagaat ctgacccgct acatctctaa tatggacatc    660
ttcgagaagg tggacgccat ctttgataag cacgaggtgc aggagatcaa ggagaagatc    720
ctgaacagcg actatgatgt ggaggatttc tttgagggcg agttctttaa ctttgtgctg    780
acacaggagg gcatcgacgt gtataacgcc atcatcggcg gcttcgtgac cgagagcggc    840
gagaagatca agggcctgaa cgagtacatc aacctgtata atcagaaaac caagcagaag    900
ctgcctaagt ttaagccact gtataagcag gtgctgagcg atcgggagtc tctgagcttc    960
tacggcgagg gctatacatc cgatgaggag gtgctggagg tgtttagaaa caccctgaac   1020
aagaacagcg agatcttcag ctccatcaag aagctggaga agctgttcaa gaattttgac   1080
gagtactcta gcgccggcat ctttgtgaag aacggccccg ccatcagcac aatctccaag   1140
gatatcttcg gcgagtggaa cgtgatccgg gacaagtgga atgccgagta tgacgatatc   1200
cacctgaaga agaaggccgt ggtgaccgag aagtacgagg acgatcggag aaagtccttc   1260
aagaagatcg gctccttttc tctggagcag ctgcaggagt acgccgacgc cgatctgtct   1320
gtggtggaga agctgaagga gatcatcatc cagaaggtgg atgagatcta caaggtgtat   1380
ggctcctctg agaagctgtt cgacgccgat tttgtgctgg agaagagcct gaagaagaac   1440
gacgccgtgg tggccatcat gaaggacctg ctggattctg tgaagagctt cgagaattac   1500
atcaaggcct tctttggcga gggcaaggag acaaacaggg acgagtcctt ctatggcgat   1560
tttgtgctgg cctacgacat cctgctgaag gtggaccaca tctacgatgc catccgcaat   1620
tatgtgaccc agaagcccta ctctaaggat aagttcaagc tgtattttca gaaccctcag   1680
ttcatgggcg gctgggacaa ggataaggag acagactatc gggccaccat cctgagatac   1740
ggctccaagt actatctggc catcatggat aagaagtacg ccaagtgcct gcagaagatc   1800
gacaaggacg atgtgaacgg caattacgag aagatcaact ataagctgct gcccggccct   1860
aataagatgc tgccaaaggt gttcttttct aagaagtgga tggcctacta taaccccagc   1920
gaggacatcc agaagatcta caagaatggc acattcaaga agggcgatat gtttaacctg   1980
aatgactgtc acaagctgat cgacttcttt aaggatagca tctcccggta tccaaagtgg   2040
tccaatgcct acgatttcaa cttttctgag acagagaagt ataaggacat cgccggcttt   2100
tacagagagg tggaggagca gggctataag gtgagcttcg agtctgccag caagaaggag   2160
gtggataagc tggtggagga gggcaagctg tatatgttcc agatctataa caaggacttt   2220
tccgataagt ctcacggcac acccaatctg cacaccatgt acttcaagct gctgtttgac   2280
gagaacaatc acggacagat caggctgagc ggaggagcag agctgttcat gaggcgcgcc   2340
tccctgaaga aggaggagct ggtggtgcac ccagccaact cccctatcgc caacaagaat   2400
ccagataatc ccaagaaaac cacaaccctg tcctacgacg tgtataagga taagaggttt   2460
tctgaggacc agtacgagct gcacatccca atcgccatca ataagtgccc caagaacatc   2520
ttcaagatca atacagaggt gcgcgtgctg ctgaagcacg acgataaccc ctatgtgatc   2580
```

ggcatcgata ggggcgagcg caatctgctg tatatcgtgg tggtggacgg caagggcaac 2640
atcgtggagc agtattccct gaacgagatc atcaacaact tcaacggcat caggatcaag 2700
acagattacc actctctgct ggacaagaag gagaaggaga ggttcgaggc ccgccagaac 2760
tggacctcca tcgagaatat caaggagctg aaggccggct atatctctca ggtggtgcac 2820
aagatctgcg agctggtgga gaagtacgat gccgtgatcg ccctggagga cctgaactct 2880
ggctttaaga atagccgcgt gaaggtggag aagcaggtgt atcagaagtt cgagaagatg 2940
ctgatcgata agctgaacta catggtggac aagaagtcta atccttgtgc aacaggcggc 3000
gccctgaagg gctatcagat caccaataag ttcgagagct ttaagtccat gtctacccag 3060
aacggcttca tcttttacat ccctgcctgg ctgacatcca agatcgatcc atctaccggc 3120
tttgtgaacc tgctgaaaac caagtatacc agcatcgccg attccaagaa gttcatcagc 3180
tcctttgaca ggatcatgta cgtgcccgag gaggatctgt tcgagtttgc cctggactat 3240
aagaacttct ctcgcacaga cgccgattac atcaagaagt ggaagctgta ctcctacggc 3300
aaccggatca gaatcttccg gaatcctaag aagaacaacg tgttcgactg ggaggaggtg 3360
tgcctgacca gcgcctataa ggagctgttc aacaagtacg gcatcaatta tcagcagggc 3420
gatatcagag ccctgctgtg cgagcagtcc gacaaggcct tctactctag ctttatggcc 3480
ctgatgagcc tgatgctgca gatgcggaac agcatcacag gccgcaccga cgtggatttt 3540
ctgatcagcc ctgtgaagaa ctccgacggc atcttctacg atagccggaa ctatgaggcc 3600
caggagaatg ccatcctgcc aaagaacgcc gacgccaatg gcgcctataa catcgccaga 3660
aaggtgctgt gggccatcgg ccagttcaag aaggccgagg acgagaagct ggataaggtg 3720
aagatcgcca tctctaacaa ggagtggctg gagtacgccc agaccagcgt gaagcacaaa 3780
aggccggcgg ccacgaaaaa ggccggccag gcaaaaaaga aaaaggaatt c 3831

<210> SEQ ID NO 82
<211> LENGTH: 3876
<212> TYPE: DNA
<213> ORGANISM: Artificial Sequence
<220> FEATURE:
<223> OTHER INFORMATION: Synthetic gene sequence; dNP2-LbCas12a

<400> SEQUENCE: 82
atgggcagca gccatcatca tcatcatcac agcagcggcc tggtgccgcg cggcagccat 60
atgaagatca agaaggttaa aaaaaagggt cgcaagggct ctaaaattaa aaaagtcaag 120
aagaaaggaa gaaaagctag cagcaagctg gagaagttta caaactgcta ctccctgtct 180
aagaccctga ggttcaaggc catccctgtg ggcaagaccc aggagaacat cgacaataag 240
cggctgctgg tggaggacga gaagagagcc gaggattata agggcgtgaa gaagctgctg 300
gatcgctact atctgtcttt tatcaacgac gtgctgcaca gcatcaagct gaagaatctg 360
aacaattaca tcagcctgtt ccggaagaaa accagaaccg agaaggagaa taaggagctg 420
gagaacctgg agatcaatct gcggaaggag atcgccaagg ccttcaaggg caacgagggc 480
tacaagtccc tgtttaagaa ggatatcatc gagacaatcc tgccagagtt cctggacgat 540
aaggacgaga tcgccctggt gaacagcttc aatggcttta ccacagcctt caccggcttc 600
tttgataaca gagagaatat gttttccgag gaggccaaga gcacatccat cgccttcagg 660
tgtatcaacg agaatctgac ccgctacatc tctaatatgg acatcttcga gaaggtggac 720
gccatctttg ataagcacga ggtgcaggag atcaaggaga agatcctgaa cagcgactat 780

```
gatgtggagg atttctttga gggcgagttc tttaactttg tgctgacaca ggagggcatc    840
gacgtgtata acgccatcat cggcggcttc gtgaccgaga gcggcgagaa gatcaagggc    900
ctgaacgagt acatcaacct gtataatcag aaaaccaagc agaagctgcc taagtttaag    960
ccactgtata agcaggtgct gagcgatcgg gagtctctga gcttctacgg cgagggctat   1020
acatccgatg aggaggtgct ggaggtgttt agaaacaccc tgaacaagaa cagcgagatc   1080
ttcagctcca tcaagaagct ggagaagctg ttcaagaatt ttgacgagta ctctagcgcc   1140
ggcatctttg tgaagaacgg ccccgccatc agcacaatct ccaaggatat cttcggcgag   1200
tggaacgtga tccgggacaa gtggaatgcc gagtatgacg atatccacct gaagaagaag   1260
gccgtggtga ccgagaagta cgaggacgat cggagaaagt ccttcaagaa gatcggctcc   1320
ttttctctgg agcagctgca ggagtacgcc gacgccgatc tgtctgtggt ggagaagctg   1380
aaggagatca tcatccagaa ggtggatgag atctacaagg tgtatggctc ctctgagaag   1440
ctgttcgacg ccgattttgt gctggagaag agcctgaaga agaacgacgc cgtggtggcc   1500
atcatgaagg acctgctgga ttctgtgaag agcttcgaga attacatcaa ggccttcttt   1560
ggcgagggca aggagacaaa cagggacgag tccttctatg gcgattttgt gctggcctac   1620
gacatcctgc tgaaggtgga ccacatctac gatgccatcc gcaattatgt gacccagaag   1680
ccctactcta aggataagtt caagctgtat tttcagaacc ctcagttcat gggcggctgg   1740
gacaaggata aggagacaga ctatcgggcc accatcctga gatacggctc caagtactat   1800
ctggccatca tggataagaa gtacgccaag tgcctgcaga agatcgacaa ggacgatgtg   1860
aacggcaatt acgagaagat caactataag ctgctgcccg gccctaataa gatgctgcca   1920
aaggtgttct tttctaagaa gtggatggcc tactataacc ccagcgagga catccagaag   1980
atctacaaga atggcacatt caagaagggc gatatgttta acctgaatga ctgtcacaag   2040
ctgatcgact tctttaagga tagcatctcc cggtatccaa agtggtccaa tgcctacgat   2100
ttcaactttt ctgagacaga gaagtataag gacatcgccg gcttttacag agaggtggag   2160
gagcagggct ataaggtgag cttcgagtct gccagcaaga aggaggtgga taagctggtg   2220
gaggagggca agctgtatat gttccagatc tataacaagg acttttccga taagtctcac   2280
ggcacaccca atctgcacac catgtacttc aagctgctgt ttgacgagaa caatcacgga   2340
cagatcaggc tgagcggagg agcagagctg ttcatgaggc gcgcctccct gaagaaggag   2400
gagctggtgg tgcacccagc caactcccct atcgccaaca agaatccaga taatcccaag   2460
aaaaccacaa ccctgtccta cgacgtgtat aaggataaga ggttttctga ggaccagtac   2520
gagctgcaca tcccaatcgc catcaataag tgccccaaga acatcttcaa gatcaataca   2580
gaggtgcgcg tgctgctgaa gcacgacgat aacccctatg tgatcggcat cgataggggc   2640
gagcgcaatc tgctgtatat cgtggtggtg gacggcaagg gcaacatcgt ggagcagtat   2700
tccctgaacg agatcatcaa caacttcaac ggcatcagga tcaagacaga ttaccactct   2760
ctgctggaca agaaggagaa ggagaggttc gaggcccgcc agaactggac ctccatcgag   2820
aatatcaagg agctgaaggc cggctatatc tctcaggtgg tgcacaagat ctgcgagctg   2880
gtggagaagt acgatgccgt gatcgccctg gaggacctga actctggctt taagaatagc   2940
cgcgtgaagg tggagaagca ggtgtatcag aagttcgaga agatgctgat cgataagctg   3000
aactacatgg tggacaagaa gtctaatcct tgtgcaacag gcggcgccct gaagggctat   3060
cagatcacca ataagttcga gagctttaag tccatgtcta cccagaacgg cttcatcttt   3120
tacatccctg cctggctgac atccaagatc gatccatcta ccggctttgt gaacctgctg   3180
```

aaaaccaagt ataccagcat cgccgattcc aagaagttca tcagctcctt tgacaggatc 3240
atgtacgtgc ccgaggagga tctgttcgag tttgccctgg actataagaa cttctctcgc 3300
acagacgccg attacatcaa gaagtggaag ctgtactcct acggcaaccg gatcagaatc 3360
ttccggaatc ctaagaagaa caacgtgttc gactgggagg aggtgtgcct gaccagcgcc 3420
tataaggagc tgttcaacaa gtacggcatc aattatcagc agggcgatat cagagccctg 3480
ctgtgcgagc agtccgacaa ggccttctac tctagcttta tggccctgat gagcctgatg 3540
ctgcagatgc ggaacagcat cacaggccgc accgacgtgg attttctgat cagccctgtg 3600
aagaactccg acggcatctt ctacgatagc cggaactatg aggcccagga gaatgccatc 3660
ctgccaaaga acgccgacgc caatggcgcc tataacatcg ccagaaaggt gctgtgggcc 3720
atcggccagt tcaagaaggc cgaggacgag aagctggata aggtgaagat cgccatctct 3780
aacaaggagt ggctggagta cgcccagacc agcgtgaagc acaaaaggcc ggcggccacg 3840
aaaaaggccg gccaggcaaa aaagaaaaag gaattc 3876

<210> SEQ ID NO 83
<211> LENGTH: 3831
<212> TYPE: DNA
<213> ORGANISM: Artificial Sequence
<220> FEATURE:
<223> OTHER INFORMATION: Synthetic gene sequence; R9-LbCas12a

<400> SEQUENCE: 83
atgggcagca gccatcatca tcatcatcac agcagcggcc tggtgccgcg cggcagccat 60
atgagacgaa gacgaagacg tagacgtaga gctagcagca agctggagaa gtttacaaac 120
tgctactccc tgtctaagac cctgaggttc aaggccatcc ctgtgggcaa gacccaggag 180
aacatcgaca ataagcggct gctggtggag gacgagaaga gagccgagga ttataagggc 240
gtgaagaagc tgctggatcg ctactatctg tcttttatca acgacgtgct gcacagcatc 300
aagctgaaga atctgaacaa ttacatcagc ctgttccgga agaaaaccag aaccgagaag 360
gagaataagg agctggagaa cctggagatc aatctgcgga aggagatcgc caaggccttc 420
aagggcaacg agggctacaa gtccctgttt aagaaggata tcatcgagac aatcctgcca 480
gagttcctgg acgataagga cgagatcgcc ctggtgaaca gcttcaatgg ctttaccaca 540
gccttcaccg gcttctttga taacagagag aatatgtttt ccgaggaggc caagagcaca 600
tccatcgcct tcaggtgtat caacgagaat ctgacccgct acatctctaa tatggacatc 660
ttcgagaagg tggacgccat ctttgataag cacgaggtgc aggagatcaa ggagaagatc 720
ctgaacagcg actatgatgt ggaggatttc tttgagggcg agttctttaa ctttgtgctg 780
acacaggagg gcatcgacgt gtataacgcc atcatcggcg gcttcgtgac cgagagcggc 840
gagaagatca agggcctgaa cgagtacatc aacctgtata atcagaaaac caagcagaag 900
ctgcctaagt ttaagccact gtataagcag gtgctgagcg atcgggagtc tctgagcttc 960
tacggcgagg gctatacatc cgatgaggag gtgctggagg tgtttagaaa caccctgaac 1020
aagaacagcg agatcttcag ctccatcaag aagctggaga agctgttcaa gaattttgac 1080
gagtactcta gcgccggcat ctttgtgaag aacggccccg ccatcagcac aatctccaag 1140
gatatcttcg gcgagtggaa cgtgatccgg gacaagtgga atgccgagta tgacgatatc 1200
cacctgaaga agaaggccgt ggtgaccgag aagtacgagg acgatcggag aaagtccttc 1260
aagaagatcg gctccttttc tctggagcag ctgcaggagt acgccgacgc cgatctgtct 1320
gtggtggaga agctgaagga gatcatcatc cagaaggtgg atgagatcta caaggtgtat 1380
ggctcctctg agaagctgtt cgacgccgat tttgtgctgg agaagagcct gaagaagaac 1440
gacgccgtgg tggccatcat gaaggacctg ctggattctg tgaagagctt cgagaattac 1500
atcaaggcct tctttggcga gggcaaggag acaaacaggg acgagtcctt ctatggcgat 1560
tttgtgctgg cctacgacat cctgctgaag gtggaccaca tctacgatgc catccgcaat 1620
tatgtgaccc agaagcccta ctctaaggat aagttcaagc tgtattttca gaaccctcag 1680
ttcatgggcg gctgggacaa ggataaggag acagactatc gggccaccat cctgagatac 1740
ggctccaagt actatctggc catcatggat aagaagtacg ccaagtgcct gcagaagatc 1800
gacaaggacg atgtgaacgg caattacgag aagatcaact ataagctgct gcccggccct 1860
aataagatgc tgccaaaggt gttcttttct aagaagtgga tggcctacta taaccccagc 1920
gaggacatcc agaagatcta caagaatggc acattcaaga agggcgatat gtttaacctg 1980
aatgactgtc acaagctgat cgacttcttt aaggatagca tctcccggta tccaaagtgg 2040
tccaatgcct acgatttcaa cttttctgag acagagaagt ataaggacat cgccggcttt 2100
tacagagagg tggaggagca gggctataag gtgagcttcg agtctgccag caagaaggag 2160
gtggataagc tggtggagga gggcaagctg tatatgttcc agatctataa caaggacttt 2220
tccgataagt ctcacggcac acccaatctg cacaccatgt acttcaagct gctgtttgac 2280
gagaacaatc acggacagat caggctgagc ggaggagcag agctgttcat gaggcgcgcc 2340
tccctgaaga aggaggagct ggtggtgcac ccagccaact cccctatcgc caacaagaat 2400
ccagataatc ccaagaaaac cacaaccctg tcctacgacg tgtataagga taagaggttt 2460
tctgaggacc agtacgagct gcacatccca atcgccatca ataagtgccc caagaacatc 2520
ttcaagatca atacagaggt gcgcgtgctg ctgaagcacg acgataaccc ctatgtgatc 2580
ggcatcgata ggggcgagcg caatctgctg tatatcgtgg tggtggacgg caagggcaac 2640
atcgtggagc agtattccct gaacgagatc atcaacaact tcaacggcat caggatcaag 2700
acagattacc actctctgct ggacaagaag gagaaggaga ggttcgaggc ccgccagaac 2760
tggacctcca tcgagaatat caaggagctg aaggccggct atatctctca ggtggtgcac 2820
aagatctgcg agctggtgga gaagtacgat gccgtgatcg ccctggagga cctgaactct 2880
ggctttaaga atagccgcgt gaaggtggag aagcaggtgt atcagaagtt cgagaagatg 2940
ctgatcgata agctgaacta catggtggac aagaagtcta atccttgtgc aacaggcggc 3000
gccctgaagg gctatcagat caccaataag ttcgagagct ttaagtccat gtctacccag 3060
aacggcttca tcttttacat ccctgcctgg ctgacatcca agatcgatcc atctaccggc 3120
tttgtgaacc tgctgaaaac caagtatacc agcatcgccg attccaagaa gttcatcagc 3180
tcctttgaca ggatcatgta cgtgcccgag gaggatctgt tcgagtttgc cctggactat 3240
aagaacttct ctcgcacaga cgccgattac atcaagaagt ggaagctgta ctcctacggc 3300
aaccggatca gaatcttccg gaatcctaag aagaacaacg tgttcgactg ggaggaggtg 3360
tgcctgacca gcgcctataa ggagctgttc aacaagtacg gcatcaatta tcagcagggc 3420
gatatcagag ccctgctgtg cgagcagtcc gacaaggcct tctactctag ctttatggcc 3480
ctgatgagcc tgatgctgca gatgcggaac agcatcacag gccgcaccga cgtggatttt 3540
ctgatcagcc ctgtgaagaa ctccgacggc atcttctacg atagccggaa ctatgaggcc 3600
caggagaatg ccatcctgcc aaagaacgcc gacgccaatg gcgcctataa catcgccaga 3660
aaggtgctgt gggccatcgg ccagttcaag aaggccgagg acgagaagct ggataaggtg 3720
aagatcgcca tctctaacaa ggagtggctg gagtacgccc agaccagcgt gaagcacaaa 3780
aggccggcgg ccacgaaaaa ggccggccag gcaaaaaaga aaaaggaatt c 3831

<210> SEQ ID NO 84
<211> LENGTH: 3837
<212> TYPE: DNA
<213> ORGANISM: Artificial Sequence
<220> FEATURE:
<223> OTHER INFORMATION: Synthetic gene sequence; TAT-LbCas12a

<400> SEQUENCE: 84
atgggcagca gccatcatca tcatcatcac agcagcggcc tggtgccgcg cggcagccat 60
atgtatggac gcaagaagcg ccgccagcgc cgccgcgcta gcagcaagct ggagaagttt 120
acaaactgct actccctgtc taagaccctg aggttcaagg ccatccctgt gggcaagacc 180
caggagaaca tcgacaataa gcggctgctg gtggaggacg agaagagagc cgaggattat 240
aagggcgtga agaagctgct ggatcgctac tatctgtctt ttatcaacga cgtgctgcac 300
agcatcaagc tgaagaatct gaacaattac atcagcctgt tccggaagaa aaccagaacc 360
gagaaggaga ataaggagct ggagaacctg gagatcaatc tgcggaagga gatcgccaag 420
gccttcaagg gcaacgaggg ctacaagtcc ctgtttaaga aggatatcat cgagacaatc 480
ctgccagagt tcctggacga taaggacgag atcgccctgg tgaacagctt caatggcttt 540
accacagcct tcaccggctt ctttgataac agagagaata tgttttccga ggaggccaag 600
agcacatcca tcgccttcag gtgtatcaac gagaatctga cccgctacat ctctaatatg 660
gacatcttcg agaaggtgga cgccatcttt gataagcacg aggtgcagga gatcaaggag 720
aagatcctga acagcgacta tgatgtggag gatttctttg agggcgagtt ctttaacttt 780
gtgctgacac aggagggcat cgacgtgtat aacgccatca tcggcggctt cgtgaccgag 840
agcggcgaga agatcaaggg cctgaacgag tacatcaacc tgtataatca gaaaaccaag 900
cagaagctgc ctaagtttaa gccactgtat aagcaggtgc tgagcgatcg ggagtctctg 960
agcttctacg gcgagggcta tacatccgat gaggaggtgc tggaggtgtt tagaaacacc 1020
ctgaacaaga acagcgagat cttcagctcc atcaagaagc tggagaagct gttcaagaat 1080
tttgacgagt actctagcgc cggcatcttt gtgaagaacg gccccgccat cagcacaatc 1140
tccaaggata tcttcggcga gtggaacgtg atccgggaca agtggaatgc cgagtatgac 1200
gatatccacc tgaagaagaa ggccgtggtg accgagaagt acgaggacga tcggagaaag 1260
tccttcaaga agatcggctc cttttctctg gagcagctgc aggagtacgc cgacgccgat 1320
ctgtctgtgg tggagaagct gaaggagatc atcatccaga aggtggatga gatctacaag 1380
gtgtatggct cctctgagaa gctgttcgac gccgattttg tgctggagaa gagcctgaag 1440
aagaacgacg ccgtggtggc catcatgaag gacctgctgg attctgtgaa gagcttcgag 1500
aattacatca aggccttctt tggcgagggc aaggagacaa acagggacga gtccttctat 1560
ggcgattttg tgctggccta cgacatcctg ctgaaggtgg accacatcta cgatgccatc 1620
cgcaattatg tgacccagaa gccctactct aaggataagt tcaagctgta ttttcagaac 1680
cctcagttca tgggcggctg ggacaaggat aaggagacag actatcgggc caccatcctg 1740
agatacggct ccaagtacta tctggccatc atggataaga agtacgccaa gtgcctgcag 1800
aagatcgaca aggacgatgt gaacggcaat tacgagaaga tcaactataa gctgctgccc 1860
ggccctaata agatgctgcc aaaggtgttc ttttctaaga agtggatggc ctactataac 1920

```
cccagcgagg acatccagaa gatctacaag aatggcacat tcaagaaggg cgatatgttt   1980
aacctgaatg actgtcacaa gctgatcgac ttctttaagg atagcatctc ccggtatcca   2040
aagtggtcca atgcctacga tttcaacttt tctgagacag agaagtataa ggacatcgcc   2100
ggcttttaca gagaggtgga ggagcagggc tataaggtga gcttcgagtc tgccagcaag   2160
aaggaggtgg ataagctggt ggaggagggc aagctgtata tgttccagat ctataacaag   2220
gacttttccg ataagtctca cggcacaccc aatctgcaca ccatgtactt caagctgctg   2280
tttgacgaga acaatcacgg acagatcagg ctgagcggag gagcagagct gttcatgagg   2340
cgcgcctccc tgaagaagga ggagctggtg gtgcacccag ccaactcccc tatcgccaac   2400
aagaatccag ataatcccaa gaaaaccaca accctgtcct acgacgtgta taaggataag   2460
aggttttctg aggaccagta cgagctgcac atcccaatcg ccatcaataa gtgccccaag   2520
aacatcttca agatcaatac agaggtgcgc gtgctgctga agcacgacga taacccctat   2580
gtgatcggca tcgatagggg cgagcgcaat ctgctgtata tcgtggtggt ggacggcaag   2640
ggcaacatcg tggagcagta ttccctgaac gagatcatca acaacttcaa cggcatcagg   2700
atcaagacag attaccactc tctgctggac aagaaggaga aggagaggtt cgaggcccgc   2760
cagaactgga cctccatcga gaatatcaag gagctgaagg ccggctatat ctctcaggtg   2820
gtgcacaaga tctgcgagct ggtggagaag tacgatgccg tgatcgccct ggaggacctg   2880
aactctggct ttaagaatag ccgcgtgaag gtggagaagc aggtgtatca gaagttcgag   2940
aagatgctga tcgataagct gaactacatg gtggacaaga agtctaatcc ttgtgcaaca   3000
ggcggcgccc tgaagggcta tcagatcacc aataagttcg agagctttaa gtccatgtct   3060
acccagaacg gcttcatctt ttacatccct gcctggctga catccaagat cgatccatct   3120
accggctttg tgaacctgct gaaaaccaag tataccagca tcgccgattc caagaagttc   3180
atcagctcct ttgacaggat catgtacgtg cccgaggagg atctgttcga gtttgccctg   3240
gactataaga acttctctcg cacagacgcc gattacatca agaagtggaa gctgtactcc   3300
tacggcaacc ggatcagaat cttccggaat cctaagaaga acaacgtgtt cgactgggag   3360
gaggtgtgcc tgaccagcgc ctataaggag ctgttcaaca agtacggcat caattatcag   3420
cagggcgata tcagagccct gctgtgcgag cagtccgaca aggccttcta ctctagcttt   3480
atggccctga tgagcctgat gctgcagatg cggaacagca tcacaggccg caccgacgtg   3540
gattttctga tcagccctgt gaagaactcc gacggcatct tctacgatag ccggaactat   3600
gaggcccagg agaatgccat cctgccaaag aacgccgacg ccaatggcgc ctataacatc   3660
gccagaaagg tgctgtgggc catcggccag ttcaagaagg ccgaggacga gaagctggat   3720
aaggtgaaga tcgccatctc taacaaggag tggctggagt acgcccagac cagcgtgaag   3780
cacaaaaggc cggcggccac gaaaaaggcc ggccaggcaa aaaagaaaaa ggaattc      3837
```

```
<210> SEQ ID NO 85
<211> LENGTH: 48
<212> TYPE: PRT
<213> ORGANISM: Artificial Sequence
<220> FEATURE:
<223> OTHER INFORMATION: Synthetic construct of General Formula 1
<220> FEATURE:
<221> NAME/KEY: VARIANT
<222> LOCATION: (15)..(18)
<223> OTHER INFORMATION: Xaa is Gly or absent
<220> FEATURE:
<221> NAME/KEY: VARIANT
<222> LOCATION: (29)..(30)
<223> OTHER INFORMATION: Xaa-Xaa at positions 29 and 30 is His-Glu or
```

absent
<220> FEATURE:
<221> NAME/KEY: VARIANT
<222> LOCATION: (31)..(32)
<223> OTHER INFORMATION: Xaa-Xaa at positions 31 and 32 is His-Glu or absent
<220> FEATURE:
<221> NAME/KEY: VARIANT
<222> LOCATION: (33)..(34)
<223> OTHER INFORMATION: Xaa-Xaa at positions 33 and 34 is His-Glu or absent
<220> FEATURE:
<221> NAME/KEY: VARIANT
<222> LOCATION: (35)..(36)
<223> OTHER INFORMATION: Xaa-Xaa at positions 35 and 36 is His-Glu or absent
<220> FEATURE:
<221> NAME/KEY: VARIANT
<222> LOCATION: (37)..(38)
<223> OTHER INFORMATION: Xaa-Xaa at positions 37 and 38 is His-Glu or absent
<220> FEATURE:
<221> NAME/KEY: VARIANT
<222> LOCATION: (39)..(40)
<223> OTHER INFORMATION: Xaa-Xaa at positions 39 and 40 is His-Glu or absent
<220> FEATURE:
<221> NAME/KEY: VARIANT
<222> LOCATION: (41)..(42)
<223> OTHER INFORMATION: Xaa-Xaa at positions 41 and 42 is His-Glu or absent
<220> FEATURE:
<221> NAME/KEY: VARIANT
<222> LOCATION: (43)..(44)
<223> OTHER INFORMATION: Xaa-Xaa at positions 43 and 44 is His-Glu or absent
<220> FEATURE:
<221> NAME/KEY: VARIANT
<222> LOCATION: (45)..(46)
<223> OTHER INFORMATION: Xaa-Xaa at positions 45 and 46 is His-Glu or absent
<220> FEATURE:
<221> NAME/KEY: VARIANT
<222> LOCATION: (47)..(48)
<223> OTHER INFORMATION: Xaa-Xaa at positions 47 and 48 is His-Glu or absent

<400> SEQUENCE: 85

```
Arg Arg Arg Trp Cys Lys Arg Arg Arg Ala Ser Gly Gly Gly Xaa Xaa
1               5                   10                  15

Xaa Xaa His Glu His Glu His Glu His Glu His Glu Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45
```

<210> SEQ ID NO 86
<211> LENGTH: 48
<212> TYPE: PRT
<213> ORGANISM: Artificial Sequence
<220> FEATURE:
<223> OTHER INFORMATION: Synthetic construct of General Formula 1
<220> FEATURE:
<221> NAME/KEY: VARIANT
<222> LOCATION: (15)..(18)
<223> OTHER INFORMATION: Xaa is Gly or absent
<220> FEATURE:
<221> NAME/KEY: VARIANT
<222> LOCATION: (37)..(38)
<223> OTHER INFORMATION: Xaa-Xaa at positions 37 and 38 is His-Glu or absent
<220> FEATURE:
<221> NAME/KEY: VARIANT
<222> LOCATION: (39)..(40)
<223> OTHER INFORMATION: Xaa-Xaa at positions 39 and 40 is His-Glu or absent
<220> FEATURE:
<221> NAME/KEY: VARIANT
<222> LOCATION: (41)..(42)
<223> OTHER INFORMATION: Xaa-Xaa at positions 41 and 42 is His-Glu or absent
<220> FEATURE:
<221> NAME/KEY: VARIANT
<222> LOCATION: (43)..(44)
<223> OTHER INFORMATION: Xaa-Xaa at positions 43 and 44 is His-Glu or absent
<220> FEATURE:
<221> NAME/KEY: VARIANT
<222> LOCATION: (45)..(46)
<223> OTHER INFORMATION: Xaa-Xaa at positions 45 and 46 is His-Glu or absent
<220> FEATURE:
<221> NAME/KEY: VARIANT
<222> LOCATION: (47)..(48)
<223> OTHER INFORMATION: Xaa-Xaa at positions 47 and 48 is His-Glu or absent

<400> SEQUENCE: 86

```
Arg Arg Arg Trp Cys Lys Arg Arg Arg Ala Ser Gly Gly Gly Xaa Xaa
1               5                   10                  15

Xaa Xaa His Glu His Glu His Glu His Glu His Glu His Glu His Glu
            20                  25                  30

His Glu His Glu Xaa Xaa Xaa Xaa Xaa Xaa Xaa Xaa Xaa Xaa Xaa Xaa
        35                  40                  45
```

<210> SEQ ID NO 87
<211> LENGTH: 42
<212> TYPE: PRT
<213> ORGANISM: Artificial Sequence
<220> FEATURE:
<223> OTHER INFORMATION: Synthetic construct of General Formula 1
<220> FEATURE:
<221> NAME/KEY: VARIANT
<222> LOCATION: (15)..(18)
<223> OTHER INFORMATION: Xaa is Gly or absent
<220> FEATURE:
<221> NAME/KEY: VARIANT
<222> LOCATION: (39)..(40)
<223> OTHER INFORMATION: Xaa-Xaa at positions 39 and 40 is His-Glu or absent
<220> FEATURE:
<221> NAME/KEY: VARIANT
<222> LOCATION: (41)..(42)
<223> OTHER INFORMATION: Xaa-Xaa at positions 41 and 42 is His-Glu or absent

<400> SEQUENCE: 87

```
Arg Arg Arg Trp Cys Lys Arg Arg Arg Ala Ser Gly Gly Gly Xaa Xaa
1               5                   10                  15

Xaa Xaa His Glu His Glu His Glu His Glu His Glu His Glu His Glu
            20                  25                  30

His Glu His Glu His Glu Xaa Xaa Xaa Xaa
        35                  40
```